(12) United States Patent
Fischl et al.

(10) Patent No.: US 11,180,479 B2
(45) Date of Patent: *Nov. 23, 2021

(54) ANTIVIRAL COMPOUNDS

(71) Applicant: HAPLOGEN GmbH, Vienna (AT)

(72) Inventors: Wolfgang Fischl, Vienna (AT);
Christopher John Yarnold, Abingdon (GB); Patricia Leonie Amouzegh, Abingdon (GB); Kevin Thewlis, Abingdon (GB); Jon Shepherd, Abingdon (GB); Mark Anthony Kerry, Abingdon (GB)

(73) Assignee: HAPLOGEN GMBH, Vienna (AT)

( * ) Notice: Subject to any disclaimer, the term of this patent is extended or adjusted under 35 U.S.C. 154(b) by 0 days.

This patent is subject to a terminal disclaimer.

(21) Appl. No.: 16/651,787

(22) PCT Filed: Oct. 5, 2018

(86) PCT No.: PCT/EP2018/077072
§ 371 (c)(1),
(2) Date: Mar. 27, 2020

(87) PCT Pub. No.: WO2019/068841
PCT Pub. Date: Apr. 11, 2019

(65) Prior Publication Data
US 2020/0239446 A1 Jul. 30, 2020

(30) Foreign Application Priority Data
Oct. 5, 2017 (EP) .................................... 17194907

(51) Int. Cl.
| | | |
|---|---|---|
| *A61K 31/40* | (2006.01) | |
| *A61K 31/4025* | (2006.01) | |
| *C07D 403/04* | (2006.01) | |
| *A61P 31/14* | (2006.01) | |
| *C07D 207/26* | (2006.01) | |
| *C07D 401/04* | (2006.01) | |
| *C07D 403/06* | (2006.01) | |
| *C07D 405/06* | (2006.01) | |
| *C07D 413/06* | (2006.01) | |

(52) U.S. Cl.
CPC ............ *C07D 403/04* (2013.01); *A61P 31/14* (2018.01); *C07D 207/26* (2013.01); *C07D 401/04* (2013.01); *C07D 403/06* (2013.01); *C07D 405/06* (2013.01); *C07D 413/06* (2013.01)

(58) Field of Classification Search
None
See application file for complete search history.

(56) References Cited
U.S. PATENT DOCUMENTS
2003/0069245 A1   4/2003   Wallace et al.

FOREIGN PATENT DOCUMENTS

| | | |
|---|---|---|
| EP | 2650292 A1 | 10/2013 |
| WO | 03/020712 A1 | 3/2003 |
| WO | 2011/160043 A2 | 12/2011 |
| WO | 2014/154829 A1 | 10/2014 |
| WO | 2015/018797 A2 | 2/2015 |

OTHER PUBLICATIONS

Jaworski et al., "AdPLA ablation increases lipolysis and prevents obesity induced by high fat feeding or leptin deficiency", Nat. Med., 2009, vol. 15, No. 2, pp. 159-68, doi:10.1038/nm.1904.
Li et al., "PLA2G16 promotes osteosarcoma metastasis and drug resistance via the MAPK pathway", Oncotarget., 2016, vol. 7, No. 14, pp. 18021-18035.
Studier et al., "Use of Bacteriophage T7 RNA Polymerase to Direct Selective High-level Expression of Cloned Genes", J. Mol. Biol., 1986, vol. 189, No. 1, pp. 113-130.
Rosenberg et al., "Vectors for selective expression of cloned DNAs by T7 RNA polymerase", Gene, 1987, vol. 56, No. 1, pp. 125-135.
Tang et al., "Discovery of a novel and potent class of anti-HIV-1 maturation inhibitors with improved virology profile against gag polymorphisms", Bioorganic & Med. Chem. Letters, 2017, vol. 27, No. 12, pp. 2689-2694, http://dx.doi.org/10.1016/j.bmcl.2017.04.042.
Xiong et al., "Pla2g16 phospholipase mediates gain-of-function activities of mutant p53", PNAS, 2014, vol. 111, No. 30, pp. 11145-11150, www.pnas.org/cgi/doi/10.1073/pnas.1404139111.
Extended European Search Report for EP 17194907.6 dated Dec. 14, 2017; 10 pages.
International Search Report for PCT/EP18/77072 dated Nov. 19, 2018; 5 pages.
Written Opinion of the ISA for PCT/EP18/77072 dated Nov. 19, 2018; 8 pages.
International Preliminary Report on Patentability for PCT/EP18/77072 dated Apr. 8, 2020; 9 pages.

(Continued)

*Primary Examiner* — Samantha L Shterengarts
(74) *Attorney, Agent, or Firm* — Loza & Loza, LLP; Michael F. Fedrick

(57) ABSTRACT

The present invention relates to novel compounds of general formula (I) wherein $R^1$ to $R^4$ and n have the meanings given in the description and claims, process for preparing these compounds and their use as for treating, preventing or ameliorating viral infections and their use for treating, preventing or ameliorating diseases which are associated with PLA2G16.

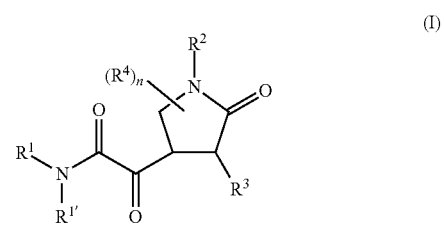

(I)

16 Claims, No Drawings

ANTIVIRAL COMPOUNDS

CROSS-REFERENCE TO RELATED APPLICATIONS

This application is the U.S. national stage of International Patent Application No. PCT/EP2018/077072, filed on Oct. 5, 2018 and entitled ANTIVIRAL COMPOUNDS, which claims the benefit of priority under 35 U.S.C. § 119 from European Patent Application No. 17194907.6, filed Oct. 5, 2017. The disclosures of the foregoing applications are incorporated herein by reference in their entirety.

FIELD OF THE INVENTION

The present invention relates to novel compounds of general formula I

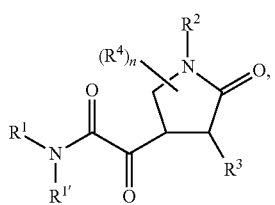

wherein $R^1$ to $R^4$ and n have the meanings given in the description and claims, process for preparing these compounds and their use as medicaments.

BACKGROUND ART

Viruses are major causes of disease and death throughout the world. Although vaccines and public health measures have greatly reduced the incidence of certain viral infections, such approaches have been less successful in tackling many viruses of significant medical and/or veterinary importance.

For example, chronic infection with hepatitis C virus (HCV) is a major health problem that affects more than 170 million people worldwide and is a causative agent of liver cirrhosis, hepatocellular carcinoma, and liver failure. Flaviviruses such as West Nile virus (WNV), Japanese Encephalitis virus (JEV), and the Dengue viruses (DENV) are significant human pathogens that cause millions of infections each year. Rhinoviruses are the most common viral infectious agents in humans and are the predominant cause of the common cold.

Pathogenic viruses can be classified into two general types with respect to the viral structure: enveloped viruses and non-enveloped viruses. Some well-known enveloped viruses include herpes virus, influenza virus, paramyxovirus, respiratory syncytial virus, corona virus, HIV, hepatitis B virus, hepatitis C virus and SARS-CoV virus. Non-enveloped viruses, sometimes referred to as "naked" viruses, include the families Picornaviridae, Reoviridae, Caliciviridae, Adenoviridae and Parvoviridae. Members of these families include rhinovirus, poliovirus, adenovirus, hepatitis A virus, norovirus, papillomavirus, and rotavirus.

The phospholipase A2, group XVI (PLA2G16) was identified as a new molecular target for antiviral drugs (WO2011160043).

PLA2G16 encodes an A2 group XVI phospholipase which is also reported to play roles in tumor metastasis (Xiong S. et al., Proc Natl Acad Sci USA. 2014 Jul. 29; 111(30), 11145-11150; Li L. et al., Oncotarget. 7(14), 18021-18035, 2016).

PLA2G16 has also been reported to play a crucial role in the development of obesity in mouse models (Jaworski K. et al., Nat. Med. 15 (2): 159-68, 2009).

However, there are still relatively few viral diseases for which effective drugs are available. Thus, there is still a need for new antiviral compounds and for new approaches to identifying such compounds. It is a further aim of the present invention to provide for new compounds which have an inhibitory effect on the enzyme PLA2G16 in vitro and in vivo and have suitable pharmacological and/or pharmacokinetic properties to enable them to be used as medicaments.

SUMMARY OF INVENTION

It has surprisingly been found, that compounds of general formula I, wherein $R^1$ to $R^4$ and n have the meanings below, act as specific inhibitors against PLA2G16. The compounds according to the invention are specifically useful as antiviral compounds.

Thus, the compounds according to the invention may be used for example for treating, preventing, and/or ameliorating viral infections.

Various objects, features, aspects, and advantages of the present invention will become more apparent from the following detailed description of embodiments of the invention.

DESCRIPTION OF EMBODIMENTS

The present invention relates to compounds of general formula I

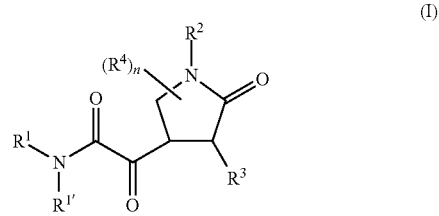

wherein
$R^1$ denotes H, $OR^a$, $-C(O)R^a$, $-(CH_2)_nC(O)OR^a$ or a group, optionally substituted by one or more, identical or different $R^a$ and/or $R^b$, selected independently from one another among $C_{1-6}$alkyl, $C_{2-6}$alkenyl, $C_{2-6}$alkynyl, $C_{3-10}$cycloalkyl, $C_{4-16}$cycloalkylalkyl, $C_{6-10}$aryl, 3-8 membered heterocycloalkyl, and 5-12 membered heteroaryl, and
$R^{1'}$ denotes H or $C_{1-4}$alkyl,
or $R^1$ and $R^{1'}$ together with the adjacent nitrogen atom form a 4- to 10-membered heterocyclic group, which optionally may be substituted by one or more, identical or different $R^a$ and/or $R^b$;
$R^2$ denotes H or a group, optionally substituted by one or more, identical or different $R^a$ and/or $R^b$, selected independently from one another among $C_{1-6}$alkyl, $C_{2-6}$alkenyl, $C_{2-6}$alkynyl, $C_{3-10}$cycloalkyl, $C_{4-16}$cycloalkylalkyl, $C_{6-10}$aryl, $C_{7-16}$arylalkyl, 3-8 membered heterocycloalkyl, 4-14 membered heterocycloalkylalkyl, 5-12 membered heteroaryl and 6-18 membered heteroarylalkyl;
$R^3$ denotes H or a group, optionally substituted by one or more, identical or different $R^a$ and/or $R^b$, selected independently from one another among $C_{1-6}$alkyl, $C_{2-6}$alkenyl, $C_{2-6}$alkynyl, $C_{3-10}$cycloalkyl, $C_{4-16}$cycloalkylalkyl, $C_{6-10}$aryl, $C_{7-16}$arylalkyl, 4-14 membered heterocycloalkylalkyl, 5-12 membered heteroaryl and 6-18 membered heterorylalkyl, $R^4$ denotes =O, halogen, or a group, optionally substituted by one or more, identical or different $R^a$ and/or $R^b$, selected independently from one another among $C_{1-6}$alkyl, $C_{2-6}$alkenyl, $C_{2-6}$alkynyl, $C_{3-6}$cycloalkyl or two $R^4$ form an optionally substituted 3 to 6 membered cycloalkyl or heterocycloalkyl ring, n denotes 0, 1, 2, 3, or 4, and each $R^a$ independently of one another denotes hydrogen or a group, optionally substituted by one or more, identical or different $R^b$ and/or $R^c$, selected from among $C_{1-6}$alkyl, $C_{2-6}$alkenyl, $C_{2-6}$alkynyl, $C_{3-10}$cycloalkyl, $C_{4-16}$cycloalkylalkyl, $C_{6-10}$aryl, $C_{7-16}$arylalkyl, 3-8 membered heterocycloalkyl, 4-14 membered heterocycloalkylalkyl, 5-12 membered heteroaryl and 6-18 membered heteroarylalkyl;

each $R^b$ is a suitable substituent and is selected in each case independently of one another from among =O, —$OR^c$, $C_{1-3}$haloalkyloxy, —$OCF_3$, =S, —$SR^c$, =$NR^c$, =$NOR^c$, =$NNR^cR^c$, =$NN(R^g)C(O)NR^cR^c$, —$NR^cR^c$, —$ONR^cR^c$, —$N(OR^c)R^c$, —$N(R^g)NR^cR^c$, halogen, —$CF_3$, —$CN$, —$NC$, —$OCN$, —$SCN$, —$NO$, —$NO_2$, =$N_2$, —$N_3$, —$S(O)R^c$, —$S(O)OR^c$, —$S(O)_2R^c$, —$S(O)_2OR^c$, —$S(O)NR^cR^c$, —$S(O)_2NR^cR^c$, —$OS(O)R^c$, —$OS(O)_2R^c$, —$OS(O)_2OR^c$, —$OS(O)NR^cR^c$, —$OS(O)_2NR^cR^c$, —$C(O)R^c$, —$C(O)OR^c$, —$C(O)SR^c$, —$C(O)NR^cR^c$, —$C(O)N(R^g)NR^cR^c$, —$C(O)N(R^g)OR^c$, —$C(NR^g)NR^cR^c$, —$C(NOH)R^c$, —$C(NOH)NR^cR^c$, —$OC(O)R^c$, —$OC(O)OR^c$, —$OC(O)SR^c$, —$OC(O)NR^cR^c$, —$OC(NR^g)NR^cR^c$, —$SC(O)R^c$, —$SC(O)OR^c$, —$SC(O)NR^cR^c$, —$SC(NR^g)NR^cR^c$, —$N(R^g)C(O)R^c$, —$N[C(O)R^c]_2$, —$N(OR^g)C(O)R^c$, —$N(R^g)C(NR^g)R^c$, —$N(R^g)N(R^g)C(O)R^c$, —$N[C(O)R^c]NR^cR^c$, —$N(R^g)C(S)R^c$, —$N(R^g)S(O)R^c$, —$N(R^g)S(O)OR^c$, —$N(R^g)S(O)_2R^c$, —$N[S(O)_2R^c]_2$, —$N(R^g)S(O)_2OR^c$, —$N(R^g)S(O)_2NR^cR^c$, —$N(R^g)[S(O)_2]_2R^c$, —$N(R^g)C(O)OR^c$, —$N(R^g)C(O)SR^c$, —$N(R^g)C(O)NR^cR^c$, —$N(R^g)C(O)NR^gNR^cR^c$, —$N(R^g)N(R^g)C(O)NR^cR^c$, —$N(R^g)C(S)NR^cR^c$, —$[N(R^g)C(O)]_2R^c$, —$N(R^g)[C(O)]_2R^c$, —$N\{[C(O)]_2R^c\}_2$, —$N(R^g)[C(O)]_2OR^c$, —$N(R^g)[C(O)]_2NR^cR^c$, —$N\{[C(O)]_2OR^c\}_2$, —$N\{[C(O)]_2NR^cR^c\}_2$, —$[N(R^g)C(O)]_2OR^c$, —$N(R^g)C(NR^g)OR^c$, —$N(R^g)C(NOH)R^c$, —$N(R^g)C(NR^g)SR^c$ and —$N(R^g)C(NR^g)NR^cR^c$;

each $R^c$ independently of one another denotes hydrogen or a group, optionally substituted by one or more, identical or different $R^d$ and/or $R^e$, selected from among $C_{1-6}$alkyl, $C_{2-6}$alkenyl, $C_{2-6}$alkynyl, $C_{3-10}$cycloalkyl, $C_{4-16}$cycloalkylalkyl, $C_{6-10}$aryl, $C_{7-16}$arylalkyl, 3-8 membered heterocycloalkyl, 4-14 membered heterocycloalkylalkyl, 5-12 membered heteroaryl and 6-18 membered heteroarylalkyl; each $R^d$ denotes a suitable substituent and is selected in each case independently of one another from among =O, —$OR^e$, $C_{1-3}$haloalkyloxy, —$OCF_3$, =S, —$SR^e$, =$NR^e$, =$NOR^e$, =$NNR^eR^e$, =$NN(R^g)C(O)NR^eR^e$, —$NR^eR^e$, —$ONR^eR^e$, —$N(OR^e)R^e$, —$N(R^g)NR^eR^e$, halogen, —$CF_3$, —$CN$, —$NC$, —$OCN$, —$SCN$, —$NO$, —$NO_2$, =$N_2$, —$N_3$, —$S(O)R^e$, —$S(O)OR^e$, —$S(O)_2R^e$, —$S(O)_2OR^e$, —$S(O)NR^eR^e$, —$S(O)_2NR^eR^e$, —$OS(O)R^e$, —$OS(O)_2R^e$, —$OS(O)_2OR^e$, —$OS(O)NR^eR^e$, —$OS(O)_2NR^eR^e$, —$C(O)R^e$, —$C(O)OR^e$, —$C(O)SR^e$, —$C(O)NR^eR^e$, —$C(O)N(R^g)NR^eR^e$, —$C(O)N(R^g)OR^e$, —$C(NR^g)NR^eR^e$, —$C(NOH)R^e$, —$C(NOH)NR^eR^e$, —$OC(O)R^e$, —$OC(O)OR^e$, —$OC(O)SR^e$, —$OC(O)NR^eR^e$, —$OC(NR^g)NR^eR^e$, —$SC(O)R^e$, —$SC(O)OR^e$, —$SC(O)NR^eR^e$, —$SC(NR^g)NR^eR^e$, —$N(R^g)C(O)R^e$, —$N[C(O)R^e]_2$, —$N(OR^g)C(O)R^e$, —$N(R^g)C(NR^g)R^e$, —$N(R^g)N(R^g)C(O)R^e$, —$N[C(O)R^e]NR^eR^e$, —$N(R^g)C(S)R^e$, —$N(R^g)S(O)R^e$, —$N(R^g)S(O)OR^e$, —$N(R^g)S(O)_2R^e$, —$N[S(O)_2R^e]_2$, —$N(R^g)S(O)_2OR^e$, —$N(R^g)S(O)_2NR^eR^e$, —$N(R^g)[S(O)_2]_2R^e$, —$N(R^g)C(O)OR^e$, —$N(R^g)C(O)SR^e$, —$N(R^g)C(O)NR^eR^e$, —$N(R^g)C(O)NR^gNR^eR^e$, —$N(R^g)N(R^g)C(O)NR^eR^e$, —$N(R^g)C(S)NR^eR^e$, —$[N(R^g)C(O)]_2R^e$, —$N(R^g)[C(O)]_2R^e$, —$N\{[C(O)]_2R^e\}_2$, —$N(R^g)[C(O)]_2OR^e$, —$N(R^g)[C(O)]_2NR^eR^e$, —$N\{[C(O)]_2OR^e\}_2$, —$N\{[C(O)]_2NR^eR^e\}_2$, —$[N(R^g)C(O)]_2OR^e$, —$N(R^g)C(NR^g)OR^e$, —$N(R^g)C(NOH)R^e$, —$N(R^g)C(NR^g)SR^e$ and —$N(R^g)C(NR^g)NR^eR^e$; and each $R^e$ independently of one another denotes hydrogen or a group selected from among $C_{1-6}$alkyl, $C_{2-6}$alkenyl, $C_{2-6}$alkynyl, $C_{3-8}$cycloalkyl, $C_{6-10}$aryl, 3-8 membered heterocycloalkyl, and 5-12 membered heteroaryl; and each $R^g$ independently of one another denotes hydrogen, $C_{1-6}$alkyl, $C_{2-6}$alkenyl, $C_{2-6}$alkynyl, $C_{3-8}$cycloalkyl, $C_{6-10}$aryl, 3-8 membered heterocycloalkyl, or 5-12 membered heteroaryl;

optionally in the form of the tautomers, the racemates, the enantiomers, the diastereomers, hydrates, isotopes, and mixtures thereof, and optionally the pharmacologically acceptable salts thereof.

One embodiment of the invention relates to compounds as described herein, wherein $R^1$ is —$R^a$, or selected from $C_{1-6}$alkyl, $C_{3-6}$cycloalkyl, $C_{4-16}$cycloalkylalkyl and 3-8 membered heterocycloalkyl, optionally substituted by one or more, identical or different $R^a$ and/or $R^b$.

One embodiment of the invention relates to compounds as described herein, wherein $R^{1'}$ is H.

One embodiment of the invention relates to compounds as described herein, wherein $R^2$ is H, $C_{1-6}$alkyl, $C_{3-10}$cycloalkyl, $C_{4-16}$cycloalkylalkyl, $C_{6-10}$aryl, $C_{7-16}$arylalkyl, 3-8 membered heterocycloalkyl, 4-14 membered heterocycloalkylalkyl, 5-12 membered heteroaryl and 6-18 membered heteroarylalkyl, optionally substituted by one or more, identical or different $R^a$ and/or $R^b$.

One embodiment of the invention relates to compounds as described herein, wherein $R^2$ is H, or $C_{1-6}$alkyl, $C_{4-16}$cycloalkylalkyl, $C_{7-16}$arylalkyl, 4-14 membered heterocycloalkylalkyl, 5-12 membered heteroaryl and 6-18 membered heteroarylalkyl, optionally substituted by one or more, identical or different $R^a$ and/or $R^b$.

One embodiment of the invention relates to compounds as described herein, wherein $R^2$ is $C_{1-6}$alkyl substituted by halogen, —$OR^a$, —$C(O)R^a$, —$C(O)NR^cR^c$, $C_{3-10}$cycloalkyl, $C_{6-10}$aryl, 3-8 membered heterocycloalkyl, and 5-12 membered heteroaryl.

One embodiment of the invention relates to compounds as described herein, wherein $R^2$ is $C_{1-2}$alkyl substituted by tetrahydropyranyl, phenyl, pyrimidinyl, triazolyl, oxazolyl, oxadiazolyl, or pyrrolidinyl, each optionally substituted by one or more, identical or different $R^a$ and/or $R^b$.

One embodiment of the invention relates to compounds as described herein, wherein $R^2$ is phenyl, pyrazolyl, pyridyl, pyrimidinyl, pyridazinyl, pyrazinyl, each optionally substituted by one or more, identical or different $R^a$ and/or $R^b$.

One embodiment of the invention relates to compounds as described herein, wherein $R^2$ is $C_{1-2}$alkyl, substituted by tetrahydropyranyl, phenyl, pyrimidinyl, triazolyl, oxazolyl, oxadiazolyl, or pyrrolidinyl, each optionally substituted by one or more, identical or different $R^a$ and/or $R^b$, or $R^2$ is phenyl, pyrazolyl, pyridyl, pyrimidinyl, pyridazinyl, pyrazinyl, each optionally substituted by one or more, identical or different $R^a$ and/or $R^b$.

One embodiment of the invention relates to compounds as described herein, wherein $R^2$ is One embodiment of the invention relates to compounds as described herein, wherein $R^3$ is $C_{3-10}$cycloalkyl, $C_{6-10}$aryl or $C_{7-16}$arylalkyl, optionally substituted by one or more, identical or different $R^a$ and/or $R^b$.

One embodiment of the invention relates to compounds as described herein, wherein $R^3$ is $C_{6-10}$aryl or $C_{7-16}$arylalkyl, optionally substituted by one or more, identical or different $R^a$ and/or $R^b$.

One embodiment of the invention relates to compounds as described herein, wherein $R^3$ is phenyl or benzyl, optionally substituted by one or more, identical or different $R^a$ and/or $R^b$.

One embodiment of the invention relates to compounds as described herein, wherein n denotes 0.

One embodiment of the invention relates to compounds as described herein, wherein the compounds are selected from Table 2.

One embodiment of the invention relates to compounds as described herein, optionally in the form of the tautomers, the racemates, the enantiomers, the diastereomers, hydrates, isotopes, and mixtures thereof, or the pharmacologically acceptable salt thereof, for use as medicament.

The invention contemplates treatment of a wide variety of viral infections in human and/or animal subjects, e.g., infection due to any virus. In some embodiments, the virus is a picornavirus, e.g., a cardiovirus, enterovirus (e.g. a coxsackievirus, a rhinovirus, a poliovirus or echovirus), or hepatovirus. In some embodiments, the virus clusters phylogenetically within the enterovirus genus. In some embodiments, the picornavirus is classified with a species selected from the group consisting of: human enterovirus A, human enterovirus B, human enterovirus C, human enterovirus D, simian enterovirus A, bovine enterovirus, porcine enterovirus B, human rhinovirus A, human rhinovirus B and human rhinovirus C. In some embodiments, the picornavirus is classified with a species selected from the group consisting of: human enterovirus A, human enterovirus B, human enterovirus C, human enterovirus D, human rhinovirus A, human rhinovirus B and human rhinovirus C.

The invention provides use of the compounds for treating diseases and medical conditions resulting from viral infection, e.g., by a picornavirus. Exemplary diseases and conditions include, e.g., asthma exacerbation, bronchiolitis, colitis, common cold, COPD exacerbation, encephalitis, encephalomyelitis, enterocolitis, foot-and-mouth disease, hand-foot-and-mouth disease, gastroenteritis, herpangina, hepatitis, meningitis, meningoencephalitis, myocarditis, pancreatitis, poliomyelitis, and pneumonia. In some aspects, the invention contemplates ex vivo uses of the PLA2G16 inhibitors.

Thus, one embodiment of the invention relates to compounds as described herein, optionally in the form of the tautomers, the racemates, the enantiomers, the diastereomers, hydrates, isotopes, and mixtures thereof, or the pharmacologically acceptable salt thereof, for use as antiviral agents.

A further embodiment of the invention relates to compounds as described herein, optionally in the form of the tautomers, the racemates, the enantiomers, the diastereomers, hydrates, isotopes, and mixtures thereof, or the pharmacologically acceptable salt thereof, for use in the treatment or prevention of infectious diseases, cancer or obesity.

One embodiment of the invention relates to compounds as described herein, optionally in the form of the tautomers, the racemates, the enantiomers, the diastereomers, hydrates, isotopes, and mixtures thereof, or the pharmacologically acceptable salt thereof, for use in treating, preventing, and/or ameliorating viral infections.

One embodiment of the invention relates to compounds as described herein, optionally in the form of the tautomers, the racemates, the enantiomers, the diastereomers, hydrates, isotopes, and mixtures thereof, or the pharmacologically acceptable salt thereof, for use in treating, preventing, and/or ameliorating viral infections caused by a picornavirus, e.g. by a rhinovirus.

One embodiment of the invention relates to pharmaceutical preparations containing as active substance one or more compounds of general formula I as described herein, optionally in the form of the tautomers, the racemates, the enantiomers, the diastereomers, hydrates, isotopes, and mixtures thereof, or the pharmacologically acceptable salt thereof, or the pharmacologically acceptable salts thereof, optionally in combination with conventional excipients and/or carriers.

One embodiment of the invention relates to pharmaceutical preparations comprising a compound of general formula I as described herein, wherein the compounds are optionally present in the form of the tautomers, racemates, enantiomers, diastereomers, hydrates, isotopes, and mixtures thereof, or also as the respective pharmacologically acceptable salts of all the above mentioned forms, and at least one further active substance different from formula I.

Definitions

As used herein, the following definitions apply, unless stated otherwise:

Unless specified otherwise, the term "alkyl", when used alone or in combination with other groups or atoms, refers to a saturated straight or branched chain consisting solely of 1 to 6 hydrogen-substituted carbon atoms, and includes methyl, ethyl, propyl, isopropyl, n-butyl, 1-methylpropyl, isobutyl, t-butyl, 2,2-dimethylbutyl, 2,2-dimethyl-propyl, n-pentyl, 2-methylpentyl, 3-methylpentyl, 4-methylpentyl, n-hexyl and the like.

Unless specified otherwise, the term "alkenyl" refers to a partially unsaturated straight or branched chain consisting solely of 2 to 6 hydrogen-substituted carbon atoms that contains at least one double bond, and includes vinyl, allyl, 2-methylprop-1-enyl, but-1-enyl, but-2-enyl, but-3-enyl, buta-1,3-dienyl, penta-1,3-dienyl, penta-2,4-dienyl, 2-methylbut-1-enyl, 2-methylpent-1-enyl, 4-methylpent-1-enyl, 4-methylpent-2-enyl, 2-methylpent-2-enyl, 4-methylpenta-1,3-dienyl, hexen-1-yl and the like.

Unless specified otherwise, the term "alkynyl" refers to a partially unsaturated straight or branched chain consisting solely of 2 to 6 hydrogen-substituted carbon atoms that contains at least one triple bond, and includes ethynyl, 1-propynyl, 2-propynyl, 2-methylprop-1-ynyl, 1-butynyl, 2-butynyl, 3-butynyl, 1,3-butadiynyl, 3-methylbut-1-ynyl, 4-methylbut-ynyl, 4-methylbut-2-ynyl, 2-methylbut-1-ynyl, 1-pentynyl, 2-pentynyl, 3-pentynyl, 4-pentynyl, 1,3-pentadiynyl, 1,4-pentadiynyl, 3-methylpent-1-ynyl, 4-methylpent-2-ynyl, 4-methylpent-2-ynyl, 1-hexynyl, and the like.

Unless specified otherwise, the term "cycloalkyl", when used alone or in combination with other groups or atoms, refers to monocyclic hydrocarbon rings, bicyclic hydrocarbon rings or spirohydrocarbon rings, which each may be either saturated or unsaturated (cycloalkenyl). The term unsaturated means that in the ring system in question there is at least one double bond, but no aromatic system is formed. In bicyclic hydrocarbon rings two rings are linked such that they have at least two carbon atoms in common. In spirohydrocarbon rings one carbon atom (spiroatom) is shared by two rings. If a cycloalkyl is substituted, the substitution may be mono- or polysubstitution in each case, at all the hydrogen-carrying carbon atoms, independently of one another. Cycloalkyl itself may be linked to the molecule as substituent via any suitable position of the ring system.

Typical examples of individual sub-groups are listed below. Monocyclic saturated hydrocarbon rings: cyclopropyl; cyclobutyl; cyclopentyl; cyclohexyl; cycloheptyl, etc.

Monocyclic unsaturated hydrocarbon rings: cycloprop-1-enyl; cycloprop-2-enyl; cyclobut-1-enyl; cyclobut-2-enyl; cyclopent-1-enyl; cyclopent-2-enyl; cyclopent-3-enyl; cyclohex-1-enyl; cyclohex-2-enyl; cyclohex-3-enyl; cyclohept-1-enyl; cyclohept-2-enyl; cyclohept-3-enyl; cyclohept-4-enyl; cyclobuta-1,3-dienyl; cyclopenta-1,4-dienyl; cyclopenta-1,3-dienyl; cyclopenta-2,4-dienyl; cyclohexa-1,3-dienyl; cyclohexa-1,5-dienyl; cyclohexa-2,4-dienyl; cyclohexa-1,4-dienyl; cyclohexa-2,5-dienyl, etc. Saturated and unsaturated bicyclic hydrocarbon rings: bicyclo[2.2.0]hexyl; bicyclo[3.2.0]heptyl; bicyclo[3.2.1]octyl; bicyclo[2.2.2]octyl; bicyclo[4.3.0]nonyl (octahydroindenyl); bicyclo[4.4.0]decyl (decahydronaphthalene); bicyclo[2,2,1]heptyl (norbornyl); (bicyclo[2.2.1]hepta-2,5-dienyl (norborna-2,5-dienyl); bicyclo[2,2,1]hept-2-enyl (norbornenyl); bicyclo[4.1.0]heptyl (norcaranyl); bicyclo-[3.1.1]heptyl (pinanyl), etc.

Saturated and unsaturated spirohydrocarbon rings: spiro[2.5]octyl, spiro[3.3]heptyl, spiro[4.5]dec-2-ene, etc.

"Cycloalkylalkyl" denotes the combination of the above-defined groups alkyl, alkenyl, alkynyl, and cycloalkyl, in each case in their broadest sense. The alkyl group as substituent is directly linked to the molecule and is in turn substituted by a cycloalkyl group. The alkyl and cycloalkyl may be linked in both groups via any carbon atoms suitable for this purpose. The respective sub-groups of alkyl and cycloalkyl are also included in the combination of the two groups.

Unless specified otherwise, the term "aryl" refers to an aromatic mono- or bicyclic group containing from 6 to 14 carbon atoms, preferably 6 to 10 carbon atoms, that may be optionally fused with a fully or partially saturated or unsaturated carbocyclic ring and may optionally be substituted with one or more, identical or different substituents, suitably one to three substituents. Examples of aryl groups include phenyl, naphthyl, indanyl, and the like.

"Arylalkyl" denotes the combination of the groups alkyl, alkenyl, alkynyl and aryl as hereinbefore defined, in each case in their broadest sense. The alkyl group as substituent is directly linked to the molecule and is in turn substituted by an aryl group. The alkyl and aryl may be linked in both groups via any carbon atoms suitable for this purpose. Typical examples include benzyl, 1-phenylethyl, 2-phenylethyl, phenylvinyl, phenylallyl, etc.

Unless specified otherwise, the term "heteroaryl" refers to an aromatic mono- or bicyclic group containing from 5 to 14 carbon atoms, preferably 5 to 12 carbon atoms, of which one to five is replaced with a heteroatom selected from N, S and O, that may optionally be reduced to a non-aromatic heterocycle and may optionally be substituted with one or more, identical or different substituents. Examples of heteroaryl groups include pyrrolyl, dihydropyrrolyl, pyrrolidinyl, oxopyrrolidinyl, indolyl, isoindolyl, indolizinyl, imidazolyl, pyrazolyl, benzimidazolyl, imidazo(1,2-a)pyridinyl, indazolyl, purinyl, pyrrolo(2,3-c)pyridinyl, pyrrolo(3,2-c)pyridinyl, pyrrolo(2,3-b)pyridinyl, pyrazolo(1,5-a)pyridinyl, 1,2,3-triazolyl, 1,2,4-triazolyl, tetrazolyl, oxazolyl, 1,2 oxazolyl, isoxazolyl, 1,3,4-oxadiazolyl, 1,2,5-oxadiazolyl, 1,2,4-oxadiazolyl, 1,2,3-oxadiazolyl, thiazolyl, isothiazolyl, 1,3,4-thiadiazolyl, 1,2,5-thiadiazolyl, 1,2,4-thiadiazolyl, 1,2,3-thiadiazolyl, furanyl, dihydrofuranyl, tetrahydrofuranyl, benzofuranyl, isobenzofuranyl, thiophenyl, dihydrothiophenyl, tetrahydrothiophenyl, benzothiophenyl, benzoisothiophenyl, pyridyl, piperidinyl, quinolinyl, isoquinolinyl, tetrahydroisoqinolinyl, quinolizinyl, pyrazinyl, pyridazinyl, pyrimidinyl, pyranyl, tetrahydropyranyl, 1,2,3-triazinyl, 1,2,4-triazinyl, 1,3,5-triazinyl, chromenyl, morpholinyl, diazepinyl, benzodiazepinyl, and the like.

"Heteroarylalkyl" denotes the combination of the alkyl, alkenyl, alkynyl, and heteroaryl groups defined hereinbefore, in each case in their broadest sense. The alkyl group as substituent is directly linked to the molecule and is in turn substituted by a heteroaryl group. The linking of the alkyl and heteroaryl may be achieved on the alkyl side via any carbon atoms suitable for this purpose and on the heteroaryl side by any carbon or nitrogen atoms suitable for this purpose.

By the term "heterocycloalkyl" are meant groups which are derived from cycloalkyl as hereinbefore defined if in the hydrocarbon rings one or more of the groups —CH$_2$— are replaced independently of one another by the groups —O—, —S— or —NH— or one or more of the groups =CH— are replaced by the group =N—, while not more than five heteroatoms may be present in total, there must be at least one carbon atom between two oxygen atoms and between two sulphur atoms or between one oxygen and one sulphur atom and the group as a whole must be chemically stable.

Heteroatoms may simultaneously be present in all the possible oxidation stages (sulphur->sulphoxide —SO—, sulphone —SO$_2$—; nitrogen->N-oxide). It is immediately apparent from the indirect definition/derivation from cycloalkyl that heterocycloalkyl is made up of the sub-groups monocyclic hetero-rings, bicyclic hetero-rings and spirohetero-rings, while each sub-group can also be further subdivided into saturated and unsaturated (heterocycloalkenyl). The term unsaturated means that in the ring system in question there is at least one double bond, but no aromatic system is formed. In bicyclic hetero-rings two rings are linked such that they have at least two atoms in common. In spirohetero-rings one carbon atom (spiroatom) is shared by two rings. If a heterocycloalkyl is substituted, the substitution may be mono- or polysubstitution in each case, at all the hydrogen-carrying carbon and/or nitrogen atoms, independently of one another. Heterocycloalkyl itself as substituent may be linked to the molecule via any suitable position of the ring system.

The term "heterocyclic group" as used herein refers to a heterocycloalkyl group which optionally may be fused to an aromatic aryl or heteroaryl group.

Typical examples of individual sub-groups are listed below: Monocyclic heterorings (saturated and unsaturated): oxolane, pyrrolidinyl, pyrrolinyl, imidazolidinyl, thiazolidinyl, imidazolinyl, pyrazolidinyl, pyrazolinyl, piperidinyl, piperazinyl, oxiranyl, aziridinyl, azetidinyl, 1,4-dioxanyl, azepanyl, diazepanyl, morpholinyl, thiomorpholinyl, homomorpholinyl, homopiperidinyl, homopiperazinyl, homothiomorpholinyl, thiomorpholinyl-S-oxide, thiomorpholinyl-S, S-dioxide, 1,3-dioxolanyl, oxane, tetrahydrothiopyranyl, 1,4-oxazepanyl, tetrahydrothienyl, homothiomorpholinyl-S, S-dioxide, oxazolidinonyl, dihydropyrazolyl, dihydropyrrolyl, dihydropyrazinyl, dihydropyridyl, dihydro-pyrimidinyl, dihydrofuryl, dihydropyranyl, tetrahydrothienyl-S-oxide, tetrahydrothienyl-S,S-dioxide, homothiomorpholinyl-S-oxide, 2,3-dihydroazet, 2H-pyrrolyl, 4H-pyranyl, 1,4-dihydropyridinyl, etc; Bicyclic heterorings (saturated and unsaturated): 8-azabicyclo[3.2.1]octyl, 8-azabicyclo[5.1.0]octyl, 2-oxa-5-azabicyclo[2.2.1]heptyl, 8-oxa-3-aza-bicyclo[3.2.1]octyl, 3,8-diaza-bicyclo[3.2.1]octyl, 2,5-diaza-bicyclo-[2.2.1]heptyl, 1-aza-bicyclo[2.2.2]octyl, 3,8-diaza-bicyclo[3.2.1]octyl, 3,9-diaza-bicyclo[4.2.1]nonyl, 2,6-diaza-bicyclo[3.2.2]nonyl, hexahydro-furo[3,2-b]furyl, etc; Spiroheterorings (saturated and unsaturated): 1,4-dioxa-spiro[4.5]decyl; 1-oxa-3,8-diaza-spiro[4.5]decyl; 2,6-diaza-spiro[3.3]heptyl; 2,7-diaza-spiro[4.4]nonyl; 2,6-diaza-spiro[3.4]octyl; 3,9-diaza-spiro[5.5]undecyl; 2,8-diaza-spiro[4.5]decyl, etc.

"Heterocycloalkylalkyl" denotes the combination of the alkyl, alkenyl, alkynyl, and heterocycloalkyl groups defined hereinbefore, in each case in their broadest sense. The alkyl group as substituent is directly linked to the molecule and is in turn substituted by a heterocycloalkyl group. The linking of the alkyl and heterocycloalkyl may be achieved on the alkyl side via any carbon atoms suitable for this purpose and on the heterocycloalkyl side by any carbon or nitrogen atoms suitable for this purpose.

By the term "suitable substituent" is meant a substituent that on the one hand is fitting on account of its valency and on the other hand leads to a system with chemical stability.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

The term "tautomers" refer to compounds that are interchangeable forms of a particular compound structure, and that vary in the displacement of hydrogen atoms and electrons. Thus, two structures may be in equilibrium through the movement of rr electrons and an atom (usually H). For example, enols and ketones are tautomers because they are rapidly interconverted by treatment with either acid or base.

It is also to be understood that compounds (e.g., dihydro bases described herein) that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively).

A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "hydrate" refers to a compound which is associated with water. Typically, the number of the water molecules contained in a hydrate of a compound is in a definite ratio to the number of the compound molecules in the hydrate.

Any formula or structure given herein, including Formula I compounds, is also intended to represent unlabeled forms as well as isotopically-labeled forms of the compounds. Isotopically-labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as, but not limited to 2H (deuterium, D), 3H (tritium), 11C, 13C, 14C, 15N, 18F, 31P, 32P, 35S, 36Cl, and 125J.

The term "pharmacologically acceptable" means compatible with the treatment of animals, in particular, humans. The term pharmacologically acceptable salt includes both pharmacologically acceptable acid addition salts and pharmacologically acceptable basic addition salts.

The term"pharmacologically acceptable acid addition salt" as used herein means any non-toxic organic or inorganic salt of any base compound of the disclosure, or any of its intermediates. Basic compounds of the disclosure that may form an acid addition salt include, for example, compounds that contain a basic nitrogen atom. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methanesulfonic acids. Either the mono-, di- or the triacid salts can be formed, and such salts may exist in either a hydrated, solvated or substantially anhydrous form. In general, the acid addition salts of the compounds of the disclosure are more soluble in water and various hydrophilic organic solvents, and generally demonstrate higher melting points in comparison to their free base forms. The selection of the appropriate salt will be known to one skilled in the art. Other non-pharmacologically acceptable acid addition salts, e.g. oxalates, may be used, for example, in the isolation of the compounds of the disclosure, for laboratory use, or for subsequent conversion to a pharmacologically acceptable acid addition salt.

The term "pharmacologically acceptable basic salt" as used herein means any non-toxic organic or inorganic basic addition salt of any acid compound of the invention, or any of its intermediates, which are suitable for or compatible with the treatment of animals, in particular humans. Acidic compounds of the invention that may form a basic addition salt include, for example compounds that contain carboxylic acid, sulfonic acid, sulfinic acid, sulfonamide, N-unsubstituted tetrazole, phosphoric acid ester, or sulfuric acid ester. Illustrative inorganic bases which form suitable salts include lithium, sodium, potassium, calcium, magnesium, or barium hydroxide. Illustrative organic bases which form suitable salts include aliphatic, alicyclic or aromatic organic amines such as methylamine, trimethylamine and picoline or ammonia. The selection of the appropriate salt will be known to a person skilled in the art. Other non-pharmacologically acceptable basic addition salts, may be used, for example, in the isolation of the compounds of the invention, for laboratory use, or for subsequent conversion to a pharmacologically acceptable basic addition salt. The formation of a desired compound salt is achieved using standard techniques. For example, the neutral compound is treated with a base in a suitable solvent and the formed salt is isolated by filtration, extraction or any other suitable method.

The term "therapeutically effective amount", "effective amount" or "sufficient amount" of a compound of the present invention is a quantity sufficient to, when administered to the subject, including a mammal, for example a human, effect beneficial or desired results, including clinical results, and, as such, an effective amount or synonym thereof depends upon the context in which it is being applied.

Abbreviations

AcOH acetic acid
atm atmosphere
$Boc_2O$ boc anhydride
$CHCl_3$ chloroform
$CO_2$ carbon dioxide
conc. concentrated
$Cs_2CO_{03}$ cesium carbonate
Cu(I)I copper (I) iodide
CV column volume
1,2-DCE 1,2-dichloroethane
DCM dichloromethane
DIPEA N,N-diisopropyl-N-ethylamine
DMF N,N-dimethylformamide
DMP Dess-Martin periodinane
DMSO dimethylsulfoxide
$D_2O$ deuterium oxide
ee enantiomeric excess
ELS Evaporative Light Scattering
ESI electron-spray ionisation
$Et_2O$ diethyl ether
EtOAc ethyl acetate
EtOH ethanol
FCC flash column chromatography
FP final product
g gram
h hour
$H_2O$ water
$H_2SO_4$ sulfuric acid
HATU 1-[bis(dimethylamino)methylene]-1H-1,2,3-triazolo[4,5-b]pyridinium 3-oxid hexafluorophosphate
HCl hydrochloric acid
HPLC high-performance liquid chromatography
I intermediate
IPA Isopropanol
$K_2CO_3$ potassium carbonate
KI potassium iodide
LC liquid chromatography
LiOH lithium hydroxide
m-CPBA meta-chloroperoxybenzoic acid
MeCN acetonitrile
MeOH methanol
mHz Mega Hertz
min minute
mL milliliter
$NaBH_4$ sodium borohydride
NaBr sodium bromide
NaH sodium hydride
$NaHCO_3$ sodium bicarbonate
NaOH sodium hydroxide
$NaNO_2$ sodium nitrite
NaOEt sodium ethoxide
NaOH sodium hydroxide
$Na_2S_2O_3$ sodium thiosulfate
$Na_2SO_3$ sodium sulfite
$Na_2SO_4$ sodium sulfate
$NH_4Cl$ ammonium chloride
$NiCl_2$ nickel chloride
NMR nuclear magnetic resonance
Pd/C palladium on charcoal
$PtO_2$ platinum dioxide
ppm parts per million
RT room temperature
Rt retention time
sat. saturated
sec second
SFC supercritical fluid chromatography
STAB sodium triacetoxyborohydride
T3P propylphosphonic anhydride
TBME tert-butyl methyl ether
THF tetrahydrofuran
UV ultraviolet
w weight

EXAMPLES

The Examples which follow are set forth to aid in the understanding of the invention but are not intended to, and should not be construed to limit the scope of the invention in any way. The Examples do not include detailed descriptions of conventional methods. Such methods are well known to those of ordinary skill in the art.

GENERAL EXPERIMENTAL DETAILS

Commercially available reagents and solvents (HPLC grade) were used without further purification. $^1H$ NMR spectra were recorded on a Bruker DRX 500 MHz spectrometer or a Bruker DPX 250 MHz spectrometer in deuterated solvents. Chemical shifts ($\delta$) are in parts per million. Compounds were purified by FCC on normal phase silica on Biotage Isolera systems using the appropriate SNAP cartridge and gradient. Alternatively, compounds were purified on reverse phase silica using Biotage Isolera systems with the appropriate SNAP C18 cartridges and reverse phase eluent or by preparative LC (if stated otherwise).

Reverse Phase Chromatography Using Acidic pH, Standard Elution Method

Purifications by FCC on reverse phase silica (acidic pH, standard elution method) were performed on Biotage Isolera systems using the appropriate SNAP C18 cartridge and a gradient of 10% B (A=0.1% formic acid in water; B=0.1% formic acid in acetonitrile) over 1.7 CV then 10-100% B over 19.5 CV and 100% B for 2 CV.

Preparative LC Using Acidic pH, Standard Elution Method

Purifications by preparative LC (acidic pH, standard elution method) were performed on a Gilson LC system using a Waters Sunfire C18 column (30 mm×10 mm, 10 μM; temperature: RT) and a gradient of 30-95% B (A=0.1% formic acid in water; B=0.1% formic acid in acetonitrile) over 11.00 min then 95% B for 2.10 min, with an injection volume of 1500 μL and a flow rate of 40 mL/min. UV spectra were recorded at 215 nm using a Gilson detector.

Preparative LC Using Acidic pH, Early Elution Method

Purifications by preparative LC (acidic pH, early elution method) were performed on a Gilson LC system using a Waters Sunfire C18 column (30 mm×100 mm, 10 μM; temperature: RT) and a gradient of 10-95% B (A=0.1% formic acid in water; B=0.1% formic acid in acetonitrile) over 14.44 min then 95% B for 2.11 min, with an injection volume of 1500 μL and a flow rate of 40 mL/min. UV spectra were recorded at 215 nm using a Gilson detector.

Method METCR0990

Analytical METCR0990 HPLC-MS were performed on a Agilent G1312A system with Waters PDA and ELS detectors using a Phenomenex Gemini-NX C18 column (2.0 mm×50 mm, 3 µM; temperature: 40° C.) and a gradient of 1-100% (A=2 mM ammonium bicarbonate, buffered to pH 10 with ammonium hydroxide solution; B=acetonitrile) over 1.8 min then 100% B for 0.3 min, with an injection volume of 3 µL and a flow rate of 1.0 mL/min. UV spectra were recorded at 215 nm using a Waters 2996 photo diode array detector. Mass spectra were obtained over the range m/z 150 to 850 at a sampling rate of 5 scans per sec using a Waters ZQ. Data were integrated and reported using Waters Mass-Lynx and OpenLynx software.

Method METCR1410

Analytical METCR1410 HPLC-MS were performed on Shimadzu LCMS-2010EV systems using reverse phase Kinetex Core shell C18 columns (2.1 mm×50 mm, 5 µm; temperature: 40° C.) and a gradient of 5-100% B (A=0.1% formic acid in water; B=0.1% formic acid in acetonitrile) over 1.2 min then 100% B for 0.1 min, with an injection volume of 3 µL and a flow rate of 1.2 mL/min. UV spectra were recorded at 215 nm using a SPD-M20A photo diode array detector. Mass spectra were obtained over the range m/z 150 to 850 at a sampling rate of 2 scans per sec using a LCMS2010EV. Data were integrated and reported using Shimadzu LCMS-Solutions and PsiPort software.

Method METCR1603

Analytical METCR1603 HPLC-MS were performed on a Agilent G1312A system with Waters 2996 PDA detector and Waters 2420 ELS detector using a Phenomenex Gemini-NX C18 column (2.0×100 mm, 3 µm column; temperature: 40° C.) and a gradient of 5-100% (A=2 mM ammonium bicarbonate, buffered to pH 10; B=acetonitrile) over 5.5 min then 100% B for 0.4 min, with an injection volume of 3 µL and a flow rate of 0.6 mL/min. UV spectra were recorded at 215 nm using a Waters Acquity photo diode array detector. Mass spectra were obtained over the range m/z 150 to 850 at a sampling rate of 5 scans per sec using a Waters ZQ mass detector. Data were integrated and reported using Waters MassLynx and OpenLynx software.

Method MET-uHPLC-AB-101

Analytical MET-uHPLC-AB-101 HPLC-MS were performed on a Waters Acquity uPLC system with Waters PDA and ELS detectors using a Phenomenex Kinetex-XB C18 column (2.1 mm×100 mm, 1.7 µM; temperature: 40° C.) and a gradient of 5-100% B (A=0.1% formic acid in water; B=0.1% formic acid in acetonitrile) over 5.3 min then 100% B for 0.5 min, with an injection solution of 3 µL and a flow rate of 0.6 mL/min. UV spectra were recorded at 215 nm using a Waters Acquity photo diode array detector. Mass spectra were obtained over the range m/z 150 to 850 at a sampling rate of 5 scans per sec using a Waters SQD. Data were integrated and reported using Waters MassLynx and OpenLynx software.

Method MET-uHPLC-AB-102

Analytical MET-uHPLC-AB-102 HPLC-MS were performed on a Waters Acquity uPLC system with Waters PDA and ELS detectors using a Waters uPLC CSH C18 column (2.1 mm×100 mm, 1.7 µM; temperature: 40° C.) and a gradient of 5-100% (A=2 mM ammonium bicarbonate, buffered to pH 10 with ammonium hydroxide solution; B=acetonitrile) over 5.3 min then 100% B for 0.5 min a flow rate of 0.6 mL/min. UV spectra were recorded at 215 nm using a Waters Acquity photo diode array detector. Mass spectra were obtained over the range m/z 150 to 850 at a sampling rate of 5 scans per sec using a Waters Quatro Premier XE. Data were integrated and reported using Waters MassLynx and OpenLynx software.

Method MET-uHPLC-1704

Analytical MET-uHPLC-1704 HPLC-MS were performed on a Waters Acquity uPLC system with Waters PDA and ELS detectors using a Waters uPLC CSH C18 column (2.1 mm×100 mm, 1.7 µM; temperature: 40° C.) and a gradient of 5-100% B (A=0.1% formic acid in water; B=0.1% formic acid in acetonitrile) over 1.1 min then 100% B for 0.25 min, with an injection solution of 2 µL and a flow rate of 0.9 mL/min. UV spectra were recorded at 215 nm using a Waters Acquity photo diode array detector. Mass spectra were obtained over the range m/z 150 to 850 at a sampling rate of 5 scans per sec using a Waters SQD. Data were integrated and reported using Waters MassLynx and OpenLynx software.

Method CAM-1

Analytical chiral SFC were performed on a Waters Resolution SFC system using Chiralpak AS-H columns (4.6 mm×250 mm, 5 µm; temperature: 40° C.) and an isocratic eluent of 7.5/2.5 $CO_2$/IPA over 10 min, with an injection volume of 10 µL and a flow rate of 4 mL/min. UV spectra were recorded at 215 nm using a Waters 2998 photo diode array detector. Data were integrated using Waters MassLynx and OpenLynx software.

Method CAM-2

Analytical CAM-2 chiral LC were performed on a Waters LC system using Chiralpak AS-H columns (4.6 mm×250 mm, 5 µm; temperature: RT) and an isocratic eluent of acetonitrile over 15 min, with an injection volume of 20 µL and a flow rate of 1 mL/min. UV spectra were recorded at 215 nm using a Waters 2996 photo diode array detector. Data were integrated and reported using Waters MassLynx and OpenLynx software.

Method CAM-3

Analytical CAM-3 chiral SFC were performed on a Waters Investigator SFC system using Chiralcel OD-H columns (4.6 mm×250 mm, 5 µm; temperature: 40° C.) and an isocratic eluent of 7.5/2.5 $CO_2$:MeCN over 10 min, with an injection volume of 10 µL and a flow rate of 4 mL/min. UV spectra were recorded at 240 nm using a Waters 2998 photo diode array detector. Data were integrated and reported using Waters MassLynx and OpenLynx software.

Method CAM-4

Analytical CAM-4 chiral LC were performed on a Waters LC system using Cellulose-4 columns (4.6 mm×250 mm, 5 µm; temperature: RT) and an isocratic eluent of MeCN over 15 min, with an injection volume of 20 µL and a flow rate of 1 mL/min. UV spectra were recorded at 215 nm using a Waters 2996 photo diode array detector. Data were integrated using Waters MassLynx and OpenLynx software.

Method CAM-5

Analytical CAM-5 chiral LC were performed on a Waters LC system using Cellulose-4 columns (4.6 mm×250 mm, 5 µm; temperature: RT) and an isocratic eluent of MeCN over 40 min, with an injection volume of 20 µL and a flow rate of 0.5 mL/min. UV spectra were recorded at 215 nm using a Waters 2996 photo diode array detector. Data were integrated using Waters MassLynx and OpenLynx software.

Method CAM-6

Analytical CAM-6 chiral LC were performed on a Waters LC system using Amylose-2 columns (4.6 mm×250 mm, 5 µm; temperature: RT) and an isocratic eluent of MeCN over 12 min, with an injection volume of 20 µL and a flow rate of 1 mL/min. UV spectra were recorded at 215 nm using a Waters 2996 photo diode array detector. Data were integrated using Waters MassLynx and OpenLynx software.

All compounds displayed a purity>95% as determined by these methods unless otherwise stated.

Compound names were generated using ChemAxon software: Instant JChem Excel IUPAC Name function.

Note: 1-(Cyanomethyl)thiolan-1-ium bromide was synthesized by the procedure described in WO2014/154829

GENERAL SCHEME 1

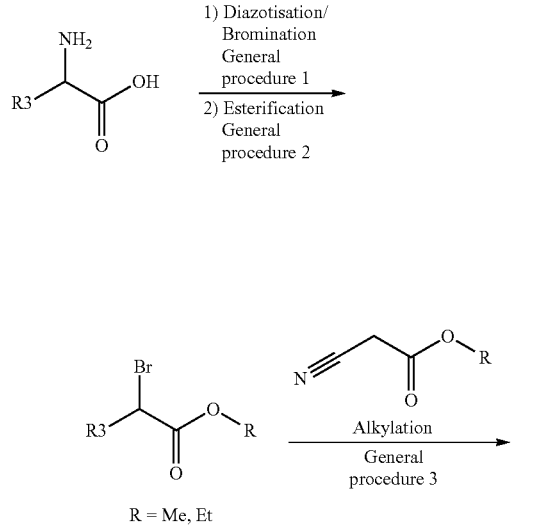

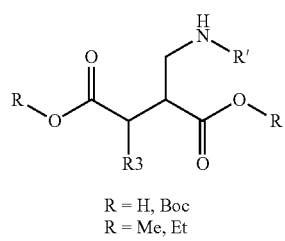

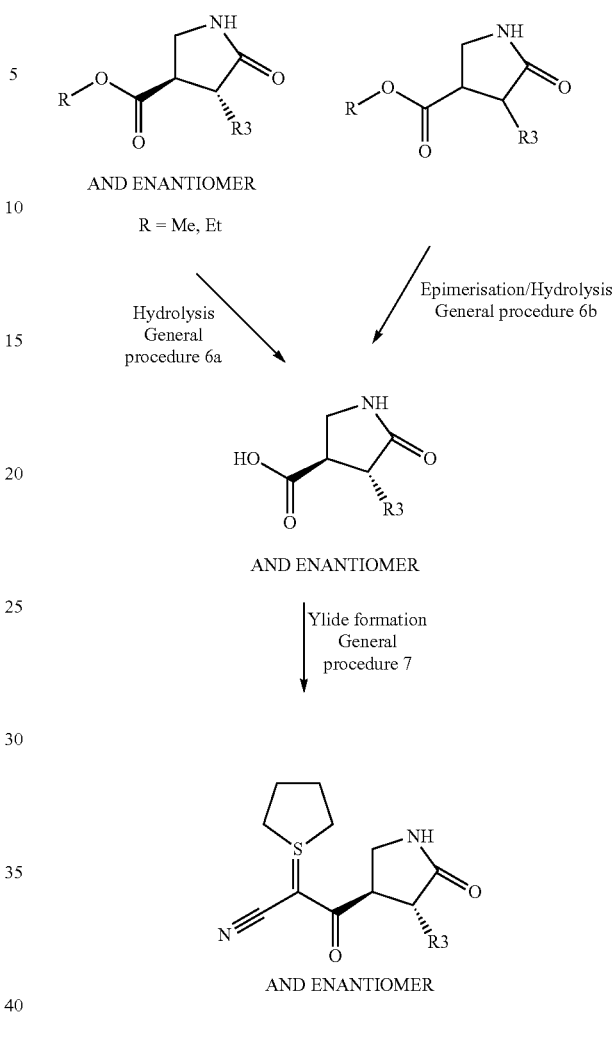

General Procedure 1 (General Scheme 1): Diazotisation/Bromination

2-Bromo-3-phenylpropanoic acid (I-1)

To an ice-cooled stirred suspension of phenylalanine (5.0 g, 30.27 mmol) in water (35 mL) was added $H_2SO_4$ (5.0 mL, 93.80 mmol) and NaBr (10.9 g, 105.94 mmol). A solution of $NaNO_2$ (2.61 g, 37.83 mmol) in water (40 mL) was added dropwise over 15 min and the reaction was stirred at 0° C. for 1 h then allowed to warm and stirred at RT for 5 h. The mixture was extracted with EtOAc (3×100 mL) and the combined organic extracts washed with brine (100 mL), dried over $Na_2SO_4$ and concentrated in vacuo to give 7.64 g of 2-bromo-3-phenylpropanoic acid as a pale yellow liquid (61% purity, 67%) which was used in the next step without further purification.

LC-MS (METCR1410): 61% (UV), Rt=1.04 min, m/z ($ESI^+$)=226.8/228.8 [M−H]$^−$ $^1$H NMR (250 MHz, Chloroform-d) δ 3.25 (dd, J=7.2, 14.2 Hz, 1H), 3.48 (dd, J=8.1, 14.2 Hz, 1H), 4.43 (dd, J=7.3, 8.1 Hz, 1H), 7.26 (s, 5H)

General Procedure 2 (General Scheme 1): Esterification

Ethyl 2-bromo-3-phenylpropanoate (I-2)

To a solution of 2-bromo-3-phenylpropanoic acid (I-1) (61% purity, 7.64 g, 20.34 mmol) in EtOH (100 mL) was added $H_2SO_4$ (610 μL, 11.44 mmol) and the mixture heated at reflux for 1.5 h, cooled to RT and concentrated in vacuo. The residue was dissolved in $Et_2O$ (100 mL), washed with sat. $NaHCO_3$ (100 mL) and brine (100 mL) and the organic phase dried over $Na_2SO_4$ and concentrated in vacuo. The residue was purified by FCC on normal phase silica (100 g SNAP KP-SIL cartridge, 0-30% EtOAc in heptane gradient) to afford 5.22 g of ethyl 2-bromo-3-phenylpropanoate as a colourless oil (97% purity, 97%).

LC-MS (METCR1410): 97% (UV), Rt=1.26 min, m/z $(ESI^+)$=256.9/258.9 $[M+H]^+$ $^1$H NMR (500 MHz, Chloroform-d) δ 1.25 (t, J=7.1 Hz, 3H), 3.27 (dd, J=14.1, 7.1 Hz, 1H), 3.48 (dd, J=14.1, 8.5 Hz, 1H), 4.16-4.24 (m, 2H), 4.41 (dd, J=8.5, 7.1 Hz, 1H), 7.22-7.26 (m, 2H), 7.28-7.35 (m, 3H)

Methyl 2-bromo-3-phenylpropanoate (I-3)

To a solution of 2-bromo-3-phenylpropanoic acid (I-1) (25 g, 109.14 mmol) in MeOH (225 mL) was added $H_2SO_4$ (3.25 mL, 63.79 mmol) and the mixture heated at reflux for 2 h, cooled to RT and concentrated in vacuo. The residue was dissolved in $Et_2O$ (220 mL), washed with sat. $NaHCO_3$ (160 mL) and brine (160 mL) and the organic phase dried over $Na_2SO_4$ and concentrated in vacuo. The residue was purified by FCC on normal phase silica (340 g SNAP KP-SIL cartridge, 0-20% EtOAc in heptane gradient) to afford 23.3 g of methyl 2-bromo-3-phenylpropanoate as a clear yellow free-flowing oil (98% purity, 86%).

LC-MS (METCR1410): 98% (UV), Rt=1.17 min, no ionisation.

$^1$H NMR (500 MHz, Chloroform-d) δ 3.25 (dd, J=7.1, 14.1 Hz, 1H), 3.47 (dd, J=8.4, 14.1 Hz, 1H), 3.73 (s, 3H), 4.41 (dd, J=7.1, 8.4 Hz, 1H), 7.19-7.23 (m, 2H), 7.24-7.29 (m, 1H), 7.29-7.34 (m, 2H)

Ethyl 2-bromo-2-(4-fluorophenyl)acetate (I-4)

To a solution of 2-bromo-2-(4-fluorophenyl)acetic acid (10 g, 41.2 mmol) in EtOH (30 mL) was added conc. HCl (354 μL, 4.24 mmol) and the reaction was heated at 50° C. for 2 h, stirred at RT for 2 h, cooled and concentrated in vacuo. The residue was purified by FCC on normal phase silica (100 g SNAP KP-SIL cartridge, 0-100% EtOAc in heptane gradient) to afford 9.9 g ethyl 2-bromo-2-(4-fluorophenyl)acetate as a colourless free-flowing oil (100% purity, 92%).

LC-MS (METCR1410): 100% (UV), Rt=1.19 min, no ionisation.

$^1$H NMR (250 MHz, Chloroform-d) δ 1.28 (t, 3H), 4.16-4.32 (m, 2H), 5.32 (s, 1H), 6.98-7.13 (m, 2H), 7.43-7.60 (m, 2H)

General Procedure 3 (General Scheme 1): Alkylation 1,4-Diethyl 2-benzyl-3-cyanobutanedioate (I-5)

To a solution of ethyl cyanoacetate (2.14 mL, 20.11 mmol) in EtOH (80 mL) was added 21% w/w NaOEt in ethanolic solution (7.85 mL, 21.02 mmol) and the mixture stirred at RT for 15 min. A solution of ethyl 2-bromo-3-phenylpropanoate (I-2) (4.7 g, 18.28 mmol) in EtOH (80 mL) was added slowly and the mixture heated at reflux for 1.5 h. The reaction was cooled to RT, quenched with AcOH (3 mL), diluted with water (200 mL) and neutralised by portionwise addition of solid $NaHCO_3$. The mixture was extracted with DCM (3×150 mL) and the combined organic extracts dried over $Na_2SO_4$ and concentrated in vacuo. The residue was purified by FCC on normal phase silica (100 g SNAP KP-SIL cartridge, 0-50% EtOAc in heptane gradient) to afford 3.29 g of 1,4-diethyl 2-benzyl-3-cyanobutanedioate as a pale yellow oil (97% purity, 60%).

LC-MS (METCR1410): 97% (UV), Rt=1.20 min, m/z $(ESI^+)$=290.0 $[M+H]^+$ 1,4-Diethyl 2-cyano-3-phenylbutanedioate (I-6)

The title compound was synthesized from ethyl 2-bromo-2-phenylacetate in a similar manner to general procedure 3 (general scheme 1) as a pale yellow viscous oil (24.3 g, 95% purity, 82%) after purification by FCC on normal phase silica (340 g SNAP KP-SIL cartridge, 0-30% EtOAc in heptane gradient).

LC-MS (METCR1410): 95% (UV), Rt=1.20 min, m/z $(ESI^+)$=276.1 $[M+H]^+$ $^1$H NMR (500 MHz, Chloroform-d) δ 1.16-1.35 (m, 6H), 3.92-4.36 (m, 6H), 7.29-7.42 (m, 5H)

1,4-Diethyl 2-cyano-3-(4-fluorophenyl)butanedioate (I-7)

The title compound was synthesized from ethyl 2-bromo-2-(4-fluorophenyl)acetate (I-4) in a similar manner to general procedure 3 (general scheme 1) as an orange oil (7.9 g, 98% purity, 70%) after purification by FCC on normal phase silica (340 g SNAP KP-SIL cartridge, 0-30% EtOAc in heptane gradient).

LC-MS (METCR1410): 98% (UV), Rt=1.77 min, m/z $(ESI^+)$=294.1 $[M+H]^+$ $^1$H NMR (500 MHz, Chloroform-d) δ 1.37-1.57 (m, 6H), 4.14-4.62 (m, 6H), 7.23-7.34 (m, 2H), 7.48-7.60 (m, 2H)

1,4-Dimethyl 2-benzyl-3-cyanobutanedioate (I-8)

To a solution of methyl 2-cyanoacetate (10 mL, 107.28 mmol) in MeOH (150 mL) was added 21% w/w NaOEt in ethanolic solution (41 mL, 109.82 mmol) and the mixture stirred at RT for 30 min. A solution of methyl 2-bromo-3-phenylpropanoate (I-3) (98% purity, 23.3 g, 93.85 mmol) in MeOH (150 mL) was added slowly and the mixture heated at reflux for 5 h. The reaction was cooled to RT, concentrated to 100 mL, quenched with AcOH (5 mL), diluted with water (200 mL) and neutralised by portionwise addition of solid $NaHCO_3$. The mixture was extracted with DCM (3×250 mL) and the combined organic extracts dried over $Na_2SO_4$ and concentrated in vacuo. The residue was purified by FCC in 2 batches on normal phase silica (340 g SNAP KP-SIL cartridge, 0-25% EtOAc in heptane gradient) to afford 9.2 g of 1,4-dimethyl 2-benzyl-3-cyanobutanedioate as a yellow oil (94% purity, 35%).

LC-MS (METCR1410): 94% (UV), Rt=1.09 min, m/z $(ESI^+)$=262.1 $[M+H]^+$ $^1$H NMR (500 MHz, Chloroform-d) δ 2.89 (dd, J=10.9, 13.5 Hz, 1H), 3.17-3.91 (m, 1H), 3.36-3.51 (m, 2H), 3.67-3.81 (m, 6H), 3.89 (d, J=7.3 Hz, 0H), 7.17-7.37 (m, 5H)

General Procedure 4 (General Scheme 1): Nitrile Reduction

Method A: Hydrogenation Using $PtO_2$ 1,4-Diethyl 2-(aminomethyl)-3-phenylbutanedioate (I-9)

To a solution of 1,4-diethyl 2-cyano-3-phenylbutanedioate (I-6) (96% purity, 10.49 g, 36.58 mmol) in EtOH (100 mL) were added 12M HCl (15 mL) and PtO$_2$ (0.83 g, 3.66 mmol) and the suspension stirred under an atmosphere of hydrogen for 18 h. The reaction was filtered through a plug of Celite and the resultant cake washed with EtOH. The combined filtrates were concentrated in vacuo and the residue dissolved in water (100 mL) and extracted with toluene (50 mL). The aqueous phase was neutralised by portionwise addition of solid NaHCO$_3$ and extracted with CHCl$_3$ (3×150 mL). The combined organic extracts were dried over Na$_2$SO$_4$ and concentrated in vacuo to give 10.35 g of 1,4-diethyl 2-(aminomethyl)-3-phenylbutanedioate as a pale yellow oil (69% purity, 70%) which was used in the next step without further purification. The compound contained 1,4-diethyl 2-(aminomethyl)-3-cyclohexylbutanedioate as a minor by-product.

LC-MS (METCR1410): 69% (UV), Rt=0.83 min, m/z (ESI$^+$)=280.0 [M+H]$^+$

Method B: Hydrogenation Using Pd/C 1,4-Diethyl 2-(aminomethyl)-3-benzylbutanedioate (I-10)

To a solution of 1,4-diethyl 2-benzyl-3-cyanobutanedioate (I-5) (2.8 g, 9.68 mmol) in EtOH (100 mL) were added 12M HCl (4.24 mL) and 10% Pd/C (0.21 g, 1.94 mmol) and the suspension stirred under an atmosphere of hydrogen for 24 h. The reaction was filtered through a plug of Celite and the resultant cake washed with EtOH. The combined filtrates were concentrated in vacuo and the residue dissolved in water (80 mL) and extracted with toluene (50 mL). The aqueous phase was neutralised by portionwise addition of solid NaHCO$_3$ and extracted with CHCl$_3$ (2×80 mL) then 3:1 CHCl$_3$/IPA (3×80 mL). The combined organic extracts were dried over Na$_2$SO$_4$ and concentrated in vacuo to give 2.56 g of 1,4-diethyl 2-(aminomethyl)-3-benzylbutanedioate as a yellow oil (71% purity, 64%) which was used in the next step without further purification.

LC-MS (METCR1410): 71% (UV), Rt=0.94 min, m/z (ESI$^+$)=294.0 [M+H]$^+$ 1,4-Diethyl 2-(aminomethyl)-3-phenylbutanedioate (I-9)

The title compound was synthesized from 1,4-diethyl 2-cyano-3-phenylbutanedioate (I-6) in a similar manner to method B, general procedure 4 (general scheme 1) as a pale yellow viscous oil (2.75 g, 91% purity, 49%) which was used in the next step without further purification.

LC-MS (METCR0990): 91% (UV), Rt=1.61 min, m/z (ESI$^+$)=280.3 [M+H]$^+$ 1,4-Dimethyl 2-(aminomethyl)-3-benzylbutanedioate (I-11)

The title compound was synthesized from 1,4-dimethyl 2-cyano-3-phenylbutanedioate (I-8) in a similar manner to method B, general procedure 4 (general scheme 1) as a yellow oil (844 mg, 64% purity, 12%) which was used in the next step without further purification.

LC-MS (METCR1410): 64% (UV), Rt=0.92 min, m/z (ESI$^+$)=266.1 [M+H]$^+$

Method C: Reduction Using NaBH$_4$ in the Presence of NiCl$_2$ 1,4-Diethyl 2-({[(tert-butoxy)carbonyl]amino}methyl)-3-(4-fluorophenyl)butanedioate (I-12)

To a solution of 1,4-diethyl 2-cyano-3-(4-fluorophenyl)butanedioate (I-7) (7.2 g, 22.83 mmol) in EtOH (300 mL) were added Boc$_2$O (12.46 g, 57.08 mmol) and NiCl$_2$.6H$_2$O (8.14 g, 34.25 mmol). The suspension was cooled to 0° C. and NaBH$_4$ (8.64 g, 228.30 mmol) added portionwise over 2 min. The mixture was stirred at 15° C. for 1.5 h, cooled to 0° C. and ethylene diamine (50 mL) added. The reaction was stirred at 0° C. for 1 h sat. NaHCO$_3$ (200 mL) added and the mixture stirred at RT for 10 min. EtOAc (200 mL) was added and the black suspension transferred to a large conical flask, diluted with sat. NaHCO$_3$ (200 mL), EtOAc (200 mL) and ethylene diamine (100 mL). Additional ethylene diamine (100 mL) was added and the suspension stirred until a solution was obtained. Brine (200 mL) was added and the two phases separated. The aqueous layer was extracted with EtOAc (3×300 mL) and the combined organic extracts washed with brine (2×200 mL), dried over MgSO$_4$ and concentrated in vacuo to afford 8.0 g of 1,4-diethyl 2-({[(tert-butoxy)carbonyl]amino}methyl)-3-(4-fluorophenyl)butane-dioate as a light orange viscous oil (91% purity by $^1$H NMR, 80%) which was used in the next step without further purification.

LC-MS (METCR0990): 97% (UV), Rt=1.95 min, m/z (ESI$^+$)=398.2 [M+H]$^+$ $^1$H NMR (500 MHz, Chloroform-d) δ 0.91-1.32 (m, 6H), 1.33-1.47 (m, 9H), 2.73-3.54 (m, 4H), 3.77-4.24 (m, 4H), 4.52-4.94 (m, 1H), 6.94-7.06 (m, 2H), 7.23-7.32 (m, 2H)

General Procedure 5a (General Scheme 1): Cyclisation

Rac-ethyl (3R,4R)-4-benzyl-5-oxopyrrolidine-3-carboxylate (I-13) and Rac-ethyl (3R,4S)-4-benzyl-5-oxopyrrolidine-3-carboxylate (I-14)

1,4-Diethyl 2-(aminomethyl)-3-benzylbutanedioate (I-10) (71% purity, 2.56 g, 8.73 mmol) was dissolved in toluene (50 mL) and the reaction mixture heated at reflux for 2 h, cooled to RT and concentrated in vacuo. The residue was purified by FCC on normal phase silica (50 g SNAP KP-SIL cartridge, 0-100% EtOAc in heptane gradient) to afford 345 mg of rac-ethyl (3R,4R)-4-benzyl-5-oxopyrrolidine-3-carboxylate as a pale yellow solid (95% purity, 15%) and 543 mg of rac-ethyl (3R,4S)-4-benzyl-5-oxopyrrolidine-3-carboxylate as an off-white solid (96% purity, 24%).

Rac-ethyl (3R,4R)-4-benzyl-5-oxopyrrolidine-3-carboxylate (I-13)

LC-MS (METCR1410): 95% (UV), Rt=0.97 min, m/z (ESI$^+$)=248.0 [M+H]$^+$ $^1$H NMR (500 MHz, Chloroform-d) δ 1.20 (t, J=7.1 Hz, 3H), 2.97-3.11 (m, 3H), 3.19 (dd, J=12.8, 3.6 Hz, 1H), 3.35 (t, J=8.7 Hz, 1H), 3.46 (dd, J=9.4, 7.8 Hz, 1H), 4.04 (qq, J=10.8, 7.1 Hz, 2H), 5.44 (s, 1H), 7.20-7.35 (m, 5H)

Rac-ethyl (3R,4S)-4-benzyl-5-oxopyrrolidine-3-carboxylate (I-14)

LC-MS (METCR1410): 96% (UV), Rt=0.96 min, m/z (ESI$^+$)=248.0 [M+H]$^+$ $^1$H NMR (500 MHz, Chloroform-d) δ 1.08 (t, J=7.1 Hz, 3H), 2.75 (dd, J=14.6, 9.8 Hz, 1H), 2.94 (ddd, J=9.6, 8.6, 4.4 Hz, 1H), 3.16 (dd, J=14.6, 4.3 Hz, 1H), 3.20-3.28 (m, 1H), 3.33-3.41 (m, 2H), 3.79-3.88 (m, 1H), 3.95-4.06 (m, 1H), 6.37 (s, 1H), 7.10-7.17 (m, 3H), 7.17-7.24 (m, 2H)

Rac-ethyl (3R,4S)-4-phenyl-5-oxopyrrolidine-3-carboxylate (I-15) and Rac-ethyl (3R,4R)-4-phenyl-5-oxopyrrolidine-3-carboxylate (I-16)

The title compounds were synthesized from crude 1,4-diethyl 2-(aminomethyl)-3-phenylbutanedioate (I-9) prepared from method A, general procedure 4 (general scheme 1) in a similar manner to general procedure 5a (general scheme 1) as off-white solids after purification by FCC on normal phase silica (340 g SNAP KP-SIL cartridge, 0-100% EtOAc in heptane gradient) to give 3.11 g of rac-ethyl (3R,4S)-4-phenyl-5-oxopyrrolidine-3-carboxylate (88% purity, 32%) and 1.05 g of rac-ethyl (3R,4R)-4-phenyl-5-oxopyrrolidine-3-carboxylate (83% purity, 10%). Both compounds contained a minor cyclohexyl by-product (8% and 10% by LC/MS respectively).

Rac-ethyl (3R,4S)-4-phenyl-5-oxopyrrolidine-3-carboxylate (I-15)

LC-MS (METCR1410): 88% (UV), Rt=0.92 min, m/z (ESI$^+$)=234.1 [M+H]$^+$

Rac-ethyl (3R,4R)-4-phenyl-5-oxopyrrolidine-3-carboxylate (I-16)

LC-MS (METCR1410): 83% (UV), Rt=0.88 min, m/z (ESI$^+$)=234.1 [M+H]$^+$

General Procedure 5b (General Scheme 1): Cyclisation

Ethyl 5-oxo-4-phenylpyrrolidine-3-carboxylate (I-17)

1,4-Diethyl 2-(aminomethyl)-3-phenylbutanedioate (I-9) (4.5 g, 16.11 mmol) prepared from method B, general procedure 4 (general scheme 1) was heated on a rotary evaporator at 50° C. under 15 mbar for 15 h then cooled to RT to afford 3.55 g of ethyl 5-oxo-4-phenylpyrrolidine-3-carboxylate as a pale yellow solid (93% purity, 88%, ~2:1 cis:trans mixture) which was used in the next step without further purification.

LC-MS (METCR0990): 63%+30% (UV), Rt=1.40 min+ 1.45 min, m/z (ESI$^+$)=234.2 [M+H]$^+$ Methyl 4-benzyl-5-oxopyrrolidine-3-carboxylate (I-18)

1,4-Dimethyl 2-(aminomethyl)-3-benzylbutanedioate (I-11) (64% purity, 844 mg, 2.04 mmol) was dissolved in toluene (15 mL) and the reaction mixture heated at reflux for 2 h, cooled to RT and concentrated in vacuo. The residue was purified by FCC on normal phase silica (50 g SNAP KP-SIL cartridge, 0-100% EtOAc in heptane gradient) to afford 544 mg of methyl 4-benzyl-5-oxopyrrolidine-3-carboxylate as a dark orange solid (94% purity, quantitative).

LC-MS (METCR1410): 94% (UV), Rt=0.91 min, m/z (ESI$^+$)=234.2 [M+H]$^+$ $^1$H NMR (500 MHz, Chloroform-d) δ 2.72-3.48 (m, 6H), 3.53-3.57 (m, 3H), 5.64-5.77 (m, 1H), 7.17-7.24 (m, 3H), 7.26-7.30 (m, 2H).

General Procedure 5c (General Scheme 1): Cyclisation after Boc Deprotection

Ethyl 4-(4-fluorophenyl)-5-oxopyrrolidine-3-carboxylate (I-19)

To a solution of 1,4-diethyl 2-({[(tert-butoxy)carbonyl]amino}methyl)-3-(4-fluorophenyl)butanedioate (I-12) (7.99 g, 19.5 mmol) in DCM (20 mL) was added 4N HCl in 1,4-dioxane (35 mL, 140 mmol) and the reaction stirred at RT for 3 h. The mixture was concentrated in vacuo and the residue partitioned between water (30 mL) and DCM (30 mL) The aqueous phase was neutralised with solid NaHCO$_3$, DCM (50 mL) added and the two phases separated. The aqueous layer was extracted with DCM (3×30 mL) and the combined organic extracts washed with brine (30 mL), dried over MgSO$_4$ and concentrated in vacuo. The material obtained was dissolved in MeCN (20 mL) and the solution heated at 80° C. for 3 h, cooled to RT and concentrated in vacuo. The residue was suspended in Et$_2$O (10 mL) and the suspension sonicated for 5 min. The resulting solid was collected by filtration and the filtrate concentrated in vacuo. The trituration process was repeated on the material obtained from the filtrate until no further solid was obtained. The solid crops were combined to afford 3.5 g ethyl 4-(4-fluorophenyl)-5-oxopyrrolidine-3-carboxylate as an off-white powder (100% purity, 71%, ~2:1 cis:trans mixture) which was used in the next step without further purification.

LC-MS (METCR0990): 63%+37% (UV), Rt=1.43 min+ 1.48 min, m/z (ESI$^+$)=252.2 [M+H]$^+$ $^1$H NMR (500 MHz, Chloroform-d) δ 0.81-1.70 (m, 3H), 3.28-4.72 (m, 6H), 6.99-8.17 (m, 5H)

General Procedure 6a (General Scheme 1): Hydrolysis of Trans-Racemic Mixture

Rac-(3R,4R)-4-benzyl-5-oxopyrrolidine-3-carboxylic acid (I-20)

To a solution of rac-ethyl (3R,4R)-4-benzyl-5-oxopyrrolidine-3-carboxylate (I-13) (345 mg, 1.40 mmol) in THF (10 mL) was added 2M NaOH (1.7 mL, 3.35 mmol) and the reaction stirred at RT for 16 h then concentrated in vacuo. The residue was diluted with water (20 mL) and extracted with Et$_2$O. The aqueous phase was acidified with 2M HCl and extracted with 3:1 CHCl$_3$:IPA (3×30 mL). The combined organic extracts were dried over Na$_2$SO$_4$ and concentrated in vacuo to give 276 mg of rac-(3R,4R)-4-benzyl-5-oxopyrrolidine-3-carboxylic acid as a pale yellow solid (90% purity, 81%) which was used in the next step without purification.

LC-MS (METCR1410): 90% (UV), Rt=0.80 min, m/z (ESI$^+$)=220.2 [M+H]$^+$ $^1$H NMR (250 MHz, Chloroform-d) δ 2.99-3.18 (m, 4H), 3.34 (t, J=9.0 Hz, 1H), 3.42-3.57 (m, 1H), 6.49 (s, 1H), 7.26 (s, 5H)

Rac-(3R,4S)-5-oxo-4-phenylpyrrolidine-3-carboxylic acid (I-21)

The title compound was synthesized from crude rac-ethyl (3R,4S)-4-phenyl-5-oxopyrrolidine-3-carboxylate (I-15) in a similar manner to general procedure 6a (general scheme 1) as an off-white solid (1.13 g, 80% purity by $^1$H NMR, 68%) obtained after work-up and used in the next step without further purification. The compound contained rac-(3R,4R)-4-cyclohexyl-5-oxopyrrolidine-3-carboxylic acid as a minor by-product.

LC-MS (METCR1410): 97% (UV), Rt=0.69 min, m/z (ESI$^+$)=206.2 [M+H]$^+$ $^1$H NMR (250 MHz, Chloroform-d) δ 3.29-3.44 (m, 1H), 3.54-3.78 (m, 2H), 3.95 (d, J=8.8 Hz, 1H), 6.80 (s, 1H), 7.18-7.34 (m, 5H)

General Procedure 6b (General Scheme 1): Epimerisation/Hydrolysis of Diastereoisomeric Mixture Rac-(3R,4S)-5-oxo-4-phenylpyrrolidine-3-carboxylic acid (I-21)

To a solution of ethyl 5-oxo-4-phenylpyrrolidine-3-carboxylate (I-17) (3.55 g, 15.22 mmol) in 3:2 MeOH:water (25 mL) was added 2M NaOH (12 mL, 24 mmol) and the mixture stirred at 60° C. for 3 h then concentrated in vacuo. The residue was diluted with water (20 mL), acidified to pH ~3 with 2N HCl and the precipitate filtered and dried in a vacuum oven at 40° C. to afford 2.6 g of rac-(3R,4S)-5-oxo-4-phenylpyrrolidine-3-carboxylic acid as an off-white solid (92% purity, 77%) which was used in the next step without further purification.

LC-MS (METCR1410): 92% (UV), Rt=0.72 min, m/z (ESI$^+$)=206.0 [M+H]$^+$ $^1$H NMR (500 MHz, Chloroform-d) δ 3.38-3.46 (m, 1H), 3.63-3.68 (m, 1H), 3.73-3.79 (m, 1H), 4.03 (d, J=8.7 Hz, 1H), 7.26-7.32 (m, 3H), 7.33-7.39 (m, 2H)

Ethyl 4-(4-fluorophenyl)-5-oxopyrrolidine-3-carboxylate (I-22)

The title compound was synthesized from ethyl 4-(4-fluorophenyl)-5-oxopyrrolidine-3-carboxylate (I-19) in a similar manner to general procedure 6b (general scheme 1) as an off-white solid (810 mg, 97% purity, 88%) obtained after work-up and used in the next step without further purification.

LC-MS (MET-uHPLC-AB-101): 97% (UV), Rt=1.38 min, m/z (ESI$^+$)=224.1 [M+H]$^+$ $^1$H NMR (500 MHz, DMSO-d6) δ 3.30-3.38 (m, 2H), 3.52-3.59 (m, 1H), 3.72-3.80 (m, 1H), 7.06-7.20 (m, 2H), 7.20-7.37 (m, 2H), 7.95 (s, 1H), 12.56 (s, 1H).

General Procedure 7 (General Scheme 1): Ylide Formation

Rac-3-[(3R,4R)-4-benzyl-5-oxopyrrolidin-3-yl]-2-(1λ$^4$-thiolan-1-ylidene)-3-oxopropanenitrile (I-23)

To a solution of rac-(3R,4R)-4-benzyl-5-oxopyrrolidine-3-carboxylic acid (I-20) (90% purity, 276 mg, 1.26 mmol) and DIPEA (658 μL, 3.78 mmol) in DCM (20 mL) was added HATU (527 mg, 1.38 mmol) and 1-(cyanomethyl)thiolan-1-ium bromide (90% purity, 349 mg, 1.51 mmol, synthesized by the procedure outlined in Note 1, general experimental details) and the mixture stirred at RT for 1.5 h. The reaction was quenched with sat. NH$_4$Cl (30 mL), the aqueous phase extracted with DCM (3×50 mL) and the combined organic phases dried over Na$_2$SO$_4$ and concentrated in vacuo. The residue was purified by FCC on normal phase silica (10 g SNAP Ultra cartridge, 0-20% MeOH in EtOAc gradient) to afford 424 mg of rac-3-[(3R,4R)-4-benzyl-5-oxopyrrolidin-3-yl]-2-(1λ$^4$-thiolan-1-ylidene)-3-oxopropanenitrile as an off-white solid (98% purity, 100%).

LC-MS (METCR1410): 98% (UV), Rt=0.82 min, m/z (ESI$^+$)=329.0 [M+H]$^+$ $^1$H NMR (250 MHz, Chloroform-d) δ 1.88-2.10 (m, 2H), 2.37-2.59 (m, 2H), 2.67 (dd, J=13.8, 10.1 Hz, 1H), 2.85-3.06 (m, 2H), 3.10-3.30 (m, 4H), 3.31-3.46 (m, 2H), 3.50-3.66 (m, 1H), 5.46 (s, 1H), 7.14-7.36 (m, 5H)

Rac-3-oxo-3-[(3R,4S)-5-oxo-4-phenylpyrrolidin-3-yl]-2-(1λ$^4$-thiolan-1-ylidene)propane-nitrile (I-24)

The title compound was synthesized from rac-(3R,4S)-5-oxo-4-phenylpyrrolidine-3-carboxylic acid (I-21) prepared from general procedure 6b (general scheme 1) in a similar manner to general procedure 7 (general scheme 1) as an off-white solid (2.20 g, 100% purity, 55%) obtained after trituration in DCM.

LC-MS (METCR1410): 100% (UV), Rt=0.79 min, m/z (ESI$^+$)=315.0 [M+H]$^+$ $^1$H NMR (500 MHz, Chloroform-d) δ 1.98-2.11 (m, 2H), 2.47-2.62 (m, 2H), 3.18-3.35 (m, 2H), 3.35-3.47 (m, 3H), 3.71 (t, J=8.9 Hz, 1H), 3.79-3.90 (m, 1H), 4.11 (d, J=9.4 Hz, 1H), 6.31 (s, 1H), 7.25-7.29 (m, 3H), 7.29-7.39 (m, 2H)

Note: Crude batches of rac-3-oxo-3-[(3R,4S)-5-oxo-4-phenylpyrrolidin-3-yl]-2-(1λ$^4$-thiolan-1-ylidene)propanenitrile (I-24) prepared from rac-(3R,4S)-5-oxo-4-phenylpyrro-lidine-3-carboxylic acid (I-21) synthesized according to general procedure 6a (general scheme 1) contained rac-3-[(3R,4R)-4-cyclohexyl-5-oxopyrrolidin-3-yl]-3-oxo-2-(1λ$^4$-thiolan-1-ylidene)propanenitrile as a minor by-product.

Rac-3-[(3R,4S)-4-(4-fluorophenyl)-5-oxopyrrolidin-3-yl]-3-oxo-2-(1λ$^4$-thiolan-1-ylidene)propanenitrile (I-25)

The title compound was synthesized from ethyl 4-(4-fluorophenyl)-5-oxopyrrolidine-3-carboxylate (I-22) in a similar manner to general procedure 7 (general scheme 1) as an off-white powder (1.08 g, 96% purity, 91%) after purification by FCC on normal phase silica (25 g SNAP KP-SIL cartridge, 0-100% EtOAc in heptane gradient followed by 0-50% MeOH in EtOAc gradient).

LC-MS (METCR1410): 100% (UV), Rt=0.79 min, m/z (ESI$^+$)=315.0 [M+H]$^+$ $^1$H NMR (500 MHz, Chloroform-d) δ 1.98-2.15 (m, 2H), 2.46-2.59 (m, 2H), 3.16-3.29 (m, 2H), 3.32-3.42 (m, 3H), 3.65 (t, J=9.0 Hz, 1H), 3.75 (q, 1H), 4.08 (d, J=9.8 Hz, 1H), 6.88 (s, 1H), 6.97-7.03 (m, 2H), 7.18-7.25 (m, 2H)

GENERAL SCHEME 2

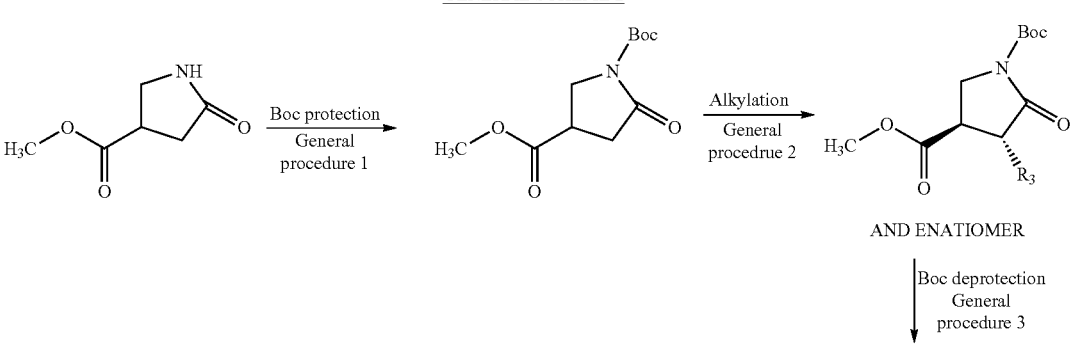

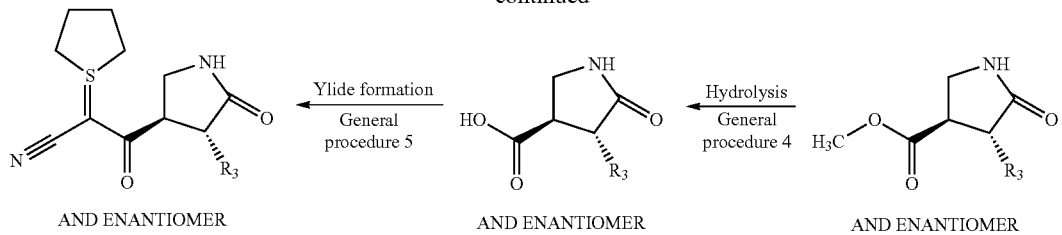

General Procedure 1 (General Scheme 2): Boc Protection

1-tert-butyl 3-methyl 5-oxopyrrolidine-1,3-dicarboxylate (I-26)

To a stirred solution of methyl 5-oxopyrrolidine-3-carboxylate (20 g, 139.72 mmol) in DCM (200 mL) was added TEA (58.4 mL, 419.16 mmol) and DMAP (1.7 g, 13.97 mmol). The mixture was stirred for 15 min at RT then Boc$_2$O (61.0 g, 279.44 mmol) was added and the reaction stirred at RT for 17 h. The solution was diluted with water (150 mL) and acidified slowly to pH 4 with 1N HCl. The aqueous layer was separated and extracted with DCM (200 mL) and the combined organic extracts washed with brine (150 mL), dried over Na$_2$SO$_4$, filtered and concentrated in vacuo. The crude material was purified by FCC on normal phase silica in two batches (340 g SNAP Ultra cartridge, 0-73% EtOAc in heptane gradient) to afford 31.6 g of 1-tert-butyl 3-methyl 5-oxopyrrolidine-1,3-dicarboxylate as a light yellow solid (98% purity, 91%).

LC-MS (METCR1410): 98% (UV), Rt=0.94 min, m/z (ESI$^+$)=188.4 [M+H-tBu]$^+$ $^1$H NMR (500 MHz, Chloroform-d) δ 1.52 (s, 9H), 2.74 (dd, J=9.5, 17.7 Hz, 1H), 2.85 (dd, J=8.0, 17.7 Hz, 1H), 3.19 (p, J=8.8 Hz, 1H), 3.75 (s, 3H), 3.90 (dd, J=7.0, 11.2 Hz, 1H), 3.97 (dd, J=8.8, 11.2 Hz, 1H)

General Procedure 2 (General Scheme 2): Alkylation

Rac-1-tert-butyl 3-methyl (3R,4R)-4-[(4-fluorophenyl)methyl]-5-oxopyrrolidine-1,3-dicarboxylate (I-27)

To a stirring solution of 1-tert-butyl 3-methyl 5-oxopyrrolidine-1,3-dicarboxylate (I-26) (98% purity, 5.43 g, 21.88 mmol) in dry THF (35 mL) under nitrogen at −78° C. was added 1M LHMDS in THF (24.0 mL, 24.06 mmol) dropwise over 15 min. The mixture was stirred at −78° C. for 1 h, 1-(bromomethyl)-4-fluorobenzene (2.9 mL, 23.28 mmol) in dry THF (10 mL) was added dropwise over 5 min and the reaction stirred at −78° C. for 2.5 h. The reaction was quenched with sat. NH$_4$Cl (40 mL) at −78° C. and extracted with EtOAc (3×25 mL). The combined organic phases were washed with brine (15 mL), dried over Na$_2$SO$_4$, filtered and concentrated in vacuo to ~25 mL. The thick emulsion was diluted with heptane (50 mL) and the product collected by filtration, washed with heptane (50 mL) and dried in vacuo in a vacuum oven at 50° C. for 15 h to afford 4.66 g of rac-1-tert-butyl 3-methyl (3R,4R)-4-[(4-fluorophenyl)methyl]-5-oxopyrrolidine-1,3-dicarboxylate as an off-white solid (99% purity, 60%).

LC-MS (METCR1410): 99% (UV), Rt=1.22 min, m/z (ESI$^+$)=252.0 [M+H-tBu]$^+$ $^1$H NMR (500 MHz, Chloroform-d) δ 1.52 (s, 9H), 2.84 (q, J=9.2 Hz, 1H), 2.96-3.04 (m, 1H), 3.10-3.18 (m, 2H), 3.61 (s, 3H), 3.63-3.69 (m, 1H), 3.76-3.83 (m, 1H), 6.93-7.00 (m, 2H), 7.15-7.20 (m, 2H)

Rac-1-tert-butyl 3-methyl (3R,4R)-4-benzyl-5-oxopyrrolidine-1,3-dicarboxylate (I-28)

The title compound was synthesized from 1-tert-butyl 3-methyl 5-oxopyrrolidine-1,3-dicarboxylate (I-26) in a similar manner to general procedure 2 (general scheme 2) as an off-white solid (20.1 g, 96% purity, 49%) after work-up and used in the next step without further purification.

LC-MS (METCR1410): 96% (UV), Rt=1.16 min, no ionisation $^1$H NMR (500 MHz, Chloroform-d) δ 1.51 (s, 9H), 2.82-2.90 (m, 1H), 2.94-3.01 (m, 1H), 3.15-3.22 (m, 2H), 3.55 (s, 3H), 3.66 (dd, J=8.8, 11.0 Hz, 1H), 3.74-3.80 (m, 1H), 7.18-7.24 (m, 3H), 7.26-7.30 (m, 2H)

Rac-1-tert-butyl 3-methyl (3R,4R)-5-oxo-4-[(pyridin-2-yl)methyl]pyrrolidine-1,3-dicarboxylate (I-29)

The title compound was synthesized from 1-tert-butyl 3-methyl 5-oxopyrrolidine-1,3-dicarboxylate (I-26) in a similar manner to general procedure 2 (general scheme 2) as a yellow solid (1.46 g, 88% purity, 48%) after purification by FCC on normal phase silica (25 g SNAP Ultra cartridge, 0-60% EtOAc in heptane gradient).

LC-MS (METCR1410): 88% (UV), Rt=0.85 min, m/z (ESI$^+$)=335.1 [M+H]$^+$ $^1$H NMR (500 MHz, Chloroform-d) δ 1.52-1.53 (m, 9H), 3.07-3.14 (m, 1H), 3.20 (q, J=9.0 Hz, 1H), 3.37-3.44 (m, 2H), 3.57-3.61 (m, 3H), 3.72 (dd, J=8.6, 11.0 Hz, 1H), 3.87-3.92 (m, 1H), 7.09-7.14 (m, 1H), 7.22 (d, J=7.8 Hz, 1H), 7.59 (td, J=1.8, 7.7 Hz, 1H), 8.45-8.52 (m, 1H)

General Procedure 3 (General Scheme 2): Boc Deprotection

Rac-methyl (3R,4R)-4-[(4-fluorophenyl)methyl]-5-oxopyrrolidine-3-carboxylate (I-30)

To a solution of rac-1-tert-butyl 3-methyl (3R,4R)-4-benzyl-5-oxopyrrolidine-1,3-dicarboxylate (I-27) (99% purity, 4.66 g, 13.14 mmol) in DCM (35 mL) was added TFA (3.0 mL, 39.42 mmol) and the mixture stirred at RT for 4 h. The reaction was quenched carefully with sat. NaHCO$_3$ (30 mL) to neutral pH and extracted with DCM (50 mL). The combined organic phases were washed with sat.

NaHCO$_3$ (25 mL) and brine (30 mL), dried over Na$_2$SO$_4$, filtered and concentrated in vacuo to give 3.24 g of rac-methyl (3R,4R)-4-[(4-fluorophenyl)methyl]-5-oxopyrrolidine-3-carboxylate as an off-white solid (100% purity; 98%).

LC-MS (METCR1410): 100% (UV), Rt=0.96 min, m/z (ESI$^+$)=252.1 [M+H]$^+$ $^1$H NMR (500 MHz, Chloroform-d) δ 2.95-3.05 (m, 3H), 3.06-3.14 (m, 1H), 3.31-3.38 (m, 1H), 3.40-3.48 (m, 1H), 3.61 (s, 3H), 5.64 (s, 1H), 6.94-7.00 (m, 2H), 7.19 (ddd, J=2.5, 5.3, 8.4 Hz, 2H)

Rac-methyl (3R,4R)-4-benzyl-5-oxopyrrolidine-3-carboxylate (I-31)

The title compound was synthesized from rac-1-tert-butyl 3-methyl (3R,4R)-4-benzyl-5-oxopyrrolidine-1,3-dicarboxylate (I-28) in a similar manner to general procedure 3 (general scheme 2) as an off-white solid (13.3 g, 98% purity, 97%) after work-up and used in the next step without further purification.

LC-MS (METCR1410): 98% (UV), Rt=0.91 min, m/z (ESI$^+$)=234.2 [M+H]$^+$ $^1$H NMR (500 MHz, Chloroform-d) δ 2.97-3.08 (m, 3H), 3.15 (dd, J=3.7, 13.0 Hz, 1H), 3.30-3.36 (m, 1H), 3.40-3.46 (m, 1H), 3.57 (s, 3H), 5.75 (s, 1H), 7.18-7.25 (m, 3H), 7.26-7.31 (m, 2H)

Rac-methyl (3R,4R)-5-oxo-4-[(pyridin-2-yl)methyl]pyrrolidine-3-carboxylate (TFA Salt) (I-32)

The title compound was synthesized from rac-1-tert-butyl 3-methyl (3R,4R)-5-oxo-4-[(pyridin-2-yl)methyl]pyrrolidine-1,3-dicarboxylate (I-29) in a similar manner to general procedure 3 (general scheme 2) as a dark oil (2.1 g, 98% purity, quantitative) after work-up and used in the next step without further purification.

LC-MS (METCR1410): 98% (UV), Rt=1.22 min, m/z (ESI$^+$)=235.2 [M+H]$^+$

General Procedure 4 (General Scheme 2): Hydrolysis

Rac-(3R,4R)-4-[(4-fluorophenyl)methyl]-5-oxopyrrolidine-3-carboxylic acid (I-33)

A solution of methyl rac-(3R,4R)-4-[(4-fluorophenyl)methyl]-5-oxo-pyrrolidine-3-carboxylate (I-30) (99% purity, 1.75 g, 6.90 mmol) in 2:1 MeOH/water (30 mL) was treated with 2M NaOH (7.6 mL), 15.20 mmol) and stirred at RT for 0.5 h. The mixture was concentrated in vacuo and the residue diluted with water (30 mL) and extracted with Et$_2$O (2×30 mL). The aqueous layer was separated, acidified to pH 1 using 6M HCl and the resulting precipitate was collected by filtration, washed with water (10 mL) and dried in a vacuum oven at 40° C. to afford 1.5 g of rac-(3R,4R)-4-[(4-fluorophenyl)-methyl]-5-oxo-pyrrolidine-3-carboxylic acid as an off-white solid (96% purity, 88%).

LC-MS (METCR1410): 96% (UV), Rt=0.83 min, m/z (ESI$^+$)=238.2 [M+H]$^+$ $^1$H NMR (500 MHz, DMSO-d$_6$) δ 2.75-2.86 (m, 3H), 2.93 (dd, J=4.5, 13.4 Hz, 1H), 3.17 (dd, J=7.2, 9.6 Hz, 1H), 3.23-3.27 (m, 1H), 7.05-7.12 (m, 2H), 7.20-7.27 (m, 2H), 7.72 (s, 1H), 12.49 (br. s, 1H)

Rac-(3R,4R)-5-oxo-4-[(pyridin-2-yl)methyl]pyrrolidine-3-carboxylic acid (HCl salt) (I-34)

The title compound was synthesized from rac-methyl (3R,4R)-5-oxo-4-[(pyridin-2-yl)methyl]pyrrolidine-3-carboxylate (TFA salt) (I-32) in a similar manner to general procedure 4 (general scheme 2) as a brown solid (2.8 g, 90% purity by $^1$H NMR, quantitative) after work-up and used in the next step without further purification.

LC-MS (METCR1410): 100% (ELS), Rt=0.16 min, m/z (ESI$^+$)=221.0 [M+H]$^+$ $^1$H NMR (500 MHz, D$_2$O) δ 3.34-3.45 (m, 3H), 3.54-3.65 (m, 2H), 3.71-3.77 (m, 1H), 7.97-8.02 (m, 1H), 8.06 (d, J=8.1 Hz, 1H), 8.57 (td, J=1.5, 8.0 Hz, 1H), 8.71-8.76 (m, 1H)

General Procedure 5 (General Scheme 2): Ylide Formation

Rac-3-[(3R,4R)-4-[(4-fluorophenyl)methyl]-5-oxopyrrolidin-3-yl]-3-oxo-2-(1λ$^4$-thiolan-1-ylidene)propanenitrile (I-35)

To a stirred solution of rac-(3R,4R)-4-[(4-fluorophenyl)methyl]-5-oxo-pyrrolidine-3-carboxylic acid (I-33) (96% purity, 1.49 g, 6.03 mmol) and DIPEA (3.4 mL, 19.52 mmol) in DCM (30 mL) was added HATU (2.52 g, 6.63 mmol) and 1-(cyanomethyl)thiolan-1-ium bromide (90% purity, 1.81 g, 7.83 mmol, synthesized by the procedure outlined in Note 1, general experimental details) and the mixture was stirred at RT under nitrogen for 1 h. The reaction was diluted with DCM (30 mL) and quenched with a sat. NH$_4$Cl (50 mL). The aqueous layer was extracted with DCM (30 mL) and the combined organic layers was dried over Na$_2$SO$_4$ and concentrated in vacuo. The residue was purified by FCC on normal phase silica (50 g SNAP KP-SIL cartridge, 0-100% EtOAc in heptane gradient followed by 0-20% MeOH in EtOAc) to afford 2.5 g of rac-3-[(3R,4R)-4-[(4-fluorophenyl)methyl]-5-oxopyrrolidin-3-yl]-3-oxo-2-(1λ$^4$-thiolan-1-ylidene)propanenitrile as an off-white gum (84% purity by $^1$H NMR, 99%).

LC-MS (METCR1410): 97% (UV), Rt=0.86 min, m/z (ESI$^+$)=347.1 [M+H]$^+$ $^1$H NMR (500 MHz, Chloroform-d) δ 1.95-2.07 (m, 2H), 2.39-2.53 (m, 2H), 2.62 (dd, J=10.2, 14.0 Hz, 1H), 2.90-2.98 (m, 1H), 2.99-3.07 (m, 1H), 3.09-3.26 (m, 4H), 3.30 (dd, J=4.3, 14.0 Hz, 1H), 3.35-3.41 (m, 1H), 3.50 (q, J=8.7 Hz, 1H), 5.72 (s, 1H), 6.91-6.98 (m, 2H), 7.21-7.28 (m, 2H)

Rac-3-oxo-3-[(3R,4R)-5-oxo-4-[(pyridin-2-yl)methyl]pyrrolidin-3-yl]-2-(1λ$^4$-thiolan-1-ylidene)propanenitrile (I-36)

The title compound was synthesized from rac-(3R,4R)-5-oxo-4-[(pyridin-2-yl)methyl]pyrrolidine-3-carboxylic acid (HCl salt) (I-34) in a similar manner to general procedure 5 (general scheme 2) as a brown gum (1 g, 76% purity by $^1$H NMR, 71%) after purification by ion-exchange flash chromatography (25 g Isolute Si II cartridge, 0-20% MeOH in EtOAc gradient then 0-10% 7N methanolic ammonia in EtOAc gradient).

LC-MS (METCR1410): 100% (UV), Rt=1.16 min, m/z (ESI$^+$)=330.2 [M+H]$^+$ $^1$H NMR (500 MHz, Chloroform-d) δ 1.97-2.06 (m, 2H), 2.49-2.58 (m, 2H), 3.03 (dd, J=8.1, 14.0 Hz, 1H), 3.10 (q, J=7.5 Hz, 1H), 3.14-3.22 (m, 1H), 3.22-3.31 (m, 3H), 3.34-3.47 (m, 3H), 3.63-3.71 (m, 1H), 5.54 (s, 1H), 7.08-7.13 (m, 1H), 7.30 (d, J=7.8 Hz, 1H), 7.59 (td, J=1.8, 7.7 Hz, 1H), 8.48-8.53 (m, 1H)

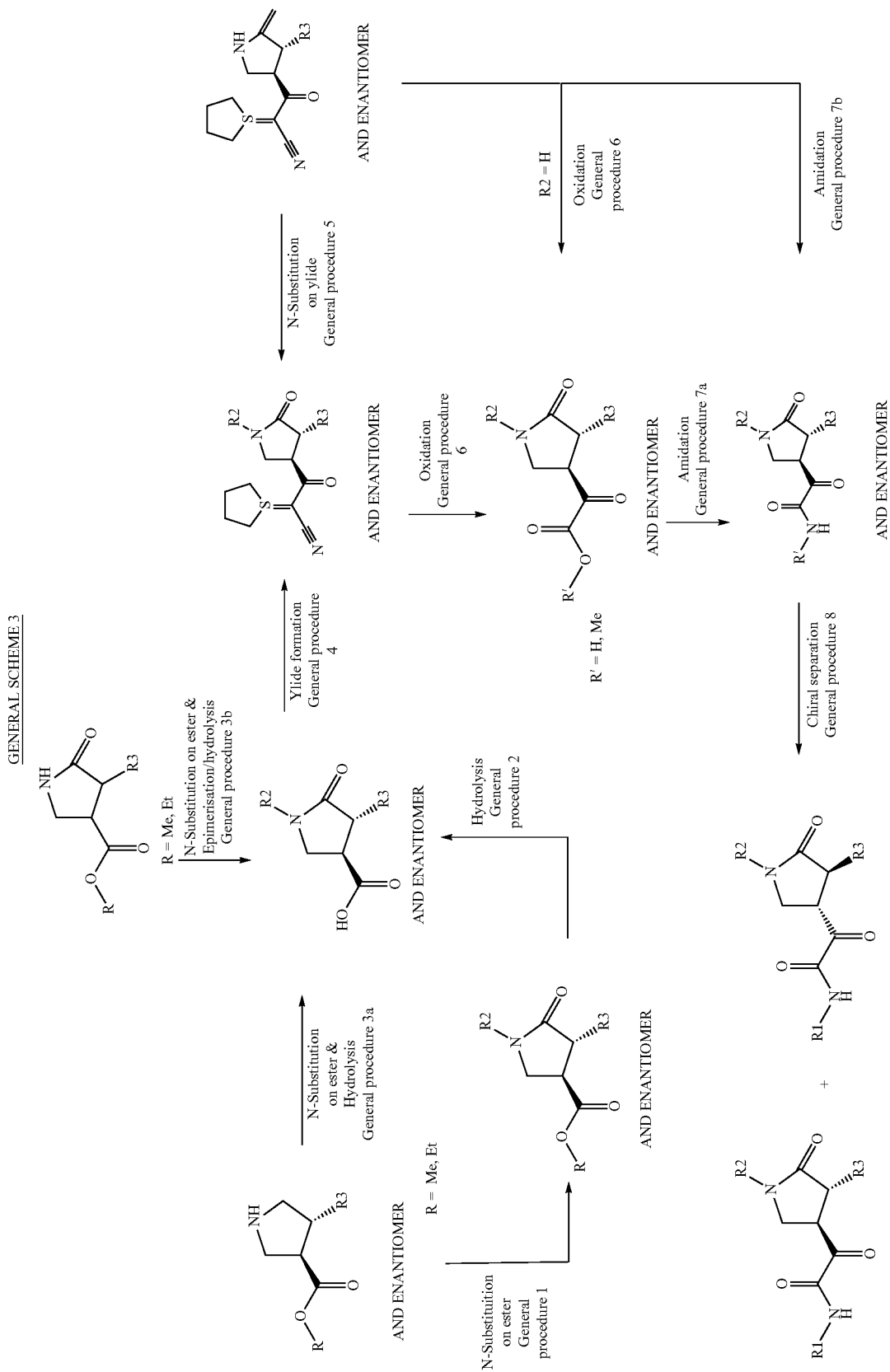

General Procedure 1 (General Scheme 3):
N-Substitution of Trans Racemic Ester

Method A: N-Alkylation Using Cs$_2$CO$_3$ in MeCN at Reflux

Rac-methyl (3R,4R)-4-benzyl-1-[(oxan-4-yl)methyl]-5-oxopyrrolidine-3-carboxylate (I-37)

To a stirring solution of rac-methyl (3R,4R)-4-benzyl-5-oxopyrrolidine-3-carboxylate (I-31) (98% purity, 1 g, 4.22 mmol) in MeCN (30 mL) was added 4-(bromomethyl)oxane (1.1 mL, 8.35 mmol), Cs$_2$CO$_3$ (5.5 g, 16.88 mmol), and KI (350 mg, 2.11 mmol) and the suspension stirred at reflux for 48 h. Further 4-(bromomethyl)-oxane (0.4 mL, 3.04 mmol) was added and the reaction stirred at reflux for 6.5 h. Further Cs$_2$CO$_3$ (6.8 g, 21.1 mmol) was added over time and the mixture stirred at reflux for 46 h. The suspension was filtered and the inorganics washed with MeCN. The combined filtrates were concentrated in vacuo to afford 2.38 g of rac-methyl (3R,4R)-4-benzyl-1-[(oxan-4-yl)methyl]-5-oxopyrrolidine-3-carboxylate as a pale yellow gum (31% purity, 53%) which was used in the next step without further purification.

LC-MS (METCR1410): 31% (UV), Rt=1.07 min, m/z (ESI$^+$)=332.1 [M+H]$^+$

Rac-methyl (3R,4R)-4-benzyl-1-[(3-methyl-1,2,4-oxadiazol-5-yl)methyl]-5-oxopyrrolidine-3-carboxylate (I-38)

The title compound was synthesized from rac-methyl (3R,4R)-4-benzyl-5-oxopyrrolidine-3-carboxylate (I-31) in a similar manner to method A, general procedure 1 (general scheme 3) as an orange solid (4.57 g, 50% purity, 66%) after work-up and used in the next step without further purification.

LC-MS (METCR1410): 50% (UV), Rt=1.02 min, m/z (ESI$^+$)=329.9 [M+H]$^+$

Method B: N-Alkylation Using NaH in DMF at RT

Rac-methyl (3R,4R)-4-benzyl-5-oxo-1-[(pyrimidin-2-yl)methyl]pyrrolidine-3-carboxylate (I-39)

To an ice-cooled stirring solution of rac-methyl (3R,4R)-4-benzyl-5-oxopyrrolidine-3-carboxylate (I-31) (98% purity, 1 g, 4.2 mmol) in dry DMF (30 mL) was added NaH (60% in mineral oil, 350 mg, 8.75 mmol) under nitrogen and the mixture was stirred at 0° C. for 30 min. 2-(Chloromethyl)pyrimidine (850 mg, 6.61 mmol) in dry DMF (3 mL) was added dropwise over 10 min followed by KI (350 mg, 2.11 mmol). The suspension was stirred at RT under nitrogen for 1 h then quenched with 0.5M HCl and extracted with DCM (4×30 mL). The combined organic layers were washed with water (30 mL) and brine (30 mL), dried over Na$_2$SO$_4$ and concentrated in vacuo to afford 1.69 g of rac-methyl (3R,4R)-4-benzyl-5-oxo-1-[(pyrimidin-2-yl)methyl]pyrrolidine-3-carboxylate as an orange gum (70% purity by $^1$H NMR, 87%).

LC-MS (METCR1410): 75% (UV), Rt=1.00 min, m/z (ESI$^+$)=326.1 [M+H]$^+$ $^1$H NMR (500 MHz, Chloroform-d) δ 2.99-3.04 (m, 2H), 3.20-3.27 (m, 2H), 3.44-3.50 (m, 1H), 3.54 (s, 3H), 3.58-3.62 (m, 1H), 4.68 (d, J=16.8 Hz, 1H), 4.75-4.79 (m, 1H), 7.15-7.31 (m, 6H), 8.67 (d, J=4.9 Hz, 2H)

Rac-methyl (3R,4R)-4-benzyl-5-oxo-1-[(pyrimidin-4-yl)methyl]pyrrolidine-3-carboxylate (I-40)

The title compound was synthesized from rac-methyl (3R,4R)-4-benzyl-5-oxopyrrolidine-3-carboxylate (I-31) in a similar manner to method B, general procedure 1 (general scheme 3) as a brown gum (1.17 g, 24% purity, 26%) after work-up and used in the next step without further purification.

LC-MS (METCR1410): 24% (UV), Rt=0.94 min, m/z (ESI$^+$)=326.0 [M+H]$^+$

General Procedure 2 (General Scheme 3): Hydrolysis

Rac-(3R,4R)-4-benzyl-1-[(oxan-4-yl)methyl]-5-oxopyrrolidine-3-carboxylic acid (I-41)

A solution of rac-methyl (3R,4R)-4-benzyl-1-[(oxan-4-yl)methyl]-5-oxo-pyrrolidine-3-carboxylate (I-37) (31% purity, 2.38 g, 2.22 mmol) in 2:1 MeOH/water (75 mL) was treated with 2M NaOH (4.4 mL) and stirred at RT for 1.5 h. The mixture was concentrated in vacuo and the residue diluted with water (50 mL) and extracted with Et$_2$O (50 mL). The aqueous layer was separated, acidified to pH 1-2 using 2M HCl and extracted with 3:1 CHCl$_3$/IPA (3×50 mL). The combined organic layers were dried over Na$_2$SO$_4$ and concentrated in vacuo to give 1.63 g of rac-(3R,4R)-4-benzyl-1-[(oxan-4-yl)methyl]-5-oxopyrrolidine-3-carboxylic acid as an orange oil (50% purity by $^1$H NMR, quantitative).

LC-MS (METCR1410): 65% (UV), Rt=0.93 min, m/z (ESI$^+$)=318.1 [M+H]$^+$ $^1$H NMR (500 MHz, Chloroform-d) δ 1.23-1.44 (m, 2H), 1.62-1.68 (m, 1H), 1.71-1.84 (m, 1H), 2.91-2.98 (m, 1H), 3.02-3.08 (m, 1H), 3.09-3.22 (m, 3H), 3.27-3.34 (m, 2H), 3.40 (td, J=2.1, 11.9 Hz, 1H), 3.45-3.49 (m, 1H), 3.51 (d, J=6.4 Hz, 1H), 3.89-3.96 (m, 2H), 3.97-4.02 (m, 1H), 7.18-7.31 (m, 5H).

Rac-(3R,4R)-4-benzyl-1-[(3-methyl-1,2,4-oxadiazol-5-yl)methyl]-5-oxopyrrolidine-3-carboxylic acid (I-42)

The title compound was synthesized from rac-methyl (3R,4R)-4-benzyl-1-[(3-methyl-1,2,4-oxadiazol-5-yl)methyl]-5-oxopyrrolidine-3-carboxylate (I-38) in a similar manner to general procedure 2 (general scheme 3) as an orange gum (3.5 g, 39% purity, 62%) obtained after work-up and used in the next step without further purification.

LC-MS (METCR1410): 39% (UV), Rt=0.92 min, m/z (ESI$^+$)=316.0 [M+H]$^+$

Rac-(3R,4R)-4-benzyl-5-oxo-1-[(pyrimidin-2-yl)methyl]pyrrolidine-3-carboxylic acid (I-43)

The title compound was synthesized from rac-methyl (3R,4R)-4-benzyl-5-oxo-1-[(pyrimidin-2-yl)methyl]pyrrolidine-3-carboxylate (I-39) in a similar manner to general procedure 2 (general scheme 3) as an orange gum (1.6 g, 76% purity, quantitative) obtained after work-up and used in the next step without further purification.

LC-MS (METCR1410): 76% (UV), Rt=0.87 min, m/z (ESI$^+$)=312.1 [M+H]$^+$ $^1$H NMR (500 MHz, Chloroform-d) δ 2.99-3.08 (m, 1H), 3.15-3.19 (m, 2H), 3.24-3.30 (m, 1H), 3.41 (t, J=9.2 Hz, 1H), 3.63 (dd, J=7.1, 9.6 Hz, 1H), 4.60 (d, J=16.9 Hz, 1H), 4.85 (d, J=16.9 Hz, 1H), 7.17-7.24 (m, 2H), 7.26 (d, J=4.4 Hz, 4H), 8.69 (d, J=4.9 Hz, 2H)

Rac-(3R,4R)-4-benzyl-5-oxo-1-[(pyrimidin-4-yl)methyl]pyrrolidine-3-carboxylic acid (I-44)

The title compound was synthesized from rac-methyl (3R,4R)-4-benzyl-5-oxo-1-[(pyrimidin-4-yl)methyl]pyrrolidine-3-carboxylate (I-40) in a similar manner to general procedure 2 (general scheme 3) as an orange gum (1.18 g, 48% purity, quantitative) obtained after work-up and used in the next step without further purification.

LC-MS (METCR1410): 48% (UV), Rt=0.86 min, m/z (ESI$^+$)=312.0 [M+H]$^+$

General Procedure 3a (General Scheme 3): N-Substitution of Trans Racemic Ester and Hydrolysis Rac-(3R,4S)-1-methyl-5-oxo-4-phenylpyrrolidine-3-carboxylic acid (I-45)

To an ice-cooled solution of crude rac-ethyl (3R,4S)-4-phenyl-5-oxopyrrolidine-3-carboxylate (I-15) (1.0 g, 4.29 mmol) in THF (30 mL) was added NaH (60% dispersion in oil, 0.51 g, 12.86 mmol) and the mixture stirred at 0° C. for 10 min. Iodomethane (534 µL, 8.57 mmol) was added and the mixture stirred for a further 30 min. The reaction was slowly quenched with water (30 mL), stirred for 15 min and extracted with Et$_2$O (30 mL). The aqueous phase was acidified with 6M HCl and extracted with 3:1 CHCl$_3$/IPA (3×50 mL). The combined organic extracts were dried over Na$_2$SO$_4$ and concentrated in vacuo. The residue was purified by FCC on normal phase silica (50 g SNAP Ultra cartridge, 0-5% MeOH in DCM gradient) to afford 835 mg of rac-(3R,4S)-1-methyl-5-oxo-4-phenylpyrrolidine-3-carboxylic acid as a yellow gum (52% purity, 46%). The compound contained rac-(3R,4R)-4-cyclohexyl-1-methyl-5-oxopyrrolidine-3-carboxylic acid as a minor by-product (10% by LC/MS).

LC-MS (METCR1410): 52% (UV), Rt=0.76 min, m/z (ESI$^+$)=220.2 [M+H]$^+$

General Procedure 3b (General Scheme 3): N-Substitution of Diastereoisomeric Ester Mixture and Epimerisation/Hydrolysis Rac-(3R,4R)-4-benzyl-1-(2-methoxyethyl)-5-oxopyrrolidine-3-carboxylic acid (I-46)

To an ice-cooled solution of methyl 4-benzyl-5-oxopyrrolidine-3-carboxylate (I-18) (94% purity, 544 mg, 2.19 mmol) in dry DMF (8 mL) was added portionwise NaH (60% dispersion in oil, 100 mg, 2.50 mmol) and the suspension stirred at 0° C. for 25 min. 2-Bromoethyl methyl ether (230 µL, 2.45 mmol) was added dropwise over 10 min and the reaction stirred at RT for 18 h. Further NaH (90 mg, 2.19 mmol) was added and the mixture stirred at RT for 30 min. Further 2-bromoethyl methyl ether (45 µL, 0.48 mmol) was added and the solution stirred at RT for 1 h. The reaction was quenched with 0.5M HCl (10 mL) and extracted with 3:1 CHCl$_3$/J.=(4×10 mL). The combined organic layers were washed with water (10 mL) and brine (5 mL), dried over Na$_2$SO$_4$ and concentrated in vacuo to afford 672 mg of rac-(3R,4R)-4-benzyl-1-(2-methoxyethyl)-5-oxopyrrolidine-3-carboxylic acid as an orange gum (42% purity, 46%) which was used in the next step without further purification.

LC-MS (METCR1410): 42% (UV), Rt=0.89 min, m/z (ESI$^+$)=278.1 [M+H]$^+$

Rac-(3R,4R)-4-benzyl-1-(carbamoylmethyl)-5-oxopyrrolidine-3-carboxylic acid (I-47)

The title compound was synthesized from methyl 4-benzyl-5-oxopyrrolidine-3-carboxylate (I-18) in a similar manner to general procedure 3b (general scheme 3) as an orange gum (701 mg, 61% purity, 67%) obtained after work-up and used in the next step without further purification.

LC-MS (METCR1410): 61% (UV), Rt=0.77 min, m/z (ESI$^+$)=277.1 [M+H]$^+$

General Procedure 4 (General Scheme 3): Ylide Formation

Rac-3-[(3R,4R)-4-benzyl-1-[(oxan-4-yl)methyl]-5-oxopyrrolidin-3-yl]-3-oxo-2-(1λ$^4$-thiolan-1-ylidene)propanenitrile (I-48)

To a solution of rac-(3R,4R)-4-benzyl-1-[(oxan-4-yl)methyl]-5-oxopyrrolidine-3-carboxylic acid (I-41) (1.55 g, 2.44 mmol) and DIPEA (2 mL, 11.43 mmol) in DCM (50 mL) was added HATU (1.39 g, 3.66 mmol) and 1-(cyanomethyl)thiolan-1-ium bromide (90%, 850 mg, 3.68 mmol, synthesized by the procedure outlined in Note 1, general experimental details) and the mixture stirred at RT for 1 h. The reaction was quenched with sat. NH$_4$Cl (30 mL), the aqueous phase extracted with DCM (3×40 mL) and the combined organic phases dried over Na$_2$SO$_4$, filtered and concentrated in vacuo. The residue was purified by FCC on normal phase silica (100 g SNAP Ultra cartridge, 0-100% EtOAc in heptane gradient followed by 0-25% MeOH in EtOAc gradient) to afford to afford 900 mg of rac-3-[(3R,4R)-4-benzyl-1-[(oxan-4-yl)methyl]-5-oxopyrrolidin-3-yl]-3-oxo-2-(1λ$^4$-thiolan-1-ylidene)propanenitrile as an orange gum (89% purity by $^1$H NMR, 77%).

LC-MS (METCR1410): 95% (UV), Rt=0.92 min, m/z (ESI$^+$)=427.1 [M+H]$^+$ $^1$H NMR (500 MHz, Chloroform-d) δ 1.28-1.36 (m, 2H), 1.46-1.54 (m, 2H), 1.76-1.86 (m, 1H), 1.94-2.03 (m, 2H), 2.40-2.53 (m, 2H), 2.68 (dd, J=9.7, 13.9 Hz, 1H), 2.91-3.02 (m, 2H), 3.09-3.21 (m, 4H), 3.21-3.29 (m, 3H), 3.29-3.37 (m, 3H), 3.39-3.46 (m, 1H), 3.90-3.98 (m, 2H), 7.12-7.18 (m, 1H), 7.20-7.30 (m, 4H)

Rac-3-[(3R,4R)-4-benzyl-1-[(3-methyl-1,2,4-oxadiazol-5-yl)methyl]-5-oxopyrrolidin-3-yl]-3-oxo-2-(1λ$^4$-thiolan-1-ylidene)propanenitrile (I-49)

The title compound was synthesized from ac-(3R,4R)-4-benzyl-1-[(3-methyl-1,2,4-oxadiazol-5-yl)methyl]-5-oxopyrrolidine-3-carboxylic acid (I-42) in a similar manner to general procedure 4 (general scheme 3) as a brown gum (1.47 g, 80% purity by $^1$H NMR, 64%) after purification by by FCC on normal phase silica (340 g SNAP Ultra cartridge, 0-100% EtOAc in heptane gradient followed by 0-30% MeOH in EtOAc gradient).

LC-MS (METCR1410): 99% (UV), Rt=0.91 min, m/z (ESI$^+$)=425.0 [M+H]$^+$ $^1$H NMR (500 MHz, Chloroform-d) δ 1.95-2.03 (m, 2H), 2.39 (s, 3H), 2.41-2.49 (m, 2H), 2.68 (dd, J=10.0, 13.9 Hz, 1H), 2.87-3.00 (m, 2H), 3.12-3.21 (m, 2H), 3.28-3.35 (m, 2H), 3.35-3.41 (m, 1H), 3.44-3.54 (m, 2H), 4.61 (d, J=16.6 Hz, 1H), 4.77 (d, J=16.6 Hz, 1H), 7.13-7.18 (m, 1H), 7.22-7.29 (m, 4H)

Rac-3-[(3R,4R)-4-benzyl-5-oxo-1-[(pyrimidin-2-yl)methyl]pyrrolidin-3-yl]-3-oxo-2-(1λ⁴-thiolan-1-ylidene)propanenitrile (I-50)

The title compound was synthesized from rac-(3R,4R)-4-benzyl-5-oxo-1-[(pyrimidin-2-yl)methyl]pyrrolidine-3-carboxylic acid (I-43) in a similar manner to general procedure 4 (general scheme 3) as an orange gum (1.74 g, 80% purity by $^1$H NMR, 88%) after purification by by FCC on normal phase silica (100 g SNAP Ultra cartridge, 0-100% EtOAc in heptane gradient followed by 0-25% MeOH in EtOAc gradient).

LC-MS (METCR1410): 98% (UV), Rt=0.87 min, m/z (ESI$^+$)=421.2 [M+H]$^+$ $^1$H NMR (500 MHz, Chloroform-d) δ 1.90-2.01 (m, 2H), 2.43 (dp, J=7.2, 20.2 Hz, 2H), 2.66 (dd, J=10.6, 13.8 Hz, 1H), 2.84-2.96 (m, 2H), 3.06-3.16 (m, 2H), 3.31-3.42 (m, 2H), 3.42-3.48 (m, 1H), 3.49-3.57 (m, 2H), 4.66 (d, J=16.6 Hz, 1H), 4.80 (d, J=16.6 Hz, 1H), 7.12-7.19 (m, 2H), 7.21-7.26 (m, 2H), 7.29-7.33 (m, 2H), 8.69 (d, J=4.9 Hz, 2H)

Rac-3-[(3R,4R)-4-benzyl-5-oxo-1-[(pyrimidin-4-yl)methyl]pyrrolidin-3-yl]-3-oxo-2-(1λ⁴-thiolan-1-ylidene)propanenitrile (I-51)

The title compound was synthesized from rac-(3R,4R)-4-benzyl-5-oxo-1-[(pyrimidin-4-yl)methyl]pyrrolidine-3-carboxylic acid (I-44) in a similar manner to general procedure 4 (general scheme 3) as a yellow solid (1.74 g, 75% purity by $^1$H NMR, 59%) after purification by by FCC on normal phase silica (600 mgg SNAP Ultra cartridge, 0-100% EtOAc in heptane gradient followed by 0-25% MeOH in EtOAc gradient).

LC-MS (METCR1410): 77% (UV), Rt=0.86 min, m/z (ESI$^+$)=421.0 [M+H]$^+$ $^1$H NMR (500 MHz, Chloroform-d) δ 1.96-2.03 (m, 2H), 2.41-2.54 (m, 2H), 2.79 (dd, J=9.0, 13.4 Hz, 1H), 2.94-3.04 (m, 2H), 3.16-3.24 (m, 2H), 3.28 (d, J=8.2 Hz, 2H), 3.30-3.37 (m, 2H), 3.50 (q, J=8.1 Hz, 1H), 4.48-4.59 (m, 2H), 7.16-7.21 (m, 2H), 7.24-7.32 (m, 4H), 8.66 (d, J=5.2 Hz, 1H), 9.12 (d, J=1.2 Hz, 1H)

Rac-3-[(3R,4R)-4-cyclohexyl-1-methyl-5-oxopyrrolidin-3-yl]-3-oxo-2-(1λ⁴-thiolan-1-ylidene)propanenitrile (I-52)

The title compound was synthesized from crude rac-(3R,4S)-1-methyl-5-oxo-4-phenylpyrrolidine-3-carboxylic acid (I-45) containing rac-(3R,4R)-4-cyclohexyl-1-methyl-5-oxopyrrolidine-3-carboxylic acid as a minor by-product in a similar manner to general procedure 4 (general scheme 3) as an off-white solid (531 mg, 91% purity, 38%) after purification by FCC on reverse phase silica (60 g SNAP Ultra C18 cartridge, acidic pH, standard elution method).

LC-MS (METCR1410): 91% (UV), Rt=0.90 min, m/z (ESI$^+$)=335.0 [M+H]$^+$ $^1$H NMR (500 MHz, Chloroform-d) δ 1.05 (qd, J=3.4, 12.5 Hz, 1H), 1.12-1.34 (m, 3H), 1.45-1.53 (m, 1H), 1.60-1.76 (m, 5H), 1.86-1.96 (m, 1H), 2.03-2.16 (m, 2H), 2.57-2.67 (m, 2H), 2.80-2.86 (m, 4H), 3.18-3.25 (m, 1H), 3.30-3.44 (m, 4H), 3.45-3.53 (m, 2H)

Rac-3-[(3R,4R)-4-benzyl-1-(2-methoxyethyl)-5-oxopyrrolidin-3-yl]-3-oxo-2-(1λ⁴-thiolan-1-ylidene)propanenitrile (I-53)

The title compound was synthesized from crude rac-(3R,4R)-4-benzyl-1-(2-methoxyethyl)-5-oxopyrrolidine-3-carboxylic acid (I-46) in a similar manner to general procedure 4 (general scheme 3) as an orange gum (582 mg, 60% purity, 89%) after purification by FCC on normal phase silica (100 g SNAP KP-SIL cartridge, 0-100% EtOAc in heptane gradient followed by 0-30% MeOH in EtOAc gradient).

LC-MS (METCR1410): 60% (UV), Rt=0.89 min, m/z (ESI$^+$)=387.1 [M+H]$^+$

Rac-2-[(3R,4R)-3-benzyl-4-[2-cyano-2-(1λ⁴-thiolan-1-ylidene)acetyl]-2-oxopyrrolidin-1-yl]acetamide (I-54)

The title compound was synthesized from crude rac-(3R,4R)-4-benzyl-1-(carbamoylmethyl)-5-oxopyrrolidine-3-carboxylic acid (I-47) in a similar manner to general procedure 4 (general scheme 3) as an orange gum (771 mg, 60% purity estimated by $^1$H NMR, 78%) after purification by FCC on normal phase silica (100 g SNAP KP-SIL cartridge, 0-100% EtOAc in heptane gradient followed by 0-30% MeOH in EtOAc gradient).

LC-MS (METCR1410): 93% (UV), Rt=0.81 min, m/z (ESI$^+$)=386.1 [M+H]$^+$

General Procedure 5 (General Scheme 3): N-Substitution of Ylide

Method A: N-Alkylation Using NaH in DMF at RT

Rac-3-[(3R,4R)-4-benzyl-1-[(5-methyl-1,2-oxazol-3-yl)methyl]-5-oxopyrrolidin-3-yl]-3-oxo-2-(1λ⁴-thiolan-1-ylidene)propanenitrile (I-55)

To a cold stirred solution of rac-3-[(3R,4R)-4-benzyl-5-oxopyrrolidin-3-yl]-3-oxo-2-(1λ⁴-thiolan-1-ylidene)propanenitrile (I-23) (85% purity by $^1$H NMR, 600 mg, 1.55 mmol) in dry DMF (12 mL) was added NaH (60% in mineral oil, 90 mg, 2.25 mmol) in one portion under nitrogen and the suspension stirred at 0° C. for 30 min. 3-(bromo-methyl)-5-methyl-isoxazole (300 mg, 1.7 mmol) in dry DMF (1 mL) was added over 3 min and the mixture stirred at RT under nitrogen for 1 h. The reaction was quenched with water (30 mL) and extracted into EtOAc (2×30 mL). The combined organic extracts were washed with brine (20 mL), dried over Na$_2$SO$_4$, filtered and concentrated in vacuo. The residue was purified by FCC on normal phase silica (10 g SNAP KP-SIL cartridge, 0-100% EtOAc in heptane gradient followed by 0-15% MeOH in EtOAc) to afford 536 mg of rac-3-[(3R,4R)-4-benzyl-1-[(5-methyl-1,2-oxazol-3-yl)methyl]-5-oxopyrrolidin-3-yl]-3-oxo-2-(1λ⁴-thiolan-1-ylidene)propanenitrile as a brown oil (86% purity by $^1$H NMR, 70%).

LC-MS (METCR1410): 100% (UV), Rt=0.94 min, m/z (ESI$^+$)=424.0 [M+H]$^+$ $^1$H NMR (500 MHz, Chloroform-d) δ 1.92-2.01 (m, 2H), 2.37-2.41 (m, 3H), 2.41-2.52 (m, 2H), 2.67 (dd, J=9.9, 13.9 Hz, 1H), 2.89-2.99 (m, 2H), 3.10-3.19 (m, 3H), 3.23-3.32 (m, 2H), 3.36 (dd, J=4.1, 13.9 Hz, 1H), 3.42 (q, J=8.7 Hz, 1H), 4.42 (d, J=15.0 Hz, 1H), 4.50 (d, J=15.0 Hz, 1H), 5.87-5.91 (m, 1H), 7.13-7.18 (m, 1H), 7.22-7.30 (m, 4H)

Rac-3-[(3R,4R)-4-benzyl-1-[(1-methyl-1H-1,2,4-triazol-5-yl)methyl]-5-oxopyrrolidin-3-yl]-3-oxo-2-(1λ⁴-thiolan-1-ylidene)propanenitrile (I-56)

The title compound was synthesized from rac-3-[(3R,4R)-4-benzyl-5-oxo-pyrrolidin-3-yl]-3-oxo-2-(1λ⁴-thiolan-1-ylidene)propanenitrile (I-23) in a similar manner to method A, general procedure 5 (general scheme 3) as an off-white solid (462 mg, 98% purity by $^1$H NMR, 67%) after purification by FCC on normal phase silica (10 g SNAP KP-SIL cartridge, 0-100% EtOAc in heptane gradient followed by 0-20% MeOH in EtOAc gradient).

LC-MS (METCR1410): 100% (UV), Rt=2.89 min, m/z (ESI$^+$)=424.1 [M+H]$^+$ $^1$H NMR (500 MHz, Chloroform-d) δ 1.94-2.02 (m, 2H), 2.40-2.53 (m, 2H), 2.70 (dd, J=9.5, 13.7 Hz, 1H), 2.89-3.01 (m, 2H), 3.12-3.21 (m, 3H), 3.22-3.28 (m, 1H), 3.29-3.37 (m, 2H), 3.42 (q, J=8.4 Hz, 1H), 3.90 (s, 3H), 4.55-4.67 (m, 2H), 7.14-7.19 (m, 1H), 7.21-7.27 (m, 4H), 7.77 (s, 1H)

Rac-2-[(3R,4R)-3-benzyl-4-[2-cyano-2-(1λ$^4$-thiolan-1-ylidene)acetyl]-2-oxopyrrolidin-1-yl]-N-methylacetamide (I-57)

The title compound was synthesized from rac-3-[(3R,4R)-4-benzyl-5-oxopyrrolidin-3-yl]-3-oxo-2-(1λ$^4$-thiolan-1-ylidene)propanenitrile (I-23) in a similar manner to method A, general procedure 5 (general scheme 3) as a pale yellow gum (603 mg, 83% purity by $^1$H NMR, 77%) after purification by FCC on normal phase silica (50 g SNAP KP-SIL cartridge, 0-100% EtOAc in heptane gradient followed by 0-25% MeOH in EtOAc gradient).

LC-MS (METCR1410): 100% (UV), Rt=0.84 min, m/z (ESI$^+$)=400.0 [M+H]$^+$ $^1$H NMR (500 MHz, Chloroform-d) δ 2.05-2.13 (m, 2H), 2.50-2.61 (m, 2H), 2.67 (dd, J=7.5, 9.5 Hz, 1H), 2.78 (d, J=4.7 Hz, 3H), 2.92-2.98 (m, 1H), 3.06 (dd, J=6.5, 13.7 Hz, 1H), 3.12-3.25 (m, 3H), 3.27 (dd, J=3.3, 9.6 Hz, 1H), 3.33-3.44 (m, 4H), 4.26 (d, J=16.8 Hz, 1H), 7.17-7.30 (m, 6H)

Rac-2-[(3R,4R)-3-benzyl-4-[2-cyano-2-(1λ$^4$-thiolan-1-ylidene)acetyl]-2-oxopyrrolidin-1-yl]-N,N-dimethylacetamide (I-58)

The title compound was synthesized from rac-3-[(3R,4R)-4-benzyl-5-oxopyrrolidin-3-yl]-3-oxo-2-(1λ$^4$-thiolan-1-ylidene)propanenitrile (I-23) in a similar manner to method A, general procedure 5 (general scheme 3) as a pale yellow gum (710 mg, 83% purity by $^1$H NMR, 88%) after purification by FCC on normal phase silica (50 g SNAP KP-SIL cartridge, 0-100% EtOAc in heptane gradient followed by 0-25% MeOH in EtOAc gradient).

LC-MS (METCR1410): 99% (UV), Rt=0.85 min, m/z (ESI$^+$)=414.0 [M+H]$^+$ $^1$H NMR (500 MHz, Chloroform-d) δ 1.90-2.02 (m, 2H), 2.40-2.52 (m, 2H), 2.65 (dd, J=10.0, 13.5 Hz, 1H), 2.90-2.99 (m, 5H), 3.01 (s, 3H), 3.10-3.18 (m, 2H), 3.28-3.40 (m, 3H), 3.48 (q, J=8.4 Hz, 1H), 3.54 (t, J=8.7 Hz, 1H), 4.04 (d, J=15.7 Hz, 1H), 4.15 (d, J=15.7 Hz, 1H), 7.12-7.17 (m, 1H), 7.21-7.31 (m, 4H)

Rac-4-{[(3R,4R)-3-benzyl-4-[2-cyano-2-(1λ$^4$-thiolan-1-ylidene)acetyl]-2-oxopyrrolidin-1-yl]methyl}benzamide (I-59)

The title compound was synthesized from rac-3-[(3R,4R)-4-benzyl-5-oxopyrrolidin-3-yl]-3-oxo-2-(1λ$^4$-thiolan-1-ylidene)propanenitrile (I-23) in a similar manner to method A, general procedure 5 (general scheme 3) as an off-white solid (588 mg, 87% purity, 82%) after purification by FCC on normal phase silica (50 g SNAP Ultra cartridge, 0-100% EtOAc in heptane gradient followed by 0-25% MeOH in EtOAc gradient).

LC-MS (METCR1410): 87% (UV), Rt=0.89 min, m/z (ESI$^+$)=461.9 [M+H]$^+$ $^1$H NMR (500 MHz, Chloroform-d) δ 1.92-2.02 (m, 2H), 2.40-2.50 (m, 2H), 2.74 (dd, J=9.6, 13.8 Hz, 1H), 2.90-2.98 (m, 2H), 3.05-3.11 (m, 1H), 3.11-3.20 (m, 3H), 3.27-3.33 (m, 1H), 3.35-3.46 (m, 2H), 4.44-4.53 (m, 2H), 5.55 (bs, 1H), 6.05 (bs, 1H), 7.13-7.20 (m, 1H), 7.23-7.28 (m, 4H), 7.28-7.31 (m, 2H), 7.72-7.78 (m, 2H)

Rac-3-[(3R,4R)-4-benzyl-1-[(3-methyl-1,2-oxazol-5-yl)methyl]-5-oxopyrrolidin-3-yl]-3-oxo-2-(1λ$^4$-thiolan-1-ylidene)propanenitrile (I-60)

The title compound was synthesized from rac-3-[(3R,4R)-4-benzyl-5-oxopyrrolidin-3-yl]-3-oxo-2-(1λ$^4$-thiolan-1-ylidene)propanenitrile (I-23) in a similar manner to method A, general procedure 5 (general scheme 3) as a brown viscous oil (367 mg, 90% purity by $^1$H NMR, 55%) after purification by FCC on normal phase silica (10 g SNAP KP-SIL cartridge, 0-100% EtOAc in heptane gradient followed by 0-20% MeOH in EtOAc gradient).

LC-MS (METCR1410): 99% (UV), Rt=0.95 min, m/z (ESI$^+$)=424.0 [M+H]$^+$ $^1$H NMR (500 MHz, Chloroform-d) δ 1.94-2.03 (m, 2H), 2.27 (s, 3H), 2.41-2.52 (m, 2H), 2.70 (dd, J=9.7, 13.8 Hz, 1H), 2.92-3.02 (m, 2H), 3.14-3.21 (m, 2H), 3.23-3.28 (m, 2H), 3.31-3.38 (m, 2H), 3.45 (q, J=8.5 Hz, 1H), 4.52 (s, 2H), 5.96 (s, 1H), 7.13-7.20 (m, 1H), 7.22-7.30 (m, 4H)

Rac-3-[(3R,4R)-4-benzyl-5-oxo-1-[2-(2-oxopyrrolidin-1-yl)ethyl]pyrrolidin-3-yl]-3-oxo-2-(1λ$^4$-thiolan-1-ylidene)propanenitrile (I-61)

The title compound was synthesized from rac-3-[(3R,4R)-4-benzyl-5-oxopyrrolidin-3-yl]-3-oxo-2-(1λ$^4$-thiolan-1-ylidene)propanenitrile (I-23) in a similar manner to method A, general procedure 5 (general scheme 3) as a pale yellow gum (598 mg, 85% purity by $^1$H NMR, 71%) after purification by FCC on normal phase silica (50 g SNAP Ultra cartridge, 0-100% EtOAc in heptane gradient followed by 0-30% MeOH in EtOAc gradient).

LC-MS (METCR1410): 89% (UV), Rt=0.87 min, m/z (ESI$^+$)=440.0 [M+H]$^+$ $^1$H NMR (500 MHz, Chloroform-d) δ 1.93-2.03 (m, 4H), 2.26-2.40 (m, 2H), 2.42-2.54 (m, 2H), 2.64 (dd, J=9.6, 13.6 Hz, 1H), 2.97-3.07 (m, 2H), 3.14-3.20 (m, 2H), 3.20-3.25 (m, 1H), 3.25-3.30 (m, 2H), 3.31-3.41 (m, 5H), 3.41-3.49 (m, 2H), 3.49-3.54 (m, 1H), 7.13-7.17 (m, 1H), 7.22-7.29 (m, 4H)

Rac-3-[(3R,4R)-4-benzyl-1-(2,2-difluoroethyl)-5-oxopyrrolidin-3-yl]-3-oxo-2-(1λ$^4$-thiolan-1-ylidene)propanenitrile (I-62)

The title compound was synthesized from rac-3-[(3R,4R)-4-benzyl-5-oxopyrrolidin-3-yl]-3-oxo-2-(1λ$^4$-thiolan-1-ylidene)propanenitrile (I-23) in a similar manner to method A, general procedure 5 (general scheme 3) as a pale yellow solid (634 mg, 93% purity by $^1$H NMR, 71%) after purification by FCC on normal phase silica (25 g SNAP KP-SIL cartridge, 0-100% EtOAc in heptane gradient followed by 0-20% MeOH in EtOAc gradient).

LC-MS (METCR1410): 100% (UV), Rt=0.93 min, m/z (ESI$^+$)=393.0 [M+H]$^+$ $^1$H NMR (500 MHz, Chloroform-d) δ 1.95-2.03 (m, 2H), 2.39-2.52 (m, 2H), 2.68 (dd, J=9.7, 13.8 Hz, 1H), 2.90-3.02 (m, 2H), 3.17-3.23 (m, 2H), 3.23-3.29 (m, 1H), 3.30-3.37

(m, 2H), 3.37-3.50 (m, 2H), 3.53-3.71 (m, 2H), 5.84 (tt, J=4.2, 55.7 Hz, 1H), 7.14-7.21 (m, 1H), 7.23-7.29 (m, 4H)

Rac-3-[(3R,4R)-4-[(4-fluorophenyl)methyl]-1-[(1-methyl-1H-1,2,4-triazol-3-yl)methyl]-5-oxopyrrolidin-3-yl]-3-oxo-2-(1λ$^4$-thiolan-1-ylidene)propanenitrile (I-63)

The title compound was synthesized from rac-3-[(3R,4R)-4-[(4-fluorophenyl)methyl]-5-oxopyrrolidin-3-yl]-3-oxo-2-(1λ$^4$-thiolan-1-ylidene)propanenitrile (I-35) in a similar manner to method A, general procedure 5 (general scheme 3) as an off-white solid (352 mg, 100% purity, 30%) after purification by FCC on normal phase silica (10 g SNAP KP-SIL cartridge, 0-100% EtOAc in heptane gradient followed by 0-20% MeOH in EtOAc gradient).

LC-MS (METCR1410): 100% (UV), Rt=0.90 min, m/z (ESI$^+$)=442.6 [M+H]$^+$ $^1$H NMR (500 MHz, Chloroform-d) δ 1.95-2.04 (m, 2H), 2.40-2.50 (m, 2H), 2.61 (dd, J=10.5, 14.0 Hz, 1H), 2.88-3.02 (m, 2H), 3.14-3.30 (m, 4H), 3.35-3.43 (m, 2H), 3.47 (t, J=8.8 Hz, 1H), 3.88 (s, 3H), 4.42 (d, J=15.3 Hz, 1H), 4.69 (d, J=15.3 Hz, 1H), 6.90-6.96 (m, 2H), 7.21-7.26 (m, 2H), 7.94 (s, 1H)

Rac-3-[(3R,4R)-4-[(4-fluorophenyl)methyl]-1-[(1-methyl-1H-1,2,4-triazol-5-yl)methyl]-5-oxopyrrolidin-3-yl]-3-oxo-2-(1λ$^4$-thiolan-1-ylidene)propanenitrile (I-64)

The title compound was synthesized from rac-3-[(3R,4R)-4-[(4-fluorophenyl)methyl]-5-oxopyrrolidin-3-yl]-3-oxo-2-(1λ$^4$-thiolan-1-ylidene)propanenitrile (I-35) in a similar manner to method A, general procedure 5 (general scheme 3) as an off-white solid (991 mg, 100% purity, 95%) after purification by FCC on normal phase silica (25 g SNAP KP-SIL cartridge, 0-100% EtOAc in heptane gradient followed by 0-50% MeOH in EtOAc gradient).

LC-MS (METCR1410): 100% (UV), Rt=0.87 min, m/z (ESI$^+$)=442.4 [M+H]$^+$ $^1$H NMR (500 MHz, Chloroform-d) δ 1.92-2.02 (m, 2H), 2.37-2.47 (m, 2H), 2.61 (dd, J=9.5, 13.7 Hz, 1H), 2.88-3.01 (m, 2H), 3.08-3.15 (m, 1H), 3.15-3.27 (m, 4H), 3.29-3.38 (m, 2H), 3.86 (s, 3H), 4.54 (d, J=15.2 Hz, 1H), 4.58 (d, J=15.2 Hz, 1H), 6.85-6.92 (m, 2H), 7.13-7.19 (m, 2H), 7.73 (s, 1H)

Method B: N-Arylation Using Pd$_2$(dba)$_3$ and Xantphos

Rac-3-[(3R,4R)-4-benzyl-5-oxo-1-(pyrimidin-5-yl)pyrrolidin-3-yl]-3-oxo-2-(1λ$^4$-thiolan-1-ylidene)propanenitrile (I-65)

To a degassed solution of rac-3-[(3R,4R)-4-benzyl-5-oxopyrrolidin-3-yl]-3-oxo-2-(1λ$^4$-thiolan-1-ylidene)propanenitrile (I-23) (80% purity by $^1$H NMR, 500 mg, 1.22 mmol) in 1,4-dioxane (10 mL) was added 5-bromopyrimidine (235 mg, 1.48 mmol), Cs$_2$CO$_3$ (555 mg, 1.7 mmol), Pd$_2$(dba)$_3$ (56 mg, 0.06 mmol) and Xantphos (106 mg, 0.18 mmol). Nitrogen was bubbled through the suspension for 5 min and the reaction heated at 100° C. for 5.5 h. The suspension was cooled to RT, diluted with DCM (10 mL) and filtered through Celite. The Celite was washed with DCM (3×15 mL) and the combined filtrates concentrated in vacuo. The residue was purified by FCC on normal phase silica (50 g SNAP KP-SIL cartridge, 0-100% EtOAc in heptane gradient followed by 0-20% MeOH in EtOAc gradient) to afford 385 mg of rac-3-[(3R,4R)-4-benzyl-5-oxo-1-(pyrimidin-5-yl)pyrrolidin-3-yl]-3-oxo-2-(1λ$^4$-thiolan-1-ylidene)propanenitrile as a pale yellow gum (90% purity by 1H NMR, 70%).

LC-MS (METCR1410): 100% (UV), Rt=0.90 min, m/z (ESI$^+$)=407.0 [M+H]$^+$ $^1$H NMR (500 MHz, Chloroform-d) δ 1.96-2.07 (m, 2H), 2.42-2.55 (m, 2H), 2.79-2.88 (m, 1H), 2.93-3.08 (m, 2H), 3.16-3.27 (m, 2H), 3.39-3.49 (m, 2H), 3.62 (q, J=8.4 Hz, 1H), 3.66-3.74 (m, 2H), 7.16-7.22 (m, 1H), 7.24-7.32 (m, 4H), 8.99 (s, 1H), 9.06 (s, 2H)

Rac-3-[(3R,4R)-4-benzyl-5-oxo-1-(pyrazin-2-yl)pyrrolidin-3-yl]-3-oxo-2-(1λ$^4$-thiolan-1-ylidene)propanenitrile (I-66)

The title compound was synthesized from rac-3-[(3R,4R)-4-benzyl-5-oxopyrrolidin-3-yl]-3-oxo-2-(1λ$^4$-thiolan-1-ylidene)propanenitrile (I-23) in a similar manner to method B, general procedure 5 (general scheme 3) as a brown viscous oil (310 mg, 82% purity by $^1$H NMR, 58%) after purification by FCC on normal phase silica (25 g SNAP KP-SIL cartridge, 0-100% EtOAc in heptane gradient followed by 0-20% MeOH in EtOAc gradient).

LC-MS (METCR1410): 91% (UV), Rt=0.97 min, m/z (ESI$^+$)=407.0 [M+H]$^+$ $^1$H NMR (500 MHz, Chloroform-d) δ 1.96-2.03 (m, 2H), 2.42-2.54 (m, 2H), 2.76-2.83 (m, 1H), 2.95-3.04 (m, 2H), 3.14-3.24 (m, 2H), 3.39-3.46 (m, 1H), 3.53-3.61 (m, 2H), 3.69-3.76 (m, 1H), 4.14-4.19 (m, 1H), 7.15-7.20 (m, 1H), 7.24-7.33 (m, 4H), 8.25-8.28 (m, 1H), 8.30 (d, J=2.6 Hz, 1H), 9.75 (d, J=1.4 Hz, 1H)#

Rac-3-[(3R,4R)-4-benzyl-5-oxo-1-(pyrimidin-2-yl)pyrrolidin-3-yl]-3-oxo-2-(1λ$^4$-thiolan-1-ylidene)propanenitrile (I-67)

The title compound was synthesized from rac-3-[(3R,4R)-4-benzyl-5-oxopyrrolidin-3-yl]-3-oxo-2-(1λ$^4$-thiolan-1-ylidene)propanenitrile (I-23) in a similar manner to method B, general procedure 5 (general scheme 3) as an orange gum (626 mg, 70% purity by $^1$H NMR, 40%) after purification by FCC on normal phase silica (100 g SNAP Ultra cartridge, 0-100% EtOAc in heptane gradient followed by 0-25% MeOH in EtOAc gradient).

LC-MS (METCR1410): 98% (UV), Rt=0.90 min, m/z (ESI$^+$)=407.0 [M+H]$^+$ $^1$H NMR (500 MHz, Chloroform-d) δ 1.92-2.03 (m, 2H), 2.40-2.55 (m, 2H), 2.79 (dd, J=9.4, 14.0 Hz, 1H), 2.92-3.04 (m, 2H), 3.10-3.22 (m, 2H), 3.47 (dd, J=4.0, 13.9 Hz, 1H), 3.50-3.60 (m, 2H), 3.79 (dd, J=8.9, 10.7 Hz, 1H), 4.18 (dd, J=8.4, 10.7 Hz, 1H), 7.02 (t, J=4.8 Hz, 1H), 7.13-7.20 (m, 1H), 7.23-7.28 (m, 2H), 7.29-7.35 (m, 2H), 8.67 (d, J=4.8 Hz, 2H)

Rac-3-[(3R,4R)-4-benzyl-1-(2-chloropyrimidin-4-yl)-5-oxopyrrolidin-3-yl]-3-oxo-2-(1λ$^4$-thiolan-1-ylidene)propanenitrile (I-68)

The title compound was synthesized from rac-3-[(3R,4R)-4-benzyl-5-oxopyrrolidin-3-yl]-3-oxo-2-(1λ$^4$-thiolan-1-ylidene)propanenitrile (I-23) in a similar manner to method B, general procedure 5 (general scheme 3) as a pale yellow viscous oil (411 mg, 96% purity, 84%) after purification by FCC on normal phase silica (25 g SNAP KP-SIL cartridge, 0-100% EtOAc in heptane gradient followed by 0-50% MeOH in EtOAc gradient).

LC-MS (METCR1410): 96% (UV), Rt=1.04 min, m/z (ESI$^+$)=441.4/443.1 [M+H]$^+$ $^1$H NMR (500 MHz, Chloroform-d) δ 1.94-2.04 (m, 2H), 2.41-2.52 (m, 2H), 2.75 (dd, J=9.2, 13.9 Hz, 1H), 2.95-3.03 (m, 2H), 3.14-3.23 (m, 2H), 3.36 (dd, J=4.2, 13.9 Hz, 1H), 3.49-3.60 (m, 2H), 3.69 (dd, J=8.5, 11.2 Hz, 1H), 4.21 (dd, J=8.5, 11.2 Hz, 1H), 7.14-7.20 (m, 1H), 7.23-7.26 (m, 4H), 8.33 (d, J=5.8 Hz, 1H), 8.44 (d, J=5.8 Hz, 1H)

Rac-3-[(3R,4R)-4-benzyl-1-(6-chloropyridazin-3-yl)-5-oxopyrrolidin-3-yl]-3-oxo-2-(1λ$^4$-thiolan-1-ylidene)propanenitrile (I-69)

The title compound was synthesized from rac-3-[(3R,4R)-4-benzyl-5-oxopyrrolidin-3-yl]-3-oxo-2-(1λ$^4$-thiolan-1-ylidene)propanenitrile (I-23) in a similar manner to method B, general procedure 5 (general scheme 3) as a pale yellow powder (362 mg, 98% purity, 75%) after purification by FCC on normal phase silica (25 g SNAP KP-SIL cartridge, 0-100% EtOAc in heptane gradient followed by 0-50% MeOH in EtOAc gradient).

LC-MS (METCR1410): 98% (UV), Rt=1.02 min, m/z (ESI$^+$)=441.0/443.1 [M+H]$^+$ $^1$H NMR (500 MHz, Chloroform-d) δ 1.95-2.04 (m, 2H), 2.43-2.57 (m, 2H), 2.74-2.84 (m, 1H), 2.96-3.10 (m, 2H), 3.14-3.26 (m, 2H), 3.37-3.45 (m, 1H), 3.54-3.63 (m, 2H), 3.82-3.92 (m, 1H), 4.29-4.37 (m, 1H), 7.16-7.22 (m, 1H), 7.26-7.30 (m, 4H), 7.48 (d, J=9.4 Hz, 1H), 8.73 (d, J=9.4 Hz, 1H)

Rac-3-oxo-3-[(3R,4S)-5-oxo-4-phenyl-1-(pyrimidin-5-yl)pyrrolidin-3-yl]-2-(1λ$^4$-thiolan-1-ylidene)propanenitrile (I-70)

The title compound was synthesized from rac-3-oxo-3-[(3R,4S)-5-oxo-4-phenylpyrrolidin-3-yl]-2-(1λ$^4$-thiolan-1-ylidene)propanenitrile (I-24) in a similar manner to method B, general procedure 5 (general scheme 3) as a yellow viscous oil (233 mg, 92% purity, 38%) after purification by FCC on normal phase silica (25 g SNAP KP-SIL cartridge, 0-100% EtOAc in heptane gradient followed by 0-50% MeOH in EtOAc gradient).

LC-MS (METCR1410): 92% (UV), Rt=0.87 min, m/z (ESI$^+$)=393.2 [M+H]$^+$ $^1$H NMR (500 MHz, Chloroform-d) δ 2.02-2.09 (m, 2H), 2.45-2.56 (m, 2H), 3.17-3.31 (m, 2H), 3.33-3.42 (m, 2H), 3.86-3.96 (m, 2H), 4.09-4.14 (m, 1H), 4.31 (d, J=9.5 Hz, 1H), 7.26-7.29 (m, 3H), 7.31-7.36 (m, 2H), 8.97 (s, 1H), 9.11 (s, 2H)

Rac-5-[(3R,4R)-3-benzyl-4-[2-cyano-2-(1λ$^4$-thiolan-1-ylidene)acetyl]-2-oxopyrrolidin-1-yl]pyrimidine-4-carbonitrile (I-71)

The title compound was synthesized from rac-3-[(3R,4R)-4-benzyl-5-oxopyrrolidin-3-yl]-3-oxo-2-(1λ$^4$-thiolan-1-ylidene)propanenitrile (I-23) in a similar manner to method B, general procedure 5 (general scheme 3) as a pale yellow powder (328 mg, 94% purity by $^1$H NMR, 83%) after purification by FCC on normal phase silica (25 g SNAP KP-SIL cartridge, 0-100% EtOAc in heptane gradient followed by 0-50% MeOH in EtOAc gradient).

LC-MS (METCR1410): 96% (UV), Rt=0.96 min, m/z (ESI$^+$)=432.0 [M+H]$^+$ $^1$H NMR (500 MHz, Chloroform-d) δ 1.96-2.09 (m, 2H), 2.45-2.57 (m, 2H), 2.91 (dd, J=9.0, 14.0 Hz, 1H), 3.00-3.11 (m, 2H), 3.19-3.29 (m, 2H), 3.39 (dd, J=4.5, 14.0 Hz, 1H), 3.46-3.53 (m, 1H), 3.65 (q, J=8.2 Hz, 1H), 3.75-3.85 (m, 1H), 3.98 (dd, J=8.0, 8.9 Hz, 1H), 7.20-7.24 (m, 1H), 7.27-7.34 (m, 4H), 9.07 (s, 1H), 9.14 (s, 1H)

Rac-3-[(3R,4R)-4-benzyl-1-(4-methylpyrimidin-5-yl)-5-oxopyrrolidin-3-yl]-3-oxo-2-(1λ$^4$-thiolan-1-ylidene)propanenitrile (I-72)

The title compound was synthesized from rac-3-[(3R,4R)-4-benzyl-5-oxopyrrolidin-3-yl]-3-oxo-2-(1λ$^4$-thiolan-1-ylidene)propanenitrile (I-23) in a similar manner to method B, general procedure 5 (general scheme 3) as an orange viscous oil (374 mg, 90% purity by $^1$H NMR, 60%) after purification by FCC on normal phase silica (25 g SNAP Ultra cartridge, 0-100% EtOAc in heptane gradient followed by 0-30% MeOH in EtOAc gradient).

LC-MS (METCR1410): 94% (UV), Rt=0.89 min, m/z (ESI$^+$)=421.1 [M+H]$^+$ $^1$H NMR (500 MHz, Chloroform-d) δ 1.97-2.07 (m, 2H), 2.43 (s, 3H), 2.44-2.55 (m, 2H), 2.92 (dd, J=8.1, 13.4 Hz, 1H), 2.99-3.09 (m, 2H), 3.20-3.28 (m, 2H), 3.31-3.42 (m, 2H), 3.42-3.47 (m, 1H), 3.60-3.69 (m, 2H), 7.20-7.24 (m, 1H), 7.28-7.34 (m, 4H), 8.37 (s, 1H), 8.98 (s, 1H)

Rac-3-[(3R,4R)-4-benzyl-1-[6-(benzyloxy)pyridin-2-yl]-5-oxopyrrolidin-3-yl]-3-oxo-2-(1λ$^4$-thiolan-1-ylidene)propanenitrile (I-73)

The title compound was synthesized from rac-3-[(3R,4R)-4-benzyl-5-oxopyrrolidin-3-yl]-3-oxo-2-(1λ$^4$-thiolan-1-ylidene)propanenitrile (I-23) in a similar manner to method B, general procedure 5 (general scheme 3) as a yellow viscous oil (342 mg, 95% purity, 61%) after purification by FCC on normal phase silica (25 g SNAP Ultra cartridge, 0-100% EtOAc in heptane gradient followed by 0-20% MeOH in EtOAc gradient).

LC-MS (METCR1410): 95% (UV), Rt=1.26 min, m/z (ESI$^+$)=512.2 [M+H]$^+$ $^1$H NMR (500 MHz, Chloroform-d) δ 1.93-2.03 (m, 2H), 2.40-2.53 (m, 2H), 2.69-2.76 (m, 1H), 2.91-3.03 (m, 2H), 3.13-3.21 (m, 2H), 3.46 (dd, J=3.7, 13.9 Hz, 1H), 3.48-3.57 (m, 2H), 3.70-3.78 (m, 1H), 4.18-4.27 (m, 1H), 5.29 (s, 2H), 6.53 (d, J=8.0 Hz, 1H), 7.14-7.19 (m, 1H), 7.24-7.29 (m, 2H), 7.29-7.33 (m, 3H), 7.33-7.38 (m, 2H), 7.40-7.44 (m, 2H), 7.61 (t, J=8.0 Hz, 1H), 7.97 (d, J=7.9 Hz, 1H)

Method C: N-Arylation using Cs$_2$CO$_3$ and Cu(I)I

Rac-3-[(3R,4R)-4-benzyl-1-(1-methyl-1H-pyrazol-4-yl)-5-oxopyrrolidin-3-yl]-3-oxo-2-(1λ$^4$-thiolan-1-ylidene)propanenitrile (I-74)

To a solution of rac-3-[(3R,4R)-4-benzyl-5-oxopyrrolidin-3-yl]-3-oxo-2-(1λ$^4$-thiolan-1-ylidene)propanenitrile (I-23) (71% purity by $^1$H NMR, 500 mg, 1.08 mmol) and 4-bromo-1-methyl-1H-pyrazole (157 mg, 0.975 mmol) in 1,4-dioxane (10 mL) was added Cs$_2$CO$_3$ (635 mg, 1.95 mmol), Cu(I)I (19 mg, 0.10 mmol) and N,N-dimethylethylenediamine (9 mg, 0.10 mmol) then the suspension was heated at 90° C. in a pressure tube for 3 h. Further 4-bromo-1-methyl-1H-pyrazole (157 mg, 0.98 mmol), Cs$_2$CO$_3$ (635 mg, 1.95 mmol), Cu(I)I (19 mg, 0.10 mmol) and N,N- dimethylethylene-diamine (9 mg, 0.10 mmol) were added and the reaction heated at 90° C. for 3 h. The mixture was cooled to RT, diluted with DCM (20 mL) and filtered. The filter cake was washed with DCM (20 mL) and the combined filtrates concentrated in vacuo. The residue was purified by FCC on normal phase silica (25 g SNAP KP-SIL cartridge, 0-100% EtOAc in heptane gradient followed by 0-50% MeOH in EtOAc gradient) to afford 248 mg of rac-3-[(3R, 4R)-4-benzyl-1-(1-methyl-1H-pyrazol-4-yl)-5-oxopyrrolidin-3-yl]-3-oxo-2-(1$\lambda^4$-thiolan-1-ylidene)propanenitrile as a pale yellow gum (90% purity by $^1$H NMR, 56%).

LC-MS (MET-uHPLC-1704): 100% (UV), Rt=0.61 min, m/z (ESI$^+$)=409.2 [M+H]$^+$ $^1$H NMR (500 MHz, DMSO-d$_6$) δ 1.92-2.06 (m, 2H), 2.15-2.29 (m, 2H), 2.72-2.81 (m, 2H), 2.93-2.99 (m, 1H), 3.07 (dd, J=4.6, 13.6 Hz, 1H), 3.10-3.16 (m, 1H), 3.35-3.56 (m, 5H), 3.80 (s, 3H), 7.16-7.22 (m, 3H), 7.22-7.31 (m, 2H), 7.56 (s, 1H), 7.96 (s, 1H)

General Procedure 6 (General Scheme 3): Oxidation

Method A: Oxone Oxidation to Ketoacid

Rac-2-[(3R,4R)-4-benzyl-5-oxopyrrolidin-3-yl]-2-oxoacetic acid (I-75)

To an ice-cooled solution of rac-3-[(3R,4R)-4-benzyl-5-oxopyrrolidin-3-yl]-2-(1$\lambda^4$-thiolan-1-ylidene)-3-oxopropanenitrile (I-23) (0.42 g, 1.29 mmol) in 3:2 THF:water (25 mL) was added Oxone (1.57 g, 2.57 mmol) and the mixture stirred at 0° C. for 1 h. The reaction was quenched with 1M HCl, stirred vigorously for 5 min and extracted with EtOAc (3×80 mL). The combined organic extracts were dried over Na$_2$SO$_4$ and concentrated in vacuo to give 490 mg of rac-2-[(3R,4R)-4-benzyl-5-oxopyrrolidin-3-yl]-2-oxoacetic acid as a pale yellow oil (70% purity by $^1$H NMR, 100%) which was used in the next step without further purification.

LC-MS (METCR1410): 91% (UV), Rt=0.67 min, m/z (ESI$^+$)=247.9 [M+H]$^+$ $^1$H NMR (500 MHz, Chloroform-d) δ 2.94 (dd, J=7.4, 13.4 Hz, 2H), 3.15-3.27 (m, 2H), 3.31-3.42 (m, 2H), 3.86-3.97 (m, 1H), 7.26 (s, 5H)

Rac-2-oxo-2-[(3R,4S)-5-oxo-4-phenylpyrrolidin-3-yl]acetic acid (I-76)

The title compound was synthesized from pure rac-3-oxo-3-[(3R,4S)-5-oxo-4-phenylpyrrolidin-3-yl]-2-(1$\lambda^4$-thiolan-1-ylidene)propanenitrile (I-24) in a similar manner to method A, general procedure 6 (general scheme 3) as a pale yellow viscous oil (550 mg, 50% purity, 39%) obtained after work-up and used in the next step without further purification.

LC-MS (METCR1410): 50% (UV), Rt=0.20-0.50 min, m/z (ESI$^+$)=234.1 [M+H]$^+$

Note: Batches of rac-2-oxo-2-[(3R,4S)-5-oxo-4-phenylpyrrolidin-3-yl]acetic acid (I-76) prepared from crude rac-3-oxo-3-[(3R,4S)-5-oxo-4-phenylpyrrolidin-3-yl]-2-(1$\lambda^4$-thiolan-1-ylidene)propanenitrile (I-24) contained rac-2-[(3R,4R)-4-cyclohexyl-5-oxopyrrolidin-3-yl]-2-oxoacetic acid as a minor by-product.

Rac-2-[(3R,4S)-4-(4-fluorophenyl)-5-oxopyrrolidin-3-yl]-2-oxoacetic acid (I-77)

The title compound was synthesized from rac-3-[(3R,4S)-4-(4-fluorophenyl)-5-oxopyrrolidin-3-yl]-3-oxo-2-(1$\lambda^4$-thiolan-1-ylidene)propanenitrile (I-25) in a similar manner to method A, general procedure 6 (general scheme 3) as a yellow viscous oil (750 mg, 50% purity, 64%) obtained after work-up and used in the next step without further purification.

LC-MS (METCR1410): 50% (UV), Rt=0.35 min, m/z (ESI$^+$)=252.0 [M+H]$^+$

Rac-2-[(3R,4R)-4-[(4-fluorophenyl)methyl]-5-oxopyrrolidin-3-yl]-2-oxoacetic acid (I-78)

The title compound was synthesized from rac-3-[(3R,4R)-4-[(4-fluorophenyl)methyl]-5-oxopyrrolidin-3-yl]-3-oxo-2-(1$\lambda^4$-thiolan-1-ylidene)propanenitrile (I-35) in a similar manner to method A, general procedure 6 (general scheme 3) as a yellow viscous oil (2.1 g, 60% purity estimated by $^1$H NMR, 60%) obtained after work-up and used in the next step without further purification.

LC-MS (METCR1410): 89% (UV), Rt=0.72 min, m/z (ESI$^+$)=266.0 [M+H]$^+$ $^1$H NMR (500 MHz, DMSO-d$_6$) δ 2.80-2.86 (m, 2H), 2.89-2.95 (m, 1H), 3.13-3.17 (m, 1H), 3.18-3.23 (m, 1H), 3.63-3.69 (m, 1H), 7.04-7.11 (m, 2H), 7.21-7.26 (m, 2H), 7.69-7.75 (m, 1H)

Rac-2-[(3R,4R)-4-benzyl-1-[(oxan-4-yl)methyl]-5-oxopyrrolidin-3-yl]-2-oxoacetic acid (I-79)

The title compound was synthesized from rac-3-[(3R,4R)-4-benzyl-1-[(oxan-4-yl)methyl]-5-oxopyrrolidin-3-yl]-3-oxo-2-(1$\lambda^4$-thiolan-1-ylidene)propanenitrile (I-48) in a similar manner to method A, general procedure 6 (general scheme 3) as a yellow viscous oil (810 mg, 60% purity estimated by $^1$H NMR, 71%) obtained after work-up and used in the next step without further purification.

LC-MS (METCR1410): 75% (UV), Rt=0.84 min, m/z (ESI$^+$)=346.2 [M+H]$^+$ $^1$H NMR (250 MHz, Chloroform-d) δ 1.31-1.49 (m, 3H), 1.68-1.90 (m, 1H), 3.05-3.22 (m, 7H), 3.25-3.45 (m, 3H), 3.75-3.86 (m, 1H), 3.88-4.02 (m, 2H), 7.16-7.32 (m, 5H)

Rac-2-[(3R,4R)-4-benzyl-1-[(3-methyl-1,2,4-oxadiazol-5-yl)methyl]-5-oxopyrrolidin-3-yl]-2-oxoacetic acid (I-80)

The title compound was synthesized from rac-3-[(3R,4R)-4-benzyl-1-[(3-methyl-1,2,4-oxadiazol-5-yl)methyl]-5-oxopyrrolidin-3-yl]-3-oxo-2-(1$\lambda^4$-thiolan-1-ylidene)propanenitrile (I-49) in a similar manner to method A, general procedure 6 (general scheme 3) as a yellow viscous oil (209 mg, 50% purity estimated by $^1$H NMR, 86%) obtained after work-up and used in the next step without further purification.

LC-MS (METCR1410): 92% (UV), Rt=0.82 min, m/z (ESI$^+$)=344.0 [M+H]$^+$

Rac-2-[(3R,4R)-4-benzyl-5-oxo-1-[(pyrimidin-2-yl)methyl]pyrrolidin-3-yl]-2-oxoacetic acid (I-81)

The title compound was synthesized from rac-3-[(3R,4R)-4-benzyl-5-oxo-1-[(pyrimidin-2-yl)methyl]pyrrolidin-3-yl]-3-oxo-2-(1$\lambda^4$-thiolan-1-ylidene)propanenitrile (I-50) in a similar manner to method A, general procedure 6 (general scheme 3) as a yellow gum (850 mg, 40% purity estimated by $^1$H NMR, 53%) obtained after work-up and used in the next step without further purification.

LC-MS (METCR1410): 70% (UV), Rt=0.78 min, m/z (ESI$^+$)=340.1 [M+H]$^+$
$^1$H NMR (250 MHz, Chloroform-d) δ 3.08-3.26 (m, 3H), 3.37-3.45 (m, 1H), 3.53-3.62 (m, 1H), 3.70-3.82 (m, 1H), 4.40 (d, J=16.9 Hz, 1H), 5.02 (d, J=17.0 Hz, 1H), 7.20-7.35 (m, 6H), 8.82 (d, J=4.7 Hz, 2H)

Rac-2-[(3R,4R)-4-benzyl-5-oxo-1-[(pyrimidin-4-yl)methyl]pyrrolidin-3-yl]-2-oxoacetic acid (I-82)

The title compound was synthesized from rac-3-[(3R,4R)-4-benzyl-5-oxo-1-[(pyrimidin-4-yl)methyl]pyrrolidin-3-yl]-3-oxo-2-(1λ$^4$-thiolan-1-ylidene)propanenitrile (I-51) in a similar manner to method A, general procedure 6 (general scheme 3) as a pale yellow gum (201 mg, 50% purity estimated by $^1$H NMR, 83%) obtained after work-up and used in the next step without further purification.
LC-MS (METCR1410): 75% (UV), Rt=0.76 min, m/z (ESI$^+$)=340.0 [M+H]$^+$

Rac-2-[(3R,4R)-4-cyclohexyl-1-methyl-5-oxopyrrolidin-3-yl]-2-oxoacetic acid (I-83)

The title compound was synthesized from rac-3-[(3R,4R)-4-cyclohexyl-1-methyl-5-oxopyrrolidin-3-yl]-3-oxo-2-(1λ$^4$-thiolan-1-ylidene)propanenitrile (I-52) in a similar manner to method A, general procedure 6 (general scheme 1) as a colourless oil (721 mg, 50% purity estimated by $^1$H NMR, 90%) obtained after work-up and used in the next step without further purification.
LC-MS (METCR1410): 89% (UV), Rt=0.75 min, m/z (ESI$^+$)=254.0 [M+H]$^+$

Rac-2-[(3R,4R)-4-benzyl-1-(2-methoxyethyl)-5-oxopyrrolidin-3-yl]-2-oxoacetic acid (I-84)

The title compound was synthesized from rac-3-[(3R,4R)-4-benzyl-1-(2-methoxyethyl)-5-oxopyrrolidin-3-yl]-3-oxo-2-(1λ$^4$-thiolan-1-ylidene)propanenitrile (I-53) in a similar manner to method A, general procedure 6 (general scheme 3) as a yellow gum (555 mg, 25% purity estimated by $^1$H NMR, 50%) obtained after work-up and used in the next step without further purification.
LC-MS (METCR1410): 54% (UV), Rt=0.79 min, m/z (ESI$^+$)=306.1 [M+H]$^+$
$^1$H NMR (500 MHz, Chloroform-d) δ 2.93-2.98 (m, 1H), 3.16-3.22 (m, 3H), 3.28 (s, 3H), 3.35-3.39 (m, 2H), 3.41-3.49 (m, 5H), 7.16-7.24 (m, 3H), 7.24-7.31 (m, 2H).

Rac-2-[(3R,4R)-4-benzyl-1-(carbamoylmethyl)-5-oxopyrrolidin-3-yl]-2-oxoacetic acid (I-85)

The title compound was synthesized from rac-2-[(3R,4R)-3-benzyl-4-[2-cyano-2-(1λ$^4$-thiolan-1-ylidene)acetyl]-2-oxopyrrolidin-1-yl]acetamide (I-54) in a similar manner to method A, general procedure 6 (general scheme 3) as a yellow gum (563 mg, 10% purity estimated by $^1$H NMR, 15%) and used in the next step without further purification.
LC-MS (METCR1410): 20% (UV), Rt=0.68 min, m/z (ESI$^+$)=305.2 [M+H]$^+$

Rac-2-[(3R,4R)-4-benzyl-1-[(5-methyl-1,2-oxazol-3-yl)methyl]-5-oxopyrrolidin-3-yl]-2-oxoacetic acid (I-86)

The title compound was synthesized from rac-3-[(3R,4R)-4-benzyl-1-[(5-methyl-1,2-oxazol-3-yl)methyl]-5-oxopyrrolidin-3-yl]-3-oxo-2-(1λ$^4$-thiolan-1-ylidene)propanenitrile (I-55) in a similar manner to method A, general procedure 6 (general scheme 3) as a brown oil (419 mg, 65% purity estimated by $^1$H NMR, 77%) and used in the next step without further purification.
LC-MS (METCR1410): 83% (UV), Rt=0.89 min, m/z (ESI$^+$)=343.0 [M+H]$^+$
$^1$H NMR (500 MHz, Chloroform-d) δ 2.39-2.41 (m, 3H), 2.97-3.06 (m, 1H), 3.16-3.26 (m, 3H), 3.28-3.34 (m, 1H), 3.74-3.82 (m, 1H), 4.44-4.46 (m, 2H), 5.83-5.88 (m, 1H), 7.14-7.19 (m, 2H), 7.20-7.27 (m, 3H)

Rac-2-[(3R,4R)-4-benzyl-1-[(1-methyl-1H-1,2,4-triazol-5-yl)methyl]-5-oxopyrrolidin-3-yl]-2-oxoacetic acid (I-87)

The title compound was synthesized from rac-3-[(3R,4R)-4-benzyl-1-[(1-methyl-1H-1,2,4-triazol-5-yl)methyl]-5-oxopyrrolidin-3-yl]-3-oxo-2-(1λ$^4$-thiolan-1-ylidene)propanenitrile (I-56) in a similar manner to method A, general procedure 6 (general scheme 3) as a colourless viscous oil (298 mg, 49% purity, 42%) and used in the next step without further purification.
LC-MS (METCR1410): 49% (UV), Rt=0.75 min, m/z (ESI$^+$)=343.0 [M+H]$^+$

Rac-2-[(3R,4R)-4-benzyl-1-[(methylcarbamoyl)methyl]-5-oxopyrrolidin-3-yl]-2-oxoacetic acid (I-88)

The title compound was synthesized from rac-2-[(3R,4R)-3-benzyl-4-[2-cyano-2-(1λ$^4$-thiolan-1-ylidene)acetyl]-2-oxopyrrolidin-1-yl]-N-methylacetamide (I-57) in a similar manner to method A, general procedure 6 (general scheme 3) as a pale yellow gum (544 mg, 45% purity by $^1$H NMR, 62%) and used in the next step without further purification.
LC-MS (METCR1410): 79% (UV), Rt=0.71 min, m/z (ESI$^+$)=319.0 [M+H]$^+$
$^1$H NMR (500 MHz, Chloroform-d) δ 2.78 (d, J=4.4 Hz, 3H), 3.08-3.20 (m, 4H), 3.39-3.46 (m, 1H), 3.66-3.83 (m, 2H), 4.02 (d, J=15.9 Hz, 1H), 6.29 (s, 1H), 7.17-7.33 (m, 5H)

Rac-2-[(3R,4R)-4-benzyl-1-[(dimethylcarbamoyl)methyl]-5-oxopyrrolidin-3-yl]-2-oxoacetic acid (I-89)

The title compound was synthesized from rac-2-[(3R,4R)-3-benzyl-4-[2-cyano-2-(1λ$^4$-thiolan-1-ylidene)acetyl]-2-oxopyrrolidin-1-yl]-N,N-dimethylacetamide (I-58) in a similar manner to method A, general procedure 6 (general scheme 3) as a pale yellow gum (670 mg, 40% purity by $^1$H NMR, 57%) and used in the next step without further purification.
LC-MS (METCR1410): 86% (UV), Rt=0.79 min, m/z (ESI$^+$)=333.1 [M+H]$^+$
$^1$H NMR (500 MHz, Chloroform-d) δ 2.94 (s, 3H), 2.96-3.00 (m, 1H), 3.01 (s, 3H), 3.15-3.23 (m, 1H), 3.27-3.36 (m, 1H), 3.51 (dd, J=4.4, 7.9 Hz, 2H), 3.67-3.80 (m, 1H), 3.95 (d, J=16.1 Hz, 1H), 4.21 (d, J=16.2 Hz, 1H), 7.14-7.25 (m, 5H)

Rac-2-[(3R,4R)-4-benzyl-1-[(4-carbamoylphenyl)methyl]-5-oxopyrrolidin-3-yl]-2-oxoacetic acid (I-90)

The title compound was synthesized from rac-4-{[(3R,4R)-3-benzyl-4-[2-cyano-2-(1λ$^4$-thiolan-1-ylidene)acetyl]-

2-oxopyrrolidin-1-yl]methyl}benzamide (I-59) in a similar manner to method A, general procedure 6 (general scheme 3) as a yellow gum (248 mg, 50% purity estimated by $^1$H NMR, 71%) and used in the next step without further purification.

LC-MS (METCR1410): 83% (UV), Rt=0.80 min, m/z (ESI$^+$)=381.2 [M+H]$^+$

Rac-2-[(3R,4R)-4-benzyl-1-[(3-methyl-1,2-oxazol-5-yl)methyl]-5-oxopyrrolidin-3-yl]-2-oxoacetic acid (I-91)

The title compound was synthesized from rac-3-[(3R,4R)-4-benzyl-1-[(3-methyl-1,2-oxazol-5-yl)methyl]-5-oxopyrrolidin-3-yl]-3-oxo-2-(1A-thiolan-1-ylidene)propanenitrile (I-60) in a similar manner to method A, general procedure 6 (general scheme 3) as a yellow oil (370 mg, 64% purity by $^1$H NMR, 90%) and used in the next step without further purification.

LC-MS (METCR1410): 90% (UV), Rt=0.86 min, m/z (ESI$^+$)=343.1 [M+H]$^+$ $^1$H NMR (500 MHz, Chloroform-d) δ 2.28 (s, 3H), 2.96-3.00 (m, 1H), 3.15-3.23 (m, 2H), 3.25-3.30 (m, 1H), 3.39 (dd, J=6.0, 9.9 Hz, 1H), 3.81-3.87 (m, 1H), 4.51 (s, 2H), 5.95 (s, 1H), 7.14-7.18 (m, 2H), 7.20-7.28 (m, 3H)

Rac-2-[(3R,4R)-4-benzyl-5-oxo-1-[2-(2-oxopyrrolidin-1-yl)ethyl]pyrrolidin-3-yl]-2-oxoacetic acid (I-92)

The title compound was synthesized from rac-3-[(3R,4R)-4-benzyl-5-oxo-1-[2-(2-oxopyrrolidin-1-yl)ethyl]pyrrolidin-3-yl]-3-oxo-2-(1A4-thiolan-1-ylidene)propanenitrile (I-61) in a similar manner to method A, general procedure 6 (general scheme 3) as a yellow gum (547 mg, 50% purity estimated by $^1$H NMR, 66%) and used in the next step without further purification.

LC-MS (METCR1410): 77% (UV), Rt=0.79 min, m/z (ESI$^+$)=359.1 [M+H]$^+$ $^1$H NMR (500 MHz, Chloroform-d) δ 1.83-2.10 (m, 6H), 2.20-2.37 (m, 5H), 2.36-2.45 (m, 1H), 2.92 (dd, J=7.6, 13.9 Hz, 1H), 3.03 (s, 6H), 3.05-3.17 (m, 2H), 3.18-3.25 (m, 2H), 3.32-3.44 (m, 2H), 3.59-3.72 (m, 3H), 3.75 (s, 5H), 7.14-7.30 (m, 5H)

Rac-2-[(3R,4R)-4-benzyl-1-(2,2-difluoroethyl)-5-oxopyrrolidin-3-yl]-2-oxoacetic acid (I-93)

The title compound was synthesized from rac-3-[(3R,4R)-4-benzyl-1-(2,2-difluoroethyl)-5-oxopyrrolidin-3-yl]-3-oxo-2-(1λ$^4$-thiolan-1-ylidene)propanenitrile (I-62) in a similar manner to method A, general procedure 6 (general scheme 3) as a pale yellow oil (346 mg, 87% purity, 64%) and used in the next step without further purification.

LC-MS (METCR1410): 87% (UV), Rt=0.86 min, m/z (ESI$^+$)=312.0 [M+H]$^+$

Rac-2-[(3R,4R)-4-[(4-fluorophenyl)methyl]-1-[(1-methyl-1H-1,2,4-triazol-3-yl)methyl]-5-oxopyrrolidin-3-yl]-2-oxoacetic acid (I-94)

The title compound was synthesized from rac-3-[(3R,4R)-4-[(4-fluorophenyl)methyl]-1-[(1-methyl-1H-1,2,4-triazol-3-yl)methyl]-5-oxopyrrolidin-3-yl]-3-oxo-2-(1λ$^4$-thiolan-1-ylidene)propanenitrile (I-63) in a similar manner to method A, general procedure 6 (general scheme 3) as a colourless gum (241 mg, 35% purity, 30%) and used in the next step without further purification.

LC-MS (METCR1410): 35% (UV), Rt=0.80 min, m/z (ESI$^+$)=361.0 [M+H]$^+$

Rac-2-[(3R,4R)-4-[(4-fluorophenyl)methyl]-1-[(1-methyl-1H-1,2,4-triazol-5-yl)methyl]-5-oxopyrrolidin-3-yl]-2-oxoacetic acid (I-95)

The title compound was synthesized from rac-3-[(3R,4R)-4-[(4-fluorophenyl)methyl]-1-[(1-methyl-1H-1,2,4-triazol-5-yl)methyl]-5-oxopyrrolidin-3-yl]-3-oxo-2-(1λ$^4$-thiolan-1-ylidene)propanenitrile (I-64) in a similar manner to method A, general procedure 6 (general scheme 3) as a yellow oil (851 mg, 40% purity estimated by $^1$H NMR, 44%) and used in the next step without further purification.

LC-MS (METCR1410): 51% (UV), Rt=0.78 min, m/z (ESI$^+$)=361.1 [M+H]$^+$

Rac-2-[(3R,4R)-4-benzyl-5-oxo-1-(pyrimidin-5-yl)pyrrolidin-3-yl]-2-oxoacetic acid (I-96)

The title compound was synthesized from rac-3-[(3R,4R)-4-benzyl-5-oxo-1-(pyrimidin-5-yl)pyrrolidin-3-yl]-3-oxo-2-(1λ$^4$-thiolan-1-ylidene)propanenitrile (I-65) in a similar manner to method A, general procedure 6 (general scheme 3) as a pale yellow gum (305 mg, 50% purity estimated by $^1$H NMR, 55%) and used in the next step without further purification.

LC-MS (METCR1410): 84% (UV), Rt=0.80 min, m/z (ESI$^+$)=344.0 [M+H]$^+$ $^1$H NMR (500 MHz, Chloroform-d) δ 3.11-3.21 (m, 1H), 3.23-3.31 (m, 1H), 3.35-3.42 (m, 1H), 3.62-3.69 (m, 1H), 3.81 (dd, J=6.3, 9.6 Hz, 1H), 3.94-4.01 (m, 1H), 7.17-7.30 (m, 5H), 8.98-9.04 (m, 1H), 9.05-9.13 (m, 2H)

Rac-2-[(3R,4R)-4-benzyl-5-oxo-1-(pyrazin-2-yl)pyrrolidin-3-yl]-2-oxoacetic acid (I-97)

The title compound was synthesized from rac-3-[(3R,4R)-4-benzyl-5-oxo-1-(pyrazin-2-yl)pyrrolidin-3-yl]-3-oxo-2-(1λ$^4$-thiolan-1-ylidene)propanenitrile (I-66) in a similar manner to method A, general procedure 6 (general scheme 3) as a brown viscous oil (206 mg, 70% purity by $^1$H NMR, 77%) and used in the next step without further purification.

LC-MS (METCR1410): 92% (UV), Rt=0.87 min, m/z (ESI$^+$)=326.0 [M+H]$^+$ $^1$H NMR (500 MHz, Chloroform-d) δ 3.00-3.06 (m, 1H), 3.33 (dd, J=5.0, 13.9 Hz, 1H), 3.49 (td, J=5.0, 8.1 Hz, 1H), 3.91 (dd, J=7.1, 11.0 Hz, 1H), 3.97-4.03 (m, 1H), 4.08-4.15 (m, 1H), 7.17-7.24 (m, 3H), 7.25-7.30 (m, 2H), 8.31-8.33 (m, 1H), 8.34 (d, J=2.6 Hz, 1H), 9.74 (d, J=1.4 Hz, 1H)

Rac-2-[(3R,4R)-4-benzyl-5-oxo-1-(pyrimidin-2-yl)pyrrolidin-3-yl]-2-oxoacetic acid (I-98)

The title compound was synthesized from rac-3-[(3R,4R)-4-benzyl-5-oxo-1-(pyrimidin-2-yl)pyrrolidin-3-yl]-3-oxo-2-(1λ$^4$-thiolan-1-ylidene)propanenitrile (I-67) in a similar manner to method A, general procedure 6 (general scheme 3) as an orange gum (566 mg, 45% purity by $^1$H NMR, 73%) and used in the next step without further purification.

LC-MS (METCR1410): 82% (UV), Rt=0.80 min, m/z (ESI$^+$)=326.0 [M+H]$^+$ $^1$H NMR (500 MHz, Chloroform-d) δ 3.06 (d, J=8.0 Hz, 1H), 3.31 (dd, J=5.0, 13.9 Hz, 1H), 3.42-3.49 (m, 1H), 3.88-3.98 (m, 2H), 7.06-7.09 (m, 1H), 7.18-7.23 (m, 3H), 7.23-7.27 (m, 3H), 8.67 (d, J=4.8 Hz, 2H)

Rac-2-[(3R,4R)-4-benzyl-1-(2-chloropyrimidin-4-yl)-5-oxopyrrolidin-3-yl]-2-oxoacetic acid (I-99)

The title compound was synthesized from rac-3-[(3R,4R)-4-benzyl-1-(2-chloropyrimidin-4-yl)-5-oxopyrrolidin-3-yl]-3-oxo-2-(1$\lambda^4$-thiolan-1-ylidene)propanenitrile (I-68) in a similar manner to method A, general procedure 6 (general scheme 3) as an off-white powder (409 mg, 75% purity by $^1$H NMR, 98%) and used in the next step without further purification.

LC-MS (METCR1410): 81% (UV), Rt=0.96 min, m/z (ESI$^+$)=360.0/362.0 [M+H]$^+$ $^1$H NMR (500 MHz, DMSO-d$_6$) δ 2.95-3.01 (m, 1H), 3.07 (dd, J=5.7, 13.8 Hz, 1H), 3.37-3.42 (m, 1H), 3.80 (dd, J=6.8, 9.2 Hz, 1H), 3.87 (dd, J=6.5, 11.3 Hz, 1H), 4.00 (dd, J=9.3, 11.3 Hz, 1H), 7.17-7.29 (m, 5H), 8.27 (d, J=5.8 Hz, 1H), 8.61 (d, J=5.8 Hz, 1H)

Rac-2-[(3R,4R)-4-benzyl-1-(6-chloropyridazin-3-yl)-5-oxopyrrolidin-3-yl]-2-oxoacetic acid (I-100)

The title compound was synthesized from rac-3-[(3R,4R)-4-benzyl-1-(6-chloropyridazin-3-yl)-5-oxopyrrolidin-3-yl]-3-oxo-2-(1$\lambda^4$-thiolan-1-ylidene)propanenitrile (I-69) in a similar manner to method A, general procedure 6 (general scheme 3) as a pale yellow oil (358 mg, 75% purity by $^1$H NMR, 95%) and used in the next step without further purification.

LC-MS (METCR1410): 87% (UV), Rt=0.93 min, m/z (ESI$^+$)=360.0/362.0 [M+H]$^+$ $^1$H NMR (500 MHz, Chloroform-d) δ 3.06 (dd, J=7.3, 13.9 Hz, 1H), 3.22 (dd, J=5.2, 13.9 Hz, 1H), 3.45-3.51 (m, 1H), 3.87-3.94 (m, 1H), 4.05 (dd, J=6.8, 11.7 Hz, 1H), 4.19 (dd, J=9.4, 11.6 Hz, 1H), 7.12-7.20 (m, 3H), 7.21-7.25 (m, 2H), 7.52 (d, J=9.4 Hz, 1H), 8.73 (d, J=9.4 Hz, 1H)

Rac-2-oxo-2-[(3R,4S)-5-oxo-4-phenyl-1-(pyrimidin-5-yl)pyrrolidin-3-yl]acetic acid (I-101)

The title compound was synthesized from rac-3-oxo-3-[(3R,4S)-5-oxo-4-phenyl-1-(pyrimidin-5-yl)pyrrolidin-3-yl]-2-(1$\lambda^4$-thiolan-1-ylidene)propanenitrile (I-70) in a similar manner to method A, general procedure 6 (general scheme 3) as a yellow viscous oil (311 mg, 36% purity, 70%) and used in the next step without further purification.

LC-MS (METCR1410): 36% (UV), Rt=0.77 min, m/z (ESI$^+$)=312.0 [M+H]$^+$

Rac-2-[(3R,4R)-4-benzyl-1-(4-cyanopyrimidin-5-yl)-5-oxopyrrolidin-3-yl]-2-oxoacetic acid (I-102)

The title compound was synthesized from rac-5-[(3R,4R)-3-benzyl-4-[2-cyano-2-(1$\lambda^4$-thiolan-1-ylidene)acetyl]-2-oxopyrrolidin-1-yl]pyrimidine-4-carbonitrile (I-71) in a similar manner to method A, general procedure 6 (general scheme 3) as a pale yellow viscous oil (241 mg, 77% purity, 76%) and used in the next step without further purification.

LC-MS (METCR1410): 77% (UV), Rt=0.88 min, m/z (ESI$^+$)=351.0 [M+H]$^+$

Rac-2-[(3R,4R)-4-benzyl-1-(4-methylpyrimidin-5-yl)-5-oxopyrrolidin-3-yl]-2-oxoacetic acid (I-103)

The title compound was synthesized from rac-3-[(3R,4R)-4-benzyl-1-(4-methylpyrimidin-5-yl)-5-oxopyrrolidin-3-yl]-3-oxo-2-(1$\lambda^4$-thiolan-1-ylidene)propanenitrile (I-72) in a similar manner to method A, general procedure 6 (general scheme 3) as a pale yellow viscous oil (227 mg, 74% purity, 67%) and used in the next step without further purification.

LC-MS (METCR1410): 74% (UV), Rt=0.79 min, m/z (ESI$^+$)=340.0 [M+H]$^+$

Rac-2-[(3R,4R)-4-benzyl-1-[6-(benzyloxy)pyridin-2-yl]-5-oxopyrrolidin-3-yl]-2-oxoacetic acid (I-104)

The title compound was synthesized from rac-3-[(3R,4R)-4-benzyl-1-[6-(benzyloxy)pyridin-2-yl]-5-oxopyrrolidin-3-yl]-3-oxo-2-(1$\lambda^4$-thiolan-1-ylidene)propane-nitrile (I-73) in a similar manner to method A, general procedure 6 (general scheme 3) as a yellow viscous oil (371 mg, 66% purity, 99%) and used in the next step without further purification.

LC-MS (METCR1410): 66% (UV), Rt=1.19 min, m/z (ESI$^+$)=431.0 [M+H]$^+$

Rac-2-[(3R,4R)-4-benzyl-1-(1-methyl-1H-pyrazol-4-yl)-5-oxopyrrolidin-3-yl]-2-oxoacetic acid (I-105)

The title compound was synthesized from rac-3-[(3R,4R)-4-benzyl-1-(1-methyl-1H-pyrazol-4-yl)-5-oxopyrrolidin-3-yl]-3-oxo-2-(1$\lambda^4$-thiolan-1-ylidene)propanenitrile (I-74) in a similar manner to method A, general procedure 6 (general scheme 3) as a yellow viscous oil (209 mg, 76% purity, 96%) and used in the next step without further purification.

LC-MS (METCR1410): 76% (UV), Rt=0.83 min, m/z (ESI$^+$)=328.0 [M+H]$^+$

Method B: m-CPBA Oxidation to Ketoester

Rac-methyl 2-oxo-2-[(3R,4S)-5-oxo-4-phenylpyrrolidin-3-yl]acetate (I-106)

To an ice-cooled solution of rac-3-oxo-3-[(3R,4S)-5-oxo-4-phenylpyrrolidin-3-yl]-2-(1$\lambda^4$-thiolan-1-ylidene)propanenitrile (I-24) (80% purity by $^1$H NMR, 450 mg, 1.21 mmol) in dry MeOH (3 mL) was added m-CPBA (70%, 598 mg, 2.45 mmol) portionwise at 0° C. and the mixture stirred at 0° C. for 1 h. The reaction was quenched with 1M Na$_2$S$_2$O$_3$ (5 mL) and extracted with DCM (3×10 mL). The organic extracts were washed with sat. NaHCO$_3$ (2×10 mL) and concentrated in vacuo to afford 150 mg of rac-methyl 2-oxo-2-[(3R,4S)-5-oxo-4-phenylpyrrolidin-3-yl]acetate as a yellow viscous oil (23% purity, 12%) which was used in the next step without further purification.

LC-MS (METCR1410): 23% (UV), Rt=0.71 min, m/z (ESI$^+$)=248.1 [M+H]$^+$

General Procedure 7a (General Scheme 3): Ketoamide Formation

Method A: T3P Coupling on Ketoacid

Rac-2-[(3R,4R)-4-benzyl-5-oxopyrrolidin-3-yl]-N-(cyclopropylmethyl)-2-oxoacetamide (FP-1)

To a solution of rac-2-[(3R,4R)-4-benzyl-5-oxopyrrolidin-3-yl]-2-oxoacetic acid (I-75) (70% purity by $^1$H NMR, 485 mg, 1.37 mmol) in DMF (3 mL) were added in quick succession T3P (50% in DMF, 2 mL, 3.43 mmol), DIPEA (718 µL, 4.12 mmol) and 1-cyclopropylmethanamine (179 µL, 2.06 mmol) and the mixture stirred at RT for 1 h. The solution was diluted with EtOAc (50 mL), washed with brine (5×50 mL) and the organic phase was dried over Na$_2$SO$_4$ and concentrated in vacuo. The residue was purified by FCC on normal phase silica (25 g SNAP KP-SIL cartridge, 0-100% EtOAc in heptane gradient) to afford 164 mg of rac-2-[(3R,4R)-4-benzyl-5-oxopyrrolidin-3-yl]-N-(cyclopropylmethyl)-2-oxoacetamide as an off-white solid (96% purity, 34%).

LC-MS (MET-uHPLC-AB-102): 96% (UV), Rt=2.45 min, m/z (ESI$^+$)=301.2 [M+H]$^+$ $^1$H NMR (500 MHz, Chloroform-d) δ 0.22 (q, J=4.7 Hz, 2H), 0.51-0.59 (m, 2H), 0.87-0.99 (m, 1H), 2.89 (dd, J=8.0, 13.7 Hz, 1H), 3.05-3.13 (m, 3H), 3.19-3.29 (m, 2H), 3.32-3.39 (m, 1H), 4.08 (ddd, J=6.9, 7.7, 9.1 Hz, 1H), 5.60-5.68 (m, 1H), 6.72-6.82 (m, 1H), 7.15-7.24 (m, 3H), 7.22-7.29 (m, 2H)

Rac-2-[(3R,4R)-4-benzyl-5-oxopyrrolidin-3-yl]-N-cyclopropyl-2-oxoacetamide (FP-2)

The title compound was synthesized from rac-2-[(3R,4R)-4-benzyl-5-oxopyrrolidin-3-yl]-2-oxoacetic acid (I-75) in a similar manner to method A, general procedure 7a (general scheme 3) as an off-white solid (22 mg, 100% purity, 11%) after purification by FCC on normal phase silica (10 g SNAP KP-SIL cartridge, 50-100% EtOAc in heptane gradient) followed by FCC on normal phase silica (10 g SNAP KP-SIL cartridge, 0-100% EtOAc in heptane gradient).

LC-MS (MET-uPLC-AB-102): 100% (UV), Rt=2.11 min, m/z (ESI$^+$)=287.1 [M+H]$^+$ $^1$H NMR (500 MHz, Chloroform-d) δ 0.49-0.60 (m, 2H), 0.79-0.89 (m, 2H), 2.65-2.74 (m, 1H), 2.88 (dd, J=8.1, 13.7 Hz, 1H), 3.03-3.11 (m, 1H), 3.18-3.28 (m, 2H), 3.30-3.38 (m, 1H), 4.08 (ddd, J=7.0, 7.8, 9.0 Hz, 1H), 5.59 (s, 1H), 6.69 (s, 1H), 7.16-7.23 (m, 3H), 7.22-7.29 (m, 2H)

Rac-2-[(3R,4R)-4-benzyl-5-oxopyrrolidin-3-yl]-N-ethyl-2-oxoacetamide (FP-3)

The title compound was synthesized from rac-2-[(3R,4R)-4-benzyl-5-oxopyrrolidin-3-yl]-2-oxoacetic acid (I-75) in a similar manner to method A, general procedure 7a (general scheme 3) as a colourless gum (63 mg, 96% purity, 29%) after purification by FCC on normal phase silica (25 g SNAP Ultra cartridge, 0-100% EtOAc in heptane gradient).

LC-MS (METCR1603): 96% (UV), Rt=3.20 min, m/z (ESI$^+$)=275.2 [M+H]$^+$ $^1$H NMR (500 MHz, Chloroform-d) δ 1.16 (t, J=7.3 Hz, 3H), 2.88 (dd, J=8.1, 13.7 Hz, 1H), 3.08 (td, J=4.7, 7.9 Hz, 1H), 3.20-3.24 (m, 1H), 3.24-3.31 (m, 3H), 3.33-3.38 (m, 1H), 4.08 (ddd, J=6.9, 7.8, 9.1 Hz, 1H), 5.68 (s, 1H), 6.66 (s, 1H), 7.17-7.23 (m, 3H), 7.23-7.27 (m, 2H)

Rac-2-[(3R,4R)-4-benzyl-5-oxopyrrolidin-3-yl]-N-(2,2-difluoroethyl)-2-oxoacetamide (FP-4)

The title compound was synthesized from rac-2-[(3R,4R)-4-benzyl-5-oxopyrrolidin-3-yl]-2-oxoacetic acid (I-75) in a similar manner to method A, general procedure 7a (general scheme 3) as an off-white solid (115 mg, 100% purity, 49%) after purification by FCC on normal phase silica (25 g SNAP Ultra cartridge, 0-100% EtOAc in heptane gradient).

LC-MS (METCR1603): 100% (UV), Rt=3.25 min, m/z (ESI$^+$)=311.2 [M+H]$^+$ $^1$H NMR (500 MHz, Chloroform-d) δ 2.85 (dd, J=8.4, 13.8 Hz, 1H), 3.10 (td, J=4.7, 8.2 Hz, 1H), 3.22-3.28 (m, 2H), 3.34-3.40 (m, 1H), 3.55-3.67 (m, 2H), 4.08 (ddd, J=7.1, 8.1, 9.0 Hz, 1H), 5.62 (s, 1H), 5.81 (tt, J=3.9, 55.4 Hz, 1H), 6.82-6.95 (m, 1H), 7.16-7.22 (m, 3H), 7.23-7.28 (m, 2H)

Rac-2-[(3R,4R)-4-benzyl-5-oxopyrrolidin-3-yl]-2-oxo-N-(propan-2-yl)acetamide (FP-5)

The title compound was synthesized from rac-2-[(3R,4R)-4-benzyl-5-oxopyrrolidin-3-yl]-2-oxoacetic acid (I-75) in a similar manner to method A, general procedure 7a (general scheme 3) as an off-white solid (89 mg, 100% purity, 38%) after purification by FCC on normal phase silica (25 g SNAP Ultra cartridge, 0-100% EtOAc in heptane gradient).

LC-MS (MET-uHPLC-AB-102): 100% (UV), Rt=3.46 min, m/z (ESI$^+$)=289.2 [M+H]$^+$ $^1$H NMR (500 MHz, Chloroform-d) δ 1.16 (dd, J=0.9, 6.6 Hz, 6H), 2.88 (dd, J=8.1, 13.7 Hz, 1H), 3.08 (td, J=4.7, 8.0 Hz, 1H), 3.20-3.27 (m, 2H), 3.31-3.38 (m, 1H), 3.90-4.03 (m, 1H), 4.09 (ddd, J=6.9, 7.8, 9.0 Hz, 1H), 5.58 (s, 1H), 6.40-6.59 (m, 1H), 7.15-7.23 (m, 3H), 7.21-7.29 (m, 2H)

Rac-2-[(3R,4R)-4-benzyl-5-oxopyrrolidin-3-yl]-N-(2-cyanoethyl)-2-oxoacetamide (FP-6)

The title compound was synthesized from rac-2-[(3R,4R)-4-benzyl-5-oxopyrrolidin-3-yl]-2-oxoacetic acid (I-75) in a similar manner to method A, general procedure 7a (general scheme 3) as an off-white solid (82 mg, 100% purity, 34%) after purification by FCC on normal phase silica (25 g SNAP Ultra cartridge, 0-100% EtOAc in heptane gradient).

LC-MS (MET-uHPLC-AB-102): 100% (UV), Rt=1.83 min, m/z (ESI$^+$)=300.1 [M+H]$^+$ $^1$H NMR (500 MHz, Chloroform-d) δ 2.52-2.68 (m, 2H), 2.82-2.90 (m, 1H), 3.10 (td, J=4.7, 8.2 Hz, 1H), 3.21-3.29 (m, 2H), 3.33-3.39 (m, 1H), 3.45-3.58 (m, 2H), 4.07 (ddd, J=7.1, 8.0, 9.0 Hz, 1H), 5.66 (s, 1H), 7.04-7.12 (m, 1H), 7.17-7.23 (m, 3H), 7.23-7.30 (m, 2H).

Rac-2-[(3R,4R)-4-benzyl-5-oxopyrrolidin-3-yl]-N-(oxan-4-yl)-2-oxoacetamide (FP-7)

The title compound was synthesized from rac-2-[(3R,4R)-4-benzyl-5-oxopyrrolidin-3-yl]-2-oxoacetic acid (I-75) in a similar manner to method A, general procedure 7a (general scheme 3) as an off-white solid (76 mg, 100% purity, 28%) after purification by FCC on normal phase silica (25 g SNAP Ultra cartridge, 0-100% EtOAc in heptane gradient) followed by trituration in Et$_2$O.

LC-MS (MET-uHPLC-AB-102): 100% (UV), Rt=2.02 min, m/z (ESI$^+$)=331.2 [M+H]$^+$ $^1$H NMR (500 MHz, Chloroform-d) δ 1.50 (dddd, J=2.2, 4.5, 9.2, 17.3 Hz, 2H), 1.80-1.87 (m, 2H), 2.88 (dd, J=8.1, 13.7 Hz, 1H), 3.08 (td, J=4.7, 8.0 Hz, 1H), 3.20-3.28 (m, 2H), 3.31-3.37 (m, 1H), 3.47 (tdd, J=2.2, 7.5, 11.6 Hz, 2H), 3.82-3.92 (m, 1H), 3.93-4.01 (m, 2H), 4.09 (ddd, J=6.9, 7.8, 9.0 Hz, 1H), 5.61 (s, 1H), 6.59 (d, J=7.9 Hz, 1H), 7.17-7.22 (m, 3H), 7.23-7.27 (m, 2H)

Rac-2-[(3R,4R)-4-benzyl-5-oxopyrrolidin-3-yl]-2-oxo-N-(propan-2-yloxy)acetamide (FP-8)

The title compound was synthesized from rac-2-[(3R,4R)-4-benzyl-5-oxopyrrolidin-3-yl]-2-oxoacetic acid (I-75) in a similar manner to method A, general procedure 7a (general scheme 3) as a colourless glass (7 mg, 90% purity by $^1$H NMR, 4%) after purification by FCC on normal phase silica (25 g SNAP Ultra cartridge, 0-100% EtOAc in heptane gradient) followed by preparative LC (acidic pH, early elution method).

LC-MS (METCR1603): 97% (UV), Rt=2.28 min, m/z (ESI⁺)=305.2 [M+H]⁺

¹H NMR (500 MHz, Chloroform-d) δ 1.20-1.30 (m, 6H), 2.83-2.92 (m, 1H), 3.04-3.12 (m, 1H), 3.19-3.28 (m, 2H), 3.34 (t, J=9.4 Hz, 1H), 4.00-4.08 (m, 1H), 4.14 (hept, J=6.0 Hz, 1H), 5.96-6.13 (m, 1H), 7.16-7.23 (m, 3H), 7.23-7.30 (m, 2H), 9.02 (s, 1H)

Rac-2-[(3R,4R)-4-benzyl-5-oxopyrrolidin-3-yl]-N-(cyclohexyloxy)-2-oxoacetamide (FP-9)

The title compound was synthesized from rac-2-[(3R,4R)-4-benzyl-5-oxopyrrolidin-3-yl]-2-oxoacetic acid (I-75) in a similar manner to method A, general procedure 7a (general scheme 3) as a colourless glass (9 mg, 84% purity by ¹H NMR, 5%) after purification by FCC on normal phase silica (25 g SNAP Ultra cartridge, 0-100% EtOAc in heptane gradient) followed by FCC on reversel phase silica (12 g SNAP C18 Ultra cartridge, acidic pH, standard elution method).

LC-MS (METCR1603): 100% (UV), Rt=2.60 min, m/z (ESI⁺)=344.2 [M+H]⁺

¹H NMR (500 MHz, Chloroform-d) δ 1.22-1.40 (m, 3H), 1.41-1.51 (m, 2H), 1.52-1.59 (m, 1H), 1.67-1.81 (m, 2H), 1.87-1.96 (m, 2H), 2.70 (dd, J=13.8, 9.3 Hz, 1H), 3.19 (dd, J=13.8, 3.8 Hz, 1H), 3.25-3.32 (m, 1H), 3.40-3.53 (m, 2H), 3.87 (q, J=8.9 Hz, 1H), 4.10-4.19 (m, 1H), 6.74 (s, 1H), 7.14-7.25 (m, 5H), 9.03 (s, 1H)

Rac-N-(cyclopropylmethyl)-2-oxo-2-[(3R,4S)-5-oxo-4-phenylpyrrolidin-3-yl]acetamide (FP-10)

The title compound was synthesized from rac-2-oxo-2-[(3R,4S)-5-oxo-4-phenylpyrrolidin-3-yl]acetic acid (I-76) in a similar manner to method A, general procedure 7a (general scheme 3) as an off-white solid (17 mg, 98% purity, 4%) after purification by FCC on normal phase silica (25 g SNAP KP-SIL cartridge, 0-100% EtOAc in heptane gradient) followed by preparative LC (acidic pH, early elution method) and FCC on normal phase silica (10 g SNAP KP-SIL cartridge, 0-100% EtOAc in heptane gradient).

LC-MS (METCR1603): 98% (UV), Rt=3.3 min, m/z (ESI⁺)=287.1 [M+H]⁺

¹H NMR (500 MHz, Chloroform-d) δ 0.19-0.26 (m, 2H), 0.51-0.59 (m, 2H), 0.90-1.02 (m, 1H), 3.08-3.21 (m, 2H), 3.38-3.46 (m, 1H), 3.94-4.01 (m, 1H), 4.07 (d, J=8.0 Hz, 1H), 4.28-4.37 (m, 1H), 6.40 (s, 1H), 7.05 (s, 1H), 7.25-7.33 (m, 3H), 7.31-7.38 (m, 2H)

Rac-N-(2,2-difluoropropyl)-2-oxo-2-[(3R,4S)-5-oxo-4-phenylpyrrolidin-3-yl]acetamide (FP-11) and

Rac-2-[(3R,4R)-4-cyclohexyl-5-oxopyrrolidin-3-yl]-N-(2,2-difluoropropyl)-2-oxoacetamide (FP-12)

The title compounds were synthesized from crude rac-2-oxo-2-[(3R,4S)-5-oxo-4-phenylpyrrolidin-3-yl]acetic acid (I-76) containing rac-2-[(3R,4R)-4-cyclohexyl-5-oxopyrrolidin-3-yl]-2-oxoacetic acid as a minor by-product in a similar manner to method A, general procedure 7a (general scheme 3) as off-white solids to give 38 mg of rac-N-(2,2-difluoropropyl)-2-oxo-2-[(3R,4S)-5-oxo-4-phenylpyrrolidin-3-yl]acetamide (100% purity, 10%) and 16 mg of rac-2-[(3R,4R)-4-cyclohexyl-5-oxopyrrolidin-3-yl]-N-(2,2-difluoropropyl)-2-oxoacetamide (97% purity, 4%).

Rac-N-(2,2-difluoropropyl)-2-oxo-2-[(3R,4S)-5-oxo-4-phenylpyrrolidin-3-yl]acetamide (FP-11)

LC-MS (METCR1603): 100% (UV), Rt=3.14 min, m/z (ESI⁺)=311.2 [M+H]⁺

¹H NMR (500 MHz, Chloroform-d) δ 1.54-1.66 (m, 3H), 3.45 (dd, J=7.1, 9.9 Hz, 1H), 3.67 (td, J=6.7, 13.8 Hz, 2H), 3.93-3.98 (m, 1H), 4.02-4.07 (m, 1H), 4.28-4.35 (m, 1H), 6.44 (s, 1H), 7.18-7.40 (m, 6H)

Rac-2-[(3R,4R)-4-cyclohexyl-5-oxopyrrolidin-3-yl]-N-(2,2-difluoropropyl)-2-oxoacetamide (FP-12)

LC-MS (METCR1603): 97% (UV), Rt=3.70 min, m/z (ESI⁺)=317.3 [M+H]⁺

¹H NMR (500 MHz, Chloroform-d) δ 0.95-1.07 (m, 1H), 1.06-1.35 (m, 4H), 1.57-1.79 (m, 8H), 1.88-1.99 (m, 1H), 2.71 (dd, J=4.2, 6.2 Hz, 1H), 3.35 (ddd, J=0.9, 5.4, 9.9 Hz, 1H), 3.62-3.77 (m, 3H), 4.08-4.17 (m, 1H), 5.77 (s, 1H), 7.24-7.30 (m, 1H)

Rac-N-(2-methylpropyl)-2-oxo-2-[(3R,4S)-5-oxo-4-phenylpyrrolidin-3-yl]acetamide (FP-13)

The title compound was synthesized from rac-2-oxo-2-[(3R,4S)-5-oxo-4-phenylpyrrolidin-3-yl]acetic acid (I-76) in a similar manner to method A, general procedure 7a (general scheme 3) as a tan powder (36 mg, 100% purity, 11%) after purification by preparative LC (acidic pH, standard elution method).

LC-MS (METCR1603): 100% (UV), Rt=3.47 min, m/z (ESI⁺)=289.2 [M+H]⁺

¹H NMR (500 MHz, Chloroform-d) δ 0.91 (d, J=6.7 Hz, 6H), 1.74-1.85 (m, 1H), 3.07-3.17 (m, 2H), 3.41 (dd, J=7.1, 9.7 Hz, 1H), 3.96 (t, J=9.6 Hz, 1H), 4.05 (d, J=7.9 Hz, 1H), 4.28-4.35 (m, 1H), 6.74 (s, 1H), 6.94-7.07 (m, 1H), 7.24-7.32 (m, 3H), 7.32-7.37 (m, 2H)

Rac-N-cyclopropyl-2-oxo-2-[(3R,4S)-5-oxo-4-phenylpyrrolidin-3-yl]acetamide (FP-14)

The title compound was synthesized from rac-2-oxo-2-[(3R,4S)-5-oxo-4-phenylpyrrolidin-3-yl]acetic acid (I-76) in a similar manner to method A, general procedure 7a (general scheme 3) as an off-white powder (25 mg, 95% purity, 7%) after purification by preparative LC (acidic pH, early elution method).

LC-MS (MET-uPLC-AB-102): 95% (UV), Rt=1.70 min, m/z (ESI⁺)=273.1 [M+H]⁺

¹H NMR (500 MHz, Chloroform-d) δ 0.55-0.63 (m, 2H), 0.82-0.90 (m, 2H), 2.72-2.80 (m, 1H), 3.38-3.48 (m, 1H), 3.99 (t, J=9.5 Hz, 1H), 4.05 (d, J=8.0 Hz, 1H), 4.28-4.35 (m, 1H), 5.84 (s, 1H), 6.96 (s, 1H), 7.27-7.32 (m, 3H), 7.31-7.38 (m, 2H)

Rac-N-ethyl-2-oxo-2-[(3R,4S)-5-oxo-4-phenylpyrrolidin-3-yl]acetamide (FP-15)

The title compound was synthesized from rac-2-oxo-2-[(3R,4S)-5-oxo-4-phenylpyrrolidin-3-yl]acetic acid (I-76) in a similar manner to method A, general procedure 7a (general scheme 3) as an off-white solid (10 mg, 90% purity by ¹H NMR, 3%) after purification by preparative LC (acidic pH, early elution method).

LC-MS (MET-uPLC-AB-102): 99% (UV), Rt=1.67 min, m/z (ESI⁺)=261.0 [M+H]⁺

¹H NMR (500 MHz, Chloroform-d) δ 1.14 (t, J=7.3 Hz, 3H), 3.20-3.33 (m, 2H), 3.33-3.41 (m, 1H), 3.92 (t, J=9.7 Hz, 1H), 4.03 (d, J=8.0 Hz, 1H), 4.21-4.33 (m, 1H), 6.80-6.99 (m, 2H), 7.21-7.27 (m, 3H), 7.28-7.37 (m, 2H)

Rac-N-(3,3-difluorocyclobutyl)-2-oxo-2-[(3R,4S)-5-oxo-4-phenylpyrrolidin-3-yl]acetamide (FP-16)

The title compound was synthesized from rac-2-oxo-2-[(3R,4S)-5-oxo-4-phenylpyrrolidin-3-yl]acetic acid (I-76) in a similar manner to method A, general procedure 7a (general scheme 3) as an off-white solid (20 mg, 96% purity by ¹H NMR, 4%) after purification by preparative LC (acidic pH, early elution method).

LC-MS (METCR1603): 100% (UV), Rt=3.30 min, m/z (ESI⁺)=323.5 [M+H]⁺

¹H NMR (500 MHz, DMSO-d₆) δ 2.69-2.91 (m, 4H), 3.35-3.39 (m, 1H), 3.66-3.73 (m, 2H), 4.01-4.17 (m, 2H), 7.23-7.27 (m, 3H), 7.28-7.36 (m, 2H), 7.97 (s, 1H), 9.22 (d, J=7.2 Hz, 1H)

Rac-N-tert-butyl-2-oxo-2-[(3R,4S)-5-oxo-4-phenylpyrrolidin-3-yl]acetamide (FP-17)

The title compound was synthesized from rac-2-oxo-2-[(3R,4S)-5-oxo-4-phenylpyrrolidin-3-yl]acetic acid (I-76) in a similar manner to method A, general procedure 7a (general scheme 3) as an off-white solid (94 mg, 96% purity by ¹H NMR, 27%) after purification by FCC on normal phase silica (10 g SNAP Ultra cartridge, 0-100% EtOAc in heptane gradient).

LC-MS (METCR1603): 100% (UV), Rt=3.62 min, m/z (ESI⁺)=289.5 [M+H]⁺

¹H NMR (500 MHz, Chloroform-d) δ 1.37 (s, 9H), 3.38-3.46 (m, 1H), 3.97 (t, J=9.7 Hz, 1H), 4.05 (d, J=8.0 Hz, 1H), 4.26-4.35 (m, 1H), 6.40 (s, 1H), 6.79 (s, 1H), 7.26-7.31 (m, 3H), 7.32-7.39 (m, 2H)

Rac-2-oxo-2-[(3R,4S)-5-oxo-4-phenylpyrrolidin-3-yl]-N-propylacetamide (FP-18)

The title compound was synthesized from rac-2-oxo-2-[(3R,4S)-5-oxo-4-phenylpyrrolidin-3-yl]acetic acid (I-76) in a similar manner to method A, general procedure 7a (general scheme 3) as an off-white solid (35 mg, 98% purity by ¹H NMR, 14%) after purification by FCC on normal phase silica (10 g SNAP Ultra cartridge, 0-100% EtOAc in heptane gradient).

LC-MS (METCR1603): 100% (UV), Rt=3.23 min, m/z (ESI⁺)=275.3 [M+H]⁺

¹H NMR (500 MHz, Chloroform-d) δ 0.93 (t, J=7.4 Hz, 3H), 1.56 (q, J=7.3 Hz, 2H), 3.19-3.31 (m, 2H), 3.41 (dd, J=7.1, 9.6 Hz, 1H), 3.97 (t, J=9.7 Hz, 1H), 4.06 (d, J=8.0 Hz, 1H), 4.29-4.37 (m, 1H), 6.43 (s, 1H), 6.97 (s, 1H), 7.26-7.32 (m, 3H), 7.32-7.38 (m, 2H)

Rac-N-cyclobutyl-2-oxo-2-[(3R,4S)-5-oxo-4-phenylpyrrolidin-3-yl]acetamide (FP-19)

The title compound was synthesized from rac-2-oxo-2-[(3R,4S)-5-oxo-4-phenylpyrrolidin-3-yl]acetic acid (I-76) in a similar manner to method A, general procedure 7a (general scheme 3) as an off-white solid (8 mg, 100% purity, 3%) after purification by FCC on normal phase silica (10 g SNAP Ultra cartridge, 0-100% EtOAc in heptane gradient) followed by trituration in MeCN.

LC-MS (METCR1603): 100% (UV), Rt=3.40 min, m/z (ESI⁺)=287.2 [M+H]⁺

¹H NMR (500 MHz, Chloroform-d) δ 1.69-1.82 (m, 2H), 1.88-2.02 (m, 2H), 2.29-2.40 (m, 2H), 3.39 (dd, J=7.2, 9.9 Hz, 1H), 3.95 (t, J=9.6 Hz, 1H), 4.05 (d, J=8.1 Hz, 1H), 4.25-4.38 (m, 2H), 6.43 (s, 1H), 7.06 (d, J=8.2 Hz, 1H), 7.26-7.30 (m, 3H), 7.31-7.36 (m, 2H)

Rac-N-(1-methylcyclopropyl)-2-oxo-2-[(3R,4S)-5-oxo-4-phenylpyrrolidin-3-yl]acetamide (FP-20)

The title compound was synthesized from rac-2-oxo-2-[(3R,4S)-5-oxo-4-phenylpyrrolidin-3-yl]acetic acid (I-76) in a similar manner to method A, general procedure 7a (general scheme 3) as an off-white solid (21 mg, 100% purity, 10%) after purification by trituration in MeCN.

LC-MS (METCR1603): 100% (UV), Rt=3.35 min, m/z (ESI⁺)=287.2 [M+H]⁺

¹H NMR (500 MHz, Chloroform-d) δ 0.66-0.73 (m, 2H), 0.74-0.80 (m, 2H), 1.37 (s, 3H), 3.42 (dd, J=7.2, 9.9 Hz, 1H), 3.96 (t, J=9.6 Hz, 1H), 4.03 (d, J=8.0 Hz, 1H), 4.23-4.33 (m, 1H), 6.44 (s, 1H), 7.17 (s, 1H), 7.26-7.31 (m, 3H), 7.31-7.38 (m, 2H)

Rac-N-(cyclobutylmethyl)-2-oxo-2-[(3R,4S)-5-oxo-4-phenylpyrrolidin-3-yl]acetamide (FP-21)

The title compound was synthesized from rac-2-oxo-2-[(3R,4S)-5-oxo-4-phenylpyrrolidin-3-yl]acetic acid (I-76) in a similar manner to method A, general procedure 7a (general scheme 3) as an off-white solid (10 mg, 100% purity, 4%) after purification by FCC on normal phase silica (10 g SNAP Ultra cartridge, 0-100% EtOAc in heptane gradient).

LC-MS (METCR1603): 100% (UV), Rt=3.54 min, m/z (ESI⁺)=301.2 [M+H]⁺

¹H NMR (500 MHz, Chloroform-d) δ 1.63-1.74 (m, 2H), 1.84-1.97 (m, 2H), 2.02-2.11 (m, 2H), 2.43-2.56 (m, 1H), 3.26-3.36 (m, 2H), 3.42-3.47 (m, 1H), 3.98 (t, J=9.5 Hz, 1H), 4.05 (d, J=8.0 Hz, 1H), 4.29-4.40 (m, 1H), 5.70 (s, 1H), 6.89 (s, 1H), 7.27-7.31 (m, 3H), 7.31-7.39 (m, 2H)

Rac-2-oxo-2-[(3R,4S)-5-oxo-4-phenylpyrrolidin-3-yl]-N-(2,2,2-trifluoroethyl)acetamide (FP-22)

The title compound was synthesized from rac-2-oxo-2-[(3R,4S)-5-oxo-4-phenylpyrrolidin-3-yl]acetic acid (I-76) in a similar manner to method A, general procedure 7a (general scheme 3) as an off-white solid (9 mg, 95% purity, 4%) after purification by trituration in Et₂O.

LC-MS (METCR1603): 95% (UV), Rt=3.09 min, m/z (ESI⁺)=315.2 [M+H]⁺

¹H NMR (500 MHz, Chloroform-d) δ 3.44-3.49 (m, 1H), 3.86-4.00 (m, 3H), 4.04 (d, J=7.9 Hz, 1H), 4.27-4.36 (m, 1H), 6.18 (s, 1H), 7.20-7.26 (m, 1H), 7.27-7.32 (m, 3H), 7.32-7.40 (m, 2H)

Rac-N-[(3,3-difluorocyclobutyl)methyl]-2-oxo-2-[(3R,4S)-5-oxo-4-phenylpyrrolidin-3-yl]acetamide (FP-23)

The title compound was synthesized from rac-2-oxo-2-[(3R,4S)-5-oxo-4-phenylpyrrolidin-3-yl]acetic acid (I-76) in a similar manner to method A, general procedure 7a (general scheme 3) as an off-white solid (27 mg, 98% purity, 11%) after purification by FCC on normal phase silica (10 g SNAP Ultra cartridge, 0-100% EtOAc in heptane gradient).

LC-MS (METCR1603): 98% (UV), Rt=3.41 min, m/z (ESI$^+$)=337.1 [M+H]$^+$ $^1$H NMR (500 MHz, Chloroform-d) δ 2.19-2.31 (m, 2H), 2.32-2.41 (m, 1H), 2.62-2.74 (m, 2H), 3.36-3.49 (m, 3H), 3.96 (t, J=9.8 Hz, 1H), 4.03 (d, J=7.9 Hz, 1H), 4.29-4.36 (m, 1H), 6.05 (s, 1H), 6.97-7.12 (m, 1H), 7.26-7.32 (m, 3H), 7.33-7.39 (m, 2H)

Rac-N-(2-cyclopropylethyl)-2-oxo-2-[(3R,4S)-5-oxo-4-phenylpyrrolidin-3-yl]acetamide (FP-24)

The title compound was synthesized from rac-2-oxo-2-[(3R,4S)-5-oxo-4-phenylpyrrolidin-3-yl]acetic acid (I-76) in a similar manner to method A, general procedure 7a (general scheme 3) as an off-white solid (43 mg, 100% purity, 21%) after purification by FCC on normal phase silica (10 g SNAP Ultra cartridge, 0-100% EtOAc in heptane gradient).

LC-MS (METCR1603): 100% (UV), Rt=3.47 min, m/z (ESI$^+$)=301.2 [M+H]$^+$ $^1$H NMR (500 MHz, Chloroform-d) δ 0.02-0.12 (m, 2H), 0.41-0.52 (m, 2H), 0.61-0.72 (m, 1H), 1.40-1.48 (m, 2H), 3.34-3.43 (m, 3H), 3.95 (t, J=9.6 Hz, 1H), 4.06 (d, J=8.0 Hz, 1H), 4.28-4.37 (m, 1H), 6.57 (s, 1H), 7.00-7.13 (m, 1H), 7.26-7.31 (m, 3H), 7.32-7.39 (m, 2H)

Rac-2-oxo-2-[(3R,4S)-5-oxo-4-phenylpyrrolidin-3-yl]-N-(2,2,3,3,3-pentafluoro-propyl)acetamide (FP-25)

The title compound was synthesized from rac-2-oxo-2-[(3R,4S)-5-oxo-4-phenylpyrrolidin-3-yl]acetic acid (I-76) in a similar manner to method A, general procedure 7a (general scheme 3) as an off-white solid (13 mg, 95% purity, 6%) after purification by FCC on normal phase silica (10 g SNAP Ultra cartridge, 0-100% EtOAc in heptane gradient).

LC-MS (METCR1603): 95% (UV), Rt=3.57 min, m/z (ESI$^+$)=365.1 [M+H]$^+$ $^1$H NMR (500 MHz, Chloroform-d) δ 3.46 (dd, J=7.0, 10.0 Hz, 1H), 3.87-4.07 (m, 4H), 4.28-4.36 (m, 1H), 6.27 (s, 1H), 7.17-7.25 (m, 1H), 7.27-7.32 (m, 3H), 7.32-7.39 (m, 2H)

Rac-N-(2,2-difluoropropyl)-2-[(3R,4S)-4-(4-fluorophenyl)-5-oxopyrrolidin-3-yl]-2-oxoacetamide (FP-26)

The title compound was synthesized from rac-2-[(3R,4S)-4-(4-fluorophenyl)-5-oxopyrrolidin-3-yl]-2-oxoacetic acid (I-77) in a similar manner to method A, general procedure 7a (general scheme 3) as an off-white solid (37 mg, 100% purity, 15%) after purification by FCC on normal phase silica (10 g SNAP Ultra cartridge, 0-100% EtOAc in heptane gradient).

LC-MS (METCR1603): 100% (UV), Rt=3.20 min, m/z (ESI$^+$)=329.2 [M+H]$^+$ $^1$H NMR (500 MHz, Chloroform-d) δ 1.61 (t, J=18.4 Hz, 3H), 3.42-3.48 (m, 1H), 3.61-3.74 (m, 2H), 3.94 (t, J=9.6 Hz, 1H), 4.02 (d, J=8.3 Hz, 1H), 4.23-4.33 (m, 1H), 6.30 (s, 1H), 7.01-7.07 (m, 2H), 7.17-7.24 (m, 1H), 7.24-7.29 (m, 2H)

Rac-2-[(3R,4S)-4-(4-fluorophenyl)-5-oxopyrrolidin-3-yl]-2-oxo-N-(propan-2-yl)acetamide (FP-27)

The title compound was synthesized from rac-2-[(3R,4S)-4-(4-fluorophenyl)-5-oxopyrrolidin-3-yl]-2-oxoacetic acid (I-77) in a similar manner to method A, general procedure 7a (general scheme 3) as an off-white solid (61 mg, 100% purity, 30%) after purification by trituration in Et$_2$O.

LC-MS (METCR1603): 100% (UV), Rt=3.17 min, m/z (ESI$^+$)=293.2 [M+H]$^+$ $^1$H NMR (500 MHz, Chloroform-od) 1.12-1.26 (m, 6H), 3.41 (dd, J=7.4, 9.9 Hz, 1H), 3.94 (t, J=9.6 Hz, 1H), 3.97-4.08 (m, 2H), 4.21-4.32 (m, 1H), 6.61 (s, 1H), 6.76 (d, J=7.5 Hz, 1H), 6.99-7.08 (m, 2H), 7.23-7.33 (m, 2H)

Rac-N-(cyclopropylmethyl)-2-[(3R,4S)-4-(4-fluorophenyl)-5-oxopyrrolidin-3-yl]-2-oxoacetamide (FP-28)

The title compound was synthesized from rac-2-[(3R,4S)-4-(4-fluorophenyl)-5-oxopyrrolidin-3-yl]-2-oxoacetic acid (I-77) in a similar manner to method A, general procedure 7a (general scheme 3) as an off-white solid (10 mg, 100% purity, 4%) after purification by FCC on normal phase silica (10 g SNAP Ultra cartridge, 0-100% EtOAc in heptane gradient) followed by trituation in Et$_2$O.

LC-MS (METCR1603): 100% (UV), Rt=3.37 min, m/z (ESI$^+$)=305.2 [M+H]$^+$ $^1$H NMR (500 MHz, Chloroform-d) δ 0.21-0.31 (m, 2H), 0.52-0.61 (m, 2H), 0.94-1.03 (m, 1H), 3.12-3.22 (m, 2H), 3.46 (dd, J=7.4, 9.9 Hz, 1H), 3.99 (t, J=9.6 Hz, 1H), 4.07 (d, J=8.3 Hz, 1H), 4.27-4.35 (m, 1H), 6.13 (s, 1H), 6.98-7.13 (m, 3H), 7.28-7.32 (m, 2H)

Rac-N-cyclopropyl-2-[(3R,4R)-4-[(4-fluorophenyl)methyl]-5-oxopyrrolidin-3-yl]-2-oxoacetamide (FP-29)

The title compound was synthesized from rac-2-[(3R,4R)-4-[(4-fluorophenyl)-methyl]-5-oxopyrrolidin-3-yl]-2-oxoacetic acid (I-78) in a similar manner to method A, general procedure 7a (general scheme 3) as an off-white solid (66 mg, 100% purity, 32%) after purification by FCC on normal phase silica (10 g SNAP Ultra cartridge, 0-100% EtOAc in heptane gradient).

LC-MS (METCR1603): 100% (UV), Rt=3.25 min, m/z (ESI$^+$)=305.2 [M+H]$^+$ $^1$H NMR (500 MHz, Chloroform-d) δ 0.52-0.61 (m, 2H), 0.81-0.90 (m, 2H), 2.68-2.77 (m, 1H), 2.89 (dd, J=7.7, 13.8 Hz, 1H), 3.02 (td, J=4.8, 7.8 Hz, 1H), 3.19 (dd, J=4.7, 13.8 Hz, 1H), 3.27 (dd, J=7.0, 9.6 Hz, 1H), 3.35 (t, J=9.4 Hz, 1H), 4.02-4.09 (m, 1H), 5.65 (s, 1H), 6.75 (s, 1H), 6.90-6.98 (m, 2H), 7.15-7.22 (m, 2H)

Rac-N-ethyl-2-[(3R,4R)-4-[(4-fluorophenyl)methyl]-5-oxopyrrolidin-3-yl]-2-oxoacetamide (FP-30)

The title compound was synthesized from rac-2-[(3R,4R)-4-[(4-fluorophenyl)methyl]-5-oxopyrrolidin-3-yl]-2-oxoacetic acid (I-78) in a similar manner to method A, general procedure 7a (general scheme 3) as an off-white solid (98 mg, 100% purity, 49%) after purification by FCC on normal phase silica (10 g SNAP Ultra cartridge, 0-100% EtOAc in heptane gradient).

LC-MS (METCR1603): 100% (UV), Rt=3.19 min, m/z (ESI$^+$)=293.2 [M+H]$^+$ $^1$H NMR (500 MHz, Chloroform-d) δ 1.17 (t, J=7.3 Hz, 3H), 2.88 (dd, J=7.8, 13.8 Hz, 1H), 3.03 (td, J=4.8, 7.9 Hz, 1H), 3.19 (dd, J=4.7, 13.9 Hz, 1H), 3.25-3.33 (m, 3H), 3.34-3.39 (m, 1H), 4.03-4.10 (m, 1H), 5.61 (s, 1H), 6.70 (s, 1H), 6.90-6.98 (m, 2H), 7.14-7.22 (m, 2H)

Rac-N-(cyclopropylmethyl)-2-[(3R,4R)-4-[(4-fluorophenyl)methyl]-5-oxopyrrolidin-3-yl]-2-oxoacetamide (FP-31)

The title compound was synthesized from rac-2-[(3R,4R)-4-[(4-fluorophenyl)methyl]-5-oxopyrrolidin-3-yl]-2-oxoacetic acid (I-78) in a similar manner to method A, general procedure 7a (general scheme 3) as an off-white solid (107 mg, 100% purity, 50%) after purification by FCC on normal phase silica (10 g SNAP Ultra cartridge, 0-85% EtOAc in heptane gradient).

LC-MS (METCR1603): 100% (UV), Rt=3.58 min, m/z (ESI$^+$)=319.2 [M+H]$^+$ $^1$H NMR (500 MHz, Chloroform-d) δ 0.18-0.28 (m, 2H), 0.51-0.62 (m, 2H), 0.90-0.99 (m, 1H), 2.89 (dd, J=7.8, 13.8 Hz, 1H), 3.04 (td, J=4.8, 7.9 Hz, 1H), 3.10 (dd, J=6.0, 7.1 Hz, 2H), 3.19 (dd, J=4.8, 13.9 Hz, 1H), 3.28 (dd, J=7.0, 9.6 Hz, 1H), 3.34-3.40 (m, 1H), 4.07 (ddd, J=7.1, 7.9, 9.0 Hz, 1H), 5.60 (s, 1H), 6.76-6.87 (m, 1H), 6.91-6.99 (m, 2H), 7.14-7.22 (m, 2H)

Rac-2-[(3R,4R)-4-benzyl-1-[(oxan-4-yl)methyl]-5-oxopyrrolidin-3-yl]-N-cyclopropyl-2-oxoacetamide (FP-32)

The title compound was synthesized from rac-2-[(3R,4R)-4-benzyl-1-[(oxan-4-yl)methyl]-5-oxopyrrolidin-3-yl]-2-oxoacetic acid (I-79) in a similar manner to method A, general procedure 7a (general scheme 3) as a pale yellow gum (135 mg, 100% purity, 50%) after purification by FCC on normal phase silica (10 g SNAP Ultra cartridge, 0-100% EtOAc in heptane gradient).

LC-MS (METCR1603): 100% (UV), Rt=3.58 min, m/z (ESI$^+$)=385.2 [M+H]$^+$ $^1$H NMR (500 MHz, Chloroform-d) δ 0.51-0.60 (m, 2H), 0.81-0.89 (m, 2H), 1.21-1.32 (m, 2H), 1.37-1.46 (m, 2H), 1.72-1.84 (m, 1H), 2.69-2.75 (m, 1H), 2.98 (dd, J=7.1, 13.5 Hz, 1H), 3.04-3.12 (m, 3H), 3.15-3.22 (m, 2H), 3.26 (dd, J=6.2, 9.8 Hz, 1H), 3.31 (td, J=2.1, 11.7 Hz, 2H), 3.90-3.98 (m, 3H), 6.74 (s, 1H), 7.16-7.26 (m, 5H)

Rac-2-[(3R,4R)-4-benzyl-1-[(oxan-4-yl)methyl]-5-oxopyrrolidin-3-yl]-N-ethyl-2-oxoacetamide (FP-33)

The title compound was synthesized from rac-2-[(3R,4R)-4-benzyl-1-[(oxan-4-yl)methyl]-5-oxopyrrolidin-3-yl]-2-oxoacetic acid (I-79) in a similar manner to method A, general procedure 7a (general scheme 3) as an off-white solid (137 mg, 100% purity, 56%) after purification by FCC on normal phase silica (25 g SNAP Ultra cartridge, 0-100% EtOAc in heptane gradient).

LC-MS (METCR1603): 100% (UV), Rt=3.55 min, m/z (ESI$^+$)=373.2 [M+H]$^+$ $^1$H NMR (500 MHz, Chloroform-d) δ 1.17 (t, J=7.3 Hz, 3H), 1.21-1.33 (m, 2H), 1.37-1.47 (m, 2H), 1.72-1.84 (m, 1H), 2.99 (dd, J=7.1, 13.5 Hz, 1H), 3.04-3.14 (m, 3H), 3.16-3.22 (m, 2H), 3.23-3.36 (m, 5H), 3.89-3.99 (m, 3H), 6.64-6.76 (m, 1H), 7.16-7.26 (m, 5H)

Rac-2-[(3R,4R)-4-benzyl-1-[(3-methyl-1,2,4-oxadiazol-5-yl)methyl]-5-oxopyrrolidin-3-yl]-N-cyclopropyl-2-oxoacetamide (FP-34)

The title compound was synthesized from rac-2-[(3R,4R)-4-benzyl-1-[(3-methyl-1,2,4-oxadiazol-5-yl)methyl]-5-oxopyrrolidin-3-yl]-2-oxoacetic acid (I-80) in a similar manner to method A, general procedure 7a (general scheme 3) as an orange solid (74 mg, 99% purity, 64%) after purification by FCC on normal phase silica (25 g SNAP Ultra cartridge, 0-100% EtOAc in heptane gradient).

LC-MS (METCR1603): 99% (UV), Rt=2.57 min, m/z (ESI$^+$)=383.2 [M+H]$^+$ $^1$H NMR (500 MHz, Chloroform-d) δ 0.51-0.58 (m, 2H), 0.80-0.88 (m, 2H), 2.38 (s, 3H), 2.67-2.73 (m, 1H), 2.94 (dd, J=7.7, 13.7 Hz, 1H), 3.15-3.21 (m, 1H), 3.26 (dd, J=4.9, 13.7 Hz, 1H), 3.37 (dd, J=6.7, 9.5 Hz, 1H), 3.43 (t, J=9.3 Hz, 1H), 4.00 (dt, J=7.0, 9.0 Hz, 1H), 4.60-4.71 (m, 2H), 6.70 (s, 1H), 7.15-7.26 (m, 5H)

Rac-2-[(3R,4R)-4-benzyl-5-oxo-1-[(pyrimidin-2-yl)methyl]pyrrolidin-3-yl]-N-cyclopropyl-2-oxoacetamide (FP-35)

The title compound was synthesized from rac-2-[(3R,4R)-4-benzyl-5-oxo-1-[(pyrimidin-2-yl)methyl]pyrrolidin-3-yl]-2-oxoacetic acid (I-81) in a similar manner to method A, general procedure 7a (general scheme 3) as a pale orange gum (63 mg, 99% purity, 28%) after purification by FCC on normal phase silica (25 g SNAP Ultra cartridge, 0-100% EtOAc in heptane gradient followed by 0-5% MeOH in EtOAc gradient).

LC-MS (METCR1603): 99% (UV), Rt=3.28 min, m/z (ESI$^+$)=373.2 [M+H]$^+$ $^1$H NMR (500 MHz, Chloroform-d) δ 0.47-0.57 (m, 2H), 0.77-0.86 (m, 2H), 2.64-2.71 (m, 1H), 2.85-2.92 (m, 1H), 3.24-3.35 (m, 2H), 3.38 (dd, J=7.2, 9.5 Hz, 1H), 3.59 (t, J=9.4 Hz, 1H), 3.99-4.08 (m, 1H), 4.72 (s, 2H), 6.64 (s, 1H), 7.14-7.26 (m, 6H), 8.67 (d, J=4.9 Hz, 2H)

Rac-2-[(3R,4R)-4-benzyl-5-oxo-1-[(pyrimidin-2-yl)methyl]pyrrolidin-3-yl]-N-ethyl-2-oxoacetamide (FP-36)

The title compound was synthesized from rac-2-[(3R,4R)-4-benzyl-5-oxo-1-[(pyrimidin-2-yl)methyl]pyrrolidin-3-yl]-2-oxoacetic acid (I-81) in a similar manner to method A, general procedure 7a (general scheme 3) as a pale orange gum (78 mg, 100% purity, 45%) after purification by FCC on normal phase silica (25 g SNAP Ultra cartridge, 0-100% EtOAc in heptane gradient followed by 0-10% MeOH in EtOAc gradient).

LC-MS (METCR1603): 100% (UV), Rt=3.25 min, m/z (ESI$^+$)=367.2 [M+H]$^+$ $^1$H NMR (500 MHz, Chloroform-d) δ 1.14 (t, J=7.3 Hz, 3H), 2.85-2.94 (m, 1H), 3.22-3.34 (m, 4H), 3.39 (dd, J=7.2, 9.5 Hz, 1H), 3.61 (t, J=9.4 Hz, 1H), 4.00-4.08 (m, 1H), 4.72 (s, 2H), 6.55-6.68 (m, 1H), 7.15-7.25 (m, 6H), 8.67 (d, J=4.9 Hz, 2H)

Rac-2-[(3R,4R)-4-benzyl-5-oxo-1-[(pyrimidin-4-yl)methyl]pyrrolidin-3-yl]-N-cyclopropyl-2-oxoacetamide (I-37)

The title compound was synthesized from rac-2-[(3R,4R)-4-benzyl-5-oxo-1-[(pyrimidin-4-yl)methyl]pyrrolidin-3-yl]-2-oxoacetic acid (I-82) in a similar manner to method A, general procedure 7a (general scheme 3) as an orange gum (38 mg, 100% purity, 34%) after purification by FCC on normal phase silica (25 g SNAP Ultra cartridge, 0-100% EtOAc in heptane gradient followed by 0-20% MeOH in EtOAc gradient).

LC-MS (METCR1603): 100% (UV), Rt=2.24 min, m/z (ESI$^+$)=379.1 [M+H]$^+$

¹H NMR (500 MHz, Chloroform-d) δ 0.52-0.60 (m, 2H), 0.81-0.90 (m, 2H), 2.68-2.75 (m, 1H), 3.05 (dd, J=6.9, 13.5 Hz, 1H), 3.14-3.19 (m, 1H), 3.21-3.27 (m, 2H), 3.33 (dd, J=6.2, 9.9 Hz, 1H), 4.03 (dt, J=6.4, 9.1 Hz, 1H), 4.45-4.55 (m, 2H), 6.76 (s, 1H), 7.01-7.05 (m, 1H), 7.20-7.28 (m, 5H), 8.64 (d, J=5.2 Hz, 1H), 9.11 (d, J=1.1 Hz, 1H)

Rac-2-[(3R,4R)-4-cyclohexyl-1-methyl-5-oxopyrrolidin-3-yl]-N-cyclopropyl-2-oxoacetamide (FP-38)

The title compound was synthesized from rac-2-[(3R,4R)-4-cyclohexyl-1-methyl-5-oxopyrrolidin-3-yl]-2-oxoacetic acid (I-83) in a similar manner to method A, general procedure 7a (general scheme 3) as a pale yellow glass (181 mg, 99% purity, 36%) after purification by FCC on normal phase silica (25 g SNAP KP-SIL cartridge, 50-100% EtOAc in heptane gradient).

LC-MS (MET-uPLC-AB-102): 99% (UV), Rt=2.52 min, m/z (ESI$^+$)=293.1 [M+H]$^+$

¹H NMR (500 MHz, Chloroform-d) δ 0.57-0.64 (m, 2H), 0.85-0.90 (m, 2H), 0.94-1.04 (m, 1H), 1.08-1.32 (m, 4H), 1.48-1.55 (m, 1H), 1.62-1.68 (m, 2H), 1.68-1.76 (m, 2H), 1.90-2.00 (m, 1H), 2.71-2.75 (m, 1H), 2.76-2.82 (m, 1H), 2.83 (s, 3H), 3.28 (dd, J=5.2, 10.2 Hz, 1H), 3.64 (t, J=9.8 Hz, 1H), 3.98 (dt, J=5.5, 9.5 Hz, 1H), 7.00 (s, 1H).

Rac-2-[(3R,4R)-4-benzyl-1-(2-methoxyethyl)-5-oxopyrrolidin-3-yl]-N-cyclopropyl-2-oxoacetamide (FP-39)

The title compound was synthesized from rac-2-[(3R,4R)-4-benzyl-1-(2-methoxyethyl)-5-oxopyrrolidin-3-yl]-2-oxoacetic acid (I-84) in a similar manner to method A, general procedure 7a (general scheme 3) as an orange gum (84 mg, 100% purity, 54%) after purification by FCC on normal phase silica (25 g SNAP Ultra cartridge, 0-100% EtOAc in heptane gradient) followed by preparative LC (acidic pH, standard elution method).

LC-MS (METCR1603): 100% (UV), Rt=3.57 min, m/z (ESI$^+$)=345.3 [M+H]$^+$

¹H NMR (500 MHz, Chloroform-d) δ 0.50-0.58 (m, 2H), 0.79-0.88 (m, 2H), 2.66-2.74 (m, 1H), 2.89 (dd, J=7.9, 13.7 Hz, 1H), 3.06-3.12 (m, 1H), 3.24 (dd, J=4.7, 13.7 Hz, 1H), 3.28 (s, 3H), 3.29-3.34 (m, 1H), 3.34-3.49 (m, 5H), 3.92-3.99 (m, 1H), 6.69 (s, 1H), 7.16-7.21 (m, 3H), 7.22-7.26 (m, 2H)

Rac-2-[(3R,4R)-4-benzyl-1-(carbamoylmethyl)-5-oxopyrrolidin-3-yl]-N-(2-methylpropyl)-2-oxoacetamide (FP-40)

The title compound was synthesized from rac-2-[(3R,4R)-4-benzyl-1-(carbamoylmethyl)-5-oxopyrrolidin-3-yl]-2-oxoacetic acid (I-85) in a similar manner to method A, general procedure 7a (general scheme 3) as a pale orange solid (5 mg, 95% purity, 4%) after purification by FCC on normal phase silica (25 g SNAP Ultra cartridge, 0-100% EtOAc in heptane gradient followed by 0-10% MeOH in EtOAc gradient) then by two FCC on reverse phase silica (12 g SNAP C18 Ultra cartridge, basic pH, standard elution method).

LC-MS (METCR1603): 95% (UV), Rt=2.39 min, m/z (ESI$^+$)=360.3 [M+H]$^+$

¹H NMR (500 MHz, Chloroform-d) δ 0.93 (d, J=6.7 Hz, 6H), 1.76-1.86 (m, 1H), 3.02-3.13 (m, 5H), 3.16-3.22 (m, 1H), 3.39 (dd, J=4.7, 9.9 Hz, 1H), 3.66 (d, J=16.5 Hz, 1H), 3.96-4.02 (m, 1H), 4.06 (d, J=16.5 Hz, 1H), 5.36 (s, 1H), 6.10 (s, 1H), 6.82-6.95 (m, 1H), 7.21-7.30 (m, 5H)

Rac-2-[(3R,4R)-4-benzyl-1-[(5-methyl-1,2-oxazol-3-yl)methyl]-5-oxopyrrolidin-3-yl]-N-cyclopropyl-2-oxoacetamide (FP-41)

The title compound was synthesized from rac-2-[(3R,4R)-4-benzyl-1-[(5-methyl-1,2-oxazol-3-yl)methyl]-5-oxopyrrolidin-3-yl]-2-oxoacetic acid (I-86) in a similar manner to method A, general procedure 7a (general scheme 3) as an off-white solid (82 mg, 100% purity, 28%) after purification by FCC on normal phase silica (10 g SNAP Ultra cartridge, 0-70% EtOAc in heptane gradient) followed by preparative LC (acidic pH, standard elution method).

LC-MS (METCR1603): 100% (UV), Rt=3.78 min, m/z (ESI$^+$)=382.2 [M+H]$^+$

¹H NMR (500 MHz, Chloroform-d) δ 0.48-0.58 (m, 2H), 0.77-0.89 (m, 2H), 2.36-2.41 (m, 3H), 2.65-2.75 (m, 1H), 2.95 (dd, J=7.5, 13.6 Hz, 1H), 3.11 (td, J=4.7, 7.4 Hz, 1H), 3.17-3.27 (m, 3H), 3.97 (q, J=7.7 Hz, 1H), 4.38-4.48 (m, 2H), 5.78-5.82 (m, 1H), 6.69 (s, 1H), 7.17-7.21 (m, 3H), 7.21-7.25 (m, 2H)

Rac-2-[(3R,4R)-4-benzyl-1-[(1-methyl-1H-1,2,4-triazol-5-yl)methyl]-5-oxopyrrolidin-3-yl]-N-cyclopropyl-2-oxoacetamide (FP-42)

The title compound was synthesized from rac-2-[(3R,4R)-4-benzyl-1-[(1-methyl-1H-1,2,4-triazol-5-yl)methyl]-5-oxopyrrolidin-3-yl]-2-oxoacetic acid (I-87) in a similar manner to method A, general procedure 7a (general scheme 3) as a yellow gum (49 mg, 100% purity, 30%) after purification by FCC on normal phase silica (10 g SNAP KP-SIL cartridge, 0-100% EtOAc in heptane gradient followed by 0-5% MeOH in EtOAc gradient).

LC-MS (METCR1603): 100% (UV), Rt=3.14 min, m/z (ESI$^+$)=382.2 [M+H]$^+$

¹H NMR (500 MHz, Chloroform-d) δ 0.51-0.57 (m, 2H), 0.79-0.88 (m, 2H), 2.66-2.75 (m, 1H), 2.94-3.00 (m, 1H), 3.06-3.12 (m, 1H), 3.17-3.26 (m, 3H), 3.88 (s, 3H), 3.92-4.02 (m, 1H), 4.50-4.64 (m, 2H), 6.71 (s, 1H), 7.13-7.17 (m, 2H), 7.17-7.24 (m, 3H), 7.77 (s, 1H)

Rac-2-[(3R,4R)-4-benzyl-1-[(methylcarbamoyl)methyl]-5-oxopyrrolidin-3-yl]-N-(2-methylpropyl)-2-oxoacetamide (FP-43)

The title compound was synthesized from rac-2-[(3R,4R)-4-benzyl-1-[(methylcarbamoyl)methyl]-5-oxopyrrolidin-3-yl]-2-oxoacetic acid (I-88) in a similar manner to method A, general procedure 7a (general scheme 3) as an off-white gum (69 mg, 100% purity, 65%) after purification by FCC on normal phase silica (10 g SNAP Ultra cartridge, 0-100% EtOAc in heptane gradient).

LC-MS (METCR1603): 100% (UV), Rt=3.55 min, m/z (ESI$^+$)=374.6 [M+H]$^+$

¹H NMR (500 MHz, Chloroform-d) δ 0.93 (d, J=6.7 Hz, 6H), 1.77-1.87 (m, 1H), 2.76 (d, J=4.8 Hz, 3H), 2.98-3.07 (m, 2H), 3.09-3.15 (m, 3H), 3.18 (dd, J=5.0, 13.6 Hz, 1H), 3.35 (dd, J=4.8, 10.0 Hz, 1H), 3.69 (d, J=16.3 Hz, 1H), 3.95-4.03 (m, 2H), 6.01-6.13 (m, 1H), 6.83-6.95 (m, 1H), 7.22-7.31 (m, 5H)

Rac-2-[(3R,4R)-3-benzyl-4-{[(2-methylpropyl)carbamoyl]carbonyl}-2-oxopyrrolidin-1-yl]-N,N-dimethylacetamide (FP-44)

The title compound was synthesized from rac-2-[(3R,4R)-4-benzyl-1-[(dimethylcarbamoyl)methyl]-5-oxopyrrolidin- 3-yl]-2-oxoacetic acid (I-89) in a similar manner to method A, general procedure 7a (general scheme 3) as a yellow gum (69 mg, 97% purity, 72%) after purification by FCC on normal phase silica (25 g SNAP Ultra cartridge, 0-100% EtOAc in heptane gradient followed by 0-5% MeOH in EtOAc gradient).

LC-MS (METCR1603): 97% (UV), Rt=3.69 min, m/z (ESI$^+$)=388.6 [M+H]$^+$ $^1$H NMR (500 MHz, Chloroform-d) δ 0.89 (dd, J=1.3, 6.7 Hz, 6H), 1.71-1.81 (m, 1H), 2.82-2.90 (m, 1H), 2.93 (s, 3H), 2.99 (s, 3H), 3.04 (t, J=6.6 Hz, 2H), 3.20-3.29 (m, 2H), 3.43 (dd, J=6.8, 9.6 Hz, 1H), 3.55 (t, J=9.5 Hz, 1H), 3.92 (d, J=16.1 Hz, 1H), 3.94-4.01 (m, 1H), 4.21 (d, J=16.1 Hz, 1H), 6.70-6.77 (m, 1H), 7.14-7.20 (m, 3H), 7.21-7.26 (m, 2H)

Rac-2-[(3R,4R)-4-benzyl-5-oxo-1-(pyrimidin-5-yl)pyrrolidin-3-yl]-N-ethyl-2-oxoacetamide (FP-45)

The title compound was synthesized from rac-2-[(3R,4R)-4-benzyl-1-[(4-carbamoylphenyl)methyl]-5-oxopyrrolidin-3-yl]-2-oxoacetic acid (I-90) in a similar manner to method A, general procedure 7a (general scheme 3) as an off-white solid (61 mg, 93% purity by $^1$H NMR, 42%) after purification by FCC on normal phase silica (25 g SNAP Ultra cartridge, 0-100% EtOAc in heptane gradient).

LC-MS (METCR1603): 100% (UV), Rt=3.29 min, m/z (ESI$^+$)=420.2 [M+H]$^+$ $^1$H NMR (500 MHz, Chloroform-d) δ 0.47-0.60 (m, 2H), 0.78-0.89 (m, 2H), 2.66-2.73 (m, 1H), 3.02 (dd, J=7.1, 13.5 Hz, 1H), 3.06-3.17 (m, 3H), 3.24 (dd, J=4.7, 13.5 Hz, 1H), 3.89-3.98 (m, 1H), 4.39-4.52 (m, 2H), 5.57 (s, 1H), 6.03 (s, 1H), 6.68-6.78 (m, 1H), 7.16-7.20 (m, 2H), 7.20-7.27 (m, 5H), 7.69-7.77 (m, 2H)

Rac-2-[(3R,4R)-4-benzyl-1-[(3-methyl-1,2-oxazol-5-yl)methyl]-5-oxopyrrolidin-3-yl]-N-cyclopropyl-2-oxoacetamide (FP-46)

The title compound was synthesized from rac-2-[(3R,4R)-4-benzyl-1-[(3-methyl-1,2-oxazol-5-yl)methyl]-5-oxopyrrolidin-3-yl]-2-oxoacetic acid (I-91) in a similar manner to method A, general procedure 7a (general scheme 3) as a yellow gum (162 mg, 100% purity, 62%) after purification by FCC on normal phase silica (10 g SNAP Ultra cartridge, 0-70% EtOAc in heptane gradient).

LC-MS (METCR1603): 100% (UV), Rt=3.69 min, m/z (ESI$^+$)=388.6 [M+H]$^+$ $^1$H NMR (500 MHz, Chloroform-d) δ 0.50-0.60 (m, 2H), 0.78-0.89 (m, 2H), 2.27 (s, 3H), 2.68-2.74 (m, 1H), 2.97 (dd, J=7.2, 13.6 Hz, 1H), 3.10 (td, J=4.8, 7.2 Hz, 1H), 3.22 (dd, J=4.0, 9.6 Hz, 1H), 3.23-3.27 (m, 1H), 3.29 (dd, J=6.3, 9.8 Hz, 1H), 3.93-4.00 (m, 1H), 4.44-4.52 (m, 2H), 5.89 (s, 1H), 6.73 (s, 1H), 7.16-7.25 (m, 5H)

Rac-2-[(3R,4R)-4-benzyl-5-oxo-1-[2-(2-oxopyrrolidin-1-yl)ethyl]pyrrolidin-3-yl]-N-(2-methylpropyl)-2-oxoacetamide (FP-47)

The title compound was synthesized from rac-2-[(3R,4R)-4-benzyl-5-oxo-1-[2-(2-oxopyrrolidin-1-yl)ethyl]pyrrolidin-3-yl]-2-oxoacetic acid (I-92) in a similar manner to method A, general procedure 7a (general scheme 3) as a yellow gum (115 mg, 100% purity, 75%) after purification by FCC on normal phase silica (25 g SNAP Ultra cartridge, 0-100% EtOAc in heptane gradient followed by 0-10% MeOH in EtOAc gradient).

LC-MS (METCR1603): 100% (UV), Rt=3.72 min, m/z (ESI$^+$)=414.2 [M+H]$^+$ $^1$H NMR (500 MHz, Chloroform-d) δ 0.91 (d, J=6.7 Hz, 6H), 1.74-1.84 (m, 1H), 1.93-2.05 (m, 2H), 2.23-2.36 (m, 2H), 2.84-2.91 (m, 1H), 3.08 (t, J=6.6 Hz, 2H), 3.09-3.20 (m, 4H), 3.29-3.36 (m, 2H), 3.38 (dd, J=5.7, 9.8 Hz, 1H), 3.49-3.55 (m, 1H), 3.55-3.62 (m, 1H), 3.62-3.70 (m, 1H), 3.84-3.91 (m, 1H), 6.90-6.97 (m, 1H), 7.15-7.20 (m, 3H), 7.21-7.26 (m, 2H)

Rac-2-[(3R,4R)-4-benzyl-5-oxo-1-[2-(2-oxopyrrolidin-1-yl)ethyl]pyrrolidin-3-yl]-N-cyclopropyl-2-oxoacetamide (FP-48)

The title compound was synthesized from rac-2-[(3R,4R)-4-benzyl-5-oxo-1-[2-(2-oxopyrrolidin-1-yl)ethyl]pyrrolidin-3-yl]-2-oxoacetic acid (I-92) in a similar manner to method A, general procedure 7a (general scheme 3) as a yellow gum (54 mg, 100% purity, 37%) after purification by FCC on normal phase silica (10 g SNAP Ultra cartridge, 0-100% EtOAc in heptane gradient followed by 0-10% MeOH in EtOAc gradient).

LC-MS (METCR1603): 100% (UV), Rt=3.23 min, m/z (ESI$^+$)=398.2 [M+H]$^+$ $^1$H NMR (500 MHz, Chloroform-d) δ 0.51-0.62 (m, 2H), 0.76-0.87 (m, 2H), 1.90-2.06 (m, 2H), 2.23-2.35 (m, 2H), 2.68-2.75 (m, 1H), 2.82-2.91 (m, 1H), 3.06-3.19 (m, 4H), 3.28-3.35 (m, 2H), 3.38 (dd, J=5.7, 9.9 Hz, 1H), 3.49-3.55 (m, 1H), 3.56-3.63 (m, 1H), 3.64-3.71 (m, 1H), 3.83-3.89 (m, 1H), 6.90 (b.s, 1H), 7.15-7.21 (m, 3H), 7.22-7.26 (m, 2H)

Rac-2-[(3R,4R)-4-benzyl-1-(2,2-difluoroethyl)-5-oxopyrrolidin-3-yl]-N-cyclopropyl-2-oxoacetamide (FP-49)

The title compound was synthesized from rac-2-[(3R,4R)-4-benzyl-1-(2,2-difluoroethyl)-5-oxopyrrolidin-3-yl]-2-oxoacetic acid (I-93) in a similar manner to method A, general procedure 7a (general scheme 3) as an off-white solid (39 mg, 100% purity, 18%) after purification by FCC on normal phase silica (10 g SNAP Ultra cartridge, 0-100% EtOAc in heptane gradient followed by 0-20% MeOH in EtOAc gradient).

LC-MS (METCR1603): 100% (UV), Rt=3.60 min, m/z (ESI$^+$)=351.2 [M+H]$^+$ $^1$H NMR (500 MHz, Chloroform-d) δ 0.48-0.61 (m, 2H), 0.82-0.89 (m, 2H), 2.67-2.75 (m, 1H), 2.95 (dd, J=7.4, 13.6 Hz, 1H), 3.07-3.15 (m, 1H), 3.23 (dd, J=4.8, 13.6 Hz, 1H), 3.28-3.37 (m, 2H), 3.51-3.67 (m, 2H), 3.96-4.03 (m, 1H), 5.78 (tt, J=4.2, 55.6 Hz, 1H), 6.72 (s, 1H), 7.16-7.23 (m, 3H), 7.24-7.28 (m, 2H)

Rac-2-[(3R,4R)-4-benzyl-1-(2,2-difluoroethyl)-5-oxopyrrolidin-3-yl]-N-ethyl-2-oxoacetamide (FP-50)

The title compound was synthesized from rac-2-[(3R,4R)-4-benzyl-1-(2,2-difluoroethyl)-5-oxopyrrolidin-3-yl]-2-oxoacetic acid (I-93) in a similar manner to method A, general procedure 7a (general scheme 3) as an off-white solid (21 mg, 100% purity, 22%) after purification by FCC on normal phase silica (10 g SNAP Ultra cartridge, 0-100% EtOAc in heptane gradient followed by 0-20% MeOH in EtOAc gradient).

LC-MS (METCR1603): 100% (UV), Rt=3.55 min, m/z (ESI$^+$)=339.2 [M+H]$^+$

¹H NMR (500 MHz, Chloroform-d) δ 1.19 (t, J=7.3 Hz, 3H), 2.97 (dd, J=7.4, 13.6 Hz, 1H), 3.11-3.17 (m, 1H), 3.24 (dd, J=4.8, 13.6 Hz, 1H), 3.29-3.40 (m, 4H), 3.53-3.68 (m, 2H), 3.97-4.06 (m, 1H), 5.80 (tt, J=4.2, 55.6 Hz, 1H), 6.74 (s, 1H), 7.18-7.25 (m, 3H), 7.25-7.30 (m, 2H)

Rac-N-cyclopropyl-2-[(3R,4R)-4-[(4-fluorophenyl)methyl]-1-[(1-methyl-1H-1,2,4-triazol-3-yl)methyl]-5-oxopyrrolidin-3-yl]-2-oxoacetamide (FP-51)

The title compound was synthesized from rac-2-[(3R,4R)-4-[(4-fluorophenyl)methyl]-1-[(1-methyl-1H-1,2,4-triazol-3-yl)methyl]-5-oxopyrrolidin-3-yl]-2-oxoacetic acid (I-94) in a similar manner to method A, general procedure 7a (general scheme 3) as a yellow viscous oil (12 mg, 100% purity, 13%) after purification by FCC on normal phase silica (10 g SNAP Ultra cartridge, 0-100% EtOAc in heptane gradient followed by 0-15% MeOH in EtOAc gradient).
LC-MS (METCR1603): 100% (UV), Rt=3.19 min, m/z (ESI⁺)=400.1 [M+H]⁺
¹H NMR (500 MHz, Chloroform-d) δ 0.50-0.57 (m, 2H), 0.78-0.89 (m, 2H), 2.66-2.73 (m, 1H), 2.88 (dd, J=8.0, 13.9 Hz, 1H), 3.12 (td, J=4.8, 7.9 Hz, 1H), 3.23 (dd, J=4.8, 13.9 Hz, 1H), 3.30 (dd, J=7.0, 9.8 Hz, 1H), 3.43 (t, J=9.5 Hz, 1H), 3.87 (s, 3H), 3.91-3.99 (m, 1H), 4.46 (d, J=15.4 Hz, 1H), 4.61 (d, J=15.4 Hz, 1H), 6.67-6.75 (m, 1H), 6.85-6.92 (m, 2H), 7.11-7.17 (m, 2H), 7.93 (s, 1H)

Rac-N-cyclopropyl-2-[(3R,4R)-4-[(4-fluorophenyl)methyl]-1-[(1-methyl-1H-1,2,4-triazol-5-yl)methyl]-5-oxopyrrolidin-3-yl]-2-oxoacetamide (FP-52)

The title compound was synthesized from rac-2-[(3R,4R)-4-[(4-fluorophenyl)methyl]-1-[(1-methyl-1H-1,2,4-triazol-5-yl)methyl]-5-oxopyrrolidin-3-yl]-2-oxoacetic acid (I-95) in a similar manner to method A, general procedure 7a (general scheme 3) as a pale yellow viscous oil (17 mg, 100% purity, 10%) after purification by FCC on normal phase silica (10 g SNAP Ultra cartridge, 0-100% EtOAc in heptane gradient followed by 0-20% MeOH in EtOAc gradient).
LC-MS (METCR1603): 100% (UV), Rt=3.26 min, m/z (ESI⁺)=400.2 [M+H]⁺
¹H NMR (500 MHz, Chloroform-d) δ 0.52-0.58 (m, 2H), 0.82-0.86 (m, 2H), 2.67-2.75 (m, 1H), 2.93 (dd, J=7.1, 13.7 Hz, 1H), 3.02-3.06 (m, 1H), 3.16 (dd, J=4.7, 13.7 Hz, 1H), 3.28 (d, J=7.7 Hz, 2H), 3.89 (s, 3H), 3.95 (q, J=7.6 Hz, 1H), 4.55 (d, J=15.3 Hz, 1H), 4.60 (d, J=15.3 Hz, 1H), 6.78 (s, 1H), 6.86-6.92 (m, 2H), 7.09-7.14 (m, 2H), 7.78 (s, 1H)

Rac-N-(2,2-difluoropropyl)-2-[(3R,4R)-4-[(4-fluorophenyl)methyl]-1-[(1-methyl-1H-1,2,4-triazol-5-yl)methyl]-5-oxopyrrolidin-3-yl]-2-oxoacetamide (FP-53)

The title compound was synthesized from rac-2-[(3R,4R)-4-[(4-fluorophenyl)methyl]-1-[(1-methyl-1H-1,2,4-triazol-5-yl)methyl]-5-oxopyrrolidin-3-yl]-2-oxoacetic acid (I-95) in a similar manner to method A, general procedure 7a (general scheme 3) as a pale yellow solid (29 mg, 100% purity, 20%) after purification by FCC on normal phase silica (10 g SNAP Ultra cartridge, 0-100% EtOAc in heptane gradient followed by 0-40% MeOH in EtOAc gradient).
LC-MS (METCR1603): 100% (UV), Rt=3.49 min, m/z (ESI⁺)=438.1 [M+H]⁺
¹H NMR (500 MHz, Chloroform-d) δ 1.60 (t, J=18.4 Hz, 3H), 2.94 (dd, J=7.1, 13.7 Hz, 1H), 3.05-3.10 (m, 1H), 3.15 (dd, J=4.7, 13.7 Hz, 1H), 3.28-3.39 (m, 2H), 3.56-3.69 (m, 2H), 3.87-3.99 (m, 4H), 4.49-4.67 (m, 2H), 6.86-6.94 (m, 2H), 7.00-7.08 (m, 1H), 7.09-7.15 (m, 2H), 7.80 (s, 1H)

Rac-2-[(3R,4R)-4-benzyl-5-oxo-1-(pyrimidin-5-yl)pyrrolidin-3-yl]-N-cyclopropyl-2-oxoacetamide (FP-54)

The title compound was synthesized from Rac-2-[(3R,4R)-4-benzyl-5-oxo-1-(pyrimidin-5-yl)pyrrolidin-3-yl]-2-oxoacetic acid (I-96) in a similar manner to method A, general procedure 7a (general scheme 3) as an off-white solid (21 mg, 100% purity, 25%) after purification by FCC on normal phase silica (10 g SNAP KP-SIL cartridge, 0-100% EtOAc in heptane gradient) followed by trituration in heptane.
LC-MS (METCR1603): 100% (UV), Rt=3.43 min, m/z (ESI⁺)=365.1 [M+H]⁺
¹H NMR (500 MHz, DMSO-d₆) δ 0.53-0.60 (m, 2H), 0.62-0.68 (m, 2H), 2.68-2.77 (m, 1H), 2.97 (dd, J=7.5, 13.7 Hz, 1H), 3.10 (dd, J=5.2, 13.7 Hz, 1H), 3.25 (td, J=5.3, 7.4 Hz, 1H), 3.79 (dd, J=6.6, 10.0 Hz, 1H), 3.87 (t, J=9.6 Hz, 1H), 4.02 (dt, J=6.9, 9.1 Hz, 1H), 7.16-7.29 (m, 5H), 8.66 (d, J=5.1 Hz, 1H), 8.95 (s, 1H), 9.07 (s, 2H)

Rac-2-[(3R,4R)-4-benzyl-5-oxo-1-(pyrimidin-5-yl)pyrrolidin-3-yl]-N-ethyl-2-oxo-acetamide (FP-55)

The title compound was synthesized from Rac-2-[(3R,4R)-4-benzyl-5-oxo-1-(pyrimidin-5-yl)pyrrolidin-3-yl]-2-oxoacetic acid (I-96) in a similar manner to method A, general procedure 7a (general scheme 3) as a yellow solid (25 mg, 97% purity, 29%) after purification by FCC on normal phase silica (10 g SNAP Ultra cartridge, 0-100% EtOAc in heptane gradient).
LC-MS (METCR1603): 97% (UV), Rt=3.38 min, m/z (ESI⁺)=353.2 [M+H]⁺
¹H NMR (500 MHz, Chloroform-d) δ 1.20 (t, J=7.3 Hz, 3H), 3.06-3.14 (m, 1H), 3.27-3.36 (m, 4H), 3.62 (t, J=9.3 Hz, 1H), 3.72 (dd, J=6.3, 9.6 Hz, 1H), 4.10-4.18 (m, 1H), 6.65-6.79 (m, 1H), 7.18-7.30 (m, 5H), 9.01 (s, 1H), 9.02 (s, 2H)

Rac-2-[(3R,4R)-4-benzyl-5-oxo-1-(pyrimidin-5-yl)pyrrolidin-3-yl]-N-(2,2-difluoropropyl)-2-oxoacetamide (FP-56)

The title compound was synthesized from rac-2-[(3R,4R)-4-benzyl-5-oxo-1-(pyrimidin-5-yl)pyrrolidin-3-yl]-2-oxoacetic acid (I-96) in a similar manner to method A, general procedure 7a (general scheme 3) as a yellow gum (94 mg, 100% purity, 58%) after purification by FCC on normal phase silica (25 g SNAP Ultra cartridge, 0-100% EtOAc in heptane gradient).
LC-MS (METCR1603): 100% (UV), Rt=3.67 min, m/z (ESI⁺)=403.2 [M+H]⁺
¹H NMR (500 MHz, Chloroform-d) δ 1.64 (t, J=18.4 Hz, 3H), 3.06-3.12 (m, 1H), 3.28-3.36 (m, 2H), 3.55-3.65 (m, 2H), 3.65-3.71 (m, 1H), 3.73 (dd, J=6.4, 9.6 Hz, 1H), 4.10-4.16 (m, 1H), 6.96-7.04 (m, 1H), 7.18-7.22 (m, 2H), 7.22-7.28 (m, 3H), 9.01 (s, 3H)

Rac-2-[(3R,4R)-4-benzyl-5-oxo-1-(pyrazin-2-yl)pyrrolidin-3-yl]-N-cyclopropyl-2-oxoacetamide (FP-57)

The title compound was synthesized from rac-2-[(3R,4R)-4-benzyl-5-oxo-1-(pyrazin-2-yl)pyrrolidin-3-yl]-2- oxoacetic acid (I-97) in a similar manner to method A, general procedure 7a (general scheme 3) as an off-white solid (62 mg, 100% purity, 39%) after purification by FCC on normal phase silica (10 g SNAP Ultra cartridge, 0-50% EtOAc in heptane gradient) followed by preparative LC (acidic pH, standard elution method).

LC-MS (METCR1603): 100% (UV), Rt=3.84 min, m/z (ESI$^+$)=365.2 [M+H]$^+$ $^1$H NMR (500 MHz, DMSO-d$_6$) δ 0.55-0.59 (m, 2H), 0.63-0.68 (m, 2H), 2.70-2.76 (m, 1H), 3.01 (dd, J=7.2, 13.7 Hz, 1H), 3.11 (dd, J=5.4, 13.7 Hz, 1H), 3.33-3.36 (m, 1H), 3.78-3.85 (m, 1H), 3.92-3.98 (m, 2H), 7.17-7.21 (m, 1H), 7.21-7.27 (m, 4H), 8.39 (d, J=2.6 Hz, 1H), 8.43 (dd, J=1.6, 2.6 Hz, 1H), 8.66 (d, J=5.1 Hz, 1H), 9.55 (d, J=1.5 Hz, 1H)

Rac-2-[(3R,4R)-4-benzyl-5-oxo-1-(pyrimidin-2-yl) pyrrolidin-3-yl]-N-cyclopropyl-2-oxoacetamide (FP-58)

The title compound was synthesized from rac-2-[(3R,4R)-4-benzyl-5-oxo-1-(pyrimidin-2-yl)pyrrolidin-3-yl]-2-oxoacetic acid (I-98) in a similar manner to method A, general procedure 7a (general scheme 3) as a yellow solid (48 mg, 98% purity, 33%) after purification by FCC on reverse phase silica (12 g SNAP C18 Ultra cartridge, acidic pH, standard elution method).

LC-MS (METCR1603): 98% (UV), Rt=3.39 min, m/z (ESI$^+$)=365.1 [M+H]$^+$ $^1$H NMR (500 MHz, Chloroform-d) δ 0.51-0.58 (m, 2H), 0.81-0.86 (m, 2H), 2.67-2.73 (m, 1H), 2.93-2.99 (m, 1H), 3.34-3.44 (m, 2H), 3.81-3.89 (m, 1H), 4.07-4.15 (m, 2H), 6.65 (b.s, 1H), 7.05 (t, J=4.8 Hz, 1H), 7.15-7.28 (m, 5H), 8.67 (d, J=4.8 Hz, 2H)

Rac-2-[(3R,4R)-4-benzyl-5-oxo-1-(pyrimidin-2-yl) pyrrolidin-3-yl]-N-ethyl-2-oxo-acetamide (FP-59)

The title compound was synthesized from rac-2-[(3R,4R)-4-benzyl-5-oxo-1-(pyrimidin-2-yl)pyrrolidin-3-yl]-2-oxoacetic acid (I-98) in a similar manner to method A, general procedure 7a (general scheme 3) as a yellow solid (65 mg, 94% purity, 45%) after purification by FCC on reverse phase silica (30 g SNAP C18 Ultra cartridge, acidic pH, standard elution method).

LC-MS (METCR1603): 94% (UV), Rt=3.38 min, m/z (ESI$^+$)=353.2 [M+H]$^+$ $^1$H NMR (500 MHz, Chloroform-d) δ 1.16 (t, J=7.3 Hz, 3H), 2.97 (dd, J=8.4, 13.7 Hz, 1H), 3.23-3.32 (m, 2H), 3.36 (dd, J=4.8, 13.7 Hz, 1H), 3.39-3.45 (m, 1H), 3.82-3.89 (m, 1H), 4.07-4.16 (m, 2H), 6.54-6.69 (m, 1H), 7.05 (t, J=4.8 Hz, 1H), 7.15-7.20 (m, 1H), 7.20-7.25 (m, 4H), 8.67 (d, J=4.8 Hz, 2H)

Rac-2-[(3R,4R)-4-benzyl-1-(2-chloropyrimidin-4-yl)-5-oxopyrrolidin-3-yl]-N-cyclopropyl-2-oxoacetamide (FP-60)

The title compound was synthesized from rac-2-[(3R,4R)-4-benzyl-1-(2-chloropyrimidin-4-yl)-5-oxopyrrolidin-3-yl]-2-oxoacetic acid (I-99) in a similar manner to method A, general procedure 7a (general scheme 3) as a pale yellow solid (99 mg, 95% purity by $^1$H NMR, 47%) after purification by FCC on normal phase silica (10 g SNAP Ultra cartridge, 0-100% EtOAc in heptane gradient).

LC-MS (METCR1603): 92% (UV), Rt=4.36 min, m/z (ESI$^+$)=399.1/401.1 [M+H]

$^1$H NMR (500 MHz, Chloroform-d) δ 0.51-0.62 (m, 2H), 0.83-0.88 (m, 2H), 2.67-2.77 (m, 1H), 2.96 (dd, J=8.1, 13.9 Hz, 1H), 3.30 (dd, J=5.0, 13.8 Hz, 1H), 3.36-3.44 (m, 1H), 3.78-3.85 (m, 1H), 4.07-4.15 (m, 2H), 6.68 (s, 1H), 7.14-7.19 (m, 2H), 7.19-7.23 (m, 1H), 7.23-7.26 (m, 2H), 8.34 (d, J=5.8 Hz, 1H), 8.48 (d, J=5.8 Hz, 1H)

Rac-2-[(3R,4R)-4-benzyl-5-oxo-1-(pyrimidin-4-yl) pyrrolidin-3-yl]-N-cyclopropyl-2-oxoacetamide (FP-61)

To a solution of rac-2-[(3R,4R)-4-benzyl-1-(2-chloropyrimidin-4-yl)-5-oxopyrrolidin-3-yl]-N-cyclopropyl-2-oxoacetamide (FP-60) (60 mg, 0.15 mmol) in EtOH (5 mL) was added 50% Pd/C (31 mg, 0.15 mmol) and the suspension stirred at RT under an atmosphere of hydrogen for 2 h. Further 50% Pd/C (31 mg, 0.15 mmol) was added and the mixture stirred at RT under an atmosphere of hydrogen for 2 h. The reaction was filtered through a plug of Celite and the resultant cake washed with EtOH.

The filtrates were combined and concentrated in vacuo. The residue was purified by FCC on normal phase silica (10 g SNAP Ultra cartridge, 0-100% EtOAc in heptane gradient) to afford 10 mg of rac-2-[(3R,4R)-4-benzyl-5-oxo-1-(pyrimidin-4-yl)pyrrolidin-3-yl]-N-cyclopropyl-2-oxoacetamide as a pale yellow viscous oil (100% purity, 18%).

LC-MS (METCR1603): 100% (UV), Rt=3.77 min, m/z (ESI$^+$)=365.1 [M+H]$^+$ $^1$H NMR (500 MHz, Chloroform-d) δ 0.52-0.59 (m, 2H), 0.83-0.87 (m, 2H), 2.68-2.75 (m, 1H), 2.96 (dd, J=8.2, 13.8 Hz, 1H), 3.31 (dd, J=4.9, 13.8 Hz, 1H), 3.38-3.44 (m, 1H), 3.80-3.86 (m, 1H), 4.07-4.14 (m, 2H), 6.69 (s, 1H), 7.16-7.22 (m, 3H), 7.22-7.26 (m, 2H), 8.40 (dd, J=0.9, 5.8 Hz, 1H), 8.55-8.69 (m, 1H), 8.91 (s, 1H)

Rac-2-[(3R,4R)-4-benzyl-1-(6-chloropyridazin-3-yl)-5-oxopyrrolidin-3-yl]-N-cyclopropyl-2-oxoacetamide (FP-62)

The title compound was synthesized from rac-2-[(3R,4R)-4-benzyl-1-(6-chloropyridazin-3-yl)-5-oxopyrrolidin-3-yl]-2-oxoacetic acid (I-100) in a similar manner to method A, general procedure 7a (general scheme 3) as a pale yellow solid (69 mg, 100% purity, 46%) after purification by FCC on normal phase silica (10 g SNAP Ultra cartridge, 0-100% EtOAc in heptane gradient).

LC-MS (METCR1603): 100% (UV), Rt=4.21 min, m/z (ESI$^+$)=399.0/401.0 [M+H]$^+$ $^1$H NMR (500 MHz, Chloroform-d) δ 0.54-0.62 (m, 2H), 0.84-0.91 (m, 2H), 2.71-2.78 (m, 1H), 3.02 (dd, J=8.0, 13.7 Hz, 1H), 3.34 (dd, J=4.9, 13.7 Hz, 1H), 3.38-3.45 (m, 1H), 3.98-4.06 (m, 1H), 4.14-4.22 (m, 2H), 6.73 (s, 1H), 7.19-7.24 (m, 3H), 7.25-7.28 (m, 2H), 7.52 (d, J=9.4 Hz, 1H), 8.73 (d, J=9.4 Hz, 1H)

Rac-N-cyclopropyl-2-oxo-2-[(3R,4S)-5-oxo-4-phenyl-1-(pyrimidin-5-yl)pyrrolidin-3-yl]acetamide (FP-63)

The title compound was synthesized from Rac-2-oxo-2-[(3R,4S)-5-oxo-4-phenyl-1-(pyrimidin-5-yl)pyrrolidin-3-yl]acetic acid (I-101) in a similar manner to method A, general procedure 7a (general scheme 3) as an off-white solid (3 mg, 90% purity by $^1$H NMR, 5%) after purification by FCC on normal phase silica (10 g SNAP KP-SIL cartridge, 0-100% EtOAc in heptane gradient) followed by preparative LC (basic pH, early elution method).

LC-MS (METCR1603): 96% (UV), Rt=3.10 min, m/z (ESI+)=351.2 [M+H]+

¹H NMR (500 MHz, DMSO-$d_6$) δ 0.54-0.61 (m, 2H), 0.62-0.67 (m, 2H), 2.70-2.78 (m, 1H), 4.05 (dd, J=6.5, 9.8 Hz, 1H), 4.17 (d, J=7.7 Hz, 1H), 4.29-4.35 (m, 1H), 4.42 (t, J=9.4 Hz, 1H), 7.30-7.39 (m, 5H), 8.81 (d, J=5.0 Hz, 1H), 8.99 (s, 1H), 9.15 (s, 2H)

Rac-N-(cyclopropylmethyl)-2-oxo-2-[(3R,4S)-5-oxo-4-phenyl-1-(pyrimidin-5-yl) pyrrolidin-3-yl] acetamide (FP-64)

The title compound was synthesized from rac-2-oxo-2-[(3R,4S)-5-oxo-4-phenyl-1-(pyrimidin-5-yl)pyrrolidin-3-yl]acetic acid (I-101) in a similar manner to method A, general procedure 7a (general scheme 3) as an off-white solid (3 mg, 95% purity by ¹H NMR, 5%) after purification by FCC on normal phase silica (10 g SNAP Ultra cartridge, 0-100% EtOAc in heptane gradient) followed by preparative LC (basic pH, early elution method).

LC-MS (METCR1603): 92% (UV), Rt=3.48 min, m/z (ESI+)=365.2 [M+H]+

¹H NMR (500 MHz, DMSO-$d_6$) δ 0.16-0.21 (m, 2H), 0.37-0.41 (m, 2H), 0.90-1.00 (m, 1H), 2.96-3.02 (m, 2H), 4.06 (dd, J=6.5, 9.6 Hz, 1H), 4.18 (d, J=7.8 Hz, 1H), 4.30-4.37 (m, 1H), 4.42 (t, J=9.4 Hz, 1H), 7.28-7.33 (m, 1H), 7.34-7.38 (m, 4H), 8.82-8.89 (m, 1H), 8.99 (s, 1H), 9.15 (s, 2H)

Rac-2-[(3R,4R)-4-benzyl-1-(4-cyanopyrimidin-5-yl)-5-oxopyrrolidin-3-yl]-N-cyclopropyl-2-oxoacetamide (FP-65)

The title compound was synthesized from rac-2-[(3R,4R)-4-benzyl-1-(4-cyanopyrimidin-5-yl)-5-oxopyrrolidin-3-yl]-2-oxoacetic acid (I-102) in a similar manner to method A, general procedure 7a (general scheme 3) as an off-white solid (41 mg, 97% purity by ¹H NMR, 39%) after purification by FCC on normal phase silica (10 g SNAP Ultra cartridge, 0-100% EtOAc in heptane gradient).

LC-MS (METCR1603): 100% (UV), Rt=3.85 min, m/z (ESI+)=390.2 [M+H]+

¹H NMR (500 MHz, Chloroform-d) δ 0.56-0.63 (m, 2H), 0.84-0.91 (m, 2H), 2.72-2.79 (m, 1H), 3.13-3.20 (m, 1H), 3.28-3.37 (m, 2H), 3.66-3.72 (m, 1H), 3.92 (dd, J=5.8, 9.5 Hz, 1H), 4.15-4.22 (m, 1H), 6.81 (s, 1H), 7.24-7.29 (m, 3H), 7.29-7.33 (m, 2H), 8.89 (s, 1H), 9.17 (s, 1H)

Rac-2-[(3R,4R)-4-benzyl-1-(4-cyanopyrimidin-5-yl)-5-oxopyrrolidin-3-yl]-N-(2,2-difluoropropyl)-2-oxoacetamide (FP-66)

The title compound was synthesized from rac-2-[(3R,4R)-4-benzyl-1-(4-cyanopyrimidin-5-yl)-5-oxopyrrolidin-3-yl]-2-oxoacetic acid (I-102) in a similar manner to method A, general procedure 7a (general scheme 3) as an off-white solid (61 mg, 99% purity by ¹H NMR, 54%) after purification by FCC on normal phase silica (10 g SNAP Ultra cartridge, 0-100% EtOAc in heptane gradient).

LC-MS (METCR1603): 100% (UV), Rt=4.07 min, m/z (ESI+)=428.1 [M+H]+

¹H NMR (500 MHz, Chloroform-d) δ 1.63 (t, J=18.4 Hz, 3H), 3.15 (dd, J=7.0, 13.7 Hz, 1H), 3.31 (dd, J=5.0, 13.7 Hz, 1H), 3.35-3.40 (m, 1H), 3.58-3.76 (m, 3H), 3.93 (dd, J=5.9, 9.5 Hz, 1H), 4.15-4.21 (m, 1H), 7.02-7.12 (m, 1H), 7.23-7.28 (m, 3H), 7.29-7.33 (m, 2H), 8.91 (s, 1H), 9.18 (s, 1H)

Rac-2-[(3R,4R)-4-benzyl-1-(4-methylpyrimidin-5-yl)-5-oxopyrrolidin-3-yl]-N-cyclopropyl-2-oxoacetamide (FP-67)

The title compound was synthesized from rac-2-[(3R,4R)-4-benzyl-1-(4-methylpyrimidin-5-yl)-5-oxopyrrolidin-3-yl]-2-oxoacetic acid (I-103) in a similar manner to method A, general procedure 7a (general scheme 3) as an off-white solid (21 mg, 96% purity, 22%) after purification by FCC on normal phase silica (10 g SNAP Ultra cartridge, 0-100% EtOAc in heptane gradient followed by 0-20% MeOH in EtOAc gradient).

LC-MS (METCR1603): 96% (UV), Rt=3.36 min, m/z (ESI+)=379.1 [M+H]+

¹H NMR (500 MHz, Chloroform-d) δ 0.56-0.65 (m, 2H), 0.85-0.92 (m, 2H), 2.37 (s, 3H), 2.74-2.80 (m, 1H), 3.18-3.25 (m, 2H), 3.25-3.31 (m, 1H), 3.31-3.36 (m, 1H), 3.60 (dd, J=5.1, 9.7 Hz, 1H), 4.17-4.23 (m, 1H), 6.86 (s, 1H), 7.27-7.36 (m, 5H), 8.25 (s, 1H), 9.00 (s, 1H)

Rac-2-[(3R,4R)-4-benzyl-1-(4-methylpyrimidin-5-yl)-5-oxopyrrolidin-3-yl]-N-(2,2-difluoropropyl)-2-oxoacetamide (FP-68)

The title compound was synthesized from rac-2-[(3R,4R)-4-benzyl-1-(4-methylpyrimidin-5-yl)-5-oxopyrrolidin-3-yl]-2-oxoacetic acid (I-103) in a similar manner to method A, general procedure 7a (general scheme 3) as a pale yellow viscous oil (12 mg, 100% purity, 12%) after purification by FCC on normal phase silica (10 g SNAP Ultra cartridge, 0-100% EtOAc in heptane gradient followed by 0-20% MeOH in EtoAc gradient).

LC-MS (METCR1603): 100% (UV), Rt=3.58 min, m/z (ESI+)=417.1 [M+H]+

¹H NMR (500 MHz, Chloroform-d) δ 1.64 (t, J=18.4 Hz, 3H), 2.38 (s, 3H), 3.15-3.30 (m, 3H), 3.32-3.40 (m, 1H), 3.58-3.77 (m, 3H), 4.15-4.26 (m, 1H), 7.07-7.16 (m, 1H), 7.31 (h, J=6.5, 7.2 Hz, 5H), 8.28 (s, 1H), 9.01 (s, 1H)

Rac-2-[(3R,4R)-4-benzyl-1-[6-(benzyloxy)pyridin-2-yl]-5-oxopyrrolidin-3-yl]-N-cyclopropyl-2-oxoacetamide (FP-69)

The title compound was synthesized from rac-2-[(3R,4R)-4-benzyl-1-[6-(benzyloxy)pyridin-2-yl]-5-oxopyrrolidin-3-yl]-2-oxoacetic acid (I-104) in a similar manner to method A, general procedure 7a (general scheme 3) as a pale yellow viscous oil (59 mg, 99% purity by ¹H NMR, 40%) after purification by FCC on normal phase silica (10 g SNAP Ultra cartridge, 0-100% EtOAc in heptane gradient).

LC-MS (METCR1603): 100% (UV), Rt=5.32 min, m/z (ESI+)=470.2 [M+H]

¹H NMR (500 MHz, Chloroform-d) δ 0.52-0.59 (m, 2H), 0.81-0.88 (m, 2H), 2.66-2.75 (m, 1H), 2.91 (dd, J=8.6, 13.6 Hz, 1H), 3.29-3.36 (m, 1H), 3.36-3.42 (m, 1H), 3.79 (dd, J=7.1, 10.9 Hz, 1H), 4.05-4.11 (m, 1H), 4.13-4.19 (m, 1H), 5.23-5.30 (m, 2H), 6.56 (d, J=8.0 Hz, 1H), 6.67 (d, 1H), 7.16-7.21 (m, 3H), 7.21-7.26 (m, 2H), 7.26-7.31 (m, 1H), 7.32-7.37 (m, 2H), 7.37-7.42 (m, 2H), 7.61 (t, J=8.0 Hz, 1H), 7.96 (d, J=7.9 Hz, 1H)

Rac-2-[(3R,4R)-4-benzyl-5-oxo-1-(6-oxo-1,6-dihydropyridin-2-yl)pyrrolidin-3-yl]-N-cyclopropyl-2-oxoacetamide (FP-70), rac-2-[(3R,4R)-4-benzyl-1-(4-chloro-6-oxo-1,6-dihydropyridin-2-yl)-5-oxopyrrolidin-3-yl]-N-cyclopropyl-2-oxoacetamide (FP-71), and rac-2-[(3R,4R)-4-benzyl-1-[6-(benzyloxy)-4-chloropyridin-2-yl]-5-oxopyrrolidin-3-yl]-N-cyclopropyl-2-oxoacetamide (FP-72)

To a solution of rac-2-[(3R,4R)-4-benzyl-1-[6-(benzyloxy)pyridin-2-yl]-5-oxopyrrolidin-3-yl]-N-cyclopropyl-2- oxoacetamide (FP-69) (71% purity, 125 mg, 0.189 mmol) in EtOAc (10 mL) was added 50% Pd/C (40 mg, 0.189 mmol) and the suspension stirred at RT under an atmosphere of hydrogen for 20 min. The reaction mixture was filtered through a plug of Celite and the resultant cake washed with EtOAc (30 mL). The filtrate was concentrated in vacuo and the crude material purified by FCC on normal phase silica (10 g SNAP KP-SIL cartridge, 0-100% EtOAc in heptane gradient followed by 0-20% MeOH in EtOAc/MeOH gradient) to give 41 mg of rac-2-[(3R,4R)-4-benzyl-5-oxo-1-(6-oxo-1,6-dihydropyridin-2-yl)pyrrolidin-3-yl]-N-cyclopropyl-2-oxoacetamide as an off-white solid (98% purity by $^1$H NMR, 56%), 8 mg of rac-2-[(3R,4R)-4-benzyl-1-(4-chloro-6-oxo-1,6-dihydropyridin-2-yl)-5-oxopyrrolidin-3-yl]-N-cyclopropyl-2-oxoacetamide as an off-white solid (100% purity, 10%) and 12 mg of rac-2-[(3R,4R)-4-benzyl-1-[6-(benzyloxy)-4-chloropyridin-2-yl]-5-oxopyrrolidin-3-yl]-N-cyclopropyl-2-oxoacetamide as an off-white solid (100% purity, 13%).

Rac-2-[(3R,4R)-4-benzyl-5-oxo-1-(6-oxo-1,6-dihydropyridin-2-yl)pyrrolidin-3-yl]-N-cyclopropyl-2-oxoacetamide (FP-70)

LC-MS (METCR1603): 100% (UV), Rt=3.06 min, m/z (ESI$^+$)=380.0 [M+H]$^+$ $^1$H NMR (500 MHz, Chloroform-d) δ 0.57-0.67 (m, 2H), 0.83-0.90 (m, 2H), 2.73-2.80 (m, 1H), 3.08 (dd, J=6.9, 13.8 Hz, 1H), 3.24 (dd, J=5.1, 13.8 Hz, 1H), 3.35-3.41 (m, 1H), 3.52-3.59 (m, 1H), 3.63 (dd, J=6.2, 10.2 Hz, 1H), 3.98-4.07 (m, 1H), 5.69 (d, J=7.4 Hz, 1H), 6.32 (d, J=9.0 Hz, 1H), 7.15-7.21 (m, 3H), 7.21-7.29 (m, 3H), 7.32-7.40 (m, 1H), 11.48 (s, 1H)

Rac-2-[(3R,4R)-4-benzyl-1-(4-chloro-6-oxo-1,6-dihydropyridin-2-yl)-5-oxopyrrolidin-3-yl]-N-cyclopropyl-2-oxoacetamide (FP-71)

LC-MS (METCR1603): 100% (UV), Rt=2.58 min, m/z (ESI$^+$)=414.2 [M+H]$^+$ $^1$H NMR (500 MHz, DMSO-d$_6$) δ 0.52-0.61 (m, 2H), 0.62-0.69 (m, 2H), 2.70-2.77 (m, 1H), 2.99 (dd, J=7.1, 13.7 Hz, 1H), 3.06 (dd, J=5.3, 13.7 Hz, 1H), 3.24-3.27 (m, 1H), 3.79 (dd, J=6.0, 10.4 Hz, 1H), 3.82-3.88 (m, 1H), 3.89-3.96 (m, 1H), 7.16-7.28 (m, 5H), 7.49-7.98 (m, 2H), 8.68 (d, J=5.2 Hz, 1H), 11.64 (s, 1H)

Rac-2-[(3R,4R)-4-benzyl-1-[6-(benzyloxy)-4-chloropyridin-2-yl]-5-oxopyrrolidin-3-yl]-N-cyclopropyl-2-oxoacetamide (FP-72)

LC-MS (METCR1603): 100% (UV), Rt=5.44 min, m/z (ESI$^+$)=504.2 [M+H]$^+$ $^1$H NMR (500 MHz, Chloroform-d) δ 0.51-0.61 (m, 2H), 0.83-0.89 (m, 2H), 2.69-2.77 (m, 1H), 2.92 (dd, J=8.3, 13.7 Hz, 1H), 3.31 (dd, J=4.8, 13.7 Hz, 1H), 3.35-3.41 (m, 1H), 3.71-3.78 (m, 1H), 4.03-4.10 (m, 2H), 5.31-5.37 (m, 2H), 6.60-6.74 (m, 1H), 7.15-7.21 (m, 3H), 7.21-7.26 (m, 2H), 7.27-7.31 (m, 1H), 7.32-7.37 (m, 2H), 7.37-7.42 (m, 2H), 7.65 (d, J=8.4 Hz, 1H), 7.95 (d, J=8.4 Hz, 1H)

Rac-2-[(3R,4R)-4-benzyl-1-[6-(benzyloxy)pyridin-2-yl]-5-oxopyrrolidin-3-yl]-N-(2,2-difluoropropyl)-2-oxoacetamide (FP-73)

The title compound was synthesized from rac-2-[(3R,4R)-4-benzyl-1-[6-(benzyloxy)pyridin-2-yl]-5-oxopyrrolidin-3-yl]-2-oxoacetic acid (I-104) in a similar manner to method A, general procedure 7a (general scheme 3) as a colourless viscous oil (5 mg, 100% purity, 2%) after purification by FCC on normal phase silica (25 g SNAP KP-SIL cartridge, 0-100% EtOAc in heptane gradient) followed by preparative LC (basic pH, early elution method).

LC-MS (METCR1603): 100% (UV), Rt=5.44 min, m/z (ESI$^+$)=508.2 [M+H]$^+$ $^1$H NMR (500 MHz, Chloroform-d) δ 1.61 (t, J=18.4 Hz, 3H), 2.91 (dd, J=8.7, 13.7 Hz, 1H), 3.34 (dd, J=4.8, 13.8 Hz, 1H), 3.39-3.45 (m, 1H), 3.54-3.70 (m, 2H), 3.81 (dd, J=7.4, 11.1 Hz, 1H), 4.03-4.10 (m, 1H), 4.16 (dd, J=9.3, 11.1 Hz, 1H), 5.26 (s, 2H), 6.56 (d, J=8.0 Hz, 1H), 6.85-6.95 (m, 1H), 7.15-7.21 (m, 3H), 7.22-7.26 (m, 2H), 7.27-7.31 (m, 1H), 7.31-7.36 (m, 2H), 7.36-7.40 (m, 2H), 7.62 (t, J=8.0 Hz, 1H), 7.96 (d, J=7.9 Hz, 1H)

Rac-2-[(3R,4R)-4-benzyl-5-oxo-1-(6-oxo-1,6-dihydropyridin-2-yl)pyrrolidin-3-yl]-N-(2,2-difluoropropyl)-2-oxoacetamide (FP-74)

To a solution of rac-2-[(3R,4R)-4-benzyl-1-[6-(benzyloxy)pyridin-2-yl]-5-oxopyrrolidin-3-yl]-N-(2,2-difluoropropyl)-2-oxoacetamide (FP-73) (62% purity, 43 mg, 0.053 mmol) in EtOAc (5 mL) was added 50% Pd/C (11 mg, 0.053 mmol) and the suspension stirred at RT under an atmosphere of hydrogen for 20 min. The reaction mixture was filtered through a plug of Celite and the filtrate concentrated in vacuo. The crude material was purified by FCC on normal phase silica (10 g SNAP KP-SIL cartridge, 0-100% EtOAc in heptane gradient) to give 2 mg of rac-2-[(3R,4R)-4-benzyl-5-oxo-1-(6-oxo-1,6-dihydropyridin-2-yl)pyrrolidin-3-yl]-N-(2,2-difluoropropyl)-2-oxoacetamide as a pale yellow viscous oil (94% purity, 9%).

LC-MS (METCR1603): 94% (UV), Rt=3.35 min, m/z (ESI$^+$)=418.1 [M+H]$^+$ $^1$H NMR (500 MHz, Chloroform-d) δ 1.64 (t, J=18.4 Hz, 3H), 3.06 (dd, J=7.2, 13.9 Hz, 1H), 3.26 (dd, J=5.1, 13.9 Hz, 1H), 3.36-3.44 (m, 1H), 3.56-3.74 (m, 4H), 3.98-4.07 (m, 1H), 5.68 (d, J=7.1 Hz, 1H), 6.33 (dd, J=0.6, 9.1 Hz, 1H), 7.01-7.11 (m, 1H), 7.15-7.19 (m, 2H), 7.26 (s, 3H), 7.35 (dd, J=7.5, 9.1 Hz, 1H), 11.29 (s, 1H)

Rac-2-[(3R,4R)-4-benzyl-1-(1-methyl-1H-pyrazol-4-yl)-5-oxopyrrolidin-3-yl]-N-cyclopropyl-2-oxoacetamide (FP-75)

The title compound was synthesized from rac-2-[(3R,4R)-4-benzyl-1-(1-methyl-1H-pyrazol-4-yl)-5-oxopyrrolidin-3-yl]-2-oxoacetic acid (I-105) in a similar manner to method A, general procedure 7a (general scheme 3) as a pale yellow solid (40 mg, 100% purity, 46%) after purification by FCC on normal phase silica (10 g SNAP Ultra cartridge, 0-100% EtOAc in heptane gradient).

LC-MS (METCR1603): 100% (UV), Rt=3.48 min, m/z (ESI$^+$)=367.2 [M+H]$^+$ $^1$H NMR (500 MHz, Chloroform-d) δ 0.53-0.61 (m, 2H), 0.83-0.88 (m, 2H), 2.69-2.77 (m, 1H), 2.98-3.05 (m, 1H), 3.22-3.30 (m, 2H), 3.57 (d, J=7.9 Hz, 2H), 3.89 (s, 3H), 4.07 (q, J=7.7 Hz, 1H), 6.75 (s, 1H), 7.16-7.21 (m, 3H), 7.21-7.25 (m, 2H), 7.37 (s, 1H), 7.95 (s, 1H)

Rac-2-[(3R,4R)-4-benzyl-1-(1-methyl-1H-pyrazol-4-yl)-5-oxopyrrolidin-3-yl]-N-(2,2-difluoropropyl)-2-oxoacetamide (FP-76)

The title compound was synthesized from rac-2-[(3R,4R)-4-benzyl-1-(1-methyl-1H-pyrazol-4-yl)-5-oxopyrrolidin-3- yl]-2-oxoacetic acid (I-105) in a similar manner to method A, general procedure 7a (general scheme 3) as a yellow oil (19 mg, 97% purity, 20%) after purification by FCC on normal phase silica (10 g SNAP Ultra cartridge, 0-100% EtOAc in heptane gradient).

LC-MS (METCR1603): 97% (UV), Rt=3.75 min, m/z (ESI$^+$)=405.0 [M+H]$^+$ $^1$H NMR (500 MHz, Chloroform-d) δ 1.62 (t, J=18.4 Hz, 3H), 2.97-3.05 (m, 1H), 3.24-3.31 (m, 2H), 3.55-3.72 (m, 4H), 3.87-3.91 (m, 3H), 4.03-4.10 (m, 1H), 6.92-7.03 (m, 1H), 7.15-7.21 (m, 3H), 7.21-7.26 (m, 2H), 7.36-7.38 (m, 1H), 7.96 (s, 1H)

Method B: HATU Coupling on Ketoacid

Rac-2-[(3R,4R)-4-[(4-fluorophenyl)methyl]-5-oxopyrrolidin-3-yl]-2-oxo-N-(propan-2-yloxy)acetamide (FP-77)

To an ice-cooled solution of rac-2-[(3R,4R)-4-[(4-fluorophenyl)methyl]-5-oxopyrrolidin-3-yl]-2-oxoacetic acid (I-78) (60% purity estimated by $^1$H NMR, 300 mg, 0.68 mmol) and DIPEA (296 μL, 1.70 mmol) in dry 1/1 DCM/DMF (6 mL) was added at 0° C. HATU (284 mg, 0.75 mmol) in one portion. The mixture was stirred at 0° C. for 15 min then 2-(aminooxy)propane hydrochloride (1:1) (76 mg, 0.68 mmol) was added.

After 15 min at 0° C., the reaction was allowed to warm up and stirred at RT for 3 h. The mixture was cooled to 0° C. then DIPEA (148 μL, 0.85 mmol) and HATU (142 mg, 0.38 mmol) were added. The mixture was stirred at 0° C. for 15 min then 2-(aminooxy)-propane hydrochloride (1:1) (38 mg, 0.34 mmol) was added. After 15 min at 0° C., the reaction was allowed to warm up and stirred at RT for 2 h. The solution was quenched with water (5 mL) and extracted with DCM (3×5 mL). The 2 layers were separated on a hydrophobic frit and the combined organic extracts were concentrated in vacuo. The crude material was purified by FCC on normal phase silica (25 g SNAP Ultra, 0-100% EtOAc in heptane gradient followed by 0-20% MeOH in EtOAc gradient) then by FCC on reverse phase silica (12 g SNAP Ultra C18, acidic pH, normal elution method) to afford 10 mg of rac-2-[(3R,4R)-4-[(4-fluorophenyl)methyl]-5-oxopyrrolidin-3-yl]-2-oxo-N-(propan-2-yloxy)acetamide as a colourless oil (85% purity by $^1$H NMR, 4%).

LC-MS (METCR1603): 95% (UV), Rt=2.37 min, m/z (ESI$^+$)=323.2 [M+H]$^+$ $^1$H NMR (500 MHz, Chloroform-d) δ 1.27 (s, 6H), 2.85-2.97 (m, 1H), 2.98-3.09 (m, 1H), 3.11-3.24 (m, 1H), 3.29 (dd, J=9.5, 7.2 Hz, 1H), 3.32-3.39 (m, 1H), 3.97-4.09 (m, 1H), 4.09-4.21 (m, 1H), 5.55 (s, 1H), 6.91-7.01 (m, 2H), 7.13-7.23 (m, 2H), 8.93 (s, 1H)

Method C: Displacement on Methyl Ketoester

Rac-2-oxo-2-[(3R,4S)-5-oxo-4-phenylpyrrolidin-3-yl]-N-(propan-2-yl)acetamide (FP-78)

To a solution of rac-methyl 2-oxo-2-[(3R,4S)-5-oxo-4-phenylpyrrolidin-3-yl]acetate (I-106) (23% purity, 100 mg, 0.08 mmol) in MeOH (3 mL) was added isopropylamine (48 mg, 0.81 mmol) and the reaction heated at reflux for 1 h then cooled to RT and concentrated in vacuo. The residue was dissolved in MeCN (1 mL) and purified by preparative LC (acidic pH, standard elution method) to afford 4 mg of rac-2-oxo-2-[(3R,4S)-5-oxo-4-phenylpyrrolidin-3-yl]-N-(propan-2-yl)acetamide as an off-white solid (93% purity, 8%).

LC-MS (METCR1603): 93% (UV), Rt=3.13 min, m/z (ESI$^+$)=275.3 [M+H]$^+$ $^1$H NMR (500 MHz, Chloroform-d) δ 1.17-1.22 (m, 6H), 3.38-3.46 (m, 1H), 3.94-4.08 (m, 3H), 4.27-4.35 (m, 1H), 6.40 (s, 1H), 6.76 (d, J=7.6 Hz, 1H), 7.24-7.38 (m, 5H)

Rac-N-cyclopentyl-2-oxo-2-[(3R,4S)-5-oxo-4-phenylpyrrolidin-3-yl]acetamide (FP-79)

The title compound was synthesized from rac-methyl 2-oxo-2-[(3R,4S)-5-oxo-4-phenylpyrrolidin-3-yl]acetate (I-106) in a similar manner to method C, general procedure 7a (general scheme 3) as an off-white powder (22 mg, 100% purity, 18%) after purification by preparative LC (acidic pH, standard elution method).

LC-MS (METCR1603): 100% (UV), Rt=3.60 min, m/z (ESI$^+$)=301.2 [M+H]$^+$ $^1$H NMR (500 MHz, Chloroform-d) δ 1.38-1.48 (m, 2H), 1.57-1.75 (m, 4H), 1.94-2.07 (m, 2H), 3.37-3.43 (m, 1H), 3.93-3.99 (m, 1H), 4.05 (d, J=8.0 Hz, 1H), 4.09-4.18 (m, 1H), 4.25-4.34 (m, 1H), 6.79 (s, 1H), 6.88 (d, J=7.7 Hz, 1H), 7.25-7.31 (m, 3H), 7.31-7.37 (m, 2H)

General Procedure 7b (General Scheme 3): Ketoamide Formation

Rac-N-(2-methylpropyl)-2-oxo-2-[(3R,4R)-5-oxo-4-[(pyridin-2-yl)methyl]pyrrolidin-3-yl]acetamide (FP-80)

To an ice-cooled stirred solution of rac-3-oxo-3-[(3R,4R)-5-oxo-4-[(pyridin-2-yl)methyl]pyrrolidin-3-yl]-2-(1λ$^4$-thiolan-1-ylidene)propanenitrile (I-36) (76% purity by $^1$H NMR, 660 mg, 1.52 mmol) in MeOH (5 mL) was added m-CPBA (70%, 750 mg, 3.04 mmol) in one portion and the mixture stirred at 0° C. for 1 h under nitrogen. Isobutylamine (1 mL, 10.06 mmol) was added and the suspension stirred at RT for 3.5 h. The mixture was concentrated in vacuo and the residue purified by ion-exchange flash chromatography (10 g Isolute Si II cartridge, 0-20% MeOH in EtOAc gradient then 0-10% 7N methanolic ammonia in EtOAc gradient) followed by preparative LC (basic pH, early elution method) to afford 128 mg of rac-N-(2-methylpropyl)-2-oxo-2-[(3R,4R)-5-oxo-4-[(pyridin-2-yl)methyl]pyrrolidin-3-yl]acetamide as an off-white powder (97% purity, 27%).

LC-MS (METCR1603): 97% (UV), Rt=3.04 min, m/z (ESI$^+$)=302.2 [M+H]$^+$ $^1$H NMR (500 MHz, Chloroform-d) δ 0.95 (d, J=6.7 Hz, 6H), 1.76-1.88 (m, 1H), 3.03 (dd, J=9.6, 15.1 Hz, 1H), 3.07-3.17 (m, 2H), 3.27 (td, J=3.8, 9.1 Hz, 1H), 3.32 (dd, J=8.1, 9.2 Hz, 1H), 3.43 (dd, J=3.8, 15.1 Hz, 1H), 3.57-3.64 (m, 1H), 4.38-4.45 (m, 1H), 5.72 (s, 1H), 6.93-7.01 (m, 1H), 7.04-7.09 (m, 1H), 7.19 (d, J=7.8 Hz, 1H), 7.56 (td, J=1.8, 7.7 Hz, 1H), 8.30-8.35 (m, 1H)

General Procedure 8 (General Scheme 3): Chiral Purification

2-[(3R,4R)-4-Benzyl-5-oxo-pyrrolidin-3-yl]-N-(cyclopropylmethyl)-2-oxo-acetamide (FP-81), and 2-[(3S,4S)-4-Benzyl-5-oxo-pyrrolidin-3-yl]-N-(cyclopropylmethyl)-2-oxo-acetamide (FP-82) ((R,R) and (S,R) Assignments Arbitrary)

Rac-2-[(3R,4R)-4-benzyl-5-oxopyrrolidin-3-yl]-N-(cyclopropylmethyl)-2-oxoacetamide (FP-1) (100 mg, 0.33 mmol) was purified by chiral separation on Berger SFC Prep [Column: Pirkle Covalent (R,R) Whelk-01 Kromasil (21.1 mm×250 mm, 5 μm) at 40° C.; Isocratic eluent: 8:2 CO$_2$: IPA; Flow rate: 50 mL/min; Detector wavelength: 210 nm; Dilution solvent: MeCN; Injection volume: 250 μL]. The samples were dissolved in MeCN/DCM/water, transferred to vials, the solvent removed under a stream of air and the residues dried in vacuo at 40° C. to afford 31 mg of 2-[(3R,4R)-4-benzyl-5-oxo-pyrrolidin-3-yl]-N-(cyclopropylmethyl)-2-oxo-acetamide as an off-white solid (96% purity, 94% ee, 30%) and 29 mg of 2-[(3S,4S)-4-benzyl-5-oxo-pyrrolidin-3-yl]-N-(cyclopropylmethyl)-2-oxo-acetamide as an off-white solid (97% purity, >99% ee, 29%).

2-[(3R,4R)-4-Benzyl-5-oxo-pyrrolidin-3-yl]-N-(cyclopropylmethyl)-2-oxo-acetamide (FP-81)

LC-MS (MET-uHPLC-AB-102): 98% (UV), Rt=2.50 min, m/z (ESI$^+$)=301.4 [M+H]$^+$
LC-MS (CAM-1): 96% (UV), Rt=2.66 min, 94% ee, m/z (ESI$^+$)=301.0 [M+H]$^+$
$^1$H NMR (500 MHz, Chloroform-d) δ 0.18-0.24 (m, 2H), 0.51-0.58 (m, 2H), 0.88-0.98 (m, 1H), 2.89 (dd, J=8.0, 13.7 Hz, 1H), 3.05-3.12 (m, 3H), 3.19-3.29 (m, 2H), 3.35 (t, J=9.4 Hz, 1H), 4.04-4.12 (m, 1H), 5.62 (s, 1H), 6.71-6.83 (m, 1H), 7.17-7.23 (m, 3H), 7.23-7.28 (m, 2H)

2-[(3S,4S)-4-Benzyl-5-oxo-pyrrolidin-3-yl]-N-(cyclopropylmethyl)-2-oxo-acetamide (FP-82)

LC-MS (MET-uHPLC-AB-102): 99% (UV), Rt=2.49 min, m/z (ESI$^+$)=301.4 [M+H]$^+$
LC-MS (CAM-1): 97% (UV), Rt=1.89 min, >99% ee, m/z (ESI$^+$)=301.0 [M+H]$^+$
$^1$H NMR (500 MHz, Chloroform-d) δ 0.18-0.25 (m, 2H), 0.51-0.59 (m, 2H), 0.87-0.99 (m, 1H), 2.89 (dd, J=8.0, 13.7 Hz, 1H), 3.05-3.13 (m, 3H), 3.19-3.29 (m, 2H), 3.35 (t, J=9.4 Hz, 1H), 4.04-4.13 (m, 1H), 5.58 (s, 1H), 6.70-6.81 (m, 1H), 7.15-7.24 (m, 4H), 7.22-7.30 (m, 2H)

2-[(3R,4R)-4-Benzyl-5-oxopyrrolidin-3-yl]-N-(2,2-difluoroethyl)-2-oxoacetamide (FP-83), and 2-[(3S,4S)-4-Benzyl-5-oxopyrrolidin-3-yl]-N-(2,2-difluoroethyl)-2-oxoacetamide (FP-84) ((R,R) and (S,S) Assignments Arbitrary)

Rac-2-[(3R,4R)-4-benzyl-5-oxopyrrolidin-3-yl]-N-(2,2-difluoroethyl)-2-oxoacetamide (FP-4) (105 mg, 0.34 mmol) was purified by chiral separation on Berger SFC Prep [Column: Pirkle Covalent (R,R) Whelk-01 Kromasil (21.1 mm×250 mm, 5 μm) at 40° C.; Isocratic eluent: 85:15 CO$_2$:IPA; Flow rate: 50 mL/min; Detector wavelength: 220 nm; Dilution solvent: IPA; Injection volume: 100 μL]. The two compounds obtained were purified by FCC on normal phase silica (10 g SNAP Ultra cartridge, 0-100% EtOAc in heptane gradient) to afford 22 mg of 2-[(3R,4R)-4-benzyl-5-oxopyrrolidin-3-yl]-N-(2,2-difluoroethyl)-2-oxoacetamide as an off-white solid (99% purity, 99% ee, 21%) and 28 mg of 2-[(3S,4S)-4-benzyl-5-oxopyrrolidin-3-yl]-N-(2,2-difluoroethyl)-2-oxoacetamide as an off-white solid (98% purity, 96% ee, 26%). 2-[(3R,4R)-4-Benzyl-5-oxopyrrolidin-3-yl]-N-(2,2-difluoroethyl)-2-oxoacetamide (FP-83)

LC-MS (METCR1603): 100% (UV), Rt=2.79 min, m/z (ESI$^+$)=311.5 [M+H]$^+$
LC-MS (CAM-2): 99% (UV), Rt=9.66 min, 99% ee
$^1$H NMR (500 MHz, Chloroform-d) δ 2.85 (dd, J=8.4, 13.8 Hz, 1H), 3.10 (td, J=4.7, 8.2 Hz, 1H), 3.21-3.29 (m, 2H), 3.34-3.41 (m, 1H), 3.61 (ttd, J=3.9, 6.5, 14.8 Hz, 2H), 4.08 (ddd, J=7.1, 8.1, 9.0 Hz, 1H), 5.62 (s, 1H), 5.81 (tt, J=3.9, 55.4 Hz, 1H), 6.84-6.94 (m, 1H), 7.16-7.23 (m, 3H), 7.23-7.27 (m, 2H) 2-[(3S,4S)-4-Benzyl-5-oxopyrrolidin-3-yl]-N-(2,2-difluoroethyl)-2-oxoacetamide (FP-84)

LC-MS (METCR1603): 100% (UV), Rt=2.79 min, m/z (ESI$^+$)=311.5 [M+H]$^+$
LC-MS (CAM-2): 98% (UV), Rt=5.96 min, 96% ee
$^1$H NMR (500 MHz, Chloroform-d) δ 2.85 (dd, J=8.4, 13.8 Hz, 1H), 3.10 (td, J=4.7, 8.2 Hz, 1H), 3.21-3.29 (m, 2H), 3.33-3.41 (m, 1H), 3.61 (ttd, J=3.9, 6.5, 14.8 Hz, 2H), 4.08 (ddd, J=7.1, 8.1, 9.0 Hz, 1H), 5.61 (s, 1H), 5.81 (tt, J=3.9, 55.4 Hz, 1H), 6.82-6.95 (m, 1H), 7.16-7.22 (m, 3H), 7.23-7.27 (m, 2H)

N-(Cyclopropylmethyl)-2-oxo-2-[(3S,4R)-5-oxo-4-phenylpyrrolidin-3-yl]acetamide (FP-85) and N-(Cyclopropylmethyl)-2-oxo-2-[(3R,4S)-5-oxo-4-phenylpyrrolidin-3-yl]acetamide (FP-86) ((R,S) and (S,R) Assignments Arbitrary)

Rac-N-(cyclopropylmethyl)-2-oxo-2-[(3R,4S)-5-oxo-4-phenylpyrrolidin-3-yl]acetamide (FP-10) (90 mg, 0.31 mmol) was purified by chiral separation on Gilson LC [Column: Chiralpak AS (20 mm×250 mm, 10 μm) at RT; Isocratic eluent: MeCN; Flow rate: 8 mL/min; Detector wavelength: 215 nm; Dilution solvent: MeCN; Injection volume: 100-1000 μL]. The samples were dissolved in MeCN, transferred to vials, the solvent removed under a stream of air and the residues dried in vacuo at 40° C. to afford 27 mg of N-(cyclopropylmethyl)-2-oxo-2-[(3S,4R)-5-oxo-4-phenylpyrrolidin-3-yl]acetamide as an off-white gum (89% purity by $^1$H NMR, 100% ee, 27%) and 26 mg of N-(cyclopropylmethyl)-2-oxo-2-[(3R,4S)-5-oxo-4-phenylpyrrolidin-3-yl]acetamide as an off-white solid (91% purity by $^1$H NMR, 96% ee, 26%).

N-(Cyclopropylmethyl)-2-oxo-2-[(3S,4R)-5-oxo-4-phenylpyrrolidin-3-yl]acetamide (FP-85)

LC-MS (METCR1603): 100% (UV), Rt=3.28 min, m/z (ESI$^+$)=287.3 [M+H]$^+$
LC-MS (CAM-2): 99% (UV), Rt=4.55 min, 100% ee
$^1$H NMR (500 MHz, Chloroform-d) δ 0.15-0.19 (m, 2H), 0.47-0.52 (m, 2H), 0.87-0.98 (m, 1H), 3.05-3.11 (m, 2H), 3.31-3.37 (m, 1H), 3.90 (t, J=9.8 Hz, 1H), 4.02 (d, J=7.9 Hz, 1H), 4.22-4.31 (m, 1H), 7.02-7.11 (m, 1H), 7.22-7.27 (m, 3H), 7.27-7.33 (m, 2H), 7.39 (s, 1H)

N-(Cyclopropylmethyl)-2-oxo-2-[(3R,4S)-5-oxo-4-phenylpyrrolidin-3-yl]acetamide (FP-86)

LC-MS (METCR1603): 100% (UV), Rt=3.24 min, m/z (ESI$^+$)=287.2 [M+H]$^+$
LC-MS (CAM-2): 95% (UV), Rt=7.92 min, 96% ee
$^1$H NMR (500 MHz, Chloroform-d) δ 0.15-0.21 (m, 2H), 0.48-0.52 (m, 2H), 0.86-0.96 (m, 1H), 3.04-3.11 (m, 2H), 3.32-3.37 (m, 1H), 3.90 (t, J=9.8 Hz, 1H), 4.03 (d, J=7.9 Hz, 1H), 4.22-4.30 (m, 1H), 7.03-7.10 (m, 1H), 7.22-7.27 (m, 3H), 7.27-7.33 (m, 2H), 7.36 (s, 1H)

N-(2,2-Difluoropropyl)-2-oxo-2-[(3S,4R)-5-oxo-4-phenylpyrrolidin-3-yl]acetamide (FP-87) and N-(2,2-Difluoropropyl)-2-oxo-2-[(3R,4S)-5-oxo-4-phenylpyrrolidin-3-yl]acetamide (FP-88) ((R,S) and (S,R) Assignments Arbitrary)

Rac-N-(2,2-difluoropropyl)-2-oxo-2-[(3R,4S)-5-oxo-4-phenylpyrrolidin-3-yl]acetamide (FP-11) (90 mg, 0.31 mmol) was purified by chiral separation on Waters Investigator SFC [Column: Chiralcel OD-H (10 mm×250 mm, 5 µm) at 40° C.; Isocratic eluent: 7.5:2.5 CO$_2$:MeCN; Flow rate: 15 mL/min; Detector wavelength: 215/254 nm; Dilution solvent: MeCN; Injection volume: 250 µL]. The samples were dissolved in EtOAc, transferred to vials, the solvent removed under a stream of air and the residues dried in vacuo at 40° C. to afford 33 mg of N-(2,2-difluoropropyl)-2-oxo-2-[(3S,4R)-5-oxo-4-phenylpyrrolidin-3-yl]acetamide as an off-white solid (88% purity by $^1$H NMR, 97% ee, 27%) and 23 mg of N-(2,2-difluoropropyl)-2-oxo-2-[(3R,4S)-5-oxo-4-phenylpyrrolidin-3-yl]acetamide as an off-white solid (92% purity by $^1$H NMR, 100% ee, 20%).

N-(2,2-Difluoropropyl)-2-oxo-2-[(3S,4R)-5-oxo-4-phenylpyrrolidin-3-yl]acetamide (FP-87)

LC-MS (MET-uHPLC-AB-102): 100% (UV), Rt=1.99 min, m/z (ESI$^+$)=311.2 [M+H]$^+$

LC-MS (CAM-3): 99% (UV), Rt=4.08 min, 97% ee, m/z (ESI$^+$)=311.0 [M+H]$^+$ $^1$H NMR (500 MHz, Chloroform-d) δ 1.60 (t, J=18.4 Hz, 3H), 3.40-3.45 (m, 1H), 3.59-3.71 (m, 2H), 3.94 (t, J=9.7 Hz, 1H), 4.04 (d, J=7.9 Hz, 1H), 4.26-4.34 (m, 1H), 7.02-7.07 (m, 1H), 7.24-7.31 (m, 4H), 7.32-7.38 (m, 2H)

N-(2,2-Difluoropropyl)-2-oxo-2-[(3R,4S)-5-oxo-4-phenylpyrrolidin-3-yl]acetamide (FP-88)

LC-MS (MET-uHPLC-AB-102): 99% (UV), Rt=1.99 min, m/z (ESI$^+$)=311.2 [M+H]$^+$

LC-MS (CAM-3): 100% (UV), Rt=5.55 min, 100% ee, m/z (ESI$^+$)=311.0 [M+H]$^+$ $^1$H NMR (500 MHz, Chloroform-d) δ 1.61 (t, J=18.4 Hz, 3H), 3.41-3.49 (m, 1H), 3.62-3.71 (m, 2H), 3.96 (t, J=9.6 Hz, 1H), 4.05 (d, J=8.0 Hz, 1H), 4.27-4.37 (m, 1H), 6.48 (s, 1H), 7.19-7.25 (m, 1H), 7.27-7.31 (m, 3H), 7.31-7.38 (m, 2H)

2-[(3R,4R)-4-benzyl-5-oxo-1-(pyrimidin-5-yl)pyrrolidin-3-yl]-N-cyclopropyl-2-oxoacetamide (FP-89) and 2-[(3S,4S)-4-benzyl-5-oxo-1-(pyrimidin-5-yl)pyrrolidin-3-yl]-N-cyclopropyl-2-oxoacetamide (FP-90) ((R,R) and (S,S) Assignments Arbitrary)

Rac-2-[(3R,4R)-4-benzyl-5-oxo-1-(pyrimidin-5-yl)pyrrolidin-3-yl]-N-cyclopropyl-2-oxoacetamide (FP-54) (91% purity by $^1$H NMR, 148 mg, 0.37 mmol) was purified by chiral separation on Gilson LC [Column: Cellulose-4 (21.2 mm×250 mm, 5 µm) at RT; Isocratic eluent: MeCN; Flow rate: 18 mL/min; Detector wavelength; 215 nm; Dilution solvent: MeCN; injection volume: 100-1000 µL] to afford 74 mg of 2-[(3R,4R)-4-benzyl-5-oxo-1-(pyrimidin-5-yl)pyrrolidin-3-yl]-N-cyclopropyl-2-oxoacetamide as an off-white solid (98% purity, 100% ee, 55%) and a second product which was further purified by FCC on normal phase silica (10 g SNAP Ultra cartridge, 0-100% EtOAc in heptane gradient) to give 38 mg of 2-[(3S,4S)-4-benzyl-5-oxo-1-(pyrimidin-5-yl)pyrrolidin-3-yl]-N-cyclopropyl-2-oxoacetamide as an off-white solid (97% purity, 94% ee, 29%).

2-[(3R,4R)-4-benzyl-5-oxo-1-(pyrimidin-5-yl)pyrrolidin-3-yl]-N-cyclopropyl-2-oxoacetamide (FP-89)

LC-MS (METCR1603): 98% (UV), Rt=3.42 min, m/z (ESI$^+$)=365.1 [M+H]$^+$

LC-MS (CAM-4): 100% (UV), Rt=7.42 min, 100% ee $^1$H NMR (500 MHz, Chloroform-d) δ 0.53-0.65 (m, 2H), 0.83-0.92 (m, 2H), 2.70-2.78 (m, 1H), 3.06-3.14 (m, 1H), 3.27-3.35 (m, 2H), 3.61 (t, J=9.3 Hz, 1H), 3.72 (dd, J=6.3, 9.6 Hz, 1H), 4.10-4.17 (m, 1H), 6.76 (b.s, 1H), 7.19-7.28 (m, 5H), 9.01 (s, 1H), 9.01 (s, 2H)

2-[(3S,4S)-4-benzyl-5-oxo-1-(pyrimidin-5-yl)pyrrolidin-3-yl]-N-cyclopropyl-2-oxoacetamide (FP-90)

LC-MS (METCR1603): 100% (UV), Rt=3.44 min, m/z (ESI$^+$)=365.2 [M+H]$^+$

LC-MS (CAM-4): 97% (UV), Rt=10.27 min, 94% ee $^1$H NMR (500 MHz, Chloroform-d) δ 0.51-0.66 (m, 2H), 0.80-0.93 (m, 2H), 2.70-2.78 (m, 1H), 3.05-3.14 (m, 1H), 3.27-3.35 (m, 2H), 3.61 (t, J=9.3 Hz, 1H), 3.72 (dd, J=6.3, 9.6 Hz, 1H), 4.13 (dt, J=6.6, 9.0 Hz, 1H), 6.76 (b.s, 1H), 7.19-7.28 (m, 5H), 9.01 (s, 1H), 9.01 (s, 2H)

2-[(3R,4R)-3-benzyl-4-{[(2-methylpropyl)carbamoyl]carbonyl}-2-oxopyrrolidin-1-yl]-N,N-dimethylacetamide (FP-91) and 2-[(3S,4S)-3-benzyl-4-{[(2-methylpropyl)carbamoyl]-carbonyl}-2-oxopyrrolidin-1-yl]-N,N-dimethylacetamide (FP-92) ((R,R) and (S,S) Assignments Arbitrary)

Rac-2-[(3R,4R)-3-benzyl-4-{[(2-methylpropyl)carbamoyl]carbonyl}-2-oxopyrrolidin-1-yl]-N,N-dimethylacetamide (FP-44) (97% purity, 58.2 mg, 0.15 mmol) was purified by chiral separation on Gilson LC [Column: Cellulose-4 (21.2 mm×250 mm, 5 µm) at RT; Isocratic eluent: MeCN; Flow rate: 9 mL/min; Detector wavelength; 215 nm; Dilution solvent: MeCN; injection volume: 100-1000 µL] to afford 17 mg of 2-[(3R,4R)-3-benzyl-4-{[(2-methylpropyl)carbamoyl]carbonyl}-2-oxopyrrolidin-1-yl]-N,N-dimethylacetamide as a pale pink solid (100% purity, 100% ee, 30%) and 23 mg of 2-[(3S,4S)-3-benzyl-4-{[(2-methylpropyl)carbamoyl]carbonyl}-2-oxopyrrolidin-1-yl]-N,N-dimethylacetamide as a pale pink glass (97% purity, 94% ee, 39%).

2-[(3S,4S)-3-benzyl-4-{[(2-methylpropyl)carbamoyl]carbonyl}-2-oxopyrrolidin-1-yl]-N,N-dimethylacetamide (FP-91)

LC-MS (METCR1603): 100% (UV), Rt=3.68 min, m/z (ESI$^+$)=388.1 [M+H]$^+$

LC-MS (CAM-5): 100% (UV), Rt=21.98 min, 100% ee $^1$H NMR (500 MHz, Chloroform-d) δ 0.87-0.92 (m, 6H), 1.71-1.81 (m, 1H), 2.83-2.90 (m, 1H), 2.93 (s, 3H), 2.99 (s, 3H), 3.05 (t, J=6.6 Hz, 2H), 3.21-3.29 (m, 2H), 3.43 (dd, J=6.8, 9.6 Hz, 1H), 3.55 (t, J=9.5 Hz, 1H), 3.92 (d, J=16.1 Hz, 1H), 3.94-4.01 (m, 1H), 4.21 (d, J=16.1 Hz, 1H), 6.73 (t, J=6.6 Hz, 1H), 7.14-7.21 (m, 3H), 7.21-7.26 (m, 2H)

2-[(3R,4R)-3-benzyl-4-{[(2-methylpropyl)carbamoyl]carbonyl}-2-oxopyrrolidin-1-yl]-N,N-dimethylacetamide (FP-92)

LC-MS (METCR1603): 100% (UV), Rt=3.68 min, m/z (ESI+)=388.1 [M+H]+
LC-MS (CAM-5): 97% (UV), Rt=25.34 min, 94% ee
$^1$H NMR (500 MHz, Chloroform-d) δ 0.87-0.91 (m, 6H), 1.71-1.80 (m, 1H), 2.83-2.90 (m, 1H), 2.93 (s, 3H), 2.99 (s, 3H), 3.04 (t, J=6.6 Hz, 2H), 3.21-3.28 (m, 2H), 3.43 (dd, J=6.8, 9.6 Hz, 1H), 3.55 (t, J=9.5 Hz, 1H), 3.92 (d, J=16.1 Hz, 1H), 3.94-4.00 (m, 1H), 4.20 (d, J=16.1 Hz, 1H), 6.70-6.78 (m, 1H), 7.14-7.20 (m, 3H), 7.21-7.25 (m, 2H)

2-[(3R,4R)-4-benzyl-5-oxo-1-(pyrazin-2-yl)pyrrolidin-3-yl]-N-cyclopropyl-2-oxo-acetamide (FP-93), and 2-[(3S,4R)-4-benzyl-5-oxo-1-(pyrazin-2-yl)pyrrolidin-3-yl]-N-cyclopropyl-2-oxoacetamide (FP-94) ((R,R) and (S,S) Assignments Arbitrary)

Rac-2-[(3R,4R)-4-benzyl-5-oxo-1-(pyrazin-2-yl)pyrrolidin-3-yl]-N-cyclopropyl-2-oxoacetamide (FP-57) (50.0 mg, 0.137 mmol) was purified by chiral separation on Gilson LC [Column: Amylose-2 (21.2 mm×250 mm, 5 μm) at RT; Isocratic eluent: MeCN; Flow rate: 18 mL/min; Detector wavelength; 215 nm; Dilution solvent: MeCN; injection volume: 100-1000 μL] to afford 22 mg of 2-[(3R,4R)-4-benzyl-5-oxo-1-(pyrazin-2-yl)pyrrolidin-3-yl]-N-cyclopropyl-2-oxoacetamide as a yellow sticky solid (93% purity, 100% ee, 41%) and 20 mg of 2-[(3S,4R)-4-benzyl-5-oxo-1-(pyrazin-2-yl)pyrrolidin-3-yl]-N-cyclopropyl-2-oxoacetamide as a yellow sticky solid (100% purity, 100% ee, 40%).
2-[(3R,4R)-4-benzyl-5-oxo-1-(pyrazin-2-yl)pyrrolidin-3-yl]-N-cyclopropyl-2-oxoacetamide (FP-93)

LC-MS (METCR1603): 100% (UV), Rt=3.84 min, m/z (ESI+)=365.2 [M+H]+
LC-MS (CAM-6): 93% (UV), Rt=4.39 min, 100% ee
$^1$H NMR (500 MHz, Chloroform-d) δ 0.52-0.60 (m, 2H), 0.81-0.91 (m, 2H), 2.69-2.75 (m, 1H), 3.00 (dd, J=8.1, 13.8 Hz, 1H), 3.34 (dd, J=4.9, 13.7 Hz, 1H), 3.41 (td, J=4.9, 8.0 Hz, 1H), 3.83 (dd, J=7.1, 11.3 Hz, 1H), 4.05 (dd, J=9.2, 11.2 Hz, 1H), 4.09-4.18 (m, 1H), 6.69 (s, 1H), 7.17-7.22 (m, 3H), 7.22-7.25 (m, 2H), 8.27 (dd, J=1.6, 2.6 Hz, 1H), 8.32 (d, J=2.6 Hz, 1H), 9.74 (d, J=1.5 Hz, 1H) 2-[(3S,4S)-4-benzyl-5-oxo-1-(pyrazin-2-yl)pyrrolidin-3-yl]-N-cyclopropyl-2-oxoacetamide (FP-94)

LC-MS (METCR1603): 100% (UV), Rt=3.82 min, m/z (ESI+)=365.2 [M+H]+
LC-MS (CAM-6): 100% (UV), Rt=7.84 min, 100% ee
$^1$H NMR (500 MHz, Chloroform-d) δ 0.50-0.62 (m, 2H), 0.78-0.92 (m, 2H), 2.68-2.75 (m, 1H), 3.00 (dd, J=8.1, 13.8 Hz, 1H), 3.34 (dd, J=4.9, 13.8 Hz, 1H), 3.38-3.44 (m, 1H), 3.83 (dd, J=7.1, 11.3 Hz, 1H), 4.05 (dd, J=9.2, 11.2 Hz, 1H), 4.10-4.17 (m, 1H), 6.69 (s, 1H), 7.17-7.22 (m, 3H), 7.22-7.26 (m, 2H), 8.27 (dd, J=1.6, 2.5 Hz, 1H), 8.32 (d, J=2.6 Hz, 1H), 9.74 (d, J=1.4 Hz, 1H)

2-[(3R,4R)-4-benzyl-5-oxo-1-(pyrimidin-5-yl)pyrrolidin-3-yl]-N-(2,2-difluoropropyl)-2-oxoacetamide (FP-95), and 2-[(3S,4S)-4-benzyl-5-oxo-1-(pyrimidin-5-yl)pyrrolidin-3-yl]-N-(2,2-difluoropropyl)-2-oxoacetamide (FP-96) ((R,R) and (S,S) Assignments Arbitrary)

Rac-2-[(3R,4R)-4-benzyl-5-oxo-1-(pyrimidin-5-yl)pyrrolidin-3-yl]-N-(2,2-difluoropropyl)-2-oxoacetamide (FP-56) (83 mg, 0.21 mmol) was purified by chiral separation on Gilson LC [Column: Cellulose-4 (21.2 mm×250 mm, 5 μm) at RT; Isocratic eluent: MeCN; Flow rate: 10 mL/min; Detector wavelength; 215 nm; Dilution solvent: MeCN; injection volume: 100-1000 μL] to afford 18 mg of 2-[(3R,4R)-4-benzyl-5-oxo-1-(pyrimidin-5-yl)pyrrolidin-3-yl]-N-(2,2-difluoropropyl)-2-oxoacetamide as a yellow sticky solid (98% purity, 100% ee, 21%) and 16 mg of 2-[(3S,4S)-4-benzyl-5-oxo-1-(pyrimidin-5-yl)pyrrolidin-3-yl]-N-(2,2-difluoropropyl)-2-oxoacetamide as a yellow sticky solid (92% purity, 84% ee, 18%).

2-[(3R,4R)-4-benzyl-5-oxo-1-(pyrimidin-5-yl)pyrrolidin-3-yl]-N-(2,2-difluoropropyl)-2-oxoacetamide (FP-95)

LC-MS (METCR1603): 98% (UV), Rt=1.53 min, m/z (ESI+)=403.1 [M+H]+
LC-MS (CAM-5): 100% (UV), Rt=10.16 min, 100% ee
$^1$H NMR (500 MHz, Chloroform-d) δ 1.63 (t, J=18.4 Hz, 3H), 3.04-3.13 (m, 1H), 3.27-3.36 (m, 2H), 3.56-3.71 (m, 3H), 3.73 (dd, J=6.4, 9.6 Hz, 1H), 4.13 (dt, J=6.5, 8.9 Hz, 1H), 7.03 (t, J=5.9 Hz, 1H), 7.17-7.28 (m, 5H), 9.01 (s, 3H)

2-[(3S,4S)-4-benzyl-5-oxo-1-(pyrimidin-5-yl)pyrrolidin-3-yl]-N-(2,2-difluoropropyl)-2-oxoacetamide D3801 (FP-96)

LC-MS (METCR1603): 100% (UV), Rt=1.54 min, m/z (ESI+)=403.1 [M+H]+
LC-MS (CAM-5): 92% (UV), Rt=12.54 min, 84% ee
$^1$H NMR (500 MHz, Chloroform-d) δ 1.63 (t, J=18.4 Hz, 3H), 3.03-3.13 (m, 1H), 3.26-3.37 (m, 2H), 3.59-3.77 (m, 4H), 4.13 (dt, J=6.6, 8.9 Hz, 1H), 7.03 (t, J=6.0 Hz, 1H), 7.17-7.29 (m, 5H), 8.99-9.03 (m, 3H)

2-[(3S,4S)-4-benzyl-1-[(1-methyl-1H-1,2,4-triazol-5-yl)methyl]-5-oxopyrrolidin-3-yl]-N-cyclopropyl-2-oxoacetamide (FP-97), and 2-[(3R,4R)-4-benzyl-1-[(1-methyl-1H-1,2,4-triazol-5-yl)methyl]-5-oxopyrrolidin-3-yl]-N-cyclopropyl-2-oxoacetamide (FP-98) ((R,R) and (S,S) Assignments Arbitrary)

Rac-2-[(3R,4R)-4-benzyl-1-[(1-methyl-1H-1,2,4-triazol-5-yl)methyl]-5-oxopyrrolidin-3-yl]-N-cyclopropyl-2-oxoacetamide (FP-42) (98% purity, 63 mg, 0.16 mmol) was purified by chiral separation on Gilson LC [Column: Cellulose-4 (21.2 mm×250 mm, 5 μm) at RT; Isocratic eluent: MeCN; Flow rate: 10 mL/min; Detector wavelength; 215 nm; Dilution solvent: MeCN; injection volume: 100-1000 μL] to afford 10 mg of 2-[(3S,4S)-4-benzyl-1-[(1-methyl-1H-1,2,4-triazol-5-yl)methyl]-5-oxopyrrolidin-3-yl]-N-cyclopropyl-2-oxoacetamide as a pale yellow viscous oil (95% purity by $^1$H NMR, 100% ee, 15%) and 9 mg of 2-[(3R,4R)-4-benzyl-1-[(1-methyl-1H-1,2,4-triazol-5-yl)methyl]-5-oxopyrrolidin-3-yl]-N-cyclopropyl-2-oxoacetamide as a pale yellow viscous oil (95% purity by $^1$H NMR, 96% ee, 14%). 2-[(3S,4S)-4-benzyl-1-[(1-methyl-1H-1,2,4-triazol-5-yl)methyl]-5-oxopyrrolidin-3-yl]-N-cyclopropyl-2-oxoacetamide (FP-97)

LC-MS (METCR1603): 100% (UV), Rt=3.16 min, m/z (ESI+)=382.2 [M+H]+
LC-MS (CAM-5): 97% (UV), Rt=15.83 min, 100% ee
$^1$H NMR (500 MHz, Chloroform-d) δ 0.50-0.57 (m, 2H), 0.80-0.86 (m, 2H), 2.66-2.73 (m, 1H), 2.96 (dd, J=7.1, 13.6 Hz, 1H), 3.05-3.10 (m, 1H), 3.15-3.26 (m, 3H), 3.87 (s, 3H), 3.93-3.98 (m, 1H), 4.53 (d, J=15.2 Hz, 1H), 4.59 (d, J=15.2 Hz, 1H), 6.74 (s, 1H), 7.12-7.16 (m, 2H), 7.16-7.21 (m, 3H), 7.76 (s, 1H) 2-[(3R,4R)-4-benzyl-1-[(1-methyl-1H-1,2,4-triazol-5-yl)methyl]-5-oxopyrrolidin-3-yl]-N-cyclopropyl-2-oxoacetamide (FP-98)

LC-MS (METCR1603): 100% (UV), Rt=3.17 min, m/z (ESI+)=382.2 [M+H]+

LC-MS (CAM-5): 94% (UV), Rt=21.13 min, 96% ee $^1$H NMR (500 MHz, Chloroform-d) δ 0.51-0.56 (m, 2H), 0.80-0.86 (m, 2H), 2.66-2.73 (m, 1H), 2.96 (dd, J=7.1, 13.6 Hz, 1H), 3.04-3.10 (m, 1H), 3.16-3.26 (m, 3H), 3.87 (s, 3H), 3.93-3.98 (m, 1H), 4.53 (d, J=15.2 Hz, 1H), 4.59 (d, J=15.3 Hz, 1H), 6.74 (s, 1H), 7.12-7.16 (m, 2H), 7.16-7.23 (m, 3H), 7.76 (s, 1H)

General Procedure 1 (General Scheme 4):
Reduction & Deprotection 1,4-Diethyl 2-(aminomethyl)-3-phenylbutanedioate hydrochloride (I-107)

To a solution of 1,4-diethyl 2-cyano-3-phenylbutanedioate (I-6) (20 g, 67.56 mmol) in EtOH (600 mL) cooled at 0° C. was added Boc$_2$O (36.9 g, 168.9 mmol) and NiCl$_2$.6H$_2$O (24.1 g, 101.34 mmol) followed by NaBH$_4$ (25.6 g, 675.6 mmol) portionwise over 2 min. The reaction was stirred at RT for 1 h, cooled to 10° C. and ethylene diamine (50 mL)

GENERAL SCHEME 4

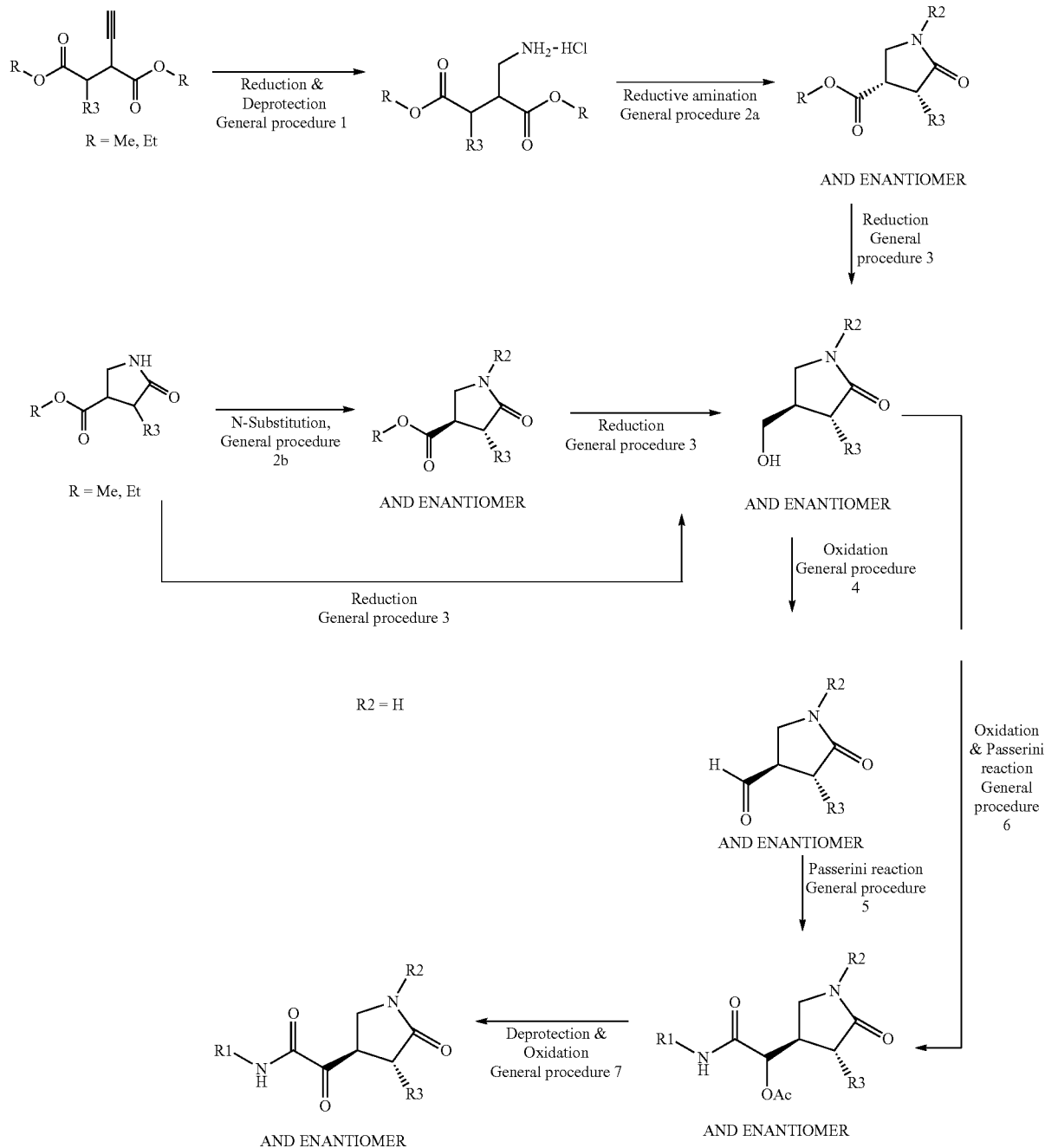

added. The mixture was stirred at 10° C. for 1 h, sat. NaHCO₃ (200 mL) added and the mixture stirred at RT for 10 min. The suspension was diluted with EtOAc (200 mL) and ethylene diamine (100 mL), stirred at RT until a purple solution was obtained. Brine (200 mL) was added and the phases separated. The aqueous layer was extracted with EtOAc (3×300 mL) and the combined organic extracts were washed with brine (2×200 mL), dried over MgSO₄ and concentrated in vacuo. The orange oil was dissolved in 4N HCl in 1,4-dioxane (100 mL, 400 mmol) and stirred at RT for 18 h. The resulting precipitate was filtered off to afford 7.66 g of 1,4-diethyl 2-(aminomethyl)-3-phenylbutanedioate hydrochloride as an off-white solid (100% purity, 36%) which was used in the next step without further purification.

LC-MS (METCR0990): 100% (UV), Rt=1.59 min, m/z (ESI⁺)=280.2 [M+H]⁺

General Procedure 2a (General Scheme 4): Reductive Amination

Rac-ethyl (3R,4R)-1-benzyl-5-oxo-4-phenylpyrrolidine-3-carboxylate (I-108)

A suspension of 1,4-diethyl 2-(aminomethyl)-3-phenylbutanedioate hydrochloride (I-6) (500 mg, 1.58 mmol) and benzaldehyde (168 mg, 1.58 mmol) in 1,2-DCE (10 mL) was stirred for 5 min then STAB (671 mg, 3.18 mmol) was added in one portion and the mixture stirred at RT for 18 h. Sat. NaHCO₃ (20 mL) and DCM (20 mL) were added and the phases separated. The aqueous phase was extracted with DCM (3×15 mL) and the combined organic phases washed with brine (30 mL), dried over MgSO₄ and concentrated in vacuo. The residue was purified by FCC on normal phase silica (25 g SNAP KP-SIL cartridge, 0-100% EtOAc in heptane gradient) to afford 153 mg of rac-ethyl (3R,4R)-1-benzyl-5-oxo-4-phenylpyrrolidine-3-carboxylate as an off-white solid (92% purity, 27%).

LC-MS (METCR1410): 92% (UV), Rt=1.13 min, m/z (ESI⁺)=324.0 [M+H]⁺

¹H NMR (500 MHz, Chloroform-d) δ 0.81 (t, J=7.2 Hz, 3H), 3.36-3.44 (m, 1H), 3.53-3.59 (m, 1H), 3.59-3.67 (m, 1H), 3.67-3.73 (m, 1H), 3.75-3.82 (m, 1H), 4.05 (d, J=10.2 Hz, 1H), 4.49 (d, J=14.6 Hz, 1H), 4.68 (d, J=14.6 Hz, 1H), 7.07-7.13 (m, 2H), 7.19-7.28 (m, 3H), 7.28-7.43 (m, 5H)

General Procedure 2b (General Scheme 4): N-Substitution on Ester

Method A: N-Alkylation Using NaH in DMF

Rac-ethyl (3R,4S)-1-[(5-methyl-1,2-oxazol-3-yl)methyl]-5-oxo-4-phenylpyrrolidine-3-carboxylate (I-109)

To a solution of ethyl 5-oxo-4-phenylpyrrolidine-3-carboxylate (I-17) (500 mg, 2.14 mmol) in DMF (4 mL) cooled at 0° C. was added NaH (60% in mineral oil, 103 mg, 2.57 mmol) portionwise. 3-(Bromomethyl)-5-methyl-1,2-oxazole (215 mg, 2.36 mmol) was added and the mixture stirred at 0° C. for 30 min then at RT for 30 min. The reaction was quenched with MeOH (5 mL), diluted with 1M HCl (5 mL) and the aqueous layer extracted with DCM (3×20 mL). The combined organic extracts were concentrated in vacuo and the residue purified by preparative LC (acidic pH, early elution method) to afford 401 mg of rac-ethyl (3R,4S)-1-[(5-methyl-1,2-oxazol-3-yl)methyl]-5-oxo-4-phenylpyrrolidine-3-carboxylate as a colourless viscous oil (99% purity, 56%).

LC-MS (METCR1410): 99% (UV), Rt=1.08 min, m/z (ESI⁺)=329.0 [M+H]⁺

¹H NMR (500 MHz, Chloroform-d) δ 1.21 (t, J=7.1 Hz, 3H), 2.42 (d, J=0.8 Hz, 3H), 3.24-3.31 (m, 1H), 3.55 (dd, J=7.7, 9.9 Hz, 1H), 3.70 (dd, J=9.0, 9.8 Hz, 1H), 4.02 (d, J=8.7 Hz, 1H), 4.11-4.19 (m, 2H), 4.55 (d, J=15.1 Hz, 1H), 4.60 (d, J=15.1 Hz, 1H), 5.98 (d, J=0.8 Hz, 1H), 7.21-7.26 (m, 2H), 7.26-7.32 (m, 1H), 7.32-7.38 (m, 2H)

Method B: N-Alkylation Using NaH in THF Followed by Hydrolysis and Methyl Ester Formation Rac-ethyl (3R,4S)-1-[(4-methoxyphenyl)methyl]-5-oxo-4-phenylpyrrolidine-3-carboxylate (I-110)

To a solution of ethyl 5-oxo-4-phenylpyrrolidine-3-carboxylate (I-17) (1 g, 4.29 mmol) in THF (30 mL) cooled at 0° C. was added NaH (60% in mineral oil, 343 mg, 8.57 mmol) portionwise and the suspension stirred at 0° C. for 30 min. 1-(chloromethyl)-4-methoxybenzene (786 μL, 4.716 mmol) was added dropwise at 0° C. over 10 min and the mixture stirred at RT for 1 h. The reaction was quenched with water (10 mL) then 2M NaOH (20 mL) was added and the mixture heated at 50° C. for 2 h. THF was removed in vacuo and the suspension acidified to pH ~3 with 2M HCl then extracted with DCM (3×20 mL). The combined organic extracts were washed with brine (30 mL), dried over MgSO₄, filtered and concentrated in vacuo. The resulting solid was dissolved in MeOH (20 mL) and conc. H₂SO₄ (100 μL) added. The solution was heated at 60° C. for 1 h then concentrated in vacuo. The residue was purified by FCC on normal phase silica (25 g SNAP KP-SIL cartridge, 0-100% EtOAc in heptane gradient) to afford 350 mg of rac-ethyl (3R,4S)-1-[(4-methoxyphenyl)methyl]-5-oxo-4-phenylpyrrolidine-3-carboxylate as a yellow viscous oil (98% purity, 24%).

LC-MS (METCR1410): 98% (UV), Rt=1.11 min, m/z (ESI⁺)=340.1 [M+H]⁺

¹H NMR (500 MHz, Chloroform-d) δ 3.22-3.31 (m, 1H), 3.43-3.50 (m, 1H), 3.54-3.58 (m, 1H), 3.70 (s, 3H), 3.84 (s, 3H), 4.07 (d, J=8.7 Hz, 1H), 4.44 (d, J=14.5 Hz, 1H), 4.59 (d, J=14.5 Hz, 1H), 6.89-6.93 (m, 2H), 7.20-7.33 (m, 5H), 7.33-7.41 (m, 2H)

General Procedure 3 (General Scheme 4): Reduction

Rac-(3R,4S)-1-benzyl-4-(hydroxymethyl)-3-phenylpyrrolidin-2-one (I-111)

To a solution of rac-ethyl (3R,4R)-1-benzyl-5-oxo-4-phenylpyrrolidine-3-carboxylate (I-108) (140 mg, 0.43 mmol) in EtOH (10 mL) was added NaBH₄ (33 mg, 0.87 mmol) and the mixture stirred at RT for 18 h. The reaction was quenched with water (10 mL) and extracted with EtOAc (3×20 mL). The combined organic extracts were washed with brine (20 mL), dried over MgSO₄, filtered and concentrated in vacuo to afford 118 mg of rac-(3R,4S)-1-benzyl-4-(hydroxymethyl)-3-phenylpyrrolidin-2-one as a viscous colourless oil (89% purity, 86%).

LC-MS (METCR1410): 89% (UV), Rt=1.02 min, m/z (ESI⁺)=282.5 [M+H]⁺

¹H NMR (500 MHz, Chloroform-d) δ 2.39-2.55 (m, 2H), 3.17 (dd, J=7.1, 9.9 Hz, 1H), 3.39 (dd, J=8.2, 9.9 Hz, 1H), 3.51 (dd, J=4.0, 9.5 Hz, 2H), 3.60 (dd, J=4.7, 10.7 Hz, 1H), 4.42 (d, J=14.6 Hz, 1H), 4.61 (d, J=14.6 Hz, 1H), 7.16-7.20 (m, 2H), 7.21-7.39 (m, 8H)

Rac-(3R,4S)-4-(hydroxymethyl)-1-[(5-methyl-1,2-oxazol-3-yl)methyl]-3-phenylpyrrolidin-2-one (I-112)

The title compound was synthesized from rac-ethyl (3R, 4S)-1-[(5-methyl-1,2-oxazol-3-yl)methyl]-5-oxo-4-phenylpyrrolidine-3-carboxylate (I-109) in a similar manner to general procedure 3 (general scheme 4) as a viscous colourless oil (197 mg, 97% purity, 57%) after purification by preparative LC (acidic pH, early elution method).

LC-MS (METCR1410): 97% (UV), Rt=0.91 min, m/z (ESI⁺)=287.1 [M+H]⁺

¹H NMR (500 MHz, Chloroform-d) δ 2.42 (d, J=0.8 Hz, 3H), 2.47-2.57 (m, 1H), 2.92 (s, 1H), 3.31 (dd, J=7.0, 9.7 Hz, 1H), 3.51-3.58 (m, 3H), 3.63 (dd, J=4.4, 10.9 Hz, 1H), 4.50-4.59 (m, 2H), 5.98 (d, J=0.7 Hz, 1H), 7.13-7.23 (m, 2H), 7.23-7.28 (m, 1H), 7.29-7.37 (m, 2H)

Rac-(3R,4S)-4-(hydroxymethyl)-1-[(4-methoxyphenyl)methyl]-3-phenylpyrrolidin-2-one (I-113)

The title compound was synthesized from rac-ethyl (3R, 4S)-1-[(4-methoxyphenyl)methyl]-5-oxo-4-phenylpyrrolidine-3-carboxylate (I-110) in a similar manner to general procedure 3 (general scheme 4) as a viscous colourless oil (320 mg, 98% purity by ¹H NMR, 98%) after work-up and used in the next step without further purification.

LC-MS (METCR1410): 83% (UV), Rt=1.01 min, m/z (ESI⁺)=312.1 [M+H]⁺

¹H NMR (500 MHz, Chloroform-d) δ 2.06 (s, 1H), 2.49-2.60 (m, 1H), 3.21 (dd, J=9.9, 7.1 Hz, 1H), 3.47 (dd, J=9.8, 8.3 Hz, 1H), 3.56 (d, J=8.3 Hz, 1H), 3.63 (dd, J=10.7, 6.8 Hz, 1H), 3.73 (dd, J=10.8, 4.7 Hz, 1H), 3.87 (s, 3H), 4.44 (d, J=14.4 Hz, 1H), 4.60 (d, J=14.4 Hz, 1H), 6.94 (d, J=8.6 Hz, 2H), 7.22-7.34 (m, 5H), 7.35-7.44 (m, 2H)

Rac-(3R,4S)-4-(hydroxymethyl)-3-phenylpyrrolidin-2-one (I-114)

The title compound was synthesized from ethyl 5-oxo-4-phenylpyrrolidine-3-carboxylate (I-17) in a similar manner to general procedure 3 (general scheme 4) as an off-white solid (1.27 g, 95% purity, 92%) after work-up and used in the next step without further purification.

LC-MS (METCR1410): 95% (UV), Rt=0.67 min, m/z (ESI⁺)=192.3 [M+H]⁺

¹H NMR (500 MHz, Methanol-d4) δ 2.57-2.66 (m, 1H), 3.28-3.36 (m, 2H), 3.49 (d, J=8.7 Hz, 1H), 3.54-3.61 (m, 2H), 3.65 (dd, J=4.7, 11.1 Hz, 1H), 7.22-7.29 (m, 3H), 7.31-7.37 (m, 2H)

General Procedure 4 (General Scheme 4): Oxidation

Rac-(3R,4S)-1-[(4-methoxyphenyl)methyl]-5-oxo-4-phenylpyrrolidine-3-carbaldehyde (I-115)

To a solution of rac-(3R,4S)-4-(hydroxymethyl)-1-[(4-methoxyphenyl)methyl]-3-phenylpyrrolidin-2-one (I-113) (280 mg, 0.90 mmol) in DCM (20 mL) was added DMP (458 mg, 1.08 mmol) and the suspension stirred at RT for 3 h. Further DMP (458 mg, 1.08 mmol) was added and the mixture stirred at RT for 18 h. The suspension was then concentrated in vacuo, diluted with EtOAc (20 mL) and washed with sat. NaHCO₃ (10 mL) and 1M Na₂SO₃ (10 mL). The aqueous phase was extracted with EtOAc (3×10 mL) and the combined organic extracts washed with brine (20 mL), dried over MgSO₄ and concentrated in vacuo to afford 290 mg of rac-(3R,4S)-1-[(4-methoxy-phenyl)methyl]-5-oxo-4-phenylpyrrolidine-3-carbaldehyde as an off-white crystalline solid (95% purity by ¹H NMR, 99%).

¹H NMR (500 MHz, Chloroform-d) δ 3.22-3.31 (m, 1H), 3.50 (dd, J=8.7, 10.2 Hz, 1H), 3.57 (dd, J=6.3, 10.3 Hz, 1H), 3.81 (s, 3H), 3.99 (d, J=7.4 Hz, 1H), 4.40 (d, J=14.5 Hz, 1H), 4.57 (d, J=14.5 Hz, 1H), 6.86-6.92 (m, 2H), 7.19-7.22 (m, 2H), 7.22-7.25 (m, 2H), 7.27-7.32 (m, 1H), 7.32-7.39 (m, 2H), 9.73 (d, J=1.0 Hz, 1H)

General Procedure 5 (General Scheme 4): Passerini Reaction

Rac-(cyclopropylcarbamoyl)[(3R,4S)-1-[(4-methoxyphenyl)methyl]-5-oxo-4-phenylpyrrolidin-3-yl]methyl acetate (I-116)

To a solution of rac-(3R,4S)-1-[(4-methoxyphenyl)methyl]-5-oxo-4-phenylpyrrolidine-3-carbaldehyde (I-115) (92 mg, 0.30 mmol) in DCM (5 mL) was added cyclopropylisocyanide (18 mg, 0.26 mmol) and the reaction stirred at RT for 5 min. Glacial acetic acid (23 µL, 0.52 mmol) was added and the mixture stirred at RT for 1 h. Sat. NaHCO₃ (10 mL) was added and the aqueous phase extracted with DCM (3×10 mL). The combined organic extracts were washed with sat. NaHCO₃ (10 mL) and brine (20 mL), dried over MgSO₄ and concentrated in vacuo. The residue was purified by FCC on normal phase silica (25 g SNAP KP-SIL cartridge, 0-100% EtOAc in heptane gradient) to afford 86 mg of rac-(cyclopropylcarbamoyl)[(3R,4S)-1-[(4-methoxyphenyl)methyl]-5-oxo-4-phenylpyrrolidin-3-yl]methyl acetate as as colourless viscous oil (92% purity, 69%).

LC-MS (METCR1410): 92% (UV), Rt=1.06 min, m/z (ESI⁺)=437.2 [M+H]⁺

¹H NMR (500 MHz, Chloroform-d) δ 0.27-0.39 (m, 2H), 0.65-0.73 (m, 2H), 2.11 (s, 3H), 2.49-2.53 (m, 1H), 2.88-2.95 (m, 1H), 3.20 (dd, J=7.0, 10.4 Hz, 1H), 3.31-3.36 (m, 1H), 3.49-3.53 (m, 1H), 3.83 (s, 3H), 4.33 (dd, J=10.4, 14.4 Hz, 1H), 4.61 (d, J=14.5 Hz, 1H), 5.10 (d, J=4.2 Hz, 1H), 6.35 (s, 1H), 6.87-6.93 (m, 2H), 7.13-7.18 (m, 2H), 7.19-7.24 (m, 2H), 7.24-7.30 (m, 1H), 7.30-7.37 (m, 2H)

General Procedure 6 (General Scheme 4): Oxidation & Passerini Reaction

Rac-[(3R,4S)-1-benzyl-5-oxo-4-phenylpyrrolidin-3-yl](cyclopropylcarbamoyl)methyl acetate (I-117)

To a solution of rac-(3R,4S)-1-benzyl-4-(hydroxymethyl)-3-phenylpyrrolidin-2-one (I-111) (99 mg, 0.352 mmol) in DCM (10 mL) was added DMP (224 mg, 0.53 mmol) and the suspension stirred at RT for 2 h. Cyclopropylisocyanide (28 mg, 0.42 mmol) was then added and the reaction stirred at RT for 1 h. The mixture was filtered and the filtrate washed successively with sat. NaHCO₃ (2×10 mL), 1M Na₂S₂O₃ (10 mL) and brine (10 mL) then dried over MgSO₄, filtered and concentrated in vacuo. The residue was purified by FCC on normal phase silica (25 g SNAP KP-SIL cartridge, 0-100% EtOAc in heptane gradient followed by 0-50% MeOH in EtOAc gradient) to afford 126 mg of rac-[(3R,4S)-1-benzyl-5-oxo-4-phenylpyrrolidin-3-yl](cyclopropyl-carbamoyl)methyl acetate as an off-white solid (43% purity, 38%).

LC-MS (METCR1410): 43% (UV), Rt=1.06 min, m/z (ESI$^+$)=407.1 [M+H]$^+$

Rac-(cyclopropylcarbamoyl)[(3R,4S)-1-[(5-methyl-1,2-oxazol-3-yl)methyl]-5-oxo-4-phenylpyrrolidin-3-yl]methyl acetate (I-118)

The title compound was synthesized from rac-(3R,4S)-4-(hydroxymethyl)-1-[(5-methyl-1,2-oxazol-3-yl)methyl]-3-phenylpyrrolidin-2-one (I-112) in a similar manner to general procedure 6 (general scheme 4) as a viscous colourless oil (127 mg, 61% purity, 47%) after purification by FCC on normal phase silica (25 g SNAP KP-SIL cartridge, 0-100% EtOAc in heptane gradient).

LC-MS (METCR1410): 61% (UV), Rt=0.97 min, m/z (ESI$^+$)=412.1 [M+H]$^+$ $^1$H NMR (500 MHz, Chloroform-d) δ 0.30-0.44 (m, 2H), 0.68-0.77 (m, 2H), 1.94-2.13 (m, 3H), 2.41-2.43 (m, 3H), 2.53-2.63 (m, 1H), 2.97-3.12 (m, 1H), 3.33-3.55 (m, 2H), 3.59-3.71 (m, 1H), 4.41-4.67 (m, 2H), 5.14-5.25 (m, 1H), 5.93-5.98 (m, 1H), 6.14-6.25 (m, 1H), 7.12-7.19 (m, 2H), 7.23-7.29 (m, 1H), 7.31-7.36 (m, 2H)

Rac-[(3R,4S)-1-[(5-methyl-1,2-oxazol-3-yl)methyl]-5-oxo-4-phenylpyrrolidin-3-yl][(propan-2-yl)carbamoyl]methyl acetate (I-119)

The title compound was synthesized from rac-(3R,4S)-4-(hydroxymethyl)-1-[(5-methyl-1,2-oxazol-3-yl)methyl]-3-phenylpyrrolidin-2-one (I-112) in a similar manner to general procedure 6 (general scheme 4) as a viscous colourless oil (31 mg, 87% purity, 41%) after purification by FCC on normal phase silica (10 g SNAP Ultra cartridge, 0-100% EtOAc in heptane gradient).

LC-MS (METCR1410): 87% (UV), Rt=1.01 min, m/z (ESI$^+$)=414.2 [M+H]$^+$ $^1$H NMR (500 MHz, Chloroform-d) δ 1.04-1.10 (m, 6H), 1.94-2.13 (m, 3H), 2.38-2.42 (m, 3H), 2.96-3.12 (m, 1H), 3.34-3.53 (m, 2H), 3.57-3.72 (m, 1H), 3.88-4.00 (m, 1H), 4.41-4.66 (m, 2H), 5.14-5.24 (m, 1H), 5.87 (dd, J=7.8, 33.9 Hz, 1H), 5.93-5.97 (m, 1H), 7.12-7.19 (m, 2H), 7.27-7.36 (m, 3H)

Rac-(butylcarbamoyl)[(3R,4S)-5-oxo-4-phenylpyrrolidin-3-yl]methyl acetate (I-120)

The title compound was synthesized from rac-(3R,4S)-4-(hydroxymethyl)-3-phenylpyrrolidin-2-one (I-114) in a similar manner to general procedure 6 (general scheme 4) as an off-white solid (297 mg, 100% purity, 43%) after purification by FCC on normal phase silica (25 g SNAP KP-SIL cartridge, 0-100% EtOAc in heptane gradient followed by 0-50% MeOH in EtOAc gradient).

LC-MS (METCR1410): 100% (UV), Rt=1.45 min, m/z (ESI$^+$)=333.2 [M+H]$^+$ $^1$H NMR (500 MHz, Chloroform-d) δ 0.83-0.92 (m, 3H), 1.20-1.31 (m, 2H), 1.32-1.44 (m, 2H), 1.93-2.18 (m, 3H), 3.02-3.24 (m, 3H), 3.27-3.61 (m, 3H), 5.13-5.38 (m, 1H), 6.09-6.22 (m, 1H), 6.98-7.07 (m, 1H), 7.15-7.21 (m, 2H), 7.22-7.29 (m, 1H), 7.30-7.36 (m, 2H)

General Procedure 7 (General Scheme 4): Deprotection & Oxidation

Rac-2-[(3R,4S)-1-benzyl-5-oxo-4-phenylpyrrolidin-3-yl]-N-cyclopropyl-2-oxoacetamide (FP-99)

To a solution of rac-[(3R,4S)-1-benzyl-5-oxo-4-phenylpyrrolidin-3-yl](cyclo-propylcarbamoyl)methyl acetate (I-117) (43% purity, 126 mg, 0.13 mmol) in MeOH (2 mL) was added K$_2$CO$_3$ (50 mg, 0.362 mmol) and the mixture stirred at RT for 30 min. The suspension was filtered and the filtrate concentrated in vacuo. The residue was dissolved in DCM (5 mL) and DMP (224 mg, 0.53 mmol) added. The suspension was stirred at RT for 5 h then sat. NaHCO$_3$ (10 mL) was added and the phases separated. The aqueous layer was extracted with DCM (3×20 mL) and the combined organic phases washed sequentially with sat. NaHCO$_3$ (20 mL), 1M Na$_2$S$_2$O$_3$ (20 mL) and brine (30 mL) then dried over MgSO$_4$, filtered and concentrated in vacuo. The residue was purified by FCC on normal phase silica (25 g SNAP KP-SIL cartridge, 0-100% EtOAc in heptane gradient) followed by preparative LC (basic pH, early elute method) to afford 10 mg of rac-2-[(3R,4S)-1-benzyl-5-oxo-4-phenylpyrrolidin-3-yl]-N-cyclopropyl-2-oxoacetamide as a colourless viscous oil (97% purity, 21%).

LC-MS (METCR1603): 97% (UV), Rt=4.03 min, m/z (ESI$^+$)=363.1 [M+H]$^+$ $^1$H NMR (500 MHz, Chloroform-d) δ 0.52-0.58 (m, 2H), 0.78-0.85 (m, 2H), 2.67-2.75 (m, 1H), 3.22-3.28 (m, 1H), 3.80-3.85 (m, 1H), 4.11-4.17 (m, 2H), 4.50 (d, J=14.6 Hz, 1H), 4.59 (d, J=14.6 Hz, 1H), 6.94 (s, 1H), 7.24-7.28 (m, 5H), 7.29-7.37 (m, 5H)

Rac-N-cyclopropyl-2-[(3R,4S)-1-[(5-methyl-1,2-oxazol-3-yl)methyl]-5-oxo-4-phenylpyrrolidin-3-yl]-2-oxoacetamide (FP-100)

The title compound was synthesized from rac-(cyclopropylcarbamoyl)[(3R,4S)-1-[(5-methyl-1,2-oxazol-3-yl)methyl]-5-oxo-4-phenylpyrrolidin-3-yl]methyl acetate (I-118) in a similar manner to general procedure 7 (general scheme 4) as an off-white solid (32 mg, 100% purity, 45%) after purification by FCC on normal phase silica (10 g SNAP Ultra cartridge, 0-100% EtOAc in heptane gradient) and further washes with 1M Na$_2$S$_2$O$_3$.

LC-MS (METCR1603): 100% (UV), Rt=3.49 min, m/z (ESI$^+$)=368.1 [M+H]$^+$ $^1$H NMR (500 MHz, Chloroform-d) δ 0.52-0.63 (m, 2H), 0.78-0.88 (m, 2H), 2.42 (d, J=0.7 Hz, 3H), 2.71-2.78 (m, 1H), 3.39 (dd, J=6.8, 10.2 Hz, 1H), 3.91-3.97 (m, 1H), 4.09 (d, J=7.6 Hz, 1H), 4.17-4.23 (m, 1H), 4.54 (d, J=15.2 Hz, 1H), 4.60 (d, J=15.2 Hz, 1H), 5.97 (d, J=0.8 Hz, 1H), 6.94 (s, 1H), 7.23-7.29 (m, 3H), 7.31-7.37 (m, 2H)

Rac-2-[(3R,4S)-1-[(5-methyl-1,2-oxazol-3-yl)methyl]-5-oxo-4-phenylpyrrolidin-3-yl]-2-oxo-N-(propan-2-yl)acetamide (FP-101)

The title compound was synthesized from rac-[(3R,4S)-1-[(5-methyl-1,2-oxazol-3-yl)methyl]-5-oxo-4-phenylpyrrolidin-3-yl][(propan-2-yl)carbamoyl]methyl acetate (I-119) in a similar manner to general procedure 7 (general scheme 4) as an off-white solid (16 mg, 100% purity, 69%) after purification by FCC on normal phase silica (10 g SNAP Ultra cartridge, 0-100% EtOAc in heptane gradient).

LC-MS (METCR1603): 100% (UV), Rt=3.76 min, m/z (ESI⁺)=370.1 [M+H]⁺

¹H NMR (500 MHz, Chloroform-d) δ 1.15-1.21 (m, 6H), 2.42 (d, J=0.6 Hz, 3H), 3.39 (dd, J=6.8, 10.2 Hz, 1H), 3.91-3.97 (m, 1H), 3.97-4.04 (m, 1H), 4.10 (d, J=7.6 Hz, 1H), 4.17-4.23 (m, 1H), 4.54 (d, J=15.2 Hz, 1H), 4.60 (d, J=15.2 Hz, 1H), 5.97 (d, J=0.5 Hz, 1H), 6.74 (d, J=7.8 Hz, 1H), 7.22-7.29 (m, 3H), 7.31-7.35 (m, 2H)

Rac-N-cyclopropyl-2-[(3R,4S)-1-[(4-methoxyphenyl)methyl]-5-oxo-4-phenylpyrrolidin-3-yl]-2-oxoacetamide (FP-102)

The title compound was synthesized from rac-(cyclopropylcarbamoyl)[(3R,4S)-1-[(4-methoxyphenyl)methyl]-5-oxo-4-phenylpyrrolidin-3-yl]methyl acetate (I-116) in a Rac-N-butyl-2-oxo-2-[(3R,4S)-5-oxo-4-phenylpyrrolidin-3-yl]acetamide (FP-103)

The title compound was synthesized from rac-(butylcarbamoyl)[(3R,4S)-5-oxo-4-phenylpyrrolidin-3-yl]methyl acetate (I-120) in a similar manner to general procedure 7 (general scheme 4) as an off-white solid (23 mg, 100% purity, 10%) after purification by FCC on normal phase silica (10 g SNAP Ultra cartridge, 0-100% EtOAc in heptane gradient) followed by preparative LC (basic pH, standard elution method).

LC-MS (METCR1603): 100% (UV), Rt=3.41 min, m/z (ESI⁺)=289.2 [M+H]⁺

¹H NMR (500 MHz, DMSO-d₆) 50.85 (t, J=7.4 Hz, 3H), 1.19-1.28 (m, 2H), 1.37-1.46 (m, 2H), 3.04-3.15 (m, 2H), 3.32-3.35 (m, 1H), 3.66-3.73 (m, 2H), 4.07-4.19 (m, 1H), 7.23-7.28 (m, 3H), 7.29-7.36 (m, 2H), 7.95 (s, 1H), 8.65-8.77 (m, 1H)

GENERAL SCHEME 5

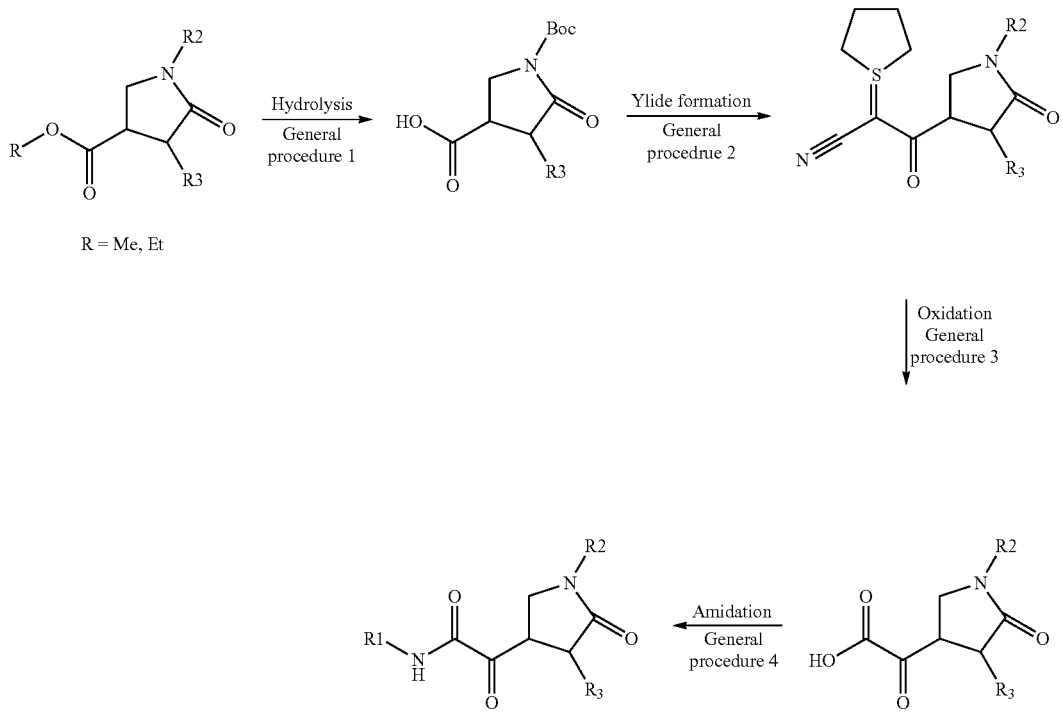

R = Me, Et similar manner to general procedure 7 (general scheme 4) as a colourless viscous oil (23 mg, 98% purity, 72%) after purification by FCC on normal phase silica (10 g SNAP Ultra cartridge, 0-100% EtOAc in heptane gradient).

LC-MS (METCR1603): 98% (UV), Rt=4.02 min, m/z (ESI⁺)=393.2 [M+H]⁺

¹H NMR (500 MHz, Chloroform-d) δ 0.50-0.57 (m, 2H), 0.78-0.84 (m, 2H), 2.66-2.75 (m, 1H), 3.20-3.25 (m, 1H), 3.77-3.82 (m, 4H), 4.07-4.13 (m, 2H), 4.42 (d, J=14.5 Hz, 1H), 4.51 (d, J=14.5 Hz, 1H), 6.84-6.90 (m, 2H), 6.94 (s, 1H), 7.17-7.21 (m, 2H), 7.21-7.27 (m, 3H), 7.27-7.33 (m, 2H)

General Procedure 1 (General Scheme 5): Hydrolysis

1-Benzyl-5-oxopyrrolidine-3-carboxylic acid (I-121)

To a solution of methyl 1-benzyl-5-oxo-pyrrolidine-3-carboxylate (5.0 g, 21.43 mmol) in 1:1:1 THF:water:MeOH (120 mL) was added LiOH monohydrate (1.35 g, 32.17 mmol) and the reaction stirred at RT for 45 min. The mixture was concentrated in vacuo to a volume of ~30 mL, diluted with water (30 mL) and washed with Et₂O (40 mL). The aqueous layer was acidified to ~pH 1 with 6N HCl and extracted with DCM (2×40 mL). The combined organic layers were dried over Na$_2$SO$_4$ and concentrated in vacuo to afford 4.67 g of 1-benzyl-5-oxo-pyrrolidine-3-carboxylic acid as an off-white solid (86% purity, 85%) which was used in the next step without further purification.

LC-MS (METCR1410): 86% (UV), Rt=0.84 min, m/z (ESI$^+$)=220.2 [M+H]$^+$ $^1$H NMR (500 MHz, DMSO-d$_6$) δ 2.47-2.53 (m, 1H), 2.59 (dd, J=9.7, 16.9 Hz, 1H), 3.17-3.25 (m, 1H), 3.36 (dd, J=5.5, 9.9 Hz, 1H), 3.45 (dd, J=8.9, 9.8 Hz, 1H), 4.33 (d, J=15.0 Hz, 1H), 4.41 (d, J=15.0 Hz, 1H), 7.19-7.23 (m, 2H), 7.25-7.30 (m, 1H), 7.32-7.36 (m, 2H)

General Procedure 2 (General Scheme 5): Ylide Formation 3-(1-Benzyl-5-oxopyrrolidin-3-yl)-3-oxo-2-(1λ$^4$-thiolan-1-ylidene)propanenitrile (I-122)

To a solution of 1-benzyl-5-oxo-pyrrolidine-3-carboxylic acid (I-121) (86% purity, 1.5 g, 5.88 mmol) and DIPEA (3.94 mL, 22.62 mmol) in DCM (30 mL) was added HATU (2.91 g, 7.65 mmol) and 1-(cyanomethyl)thiolan-1-ium bromide (90% purity, 1.60 g, 6.92 mmol, synthesized by the procedure outlined in Note 1, general experimental details. The mixture was stirred at RT under nitrogen for 1 h then quenched with sat. NH$_4$Cl (50 mL). The aqueous layer was extracted with DCM (2×40 mL) and the combined organic layers were washed with brine (30 mL), dried over Na$_2$SO$_4$ and concentrated in vacuo. The residue was purified by FCC on normal phase silica (100 g SNAP KP-SIL cartridge, 0-100% EtOAc in heptane gradient then 0-25% MeOH in EtOAc gradient) to afford 2.19 g of 3-(1-benzyl-5-oxopyrrolidin-3-yl)-3-oxo-2-(1λ$^4$-thiolan-1-ylidene)propanenitrile as a brown viscous oil (87% purity by $^1$H NMR, 99%).

LC-MS (METCR1410): 98% (UV), Rt=0.88 min, m/z (ESI$^+$)=329.0 [M+H]$^+$ $^1$H NMR (500 MHz, Chloroform-d) δ 2.05-2.13 (m, 2H), 2.53-2.67 (m, 3H), 2.77 (dd, J=7.7, 17.0 Hz, 1H), 3.25-3.41 (m, 5H), 3.44 (t, J=9.3 Hz, 1H), 3.56-3.64 (m, 1H), 4.38-4.44 (m, 1H), 4.45-4.50 (m, 1H), 7.20-7.24 (m, 2H), 7.24-7.34 (m, 3H).

General Procedure 3 (General Scheme 5): Oxidation 2-(1-Benzyl-5-oxopyrrolidin-3-yl)-2-oxoacetic acid (I-123)

To an ice-cooled solution of 3-(1-benzyl-5-oxopyrrolidin-3-yl)-3-oxo-2-(1λ4-thiolan-1-ylidene)propanenitrile (I-122) (87% purity by $^1$H NMR, 2.18 g, 5.77 mmol) in 2:1 THF/water (45 mL) was added at 0° C. Oxone (7.1 g, 11.55 mmol) in one portion. The mixture was stirred at 0° C. for 45 min, quenched slowly with 1N HCl (30 mL) and extracted with EtOAc (50 mL). The organic layer was washed with 1N HCl (30 mL) and the combined aqueous layers extracted with EtOAc (2×30 mL). The combined organic extracts were dried over Na$_2$SO$_4$ and concentrated in vacuo to give 1.86 g of 2-(1-benzyl-5-oxo-pyrrolidin-3-yl)-2-oxo-acetic acid as a yellow oil (51% purity by $^1$H NMR, 66%) which was used in the next step without further purification.

LC-MS (METCR1410): 76% (UV), Rt=0.73 min, m/z (ESI$^+$)=248.0 [M+H]$^+$ $^1$H NMR (250 MHz, Chloroform-d) δ 2.70-2.94 (m, 2H), 3.45-3.66 (m, 2H), 3.84-4.04 (m, 1H), 4.36-4.48 (m, 1H), 4.48-4.59 (m, 1H), 7.17-7.26 (m, 2H), 7.27-7.40 (m, 3H).

General Procedure 4 (General Scheme 5): Amidation 2-(1-Benzyl-5-oxopyrrolidin-3-yl)-N-cyclopropyl-2-oxoacetamide (FP-104)

To a cooled solution of 2-(1-benzyl-5-oxopyrrolidin-3-yl)-2-oxoacetic acid (I-123) (51% purity by $^1$H NMR, 520 mg, 1.07 mmol) in DMF (10 mL) was added cyclopropylamine (0.15 mL, 2.16 mmol), DIPEA (0.58 mL, 3.33 mmol) and T3P (50% in DMF, 1.9 mL, 3.22 mmol) in quick succession. The mixture was stirred at RT under nitrogen for 45 min, diluted with EtOAc (30 mL) and washed with water (3×15 mL). The combined aqueous layers were washed with EtOAc (20 mL) and the combined organic extracts were washed with brine (20 mL), dried over Na$_2$SO$_4$ and concentrated in vacuo. The residue was purified by FCC on normal phase silica (10 g SNAP KP-SIL cartridge, 0-65% EtOAc in heptane gradient then 0-25% MeOH in EtOAc gradient) followed by preparative LC (acidic pH, standard elution method) to afford 57 mg of 2-(1-benzyl-5-oxo-pyrrolidin-3-yl)-N-cyclopropyl-2-oxo-acetamide as a colourless oil (100% purity, 19%).

LC-MS (METCR1603): 100% (UV), Rt=3.32 min, m/z (ESI$^+$)=287.2 [M+H]$^+$ $^1$H NMR (500 MHz, Chloroform-d) δ 0.52-0.64 (m, 2H), 0.80-0.90 (m, 2H), 2.70-2.79 (m, 3H), 3.36 (dd, J=5.8, 10.4 Hz, 1H), 3.61 (dd, J=9.4, 10.3 Hz, 1H), 4.09 (qd, J=5.8, 8.4 Hz, 1H), 4.39-4.50 (m, 2H), 6.95 (br. s, 1H), 7.19-7.24 (m, 2H), 7.26-7.35 (m, 3H).

TABLE 1

Intermediates (I-1-I-123)

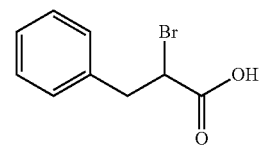 [SMILES: O=C(O)C(Br)Cc1ccccc1]

I-1

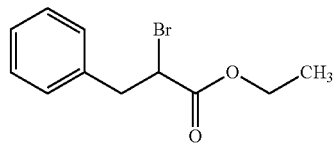

I-2

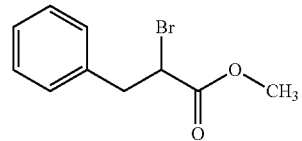

I-3

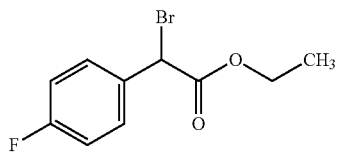

I-4

TABLE 1-continued
Intermediates (I-1-I-123)
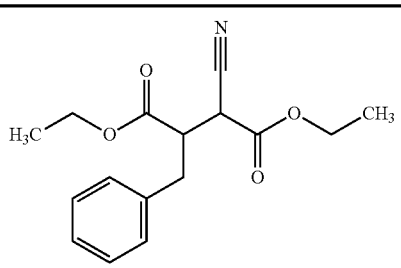 I-5
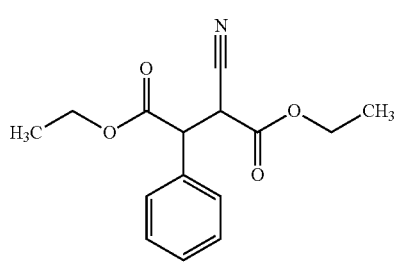 [SMILES: CCOC(=O)C(C#N)C(C(=O)OCC)c1ccccc1] I-6
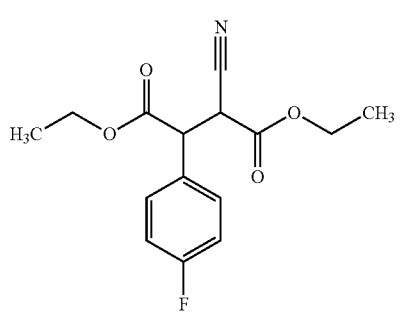 [SMILES: CCOC(=O)C(C#N)C(C(=O)OCC)c1ccc(F)cc1] I-7
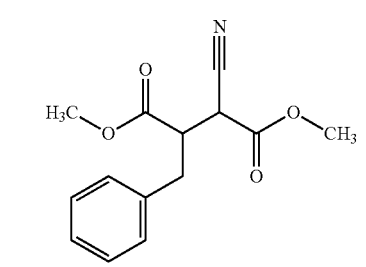 I-8
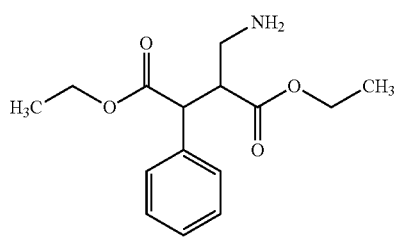 [SMILES: CCOC(=O)C(CN)C(C(=O)OCC)c1ccccc1] I-9
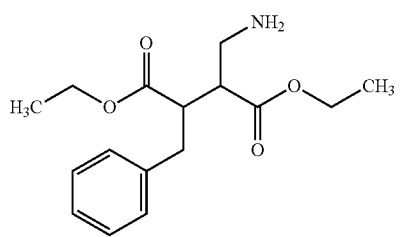 [SMILES: CCOC(=O)C(CN)C(Cc1ccccc1)C(=O)OCC] I-10
TABLE 1-continued
Intermediates (I-1-I-123)
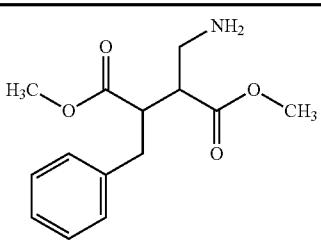 I-11
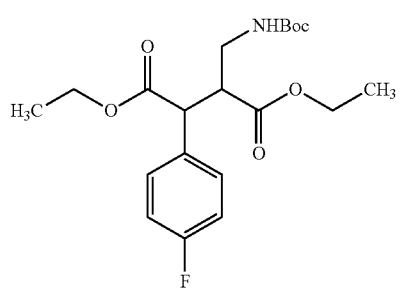 [SMILES: CCOC(=O)C(CNC(=O)OC(C)(C)C)C(C(=O)OCC)c1ccc(F)cc1] I-12
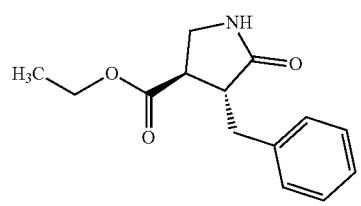 [SMILES: CCOC(=O)[C@H]1CNC(=O)[C@@H]1Cc1ccccc1] I-13
AND ENANTIOMER
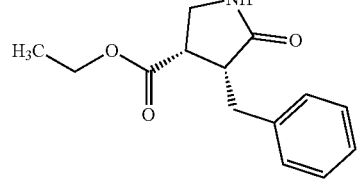 I-14
AND ENANTIOMER
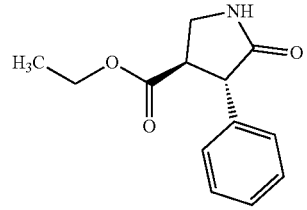 [SMILES: CCOC(=O)[C@H]1CNC(=O)[C@@H]1c1ccccc1] I-15
AND ENANTIOMER
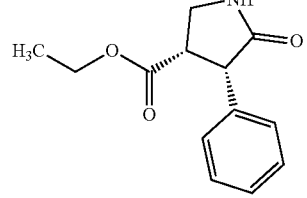 I-16
AND ENANTIOMER TABLE 1-continued
Intermediates (I-1-I-123)
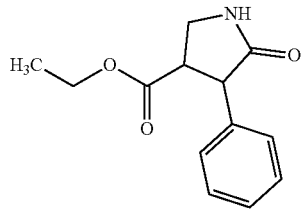 [SMILES: CCOC(=O)C1CNC(=O)C1c1ccccc1] I-17
 I-18
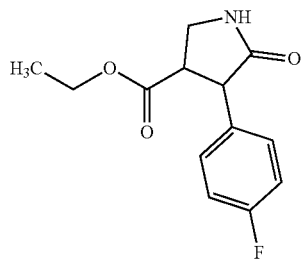 [SMILES: CCOC(=O)C1CNC(=O)C1c1ccc(F)cc1] I-19
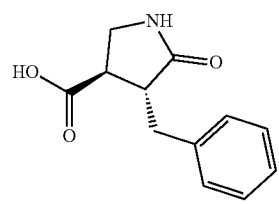 [SMILES: O=C(O)[C@H]1CNC(=O)[C@@H]1Cc1ccccc1] I-20
AND ENANTIOMER
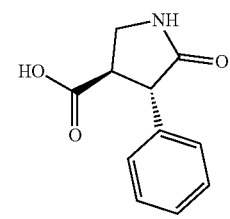 I-21
AND ENANTIOMER
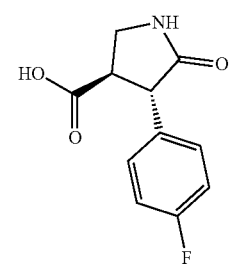 [SMILES: O=C(O)[C@H]1CNC(=O)[C@@H]1c1ccc(F)cc1] I-22
AND ENANTIOMER
TABLE 1-continued
Intermediates (I-1-I-123)
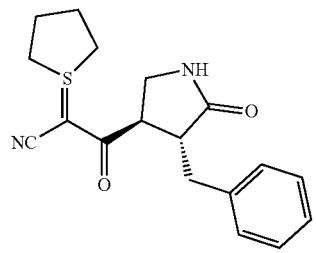 [SMILES: N#CC(C(=O)[C@H]1CNC(=O)[C@@H]1Cc1ccccc1)=S1CCCC1] I-23
AND ENANTIOMER
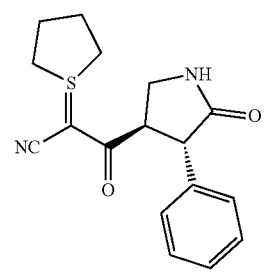 [SMILES: N#CC(C(=O)[C@H]1CNC(=O)[C@@H]1c1ccccc1)=S1CCCC1] I-24
AND ENANTIOMER
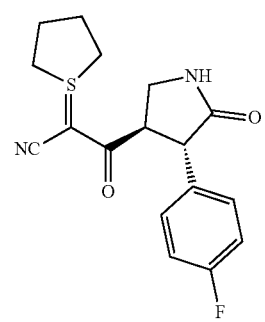 [SMILES: N#CC(C(=O)[C@H]1CNC(=O)[C@@H]1c1ccc(F)cc1)=S1CCCC1] I-25
AND ENANTIOMER
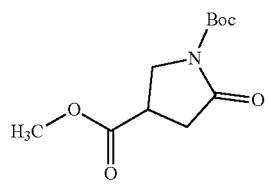 I-26
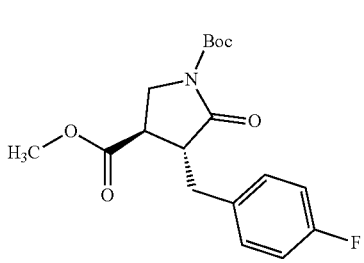 [SMILES: COC(=O)[C@H]1CN(C(=O)OC(C)(C)C)C(=O)[C@@H]1Cc1ccc(F)cc1] I-27
AND ENANTIOMER TABLE 1-continued
Intermediates (I-1-I-123)
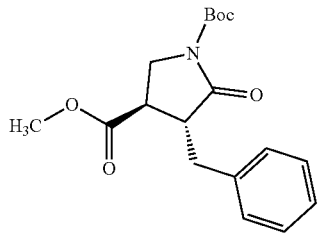 [SMILES: COC(=O)[C@H]1CN(C(=O)OC(C)(C)C)C(=O)[C@@H]1Cc1ccccc1]
AND ENANTIOMER
I-28
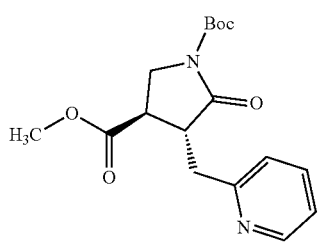 [SMILES: COC(=O)[C@H]1CN(C(=O)OC(C)(C)C)C(=O)[C@@H]1Cc1ccccn1]
AND ENANTIOMER
I-29
AND ENANTIOMER
I-30
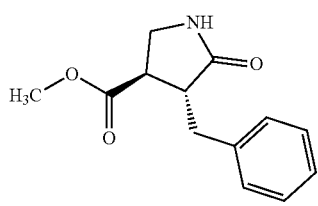 [SMILES: COC(=O)[C@H]1CNC(=O)[C@@H]1Cc1ccccc1]
AND ENANTIOMER
I-31
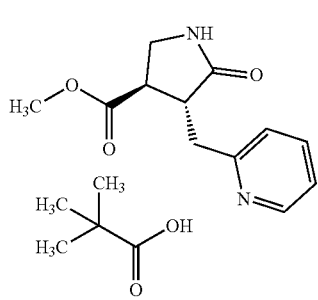
AND ENANTIOMER
I-32
TABLE 1-continued
Intermediates (I-1-I-123)
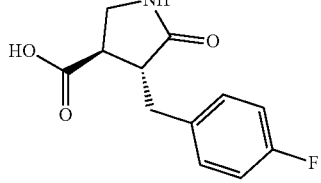
AND ENANTIOMER
I-33
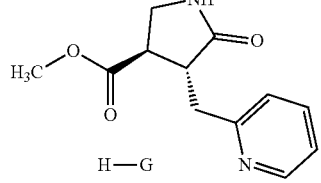
H—G
AND ENANTIOMER
I-34
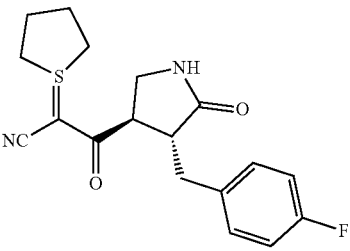 [SMILES: N#CC(C(=O)[C@H]1CNC(=O)[C@@H]1Cc1ccc(F)cc1)=S1CCCC1]
AND ENANTIOMER
I-35
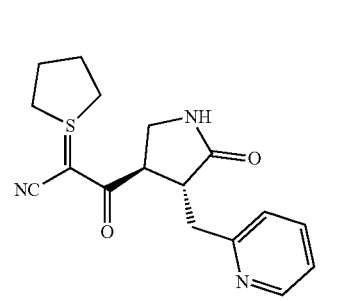 [SMILES: N#CC(C(=O)[C@H]1CNC(=O)[C@@H]1Cc1ccccn1)=S1CCCC1]
AND ENANTIOMER
I-36
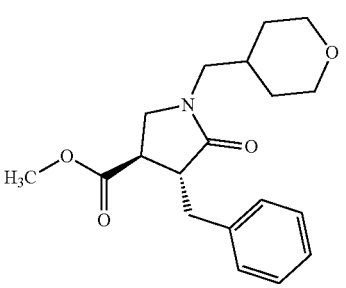 [SMILES: COC(=O)[C@H]1CN(CC2CCOCC2)C(=O)[C@@H]1Cc1ccccc1]
AND ENANTIOMER
I-37

TABLE 1-continued
Intermediates (I-1-I-123)
I-38
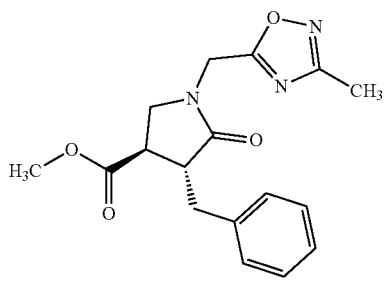
AND ENANTIOMER
I-39
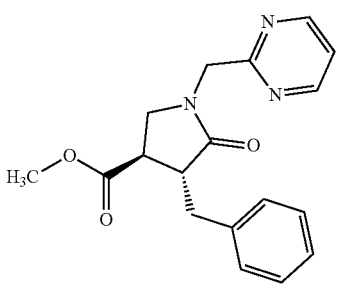 [SMILES: COC(=O)[C@H]1CN(Cc2ncccn2)C(=O)[C@@H]1Cc1ccccc1]
AND ENANTIOMER
I-40
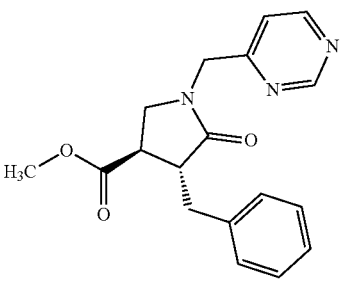 [SMILES: COC(=O)[C@H]1CN(Cc2ccncn2)C(=O)[C@@H]1Cc1ccccc1]
AND ENANTIOMER
I-41
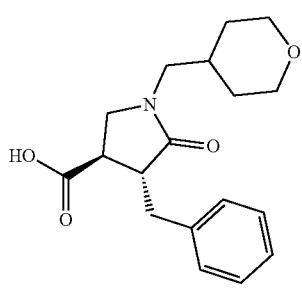 [SMILES: O=C(O)[C@H]1CN(CC2CCOCC2)C(=O)[C@@H]1Cc1ccccc1]
AND ENANTIOMER
I-42
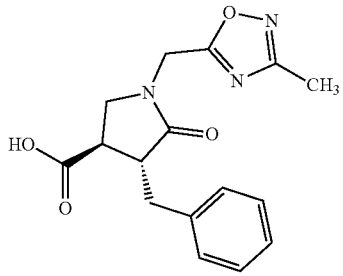 [SMILES: Cc1noc(CN2C[C@H](C(=O)O)[C@@H](Cc3ccccc3)C2=O)n1]
AND ENANTIOMER
I-43
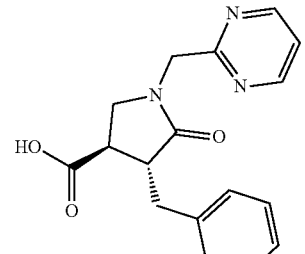
AND ENANTIOMER
I-44
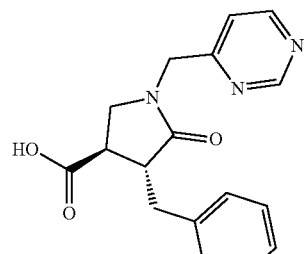
AND ENANTIOMER
I-45
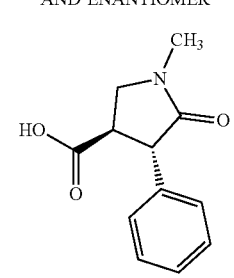
AND ENANTIOMER
I-46
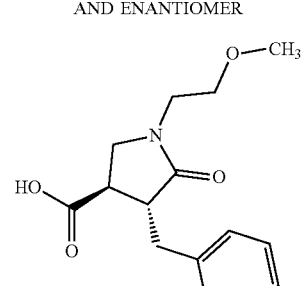
AND ENANTIOMER

TABLE 1-continued

Intermediates (I-1-I-123)

I-47: (structure with carboxylic acid, pyrrolidinone, N-CH2C(O)NH2, and benzyl substituents)
AND ENANTIOMER I-48: (structure with tetrahydrothiophene-ylidene, cyano, ketone, pyrrolidinone, N-CH2-tetrahydropyran, and benzyl)
AND ENANTIOMER I-49: (structure with tetrahydrothiophene-ylidene, cyano, ketone, pyrrolidinone, N-CH2-(3-methyl-1,2,4-oxadiazol-5-yl), and benzyl)
AND ENANTIOMER I-50: (structure with tetrahydrothiophene-ylidene, cyano, ketone, pyrrolidinone, N-CH2-pyrimidin-2-yl, and benzyl)
AND ENANTIOMER I-51: (structure with tetrahydrothiophene-ylidene, cyano, ketone, pyrrolidinone, N-CH2-pyrimidin-4-yl, and benzyl)
AND ENANTIOMER I-52: (structure with tetrahydrothiophene-ylidene, cyano, ketone, pyrrolidinone, N-CH3, and cyclohexyl)
AND ENANTIOMER I-53: (structure with tetrahydrothiophene-ylidene, cyano, ketone, pyrrolidinone, N-CH2CH2OCH3, and benzyl)
AND ENANTIOMER I-54: (structure with tetrahydrothiophene-ylidene, cyano, ketone, pyrrolidinone, N-CH2C(O)NH2, and benzyl)
AND ENANTIOMER I-55: (structure with tetrahydrothiophene-ylidene, cyano, ketone, pyrrolidinone, N-CH2-(5-methylisoxazol-3-yl), and benzyl)
AND ENANTIOMER TABLE 1-continued
Intermediates (I-1-I-123)
I-56
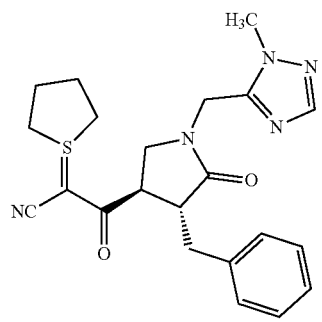 [SMILES: Cn1ncnc1CN1C[C@H](C(=O)C(C#N)=S2CCCC2)[C@@H](Cc2ccccc2)C1=O]
AND ENANTIOMER
I-57
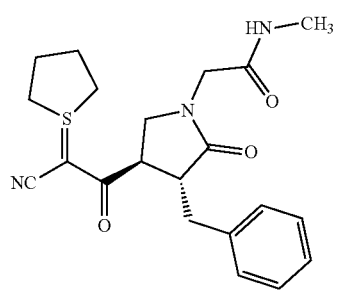 [SMILES: CNC(=O)CN1C[C@H](C(=O)C(C#N)=S2CCCC2)[C@@H](Cc2ccccc2)C1=O]
AND ENANTIOMER
I-58
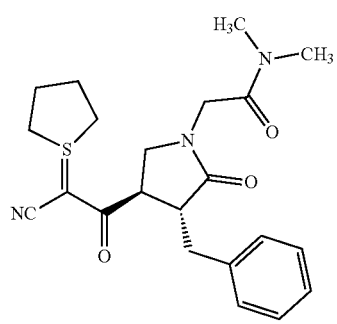 [SMILES: CN(C)C(=O)CN1C[C@H](C(=O)C(C#N)=S2CCCC2)[C@@H](Cc2ccccc2)C1=O]
AND ENANTIOMER
I-59
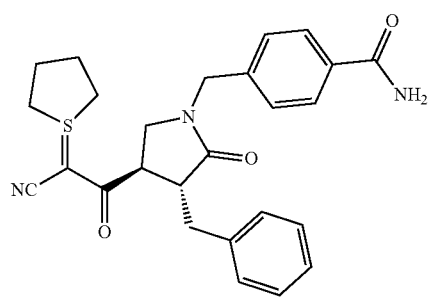 [SMILES: N#CC(C(=O)[C@H]1CN(Cc2ccc(C(N)=O)cc2)C(=O)[C@@H]1Cc1ccccc1)=S1CCCC1]
AND ENANTIOMER
TABLE 1-continued
Intermediates (I-1-I-123)
I-60
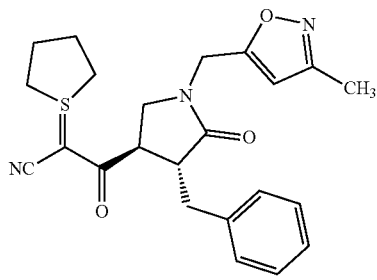 [SMILES: Cc1cc(CN2C[C@H](C(=O)C(C#N)=S3CCCC3)[C@@H](Cc3ccccc3)C2=O)on1]
AND ENANTIOMER
I-61
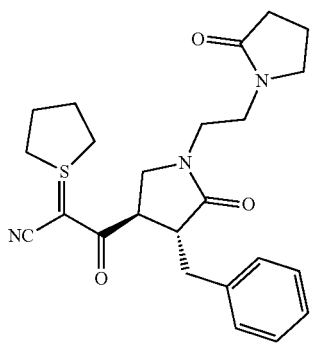 [SMILES: N#CC(C(=O)[C@H]1CN(CCN2CCCC2=O)C(=O)[C@@H]1Cc1ccccc1)=S1CCCC1]
AND ENANTIOMER
I-62
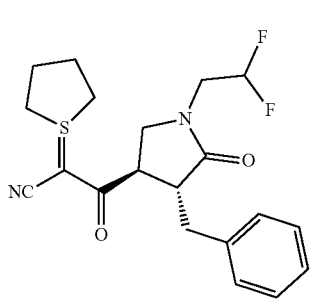 [SMILES: N#CC(C(=O)[C@H]1CN(CC(F)F)C(=O)[C@@H]1Cc1ccccc1)=S1CCCC1]
AND ENANTIOMER
I-63
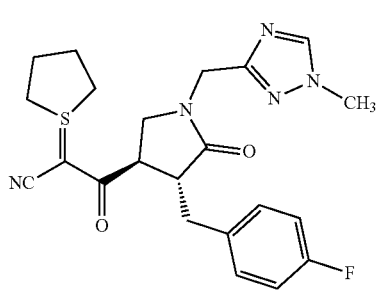 [SMILES: Cn1cnc(CN2C[C@H](C(=O)C(C#N)=S3CCCC3)[C@@H](Cc3ccc(F)cc3)C2=O)n1]
AND ENANTIOMER TABLE 1-continued
Intermediates (I-1-I-123)
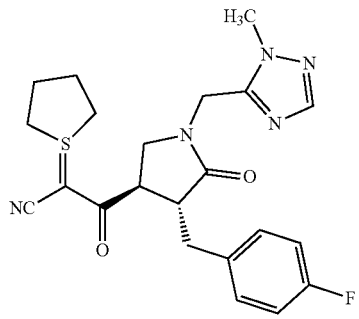 [SMILES: Cn1ncnc1CN1C[C@H](C(=O)C(C#N)=S2CCCC2)[C@@H](Cc2ccc(F)cc2)C1=O]
I-64
AND ENANTIOMER
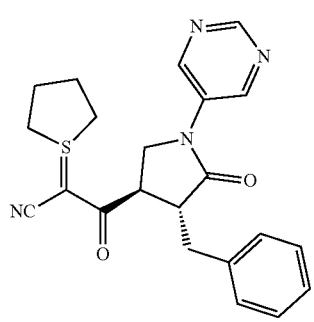 [SMILES: N#CC(C(=O)[C@H]1CN(c2cncnc2)C(=O)[C@@H]1Cc1ccccc1)=S1CCCC1]
I-65
AND ENANTIOMER
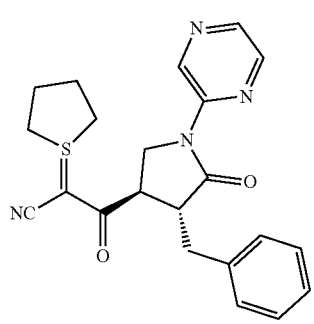 [SMILES: N#CC(C(=O)[C@H]1CN(c2cnccn2)C(=O)[C@@H]1Cc1ccccc1)=S1CCCC1]
I-66
AND ENANTIOMER
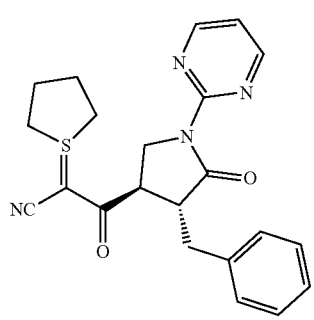 [SMILES: N#CC(C(=O)[C@H]1CN(c2ncccn2)C(=O)[C@@H]1Cc1ccccc1)=S1CCCC1]
I-67
AND ENANTIOMER
TABLE 1-continued
Intermediates (I-1-I-123)
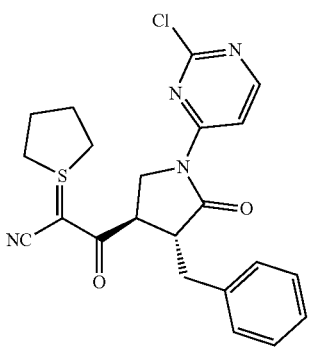 [SMILES: N#CC(C(=O)[C@H]1CN(c2ccnc(Cl)n2)C(=O)[C@@H]1Cc1ccccc1)=S1CCCC1]
I-68
AND ENANTIOMER
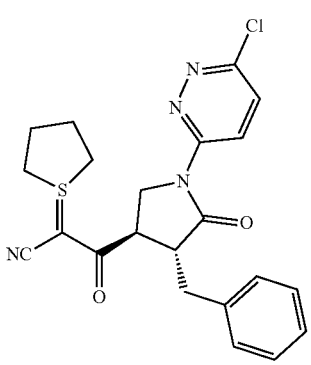 [SMILES: N#CC(C(=O)[C@H]1CN(c2ccc(Cl)nn2)C(=O)[C@@H]1Cc1ccccc1)=S1CCCC1]
I-69
AND ENANTIOMER
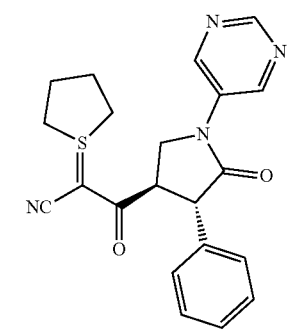 [SMILES: N#CC(C(=O)[C@H]1CN(c2cncnc2)C(=O)[C@@H]1c1ccccc1)=S1CCCC1]
I-70
AND ENANTIOMER
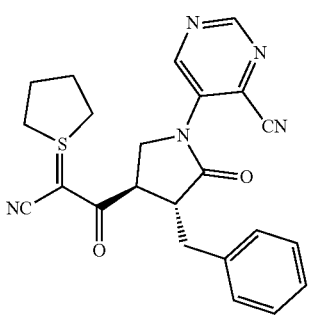 [SMILES: N#CC(C(=O)[C@H]1CN(c2cncnc2C#N)C(=O)[C@@H]1Cc1ccccc1)=S1CCCC1]
I-71
AND ENANTIOMER TABLE 1-continued
Intermediates (I-1-I-123)
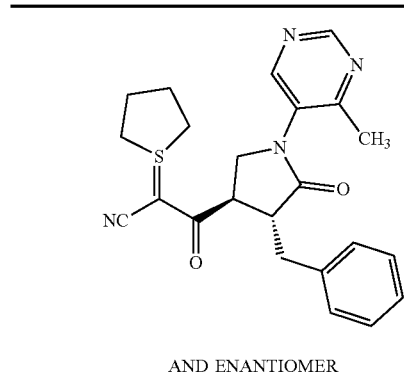
I-72
AND ENANTIOMER
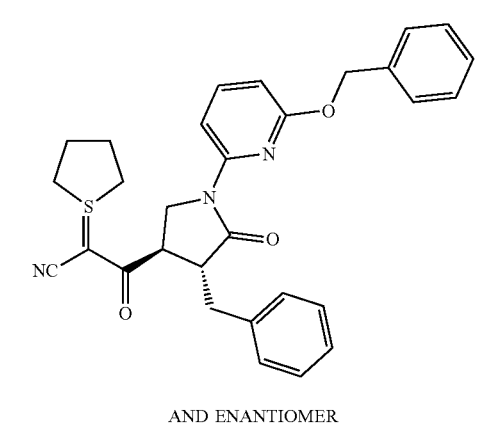
I-73
AND ENANTIOMER
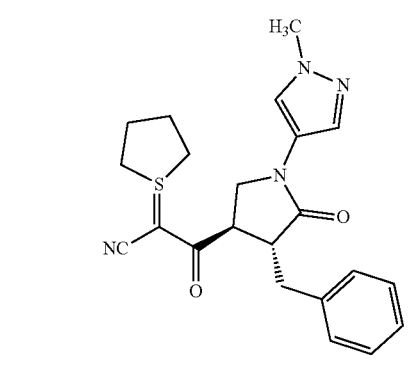 [SMILES: Cn1cc(N2C[C@H](C(=O)C(C#N)=S3CCCC3)[C@@H](Cc3ccccc3)C2=O)cn1]
I-74
AND ENANTIOMER
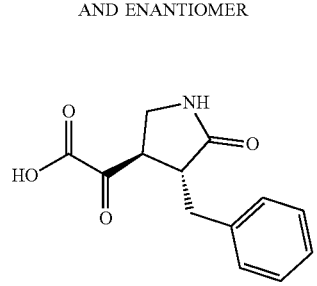
I-75
AND ENANTIOMER
TABLE 1-continued
Intermediates (I-1-I-123)
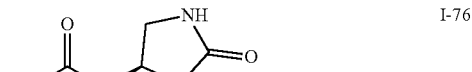
I-76
AND ENANTIOMER
I-77
AND ENANTIOMER
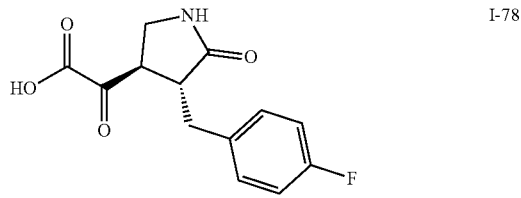
I-78
AND ENANTIOMER
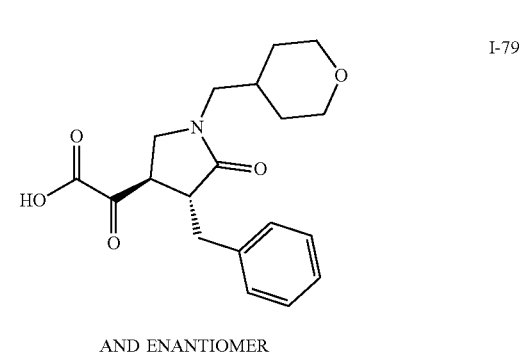
I-79
AND ENANTIOMER
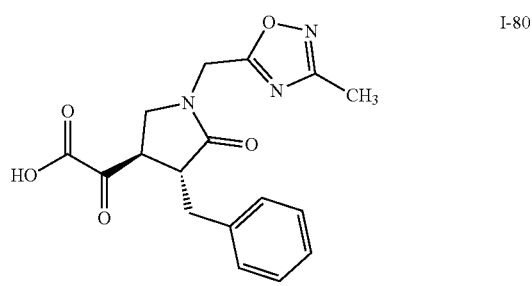
I-80
AND ENANTIOMER TABLE 1-continued
Intermediates (I-1-I-123)
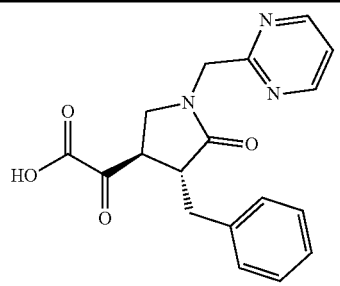
I-81
AND ENANTIOMER
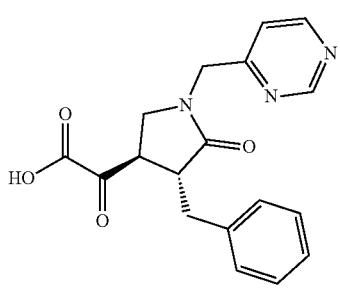 [SMILES: O=C(O)C(=O)[C@H]1CN(Cc2ccncn2)C(=O)[C@@H]1Cc1ccccc1]
I-82
AND ENANTIOMER
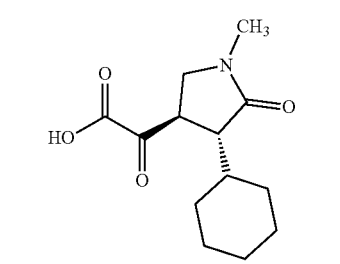 [SMILES: CN1C[C@H](C(=O)C(=O)O)[C@@H](C2CCCCC2)C1=O]
I-83
AND ENANTIOMER
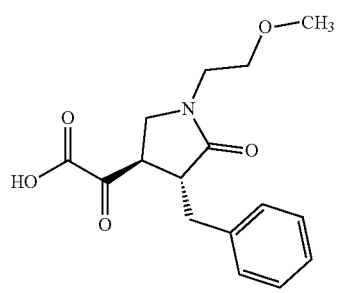 [SMILES: COCCN1C[C@H](C(=O)C(=O)O)[C@@H](Cc2ccccc2)C1=O]
I-84
AND ENANTIOMER
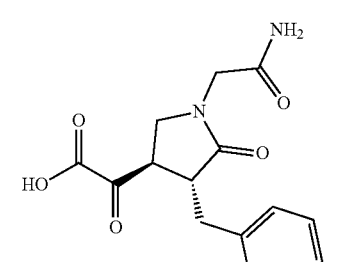
I-85
AND ENANTIOMER
TABLE 1-continued
Intermediates (I-1-I-123)
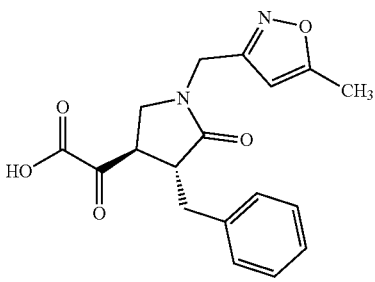 [SMILES: Cc1cc(CN2C[C@H](C(=O)C(=O)O)[C@@H](Cc3ccccc3)C2=O)no1]
I-86
AND ENANTIOMER
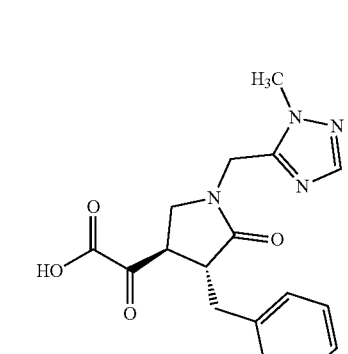
I-87
AND ENANTIOMER
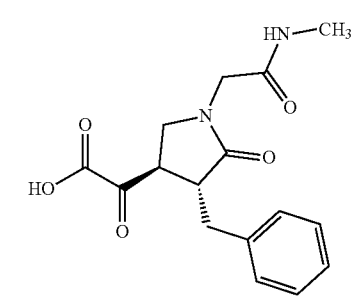 [SMILES: CNC(=O)CN1C[C@H](C(=O)C(=O)O)[C@@H](Cc2ccccc2)C1=O]
I-88
AND ENANTIOMER
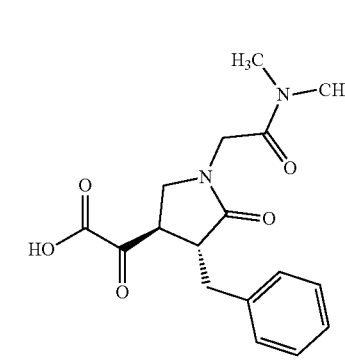
I-89
AND ENANTIOMER TABLE 1-continued
Intermediates (I-1-I-123)
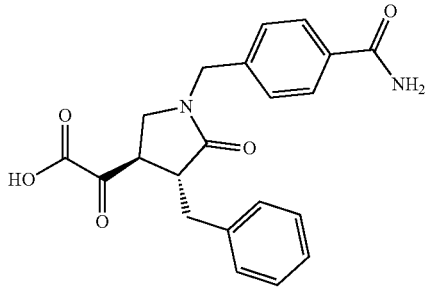 [SMILES: NC(=O)c1ccc(CN2C[C@H](C(=O)C(=O)O)[C@@H](Cc3ccccc3)C2=O)cc1]
I-90
AND ENANTIOMER
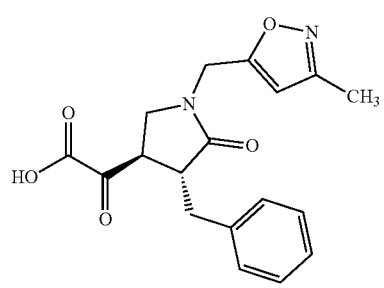 [SMILES: Cc1cc(CN2C[C@H](C(=O)C(=O)O)[C@@H](Cc3ccccc3)C2=O)on1]
I-91
AND ENANTIOMER
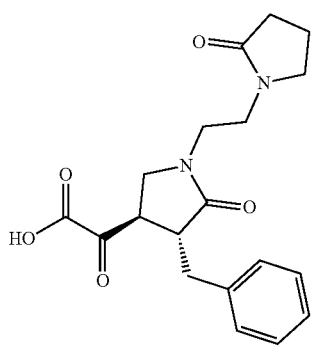 [SMILES: O=C(O)C(=O)[C@H]1CN(CCN2CCCC2=O)C(=O)[C@@H]1Cc1ccccc1]
I-92
AND ENANTIOMER
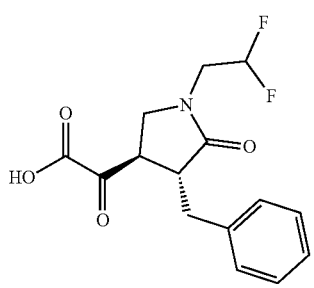 [SMILES: O=C(O)C(=O)[C@H]1CN(CC(F)F)C(=O)[C@@H]1Cc1ccccc1]
I-93
AND ENANTIOMER
TABLE 1-continued
Intermediates (I-1-I-123)
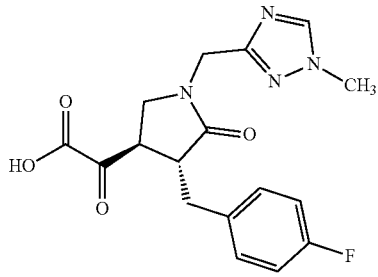 [SMILES: Cn1cnc(CN2C[C@H](C(=O)C(=O)O)[C@@H](Cc3ccc(F)cc3)C2=O)n1]
I-94
AND ENANTIOMER
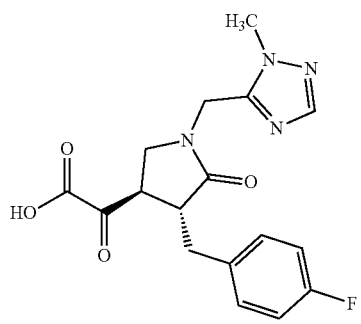 [SMILES: Cn1ncnc1CN1C[C@H](C(=O)C(=O)O)[C@@H](Cc2ccc(F)cc2)C1=O]
I-95
AND ENANTIOMER
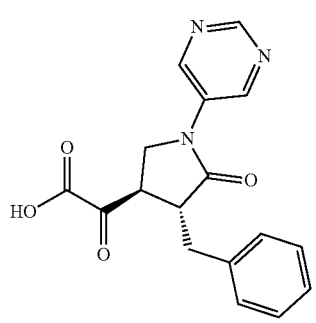 [SMILES: O=C(O)C(=O)[C@H]1CN(c2cncnc2)C(=O)[C@@H]1Cc1ccccc1]
I-96
AND ENANTIOMER
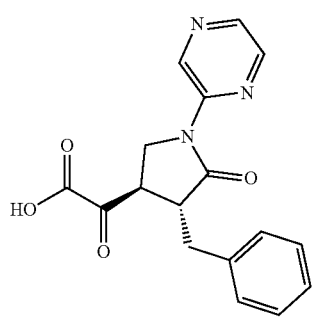 [SMILES: O=C(O)C(=O)[C@H]1CN(c2cnccn2)C(=O)[C@@H]1Cc1ccccc1]
I-97
AND ENANTIOMER TABLE 1-continued
Intermediates (I-1-I-123)
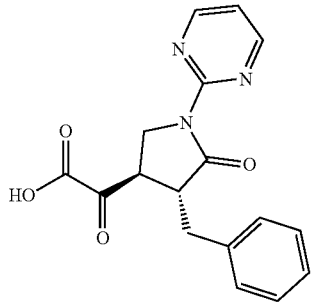 [SMILES: O=C(O)C(=O)[C@H]1CN(c2ncccn2)C(=O)[C@@H]1Cc1ccccc1]
I-98
AND ENANTIOMER
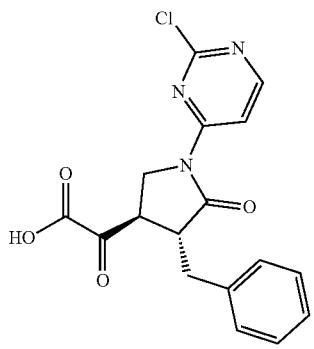 [SMILES: O=C(O)C(=O)[C@H]1CN(c2ccnc(Cl)n2)C(=O)[C@@H]1Cc1ccccc1]
I-99
AND ENANTIOMER
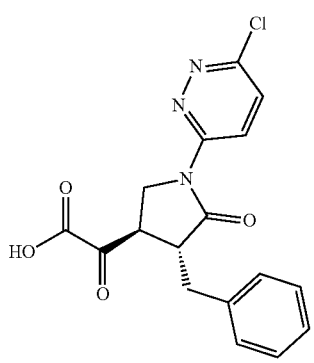 [SMILES: O=C(O)C(=O)[C@H]1CN(c2ccc(Cl)nn2)C(=O)[C@@H]1Cc1ccccc1]
I-100
AND ENANTIOMER
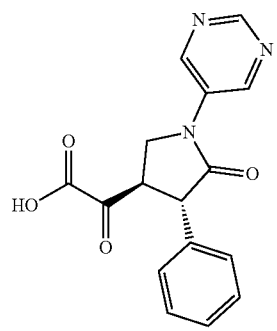 [SMILES: O=C(O)C(=O)[C@H]1CN(c2cncnc2)C(=O)[C@@H]1c1ccccc1]
I-101
AND ENANTIOMER
TABLE 1-continued
Intermediates (I-1-I-123)
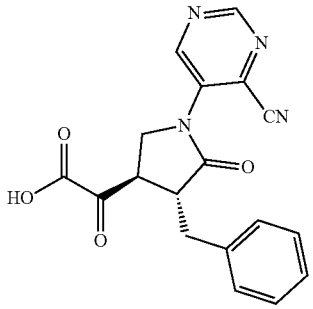
I-102
AND ENANTIOMER
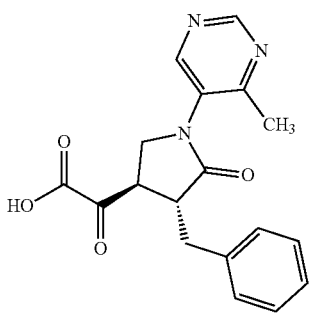 [SMILES: N#Cc1ncncc1N1C[C@H](C(=O)C(=O)O)[C@@H](Cc2ccccc2)C1=O]
I-103
AND ENANTIOMER
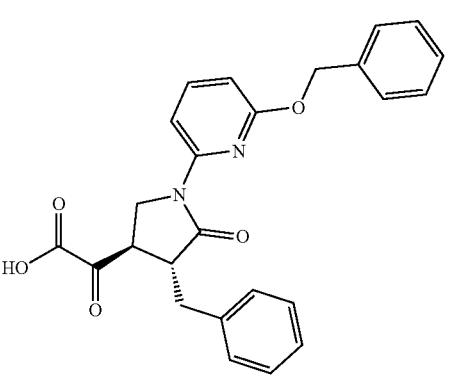 [SMILES: O=C(O)C(=O)[C@H]1CN(c2cccc(OCc3ccccc3)n2)C(=O)[C@@H]1Cc1ccccc1]
I-104
AND ENANTIOMER
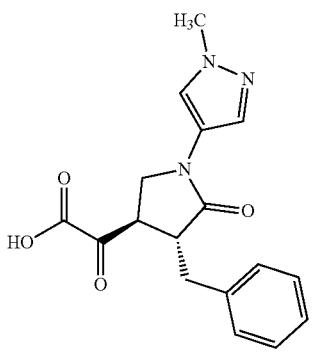 [SMILES: Cn1cc(N2C[C@H](C(=O)C(=O)O)[C@@H](Cc3ccccc3)C2=O)cn1]
I-105
AND ENANTIOMER

TABLE 1-continued
Intermediates (I-1-I-123)
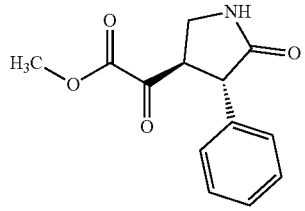 [SMILES: COC(=O)C(=O)[C@H]1CNC(=O)[C@@H]1c1ccccc1]
I-106
AND ENANTIOMER
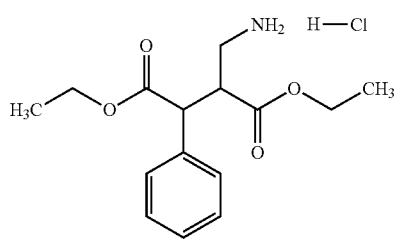
I-107
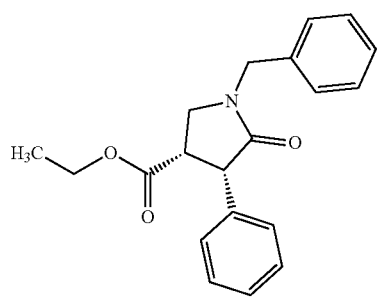 [SMILES: CCOC(=O)[C@@H]1CN(Cc2ccccc2)C(=O)[C@@H]1c1ccccc1]
I-108
AND ENANTIOMER
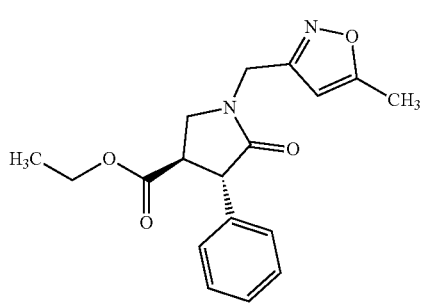 [SMILES: CCOC(=O)[C@H]1CN(Cc2cc(C)on2)C(=O)[C@@H]1c1ccccc1]
I-109
AND ENANTIOMER
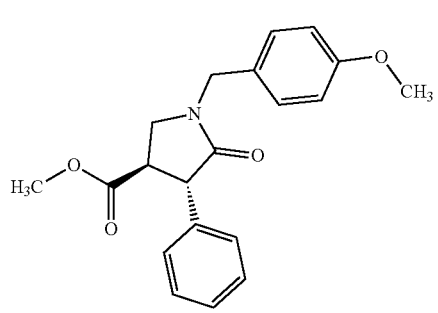
I-110
AND ENANTIOMER
TABLE 1-continued
Intermediates (I-1-I-123)
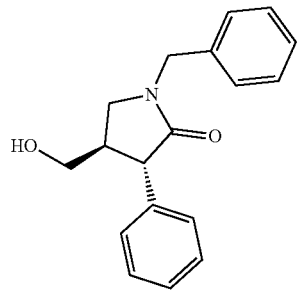 [SMILES: O=C1[C@H](c2ccccc2)[C@@H](CO)CN1Cc1ccccc1]
I-111
AND ENANTIOMER
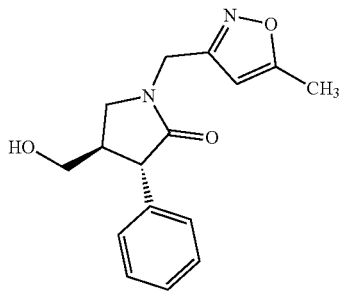 [SMILES: Cc1cc(CN2C[C@H](CO)[C@@H](c3ccccc3)C2=O)no1]
I-112
AND ENANTIOMER
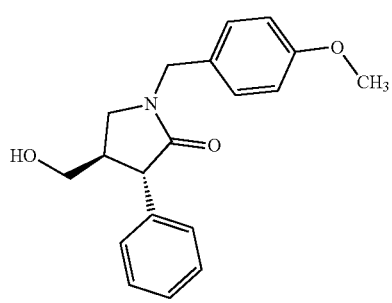 [SMILES: COc1ccc(CN2C[C@H](CO)[C@@H](c3ccccc3)C2=O)cc1]
I-113
AND ENANTIOMER
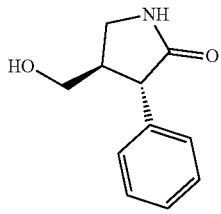 [SMILES: O=C1NC[C@H](CO)[C@H]1c1ccccc1]
I-114
AND ENANTIOMER TABLE 1-continued
Intermediates (I-1-I-123)
I-115
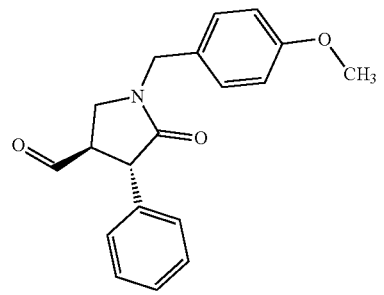 [SMILES: COc1ccc(CN2C[C@H](C=O)[C@@H](c3ccccc3)C2=O)cc1]
AND ENANTIOMER
I-116
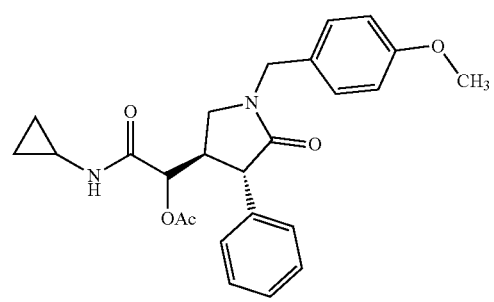 [SMILES: COc1ccc(CN2C[C@H](C(OC(C)=O)C(=O)NC3CC3)[C@@H](c3ccccc3)C2=O)cc1]
AND ENANTIOMER
I-117
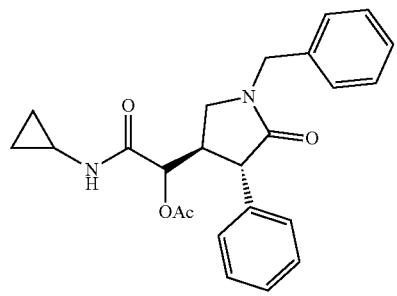 [SMILES: CC(=O)OC(C(=O)NC1CC1)[C@H]1CN(Cc2ccccc2)C(=O)[C@@H]1c1ccccc1]
AND ENANTIOMER
I-118
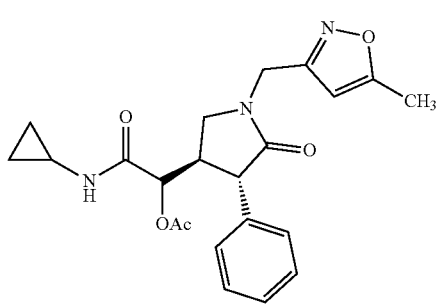 [SMILES: CC(=O)OC(C(=O)NC1CC1)[C@H]1CN(Cc2cc(C)on2)C(=O)[C@@H]1c1ccccc1]
AND ENANTIOMER
TABLE 1-continued
Intermediates (I-1-I-123)
I-119
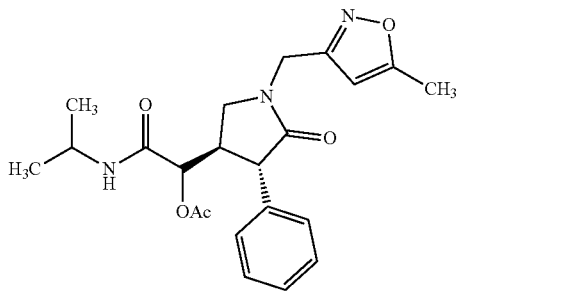 [SMILES: CC(=O)OC(C(=O)NC(C)C)[C@H]1CN(Cc2cc(C)on2)C(=O)[C@@H]1c1ccccc1]
AND ENANTIOMER
I-120
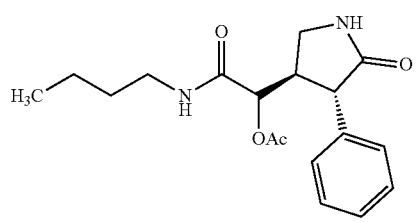 [SMILES: CCCCNC(=O)C(OC(C)=O)[C@H]1CNC(=O)[C@@H]1c1ccccc1]
AND ENANTIOMER
I-121
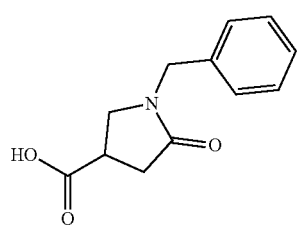 [SMILES: O=C(O)C1CC(=O)N(Cc2ccccc2)C1]
I-122
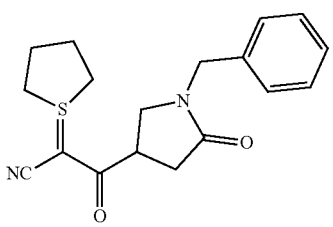 [SMILES: N#CC(C(=O)C1CC(=O)N(Cc2ccccc2)C1)=S1CCCC1]
I-123
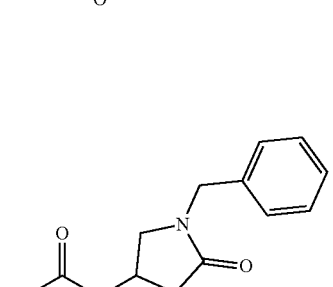

TABLE 2
Compounds FP-1-FP-104
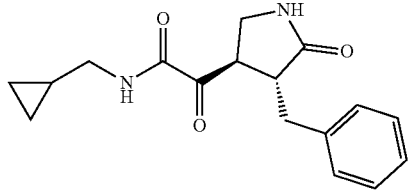 [SMILES: O=C(NCC1CC1)C(=O)[C@H]1CNC(=O)[C@@H]1Cc1ccccc1] FP-1 (A/I)
AND ENANTIOMER
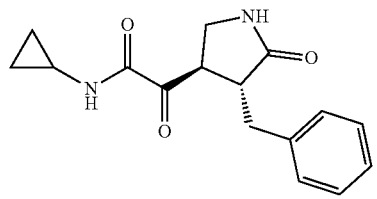 [SMILES: O=C(NC1CC1)C(=O)[C@H]1CNC(=O)[C@@H]1Cc1ccccc1] FP-2 (A/I)
AND ENANTIOMER
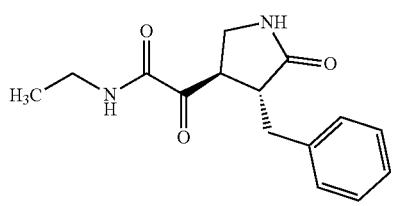 [SMILES: CCNC(=O)C(=O)[C@H]1CNC(=O)[C@@H]1Cc1ccccc1] FP-3 (A/I)
AND ENANTIOMER
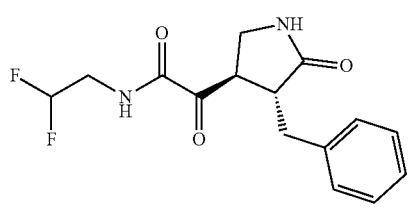 [SMILES: O=C(NCC(F)F)C(=O)[C@H]1CNC(=O)[C@@H]1Cc1ccccc1] FP-4 (A/I)
AND ENANTIOMER
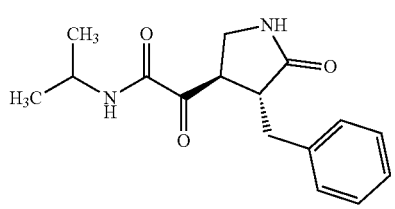 [SMILES: CC(C)NC(=O)C(=O)[C@H]1CNC(=O)[C@@H]1Cc1ccccc1] FP-5 (A/I)
AND ENANTIOMER
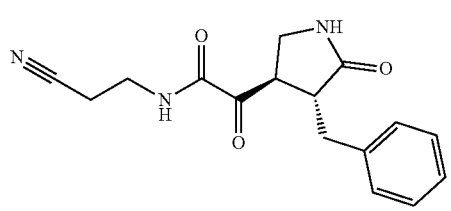 [SMILES: N#CCCNC(=O)C(=O)[C@H]1CNC(=O)[C@@H]1Cc1ccccc1] FP-6 (A/II)
AND ENANTIOMER
TABLE 2-continued
Compounds FP-1-FP-104
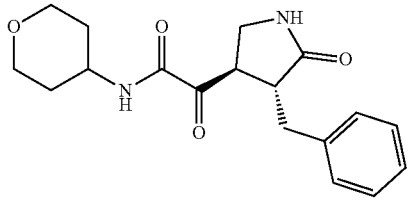 [SMILES: O=C(NC1CCOCC1)C(=O)[C@H]1CNC(=O)[C@@H]1Cc1ccccc1] FP-7 (A/II)
AND ENANTIOMER
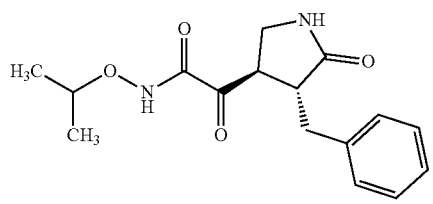 [SMILES: CC(C)ONC(=O)C(=O)[C@H]1CNC(=O)[C@@H]1Cc1ccccc1] FP-8 (A/II)
AND ENANTIOMER
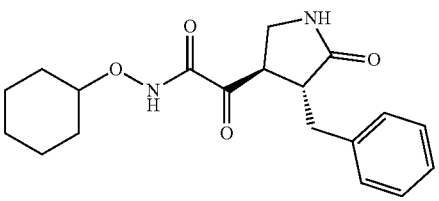 [SMILES: O=C(NOC1CCCCC1)C(=O)[C@H]1CNC(=O)[C@@H]1Cc1ccccc1] FP-9 (A/II)
AND ENANTIOMER
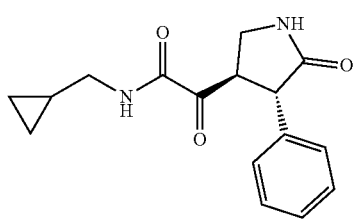 [SMILES: O=C(NCC1CC1)C(=O)[C@H]1CNC(=O)[C@@H]1c1ccccc1] FP-10 (A/I)
AND ENANTIOMER
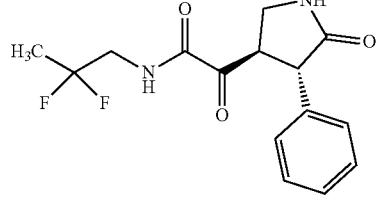 FP-11 (A/II)
AND ENANTIOMER
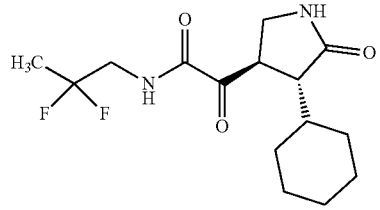 [SMILES: CC(F)(F)CNC(=O)C(=O)[C@H]1CNC(=O)[C@@H]1C1CCCCC1] FP-12 (A/I)
AND ENANTIOMER TABLE 2-continued
Compounds FP-1-FP-104
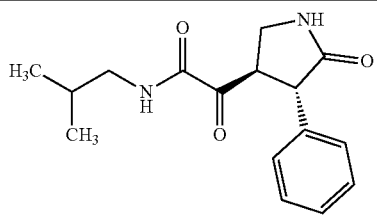
FP-13 (A/I)
AND ENANTIOMER
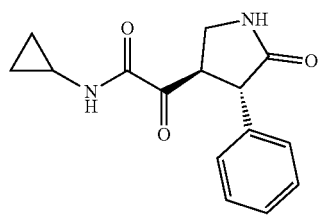 [SMILES: O=C(NC1CC1)C(=O)[C@H]1CNC(=O)[C@@H]1c1ccccc1]
FP-14 (A/II)
AND ENANTIOMER
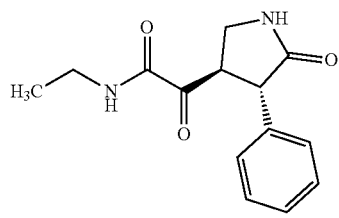 [SMILES: CCNC(=O)C(=O)[C@H]1CNC(=O)[C@@H]1c1ccccc1]
FP-15 (A/II)
AND ENANTIOMER
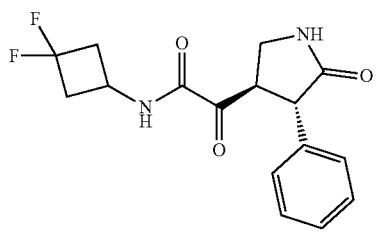 [SMILES: O=C(NC1CC(F)(F)C1)C(=O)[C@H]1CNC(=O)[C@@H]1c1ccccc1]
FP-16 (A/II)
AND ENANTIOMER
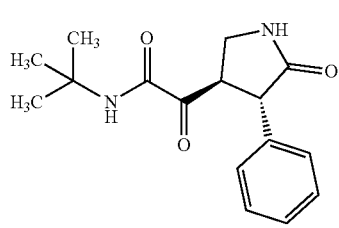 [SMILES: CC(C)(C)NC(=O)C(=O)[C@H]1CNC(=O)[C@@H]1c1ccccc1]
FP-17 (A/I)
AND ENANTIOMER
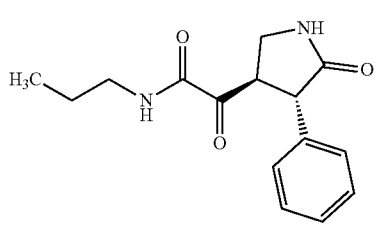 [SMILES: CCCNC(=O)C(=O)[C@H]1CNC(=O)[C@@H]1c1ccccc1]
FP-18 (A/II)
AND ENANTIOMER
TABLE 2-continued
Compounds FP-1-FP-104
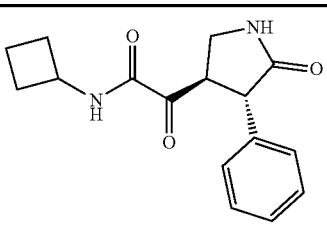
FP-19 (A/I)
AND ENANTIOMER
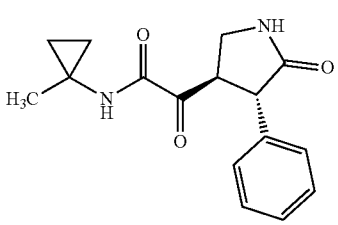 [SMILES: CC1(NC(=O)C(=O)[C@H]2CNC(=O)[C@@H]2c2ccccc2)CC1]
FP-20 (A/II)
AND ENANTIOMER
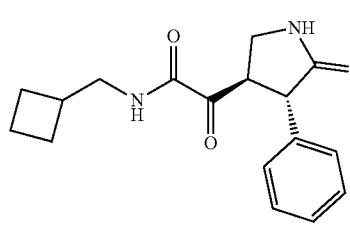
FP-21 (A/I)
AND ENANTIOMER
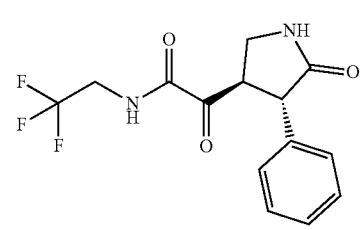 [SMILES: O=C(NCC(F)(F)F)C(=O)[C@H]1CNC(=O)[C@@H]1c1ccccc1]
FP-22 (A/II)
AND ENANTIOMER
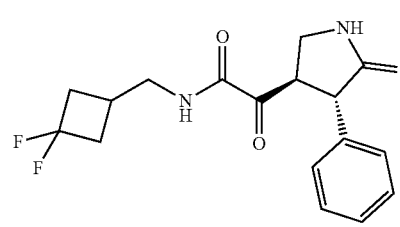
FP-23 (A/I)
AND ENANTIOMER
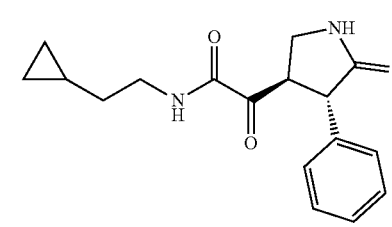
FP-24 (A/I)
AND ENANTIOMER TABLE 2-continued
Compounds FP-1-FP-104
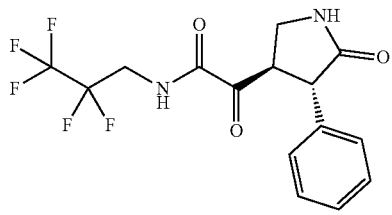 [SMILES: O=C(NCC(F)(F)C(F)(F)F)C(=O)[C@H]1CNC(=O)[C@@H]1c1ccccc1]
FP-25 (A/II)
AND ENANTIOMER
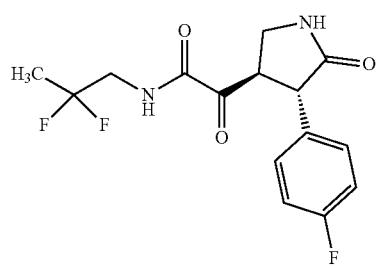 [SMILES: CC(F)(F)CNC(=O)C(=O)[C@H]1CNC(=O)[C@@H]1c1ccc(F)cc1]
FP-26 (A/II)
AND ENANTIOMER
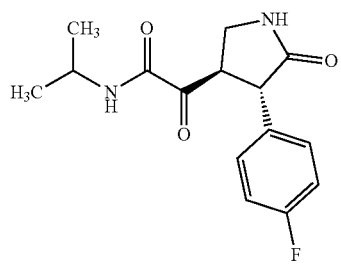 [SMILES: CC(C)NC(=O)C(=O)[C@H]1CNC(=O)[C@@H]1c1ccc(F)cc1]
FP-27 (A/II)
AND ENANTIOMER
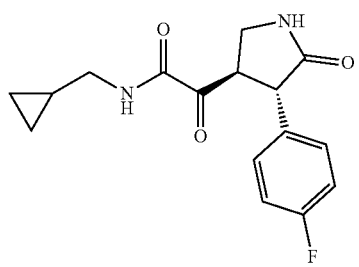 [SMILES: O=C(NCC1CC1)C(=O)[C@H]1CNC(=O)[C@@H]1c1ccc(F)cc1]
FP-28 (A/I)
AND ENANTIOMER
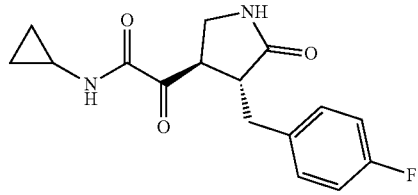 [SMILES: O=C(NC1CC1)C(=O)[C@H]1CNC(=O)[C@@H]1Cc1ccc(F)cc1]
FP-29 (A/I)
AND ENANTIOMER
TABLE 2-continued
Compounds FP-1-FP-104
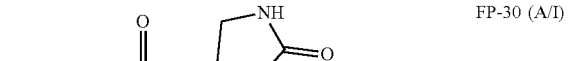
FP-30 (A/I)
AND ENANTIOMER
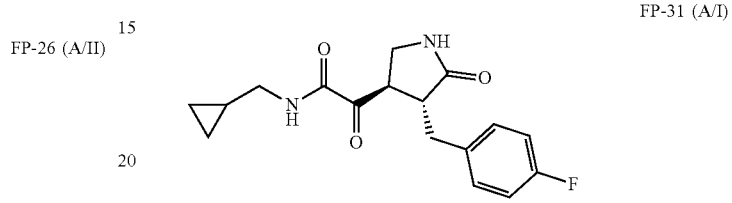
FP-31 (A/I)
AND ENANTIOMER
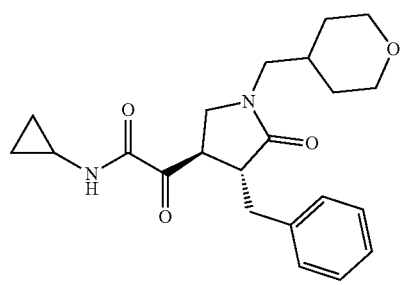 [SMILES: O=C(NC1CC1)C(=O)[C@H]1CN(CC2CCOCC2)C(=O)[C@@H]1Cc1ccccc1]
FP-32 (A/I)
AND ENANTIOMER
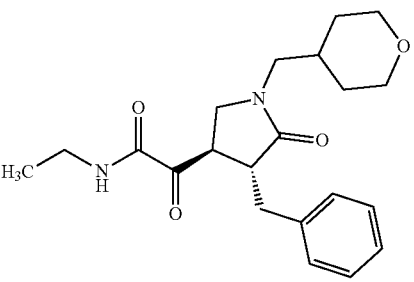 [SMILES: CCNC(=O)C(=O)[C@H]1CN(CC2CCOCC2)C(=O)[C@@H]1Cc1ccccc1]
FP-33 (A/I)
AND ENANTIOMER
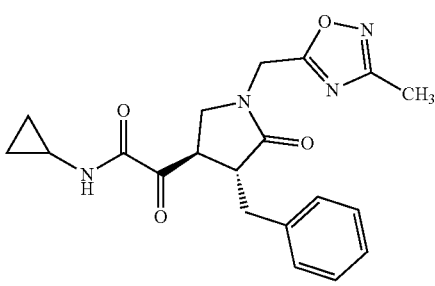 [SMILES: Cc1noc(CN2C[C@H](C(=O)C(=O)NC3CC3)[C@@H](Cc3ccccc3)C2=O)n1]
FP-34 (A/II)
AND ENANTIOMER TABLE 2-continued
Compounds FP-1-FP-104
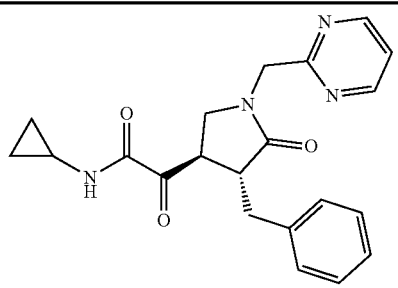
FP-35 (A/II)
AND ENANTIOMER
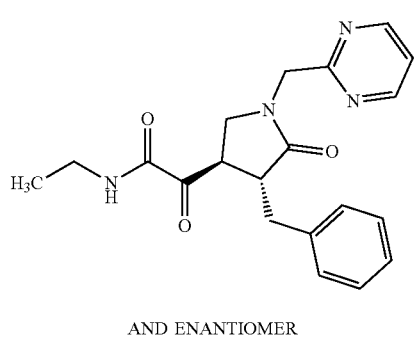
FP-36 (A/II)
AND ENANTIOMER
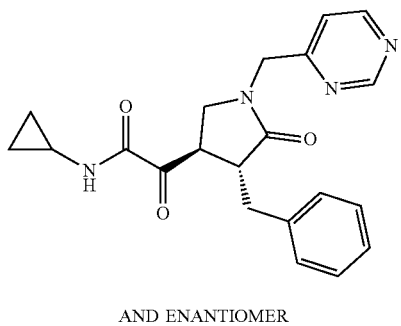
FP-37 (A/II)
AND ENANTIOMER
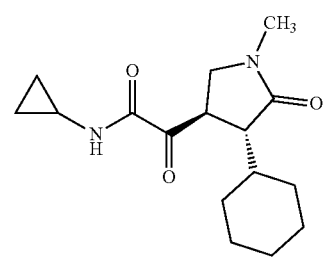 [SMILES: CN1C[C@H](C(=O)C(=O)NC2CC2)[C@@H](C2CCCCC2)C1=O]
FP-38 (A/II)
AND ENANTIOMER
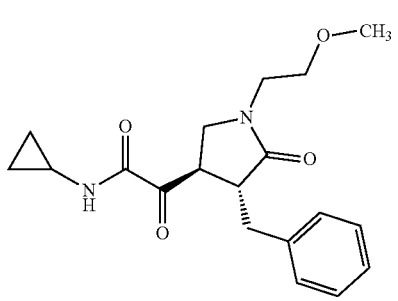 [SMILES: COCCN1C[C@H](C(=O)C(=O)NC2CC2)[C@@H](Cc2ccccc2)C1=O]
FP-39 (A/II)
AND ENANTIOMER
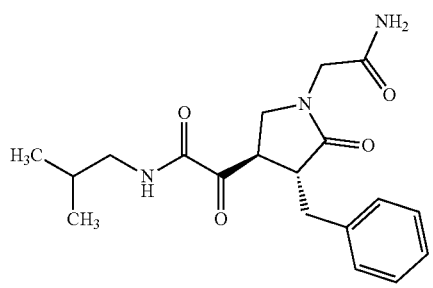 [SMILES: CC(C)CNC(=O)C(=O)[C@H]1CN(CC(N)=O)C(=O)[C@@H]1Cc1ccccc1]
FP-40 (A/I)
AND ENANTIOMER
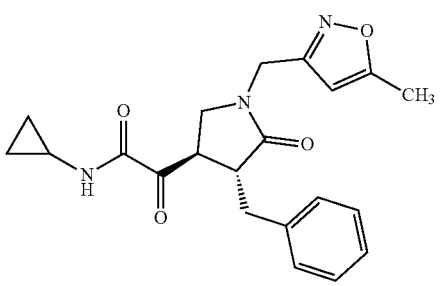 [SMILES: Cc1cc(CN2C[C@H](C(=O)C(=O)NC3CC3)[C@@H](Cc3ccccc3)C2=O)no1]
FP-41 (A/I)
AND ENANTIOMER
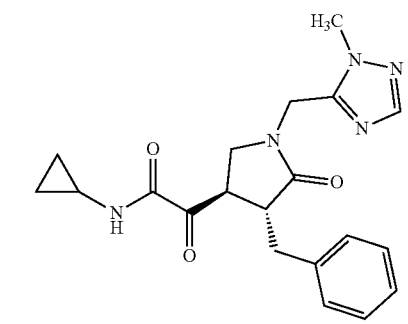 [SMILES: Cn1ncnc1CN1C[C@H](C(=O)C(=O)NC2CC2)[C@@H](Cc2ccccc2)C1=O]
FP-42 (A/II)
AND ENANTIOMER
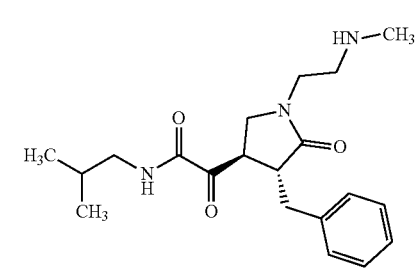 [SMILES: CNCCN1C[C@H](C(=O)C(=O)NCC(C)C)[C@@H](Cc2ccccc2)C1=O]
FP-43 (A/II)
AND ENANTIOMER TABLE 2-continued
Compounds FP-1-FP-104
FP-44 (A/I)
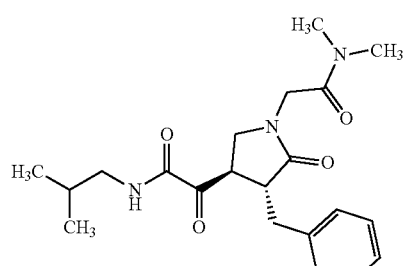
AND ENANTIOMER
FP-45 (A/II)
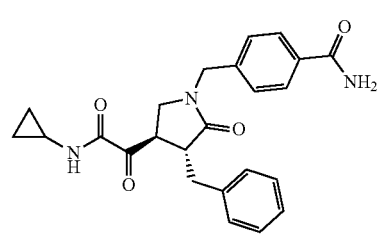 [SMILES: NC(=O)c1ccc(CN2C[C@H](C(=O)C(=O)NC3CC3)[C@@H](Cc3ccccc3)C2=O)cc1]
AND ENANTIOMER
FP-46 (A/II)
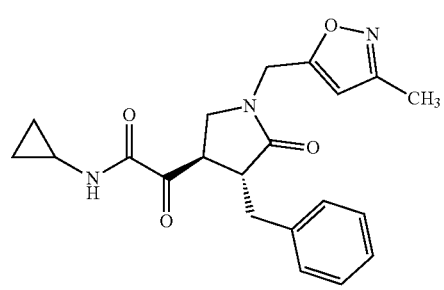 [SMILES: Cc1cc(CN2C[C@H](C(=O)C(=O)NC3CC3)[C@@H](Cc3ccccc3)C2=O)on1]
AND ENANTIOMER
FP-47 (A/II)
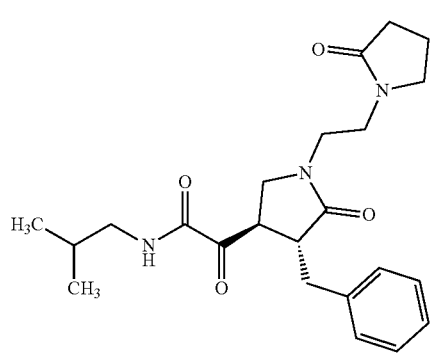 [SMILES: CC(C)CNC(=O)C(=O)[C@H]1CN(CCN2CCCC2=O)C(=O)[C@@H]1Cc1ccccc1]
AND ENANTIOMER
TABLE 2-continued
Compounds FP-1-FP-104
FP-48 (A/II)
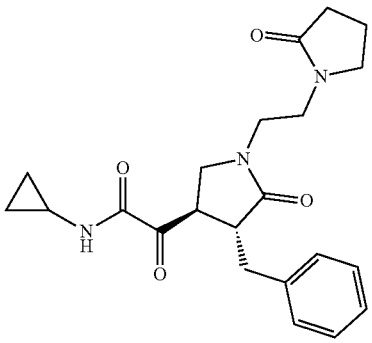 [SMILES: O=C(NC1CC1)C(=O)[C@H]1CN(CCN2CCCC2=O)C(=O)[C@@H]1Cc1ccccc1]
AND ENANTIOMER
FP-49 (A/I)
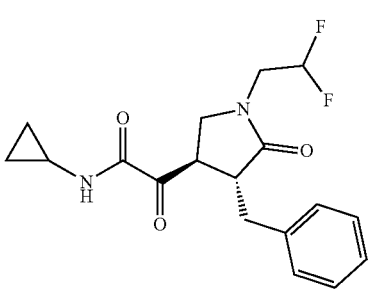 [SMILES: O=C(NC1CC1)C(=O)[C@H]1CN(CC(F)F)C(=O)[C@@H]1Cc1ccccc1]
AND ENANTIOMER
FP-50 (A/I)
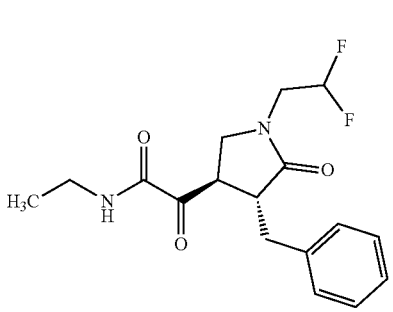 [SMILES: CCNC(=O)C(=O)[C@H]1CN(CC(F)F)C(=O)[C@@H]1Cc1ccccc1]
AND ENANTIOMER
FP-51 (A/II)
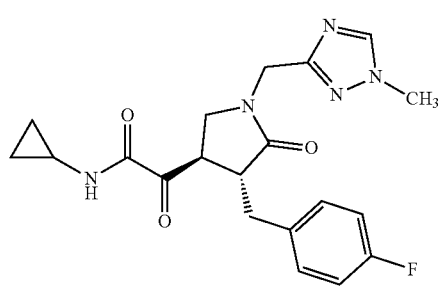 [SMILES: Cn1cnc(CN2C[C@H](C(=O)C(=O)NC3CC3)[C@@H](Cc3ccc(F)cc3)C2=O)n1]
AND ENANTIOMER TABLE 2-continued
Compounds FP-1-FP-104
FP-52 (A/III)
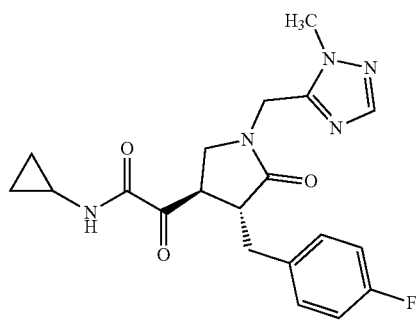 [SMILES: Cn1ncnc1CN1C[C@H](C(=O)C(=O)NC2CC2)[C@@H](Cc2ccc(F)cc2)C1=O]
AND ENANTIOMER
FP-53 (A/II)
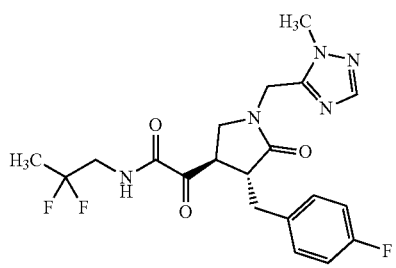 [SMILES: Cn1ncnc1CN1C[C@H](C(=O)C(=O)NCC(C)(F)F)[C@@H](Cc2ccc(F)cc2)C1=O]
AND ENANTIOMER
FP-54 (A/I)
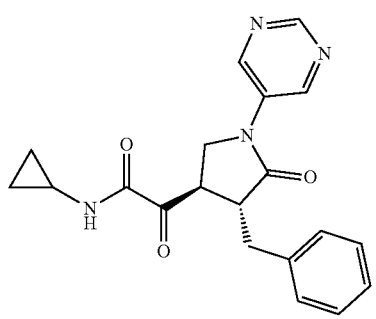 [SMILES: O=C(NC1CC1)C(=O)[C@H]1CN(c2cncnc2)C(=O)[C@@H]1Cc1ccccc1]
AND ENANTIOMER
FP-55 (A/I)
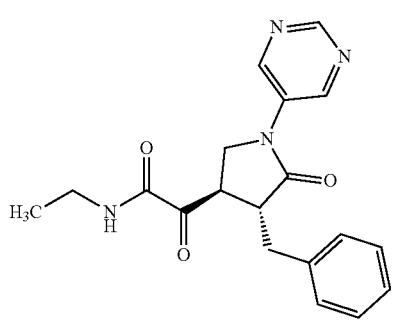 [SMILES: CCNC(=O)C(=O)[C@H]1CN(c2cncnc2)C(=O)[C@@H]1Cc1ccccc1]
AND ENANTIOMER
TABLE 2-continued
Compounds FP-1-FP-104
FP-56 (A/I)
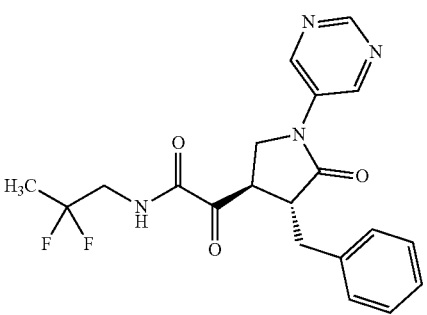 [SMILES: CC(F)(F)CNC(=O)C(=O)[C@H]1CN(c2cncnc2)C(=O)[C@@H]1Cc1ccccc1]
AND ENANTIOMER
FP-57 (A/I)
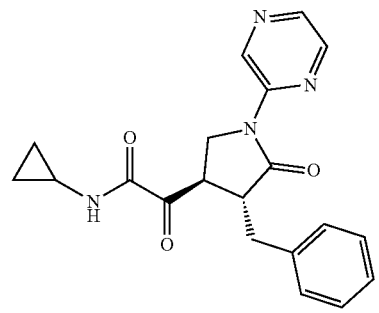 [SMILES: O=C(NC1CC1)C(=O)[C@H]1CN(c2cnccn2)C(=O)[C@@H]1Cc1ccccc1]
AND ENANTIOMER
FP-58 (A/II)
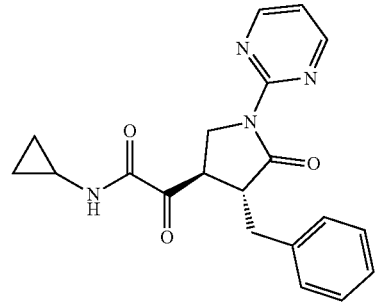 [SMILES: O=C(NC1CC1)C(=O)[C@H]1CN(c2ncccn2)C(=O)[C@@H]1Cc1ccccc1]
AND ENANTIOMER
FP-59 (A/II)
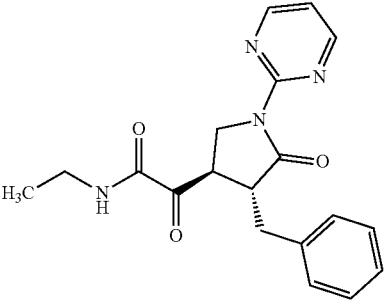 [SMILES: CCNC(=O)C(=O)[C@H]1CN(c2ncccn2)C(=O)[C@@H]1Cc1ccccc1]
AND ENANTIOMER TABLE 2-continued
Compounds FP-1-FP-104
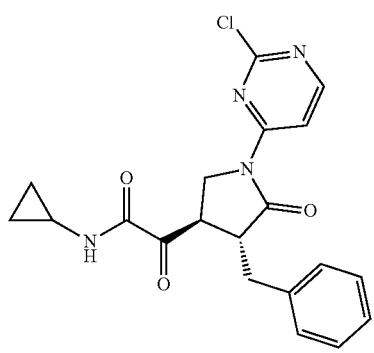 [SMILES: O=C(NC1CC1)C(=O)[C@H]1CN(c2ccnc(Cl)n2)C(=O)[C@@H]1Cc1ccccc1]
FP-60 (A/II)
AND ENANTIOMER
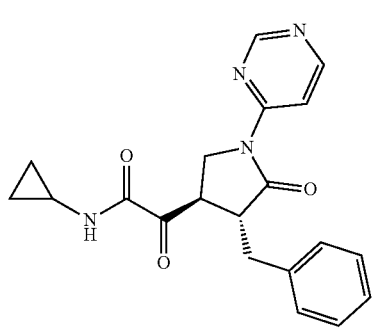 [SMILES: O=C(NC1CC1)C(=O)[C@H]1CN(c2ccncn2)C(=O)[C@@H]1Cc1ccccc1]
FP-61 (A/II)
AND ENANTIOMER
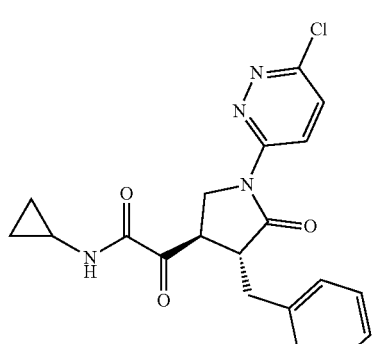
FP-62 (A/I)
AND ENANTIOMER
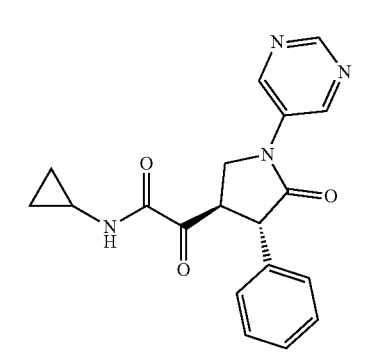 [SMILES: O=C(NC1CC1)C(=O)[C@H]1CN(c2cncnc2)C(=O)[C@@H]1c1ccccc1]
FP-63 (A/II)
AND ENANTIOMER
TABLE 2-continued
Compounds FP-1-FP-104
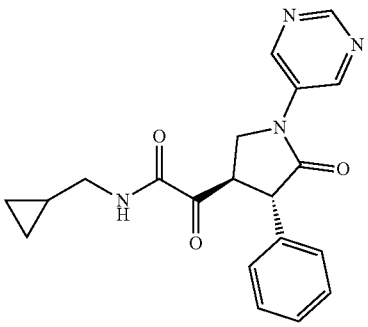 [SMILES: O=C(NCC1CC1)C(=O)[C@H]1CN(c2cncnc2)C(=O)[C@@H]1c1ccccc1]
FP-64 (A/II)
AND ENANTIOMER
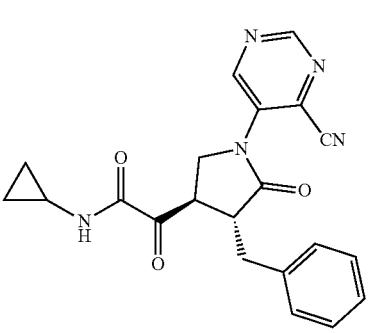 [SMILES: N#Cc1ncncc1N1C[C@H](C(=O)C(=O)NC2CC2)[C@@H](Cc2ccccc2)C1=O]
FP-65 (A/II)
AND ENANTIOMER
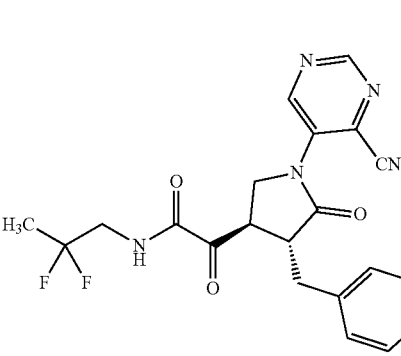
FP-66 (A/II)
AND ENANTIOMER
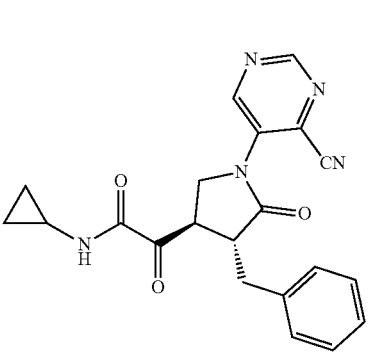 [SMILES: N#Cc1ncncc1N1C[C@H](C(=O)C(=O)NC2CC2)[C@@H](Cc2ccccc2)C1=O]
FP-67 (A/II)
AND ENANTIOMER TABLE 2-continued
Compounds FP-1-FP-104
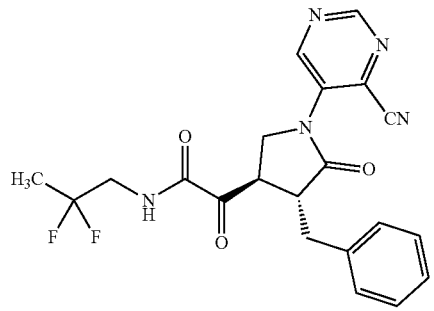 [SMILES: CC(F)(F)CNC(=O)C(=O)[C@H]1CN(c2cncnc2C#N)C(=O)[C@@H]1Cc1ccccc1]
FP-68 (A/II)
AND ENANTIOMER
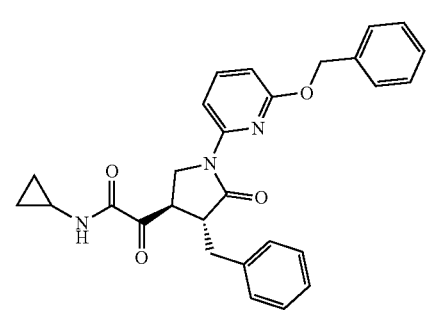 [SMILES: O=C(NC1CC1)C(=O)[C@H]1CN(c2cccc(OCc3ccccc3)n2)C(=O)[C@@H]1Cc1ccccc1]
FP-69 (A/I)
AND ENANTIOMER
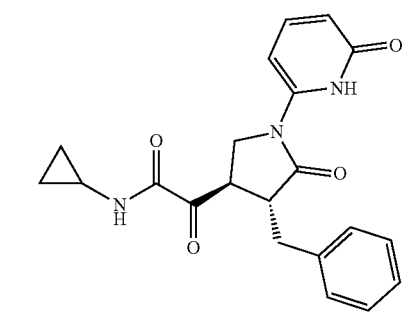 [SMILES: O=C(NC1CC1)C(=O)[C@H]1CN(c2cccc(=O)[nH]2)C(=O)[C@@H]1Cc1ccccc1]
FP-70 (A/I)
AND ENANTIOMER
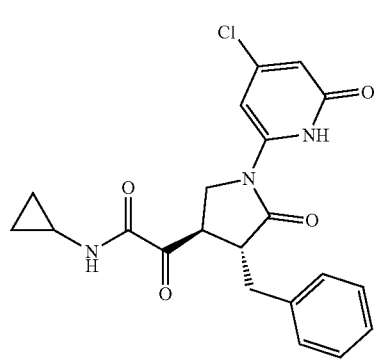 [SMILES: O=C(NC1CC1)C(=O)[C@H]1CN(c2cc(Cl)cc(=O)[nH]2)C(=O)[C@@H]1Cc1ccccc1]
FP-71 (A/I)
AND ENANTIOMER
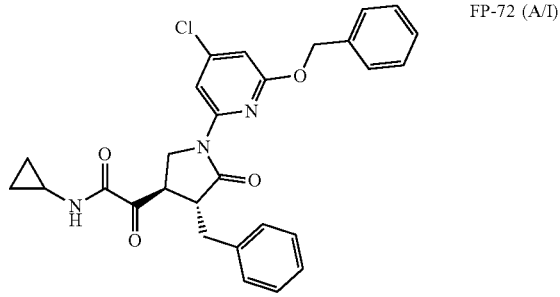
FP-72 (A/I)
AND ENANTIOMER
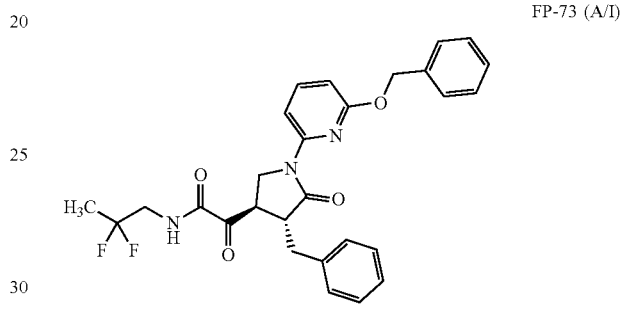
FP-73 (A/I)
AND ENANTIOMER
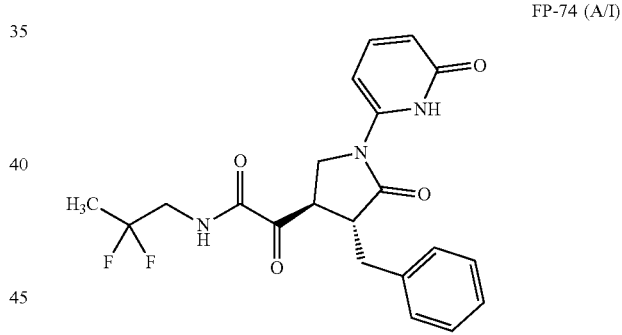
FP-74 (A/I)
AND ENANTIOMER
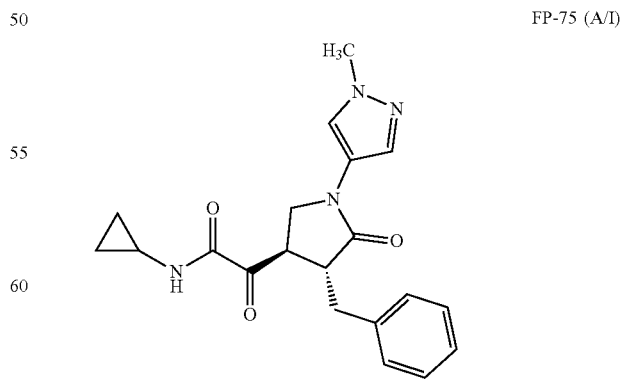
FP-75 (A/I)
AND ENANTIOMER TABLE 2-continued
Compounds FP-1-FP-104
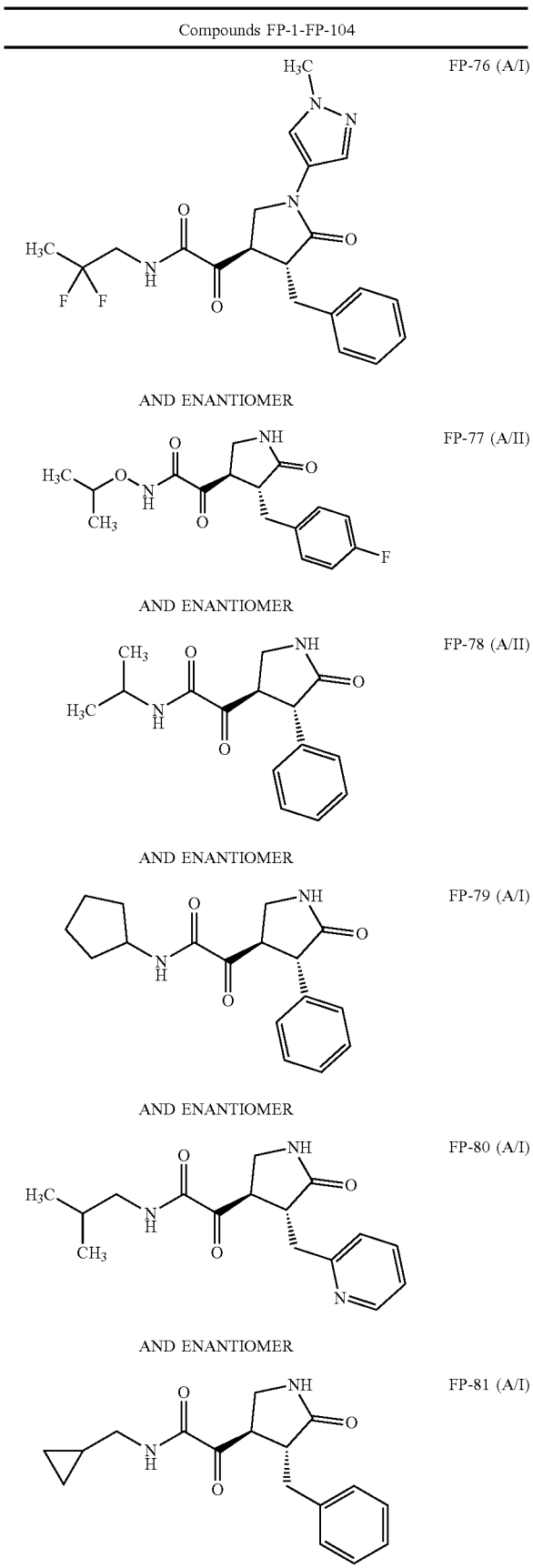
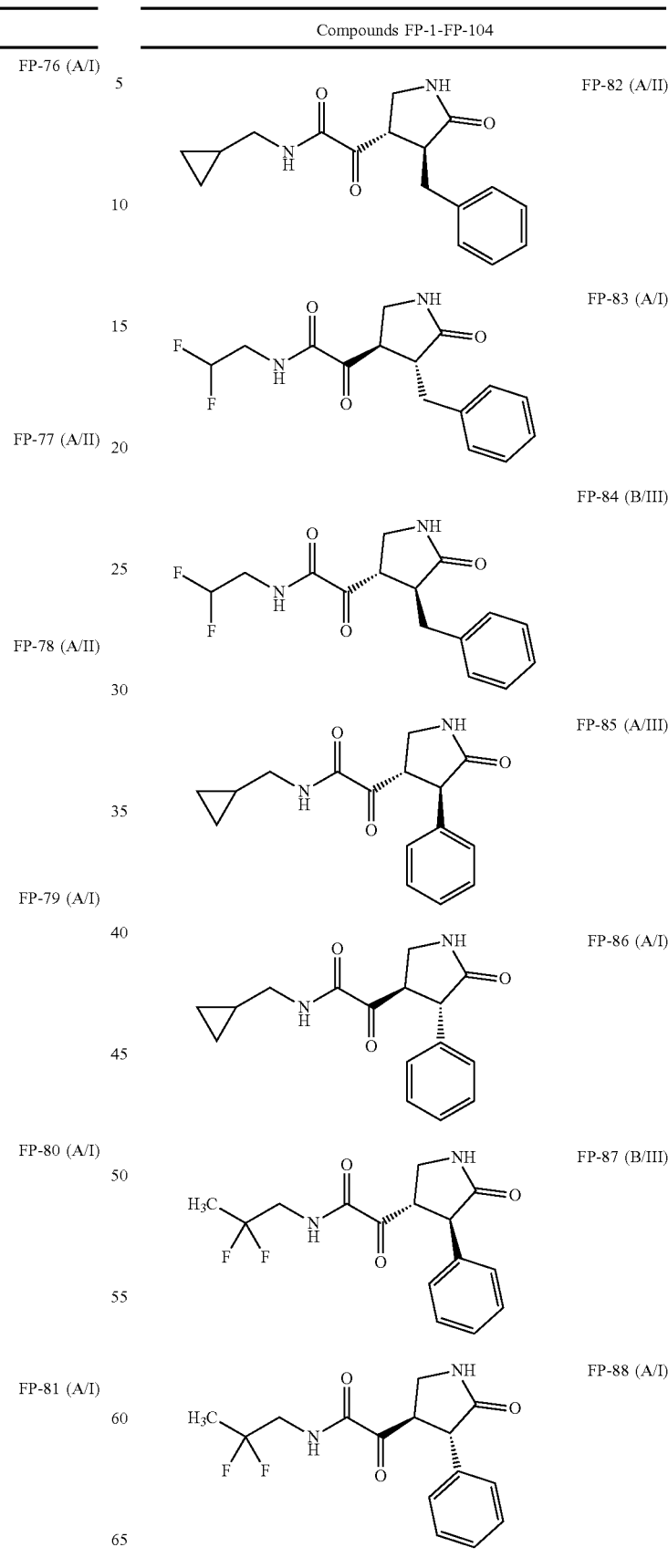

TABLE 2-continued
Compounds FP-1-FP-104
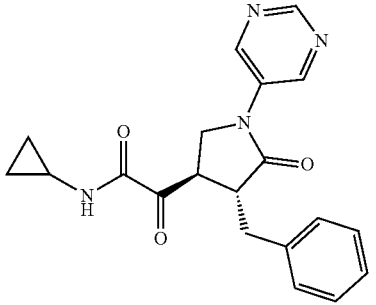 [SMILES: O=C(NC1CC1)C(=O)[C@H]1CN(c2cncnc2)C(=O)[C@@H]1Cc1ccccc1] FP-89 (A/I)
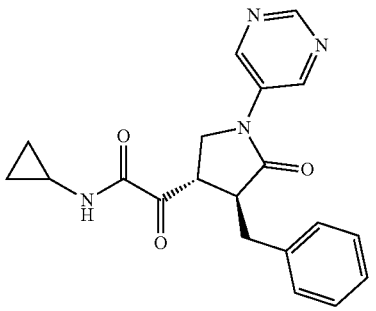 [SMILES: O=C(NC1CC1)C(=O)[C@@H]1CN(c2cncnc2)C(=O)[C@H]1Cc1ccccc1] FP-90 (A/II)
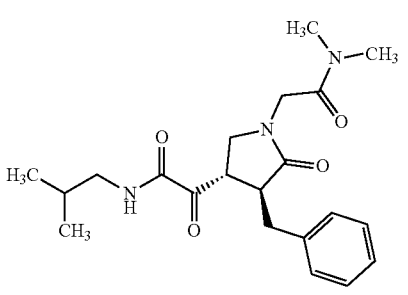 [SMILES: CC(C)CNC(=O)C(=O)[C@@H]1CN(CC(=O)N(C)C)C(=O)[C@H]1Cc1ccccc1] FP-91 (B/III)
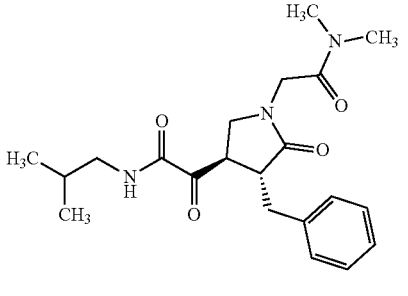 [SMILES: CC(C)CNC(=O)C(=O)[C@H]1CN(CC(=O)N(C)C)C(=O)[C@@H]1Cc1ccccc1] FP-92 (A/II)
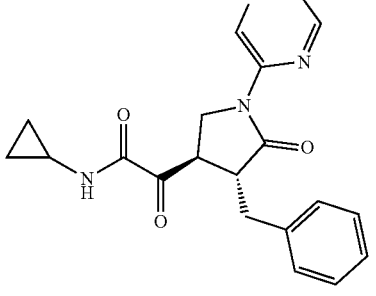 FP-93 (A/I)
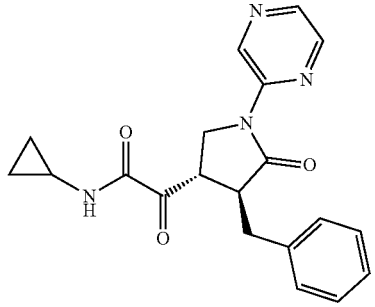 [SMILES: O=C(NC1CC1)C(=O)[C@@H]1CN(c2cnccn2)C(=O)[C@H]1Cc1ccccc1] FP-94 (A/II)
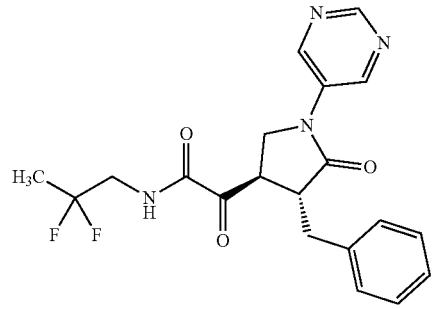 [SMILES: CC(F)(F)CNC(=O)C(=O)[C@H]1CN(c2cncnc2)C(=O)[C@@H]1Cc1ccccc1] FP-95 (A/I)
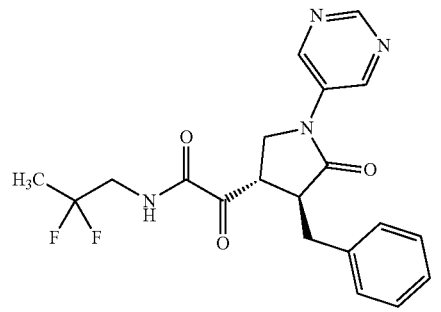 [SMILES: CC(F)(F)CNC(=O)C(=O)[C@@H]1CN(c2cncnc2)C(=O)[C@H]1Cc1ccccc1] FP-96 (A/II)
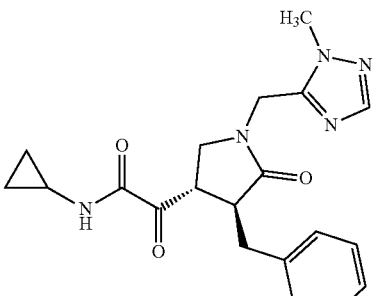 FP-97 (B/III)
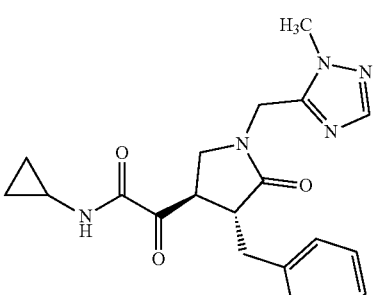 FP-98 (A/II)

TABLE 2-continued

Compounds FP-1-FP-104

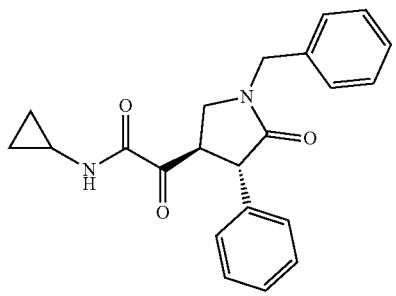 [SMILES: O=C(NC1CC1)C(=O)[C@H]1CN(Cc2ccccc2)C(=O)[C@@H]1c1ccccc1]
FP-99 (A/II)

AND ENANTIOMER

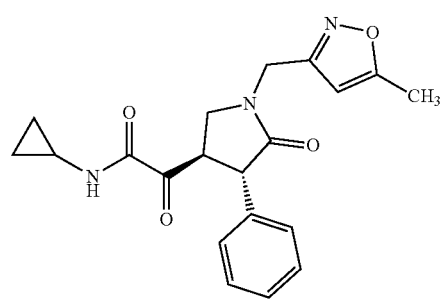 [SMILES: Cc1cc(CN2C[C@H](C(=O)C(=O)NC3CC3)[C@@H](c3ccccc3)C2=O)no1]
FP-100 (A/II)

AND ENANTIOMER

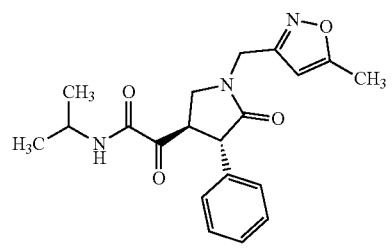 [SMILES: Cc1cc(CN2C[C@H](C(=O)C(=O)NC(C)C)[C@@H](c3ccccc3)C2=O)no1]
FP-101 (A/II)

AND ENANTIOMER

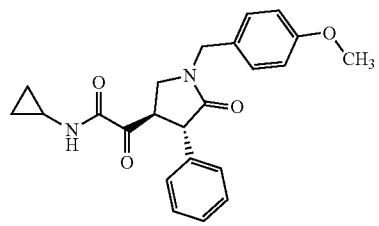 [SMILES: COc1ccc(CN2C[C@H](C(=O)C(=O)NC3CC3)[C@@H](c3ccccc3)C2=O)cc1]
FP-102 (A/I)

AND ENANTIOMER

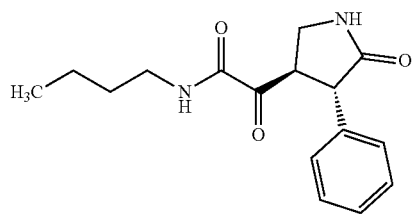 [SMILES: CCCCNC(=O)C(=O)[C@H]1CNC(=O)[C@@H]1c1ccccc1]
FP-103 (A/I)

AND ENANTIOMER

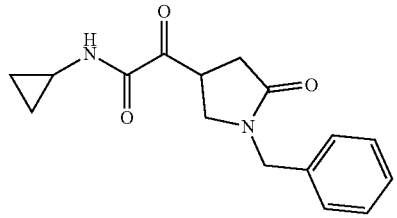 [SMILES: O=C(NC1CC1)C(=O)C1CC(=O)N(Cc2ccccc2)C1]
FP-104 (A/II)

IC$_{50}$ values of the compounds determined in the enzyme activity assay for PLA2G16 described below and EC$_{50}$ values of the compounds determined in the anti-picornavirus assay described below are given in parentheses. Compounds with IC$_{50}$ values <1 µM (class "A") in the enzymatic activity assay are considered as highly active, compounds with IC$_{50}$ values between 1 and 10 µM (class "B") are considered as medium active and compounds with IC$_{50}$ values greater than 10 µM, but below 50 µM (class "C") are considered as weakly active. Antiviral activity against four different picornaviruses is categorized analogously, where class "I" denotes compounds with EC$_{50}$ < 1 µM, class "II" with EC$_{50}$ between 1 µM and 10 µM and class "III" with EC$_{50}$ > 10 µM.
ND: not determined Purification and Enzyme Activity Assay for PLA2G16

A cDNA for PLA2G16 (NM_007069) was custom-synthesized by Genscript (Piscataway, USA) and inserted into a pET-based bacterial expression vector [Moffatt, B. A. and Studier, F. W. (1986) J. Mol. Biol. 189, 113-130; Rosenberg, A. H., Lade, B. N., Chui, D., Lin, S., Dunn, J. J., and Studier, F. W. (1987) Gene 56, 125-135], enabling the expression of N-terminally Hexa-His-tagged PLA2G16. E. coli BL21 (DE3) (Agilent) were transformed with pET-His-PLA2G16 according to the manufacturer's instructions and plated on Carbenicillin-containing agar plates (final concentration: 100 µg/mL). A single clone was inoculated in 100 mL LB medium supplemented with 100 µg/mL Carbenicillin and the inoculated culture was grown at 37° C. overnight in a rotary shaker. On the next day, the bacterial culture was diluted in LB medium supplemented with 100 µg/mL Carbenicillin (30 mL overnight culture in 800 mL total culture volume). Bacteria were grown at 37° C. until the OD$_{600}$ reached 0.6. Gene expression was induced by addition of 1 mM isopropyl-β-D-thiogalactopyranosid (IPTG) for 2 h at 18° C. Subsequently, bacteria were harvested by centrifugation (15 min; 10,000×g; 4° C.) and frozen at −80° C. The bacterial pellet was resuspended in Buffer A (50 mM Tris/HCl pH 7.5, 500 mM NaCl, 5% glycerol, 5 mM β-Mercaptoethanol and 1 mM PMSF) and lysed by addition of 1 mg/mL lysozyme (Sigma Aldrich) and 100 µg/mL DNaseI-(Roche). The sample was incubated at 30° C. for 30 min to allow lysis to occur. Then, the lysate was cleared by centrifugation (15,000×g, 15 min, 4° C.) and incubated with 1.5 mL Ni-NTA agarose suspension (Qiagen) for 60 min at 4° C. The Ni-NTA agarose was washed with 10 mL Buffer A. Bound protein was eluted by applying a manual gradient of Buffer A supplemented with increasing concentrations of imidazole (Sigma Aldrich; 25/50/75/100/250 mM). Purified fractions were analyzed by SDS-PAGE followed by Coomassie staining to assess the purity.

Activity of the protein was assessed as follows:
Red/Green BODIPY® PC-A2 (Invitrogen, 1 mM in DMSO) was mixed with equal volumes of 1,2-Dioleoyl-sn-glycero-3-phosphocholine (DOPC; Sigma Aldrich, 10 mM in Ethanol) and 1,2-Dioleoyl-sn-glycero-3-phospho-rac-(1-glycerol) (DOPG; Sigma Aldrich, 10 mM in Ethanol) and 0.5 volumes of Cholesterol (CHOL; Sigma Aldrich, 10 mM in Ethanol) and vortexed for 5 s. The mixture (Red/Green BODIPY® PC-A2/DOPC/DOPG/CHOL) was diluted 1:91.4 in activity assay buffer (50 mM Tris/HCl pH 8.5, 100 mM NaCl) using a small-orifice pipette tip under constant vortexing. In the following, this preparation will be referred to as the "substrate solution".

In order to evaluate their inhibitory potential, compounds were dissolved at 10 mM concentration in DMSO and directly spotted into assay plates (Corning, Cat. No. 3576) using acoustic liquid transfer (Labcyte Echo 525). Each compound was spotted at increasing concentrations, ranging from 2 nM to 50 µM (concentration in the final assay volume). 50 µl of PLA2G16 enzyme solution (diluted in activity buffer, supplemented with 5 mM L-Glutathione; Sigma Aldrich) was pre-incubated with compounds for 4 min., followed by addition of 50 µl of substrate solution. Fluorescence was recorded immediately after substrate addition for a total time of 10 min. using a SpectraMax M5 multimode reader (Excitation wavelength: 480 nm, emission wavelength: 530 nm). The relative increase of fluorescence over time is referred to as the enzyme activity. Half-maximal inhibitory concentrations ($IC_{50}$) were derived by non-linear regression analysis using the drc package in R (R Development. Core Team, 2005).

The results of the enzyme activity assay for PLA2G16 are presented in Table 2.

Anti-Picornavirus Assay in Mammalian Cell Culture

The antiviral activity of selected compounds was tested using a cytopathic effect (CPE) reduction assay on HeLa H1 cells (ATCC CRL-1958). Briefly, cells were seeded in 96-well dishes ($2 \times 10^4$ cells/well) in DMEM medium (Life technologies) supplemented with 10% FBS and PenStrep solution (100 U/mL Penicillin and 100 µg/mL streptomycin) and incubated at 37° C., 5% $CO_2$ overnight. The next day, cells were pre-treated with serial dilutions of the compound in DMEM medium supplemented with 2% FBS and PenStrep for 2 h at 37° C., 5% $CO_2$. Next, cells were infected with virus (CVB1, HRV-A2, HRV-A23, EV-68) at an multiplicity of infection (MOI) which results in a complete virus-induced CPE within 2 days in control wells (infected and vehicle-treated). After 48 h, supernatants were aspirated and 50 µl/well of CellTiterBlue reagent (Promega) diluted 1:5 in DMEM+2% FBS, was added to the cells. Plates were returned to the incubator and allowed to develop for 1.5 h. After that, plates were equilibrated to RT and subsequently, fluorescence was recorded (Excitation wavelength: 560 nm; emission wavelength: 590 nm) using a SpectraMax M5 multimode plate reader. Viability of cells was calculated according to the formula: $V=(RFU_{Cpd}-RFU_{Veh})/(RFU_M-RFU_{Veh})$, where $RFU_{Cpd}$ refers to infected and compound-treated cells, $RFU_{Veh}$ to infected and vehicle-treated cells and $RFU_M$ to uninfected and vehicle treated cells. Half-maximal effective concentrations ($EC_{50}$) were calculated by non-linear regression analysis using the drc package in R (R Development. Core Team, 2005). $EC_{50}$ categories as presented in Table 2 were calculated by averaging the $EC_{50}$ values from four picornaviruses (CVB1, HRV-A2, HRV-A23, EV68).

The invention claimed is:
1. A compound of general formula I,

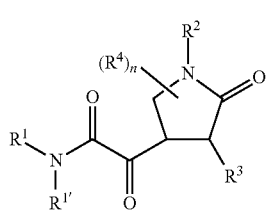

(I)

wherein
$R^1$ denotes H, —$OR^a$, —$C(O)R^a$, —$(CH_2)_nC(O)OR^a$ or a group, optionally substituted by one or more, identical or different $R^a$ and/or $R^b$, selected independently from one another among $C_{1-6}$ alkyl, $C_{2-6}$ alkenyl, $C_{2-6}$ alkynyl, $C_{3-10}$ cycloalkyl, $C_{4-16}$ cycloalkylalkyl, $C_{6-10}$ aryl, 3-8 membered heterocycloalkyl, and 5-12 membered heteroaryl, and
$R^{1'}$ denotes H or $C_{1-4}$alkyl,
or $R^1$ and $R^{1'}$ together with the adjacent nitrogen atom form a 4- to 10-membered heterocyclic group, which optionally may be substituted by one or more, identical or different $R^a$ and/or $R^b$;
$R^2$ denotes H or a group, optionally substituted by one or more, identical or different $R^a$ and/or $R^b$, selected independently from one another among $C_{1-6}$ alkyl, $C_{2-6}$ alkenyl, $C_{2-6}$ alkynyl, $C_{3-10}$ cycloalkyl, $C_{4-16}$ cycloalkylalkyl, $C_{6-10}$ aryl, $C_{7-16}$ arylalkyl, 3-8 membered heterocycloalkyl, 4-14 membered heterocycloalkylalkyl, 5-12 membered heteroaryl and 6-18 membered heteroarylalkyl;
$R^3$ denotes H or a group, optionally substituted by one or more, identical or different $R^a$ and/or $R^b$, selected independently from one another among $C_{1-6}$ alkyl, $C_{2-6}$ alkenyl, $C_{2-6}$ alkynyl, $C_{3-10}$ cycloalkyl, $C_{4-16}$ cycloalkylalkyl, $C_{6-10}$ aryl,
$C_{7-16}$ arylalkyl, 4-14 membered heterocycloalkylalkyl, 5-12 membered heteroaryl and 6-18 membered heteroarylalkyl,
$R^4$ denotes =O, halogen, or a group, optionally substituted by one or more, identical or different $R^a$ and/or $R^b$, selected independently from one another among $C_{1-6}$ alkyl, $C_{2-6}$ alkenyl, $C_{2-6}$ alkynyl, $C_{3-6}$ cycloalkyl
or two $R^4$ form an optionally substituted 3 to 6 membered cycloalkyl or heterocycloalkyl ring,
n denotes 0, 1, 2, 3, or 4, and
each $R^a$ independently of one another denotes hydrogen or a group, optionally substituted by one or more, identical or different $R^b$ and/or $R^c$, selected from among $C_{1-6}$ alkyl, $C_{2-6}$ alkenyl, $C_{2-6}$ alkynyl, $C_{3-10}$ cycloalkyl, $C_{4-16}$ cycloalkylalkyl,
$C_{6-10}$ aryl, $C_{7-16}$ arylalkyl, 3-8 membered heterocycloalkyl, 4-14 membered heterocycloalkylalkyl, 5-12 membered heteroaryl and 6-18 membered heteroarylalkyl;
each $R^b$ is a suitable substituent and is selected in each case independently of one another from among =O, —$OR^c$, $C_{1-3}$ haloalkyloxy, —$OCF_3$, =S, —$SR^c$, =$NR^c$, =$NOR^c$, =$NNR^cR^c$, =$NN(R^g)C(O)NR^cR^c$, —$NR^cR^c$, —$ONR^cR^c$, —$N(OR^c)R^c$, —$N(R^g)NR^cR^c$, halogen, —$CF_3$, —CN, —NC, —OCN, —SCN, —NO, —$NO_2$, =$N_2$, —$N_3$, —$S(O)R^c$, —$S(O)OR^c$, —$S(O)_2R^c$, —$S(O)_2OR^c$, —$S(O)NR^cR^c$, —$S(O)_2$-$NR^cR^c$, —$OS(O)R^c$, —$OS(O)_2R^c$, —$OS(O)_2OR^c$, —$OS(O)NR^cR^c$, —$OS(O)_2NR^cR^c$, —$C(O)R^c$, —$C(O)$ $OR^c$, —$C(O)SR^c$, —$C(O)NR^cR^c$, —$C(O)N(R^g)NR^cR^c$, —$C(O)N(R^g)OR^c$, —$C(NR^g)NR^cR^c$, —$C(NOH)R^c$, —$C(NOH)NR^cR^c$, —$OC(O)R^c$, —$OC(O)OR^c$, —$OC(O)SR^c$, —$OC(O)NR^cR^c$, —$OC(NR^g)NR^cR^c$, —$SC(O)R^c$, —$SC(O)OR^c$, —$SC(O)NR^cR^c$, —$SC(NR^g)$-$NR^cR^c$, —$N(R^g)C(O)R^c$, —$N[C(O)R^c]_2$, —$N(OR^g)C(O)R^c$, —$N(R^g)C(NR^g)R^c$, —$N(R^g)N(R^g)C(O)R^c$, —$N[C(O)R^c]NR^cR^c$, —$N(R^g)C(S)R^c$, —$N(R^g)S(O)R^c$, —$N(R^g)S(O)OR^c$, —$N(R^g)S(O)_2R^c$, —$N[S(O)_2R^c]_2$, —$N(R^g)S(O)_2OR^c$, —$N(R^g)S(O)_2NR^cR^c$, —$N(R^g)[S(O)_2]_2R^c$, —$N(R^g)C(O)OR^c$, —$N(R^g)C(O)$ $SR^c$, —$N(R^g)C(O)NR^cR^c$, —$N(R^g)C(O)NR^gNR^cR^c$, —$N(R^g)N(R^g)C(O)NR^cR^c$, —$N(R^g)C(S)NR^cR^c$, —[N (R$^g$)C(O)]$_2$R$^c$, —N(R$^g$)[C(O)]$_2$R$^c$, —N{[C(O)]$_2$R$^c$}$_2$, —N(R$^g$)[C(O)]$_2$OR$^c$, —N(R$^g$)[C(O)]$_2$NR$^c$R$^c$, —N{[C(O)]$_2$OR$^c$}$_2$, —N{[C(O)]$_2$NR$^c$R$^c$}$_2$, —[N(R$^g$)C(O)]$_2$OR$^c$, —N(R$^g$)C(NR$^g$)OR$^c$, —N(R$^g$)C(NOH)R$^c$, —N(R$^g$)C(NR$^g$)SR$^c$ and —N(R$^g$)C(NR$^g$)NR$^c$R$^c$;

each R$^c$ independently of one another denotes hydrogen or a group, optionally substituted by one or more, identical or different R$^d$ and/or R$^e$, selected from among C$_{1-6}$ alkyl, C$_{2-6}$ alkenyl, C$_{2-6}$ alkynyl, C$_{3-10}$ cycloalkyl, C$_{4-16}$ cycloalkylalkyl, C$_{6-10}$ aryl, C$_{7-16}$ arylalkyl, 3-8 membered heterocycloalkyl, 4-14 membered heterocycloalkylalkyl, 5-12 membered heteroaryl and 6-18 membered heteroarylalkyl;

each R$^d$ denotes a suitable substituent and is selected in each case independently of one another from among =O, —OR$^e$, C$_{1-3}$haloalkyloxy, —OCF$_3$, =S, —SR$^e$, =NR$^e$, =NOR$^e$, =NNR$^e$R$^e$, =NN(R$^g$)C(O)NR$^e$R$^e$, —NR$^e$R$^e$, —ONR$^e$R$^e$, —N(OR$^e$)R$^e$, —N(R$^g$)NR$^e$R$^e$, halogen, —CF$_3$, —CN, —NC, —OCN, —SCN, —NO, —NO$_2$, =N$_2$, —N$_3$, —S(O)R$^e$, —S(O)OR$^e$, —S(O)$_2$R$^e$, —S(O)$_2$OR$^e$, —S(O)NR$^e$R$^e$, —S(O)$_2$NR$^e$R$^e$, —OS(O)R$^e$, —OS(O)$_2$R$^e$, —OS(O)$_2$OR$^e$, —OS(O)NR$^e$R$^e$, —OS(O)$_2$NR$^e$R$^e$, —C(O)R$^e$, —C(O)OR$^e$, —C(O)SR$^e$, —C(O)NR$^e$R$^e$, —C(O)N(R$^g$)NR$^e$R$^e$, —C(O)N(R$^g$)OR$^e$, —C(NR$^g$)NR$^e$R$^e$, —C(NOH)R$^e$, —C(NOH)NR$^e$R$^e$, —OC(O)R$^e$, —OC(O)OR$^e$, —OC(O)SR$^e$, —OC(O)NR$^e$R$^e$, —OC(NR$^g$)NR$^e$R$^e$, —SC(O)R$^e$, —SC(O)OR$^e$, —SC(O)NR$^e$R$^e$, —SC(NR$^g$)NR$^e$R$^e$, —N(R$^g$)C(O)R$^e$, —N[C(O)R$^e$]$_2$, —N(OR$^g$)C(O)R$^e$, —N(R$^g$)C(NR$^g$)R$^e$, —N(R$^g$)N(R$^g$)C(O)R$^e$, —N[C(O)R$^e$]NR$^e$R$^e$, —N(R$^g$)C(S)R$^e$, —N(R$^g$)S(O)R$^e$, —N(R$^g$)S(O)OR$^e$, —N(R$^g$)S(O)$_2$R$^e$, —N[S(O)$_2$R$^e$]$_2$, —N(R$^g$)S(O)$_2$OR$^e$, —N(R$^g$)S(O)$_2$NR$^e$R$^e$, —N(R$^g$)[S(O)$_2$]$_2$R$^e$, —N(R$^g$)C(O)OR$^e$, —N(R$^g$)C(O)SR$^e$, —N(R$^g$)C(O)NR$^e$R$^e$, —N(R$^g$)C(O)NR$^g$NR$^e$R$^e$, —N(R$^g$)N(R$^g$)C(O)NR$^e$R$^e$, —N(R$^g$)C(S)NR$^e$R$^e$, —[N(R$^g$)C(O)]$_2$R$^e$, —N(R$^g$)[C(O)]$_2$R$^e$, —N{[C(O)]$_2$R$^e$}$_2$, —N(R$^g$)[C(O)]$_2$OR$^e$, —N(R$^g$)[C(O)]$_2$NR$^e$R$^e$, —N{[C(O)]$_2$OR$^e$}$_2$, —N{[C(O)]$_2$NR$^e$R$^e$}$_2$, —[N(R$^g$)C(O)]$_2$OR$^e$, —N(R$^g$)C(NR$^g$)OR$^e$, —N(R$^g$)C(NOH)R$^e$, —N(R$^g$)C(NR$^g$)SR$^e$ and —N(R$^g$)C(NR$^g$)NR$^e$R$^e$; and each R$^e$ independently of one another denotes hydrogen or a group selected from among C$_{1-6}$ alkyl, C$_{2-6}$ alkenyl, C$_{2-6}$ alkynyl, C$_{3-8}$ cycloalkyl, C$_{6-10}$ aryl, 3-8 membered heterocycloalkyl, and 5-12 membered heteroaryl; and each R$^g$ independently of one another denotes hydrogen, C$_{1-6}$ alkyl, C$_{2-6}$ alkenyl, C$_{2-6}$ alkynyl, C$_{3-8}$ cycloalkyl, C$_{6-10}$ aryl, 3-8 membered heterocycloalkyl, or 5-12 membered heteroaryl;

optionally in the form of tautomers, racemates, enantiomers, diastereomers, hydrates, isotopes, or mixtures thereof, and optionally in the form of pharmacologically acceptable salts thereof.

2. The compound according to claim 1, wherein R$^1$ is —R$^a$, or is selected from the group consisting of C$_{1-6}$ alkyl, C$_{3-6}$ cycloalkyl, C$_{4-16}$ cycloalkylalkyl and 3-8 membered heterocycloalkyl, optionally substituted by one or more identical or different R$^a$ and/or R$^b$.

3. The compound according to claim 1, wherein R$^{1'}$ is H.

4. The compound according to claim 1, wherein R$^2$ is selected from the group consisting of H, C$_{1-6}$ alkyl, C$_{3-10}$ cycloalkyl, C$_{4-16}$ cycloalkylalkyl, C$_{6-10}$ aryl, C$_{7-16}$ arylalkyl, 3-8 membered heterocycloalkyl, 4-14 membered heterocycloalkylalkyl, 5-12 membered heteroaryl and 6-18 membered heteroarylalkyl, optionally substituted by one or more; identical or different R$^a$ and/or R$^b$.

5. The compound according to claim 1, wherein R$^2$ is selected from the group consisting of H, C$_{1-6}$alkyl, C$_{3-10}$ cycloalkyl, C$_{4-16}$ cycloalkylalkyl, C$_{6-10}$ aryl, C$_{7-16}$ arylalkyl, 3-8 membered heterocycloalkyl, 4-14 membered heterocycloalkylalkyl, 5-12 membered heteroaryl and 6-18 membered heteroarylalkyl, optionally substituted by one or more identical or different R$^a$ and/or R$^b$.

6. The compound according to claim 4, wherein R$^2$ is selected from the group consisting of C$_{1-6}$ alkyl substituted by halogen, —OR$^a$, —C(O)R$^a$, —C(O)NR$^c$R$^c$, C$_{3-10}$ cycloalkyl, C$_{6-10}$ aryl, 3-8 membered heterocycloalkyl, and 5-12 membered heteroaryl.

7. The compound according to claim 6, wherein R$^2$ is selected from the group consisting of C$_{1-2}$alkyl substituted by tetrahydropyranyl, phenyl, pyrimidinyl, triazolyl, oxazolyl, oxadiazolyl, or pyrrolidinyl, each optionally substituted by one or more identical or different R$^a$ and/or R$^b$.

8. The compound according to claim 4, wherein R$^2$ is selected from the group consisting of phenyl, pyrazolyl, pyridyl, pyrimidinyl, pyridazinyl, pyrazinyl, each optionally substituted by one or more identical or different R$^a$ and/or R$^b$.

9. The compound according to claim 1, wherein R$^3$ is selected from the group consisting of C$_{3-10}$cycloalkyl, C$_{6-10}$aryl or C$_{7-16}$ arylalkyl, optionally substituted by one or more identical or different R$^a$ and/or R$^b$.

10. The compound according to claim 9, wherein R$^3$ is selected from the group consisting of C$_{6-10}$ aryl or C$_{7-16}$ arylalkyl, optionally substituted by one or more identical or different R$^a$ and/or R$^b$.

11. The compound according to claim 10, wherein R$^3$ is selected from the group consisting of phenyl or benzyl, optionally substituted by one or more identical or different R$^a$ and/or R$^b$.

12. The compound according to claim 1, wherein n denotes 0.

13. The compound according to claim 1, wherein the compound is selected from the group consisting of one of the following compounds:

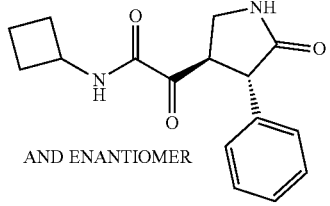 [SMILES: O=C(NC1CCC1)C(=O)[C@H]1CNC(=O)[C@@H]1c1ccccc1]

FP-19 (A/I)

AND ENANTIOMER

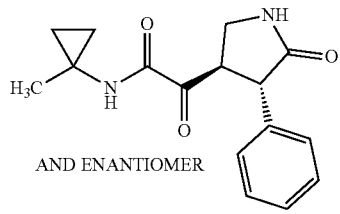 [SMILES: CC1(NC(=O)C(=O)[C@H]2CNC(=O)[C@@H]2c2ccccc2)CC1]

FP-20 (A/II)

AND ENANTIOMER

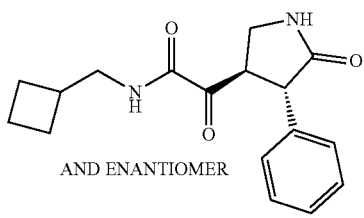 [SMILES: O=C(NCC1CCC1)C(=O)[C@H]1CNC(=O)[C@@H]1c1ccccc1]

FP-21 (A/I)

AND ENANTIOMER

FP-22 (A/II)
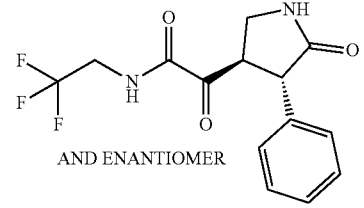 [SMILES: O=C(NCC(F)(F)F)C(=O)[C@H]1CNC(=O)[C@@H]1c1ccccc1]
AND ENANTIOMER
FP-23 (A/I)
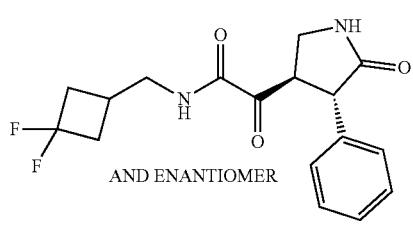 [SMILES: O=C(NCC1CC(F)(F)C1)C(=O)[C@H]1CNC(=O)[C@@H]1c1ccccc1]
AND ENANTIOMER
FP-24 (A/I)
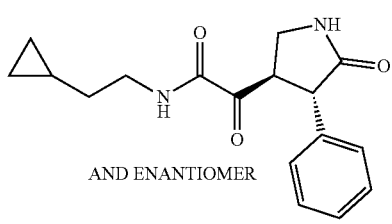 [SMILES: O=C(NCCC1CC1)C(=O)[C@H]1CNC(=O)[C@@H]1c1ccccc1]
AND ENANTIOMER
FP-25 (A/II)
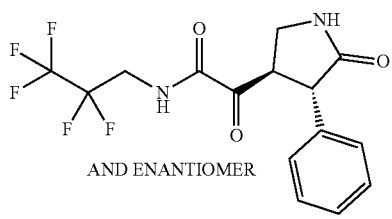 [SMILES: O=C(NCC(F)(F)C(F)(F)F)C(=O)[C@H]1CNC(=O)[C@@H]1c1ccccc1]
AND ENANTIOMER
FP-26 (A/II)
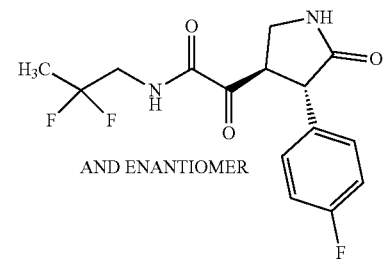 [SMILES: CC(F)(F)CNC(=O)C(=O)[C@H]1CNC(=O)[C@@H]1c1ccc(F)cc1]
AND ENANTIOMER
FP-27 (A/II)
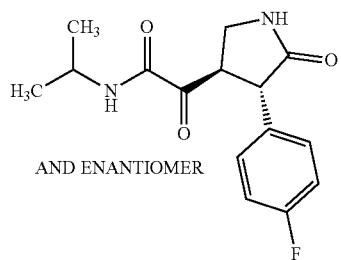 [SMILES: CC(C)NC(=O)C(=O)[C@H]1CNC(=O)[C@@H]1c1ccc(F)cc1]
AND ENANTIOMER
FP-28 (A/I)
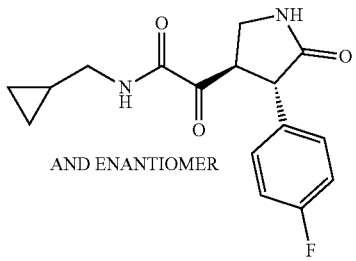 [SMILES: O=C(NCC1CC1)C(=O)[C@H]1CNC(=O)[C@@H]1c1ccc(F)cc1]
AND ENANTIOMER
FP-29 (A/I)
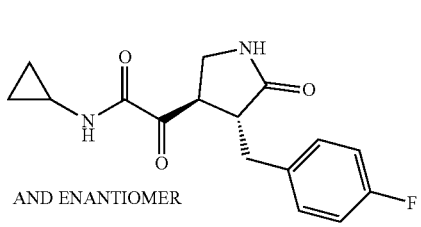 [SMILES: O=C(NC1CC1)C(=O)[C@H]1CNC(=O)[C@@H]1Cc1ccc(F)cc1]
AND ENANTIOMER
FP-30 (A/I)
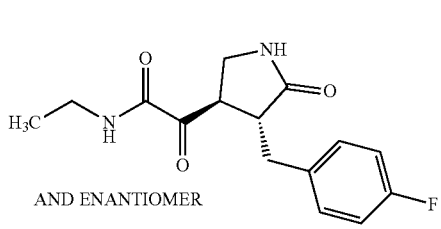 [SMILES: CCNC(=O)C(=O)[C@H]1CNC(=O)[C@@H]1Cc1ccc(F)cc1]
AND ENANTIOMER
FP-31 (A/I)
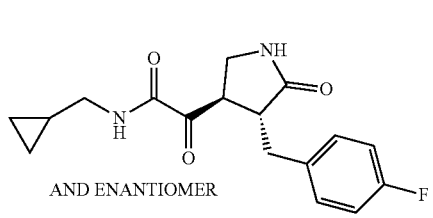 [SMILES: O=C(NCC1CC1)C(=O)[C@H]1CNC(=O)[C@@H]1Cc1ccc(F)cc1]
AND ENANTIOMER
FP-32 (A/I)
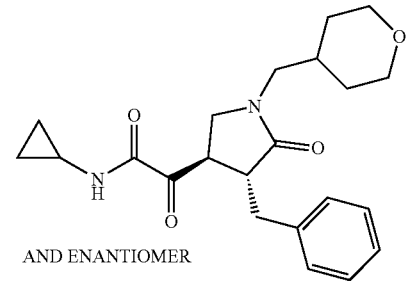 [SMILES: O=C(NC1CC1)C(=O)[C@H]1CN(CC2CCOCC2)C(=O)[C@@H]1Cc1ccccc1]
AND ENANTIOMER
FP-33 (A/I)
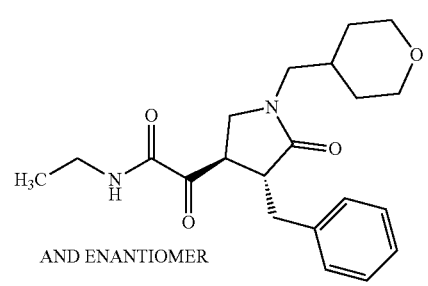 [SMILES: CCNC(=O)C(=O)[C@H]1CN(CC2CCOCC2)C(=O)[C@@H]1Cc1ccccc1]
AND ENANTIOMER

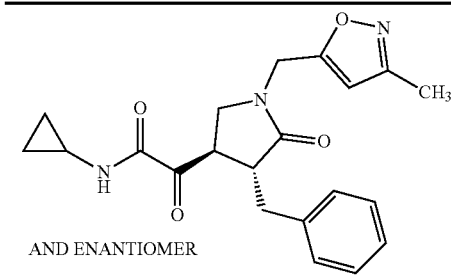
FP-34 (A/II)
AND ENANTIOMER
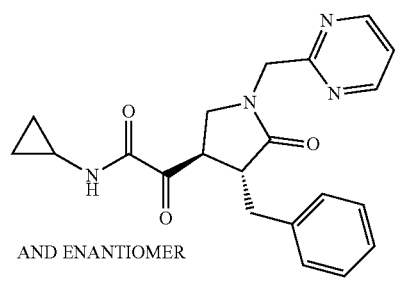 [SMILES: O=C(NC1CC1)C(=O)[C@H]1CN(Cc2ncccn2)C(=O)[C@@H]1Cc1ccccc1]
FP-35 (A/II)
AND ENANTIOMER
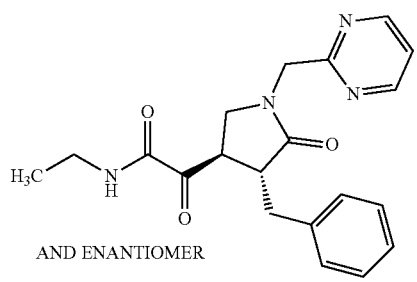 [SMILES: CCNC(=O)C(=O)[C@H]1CN(Cc2ncccn2)C(=O)[C@@H]1Cc1ccccc1]
FP-36 (A/II)
AND ENANTIOMER
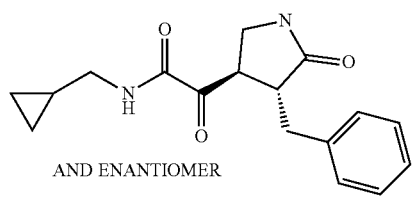 [SMILES: O=C(NCC1CC1)C(=O)[C@H]1CNC(=O)[C@@H]1Cc1ccccc1]
FP-1 (A/I)
AND ENANTIOMER
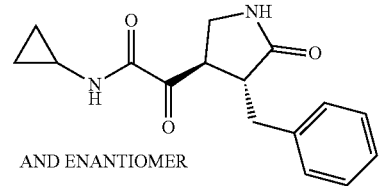 [SMILES: O=C(NC1CC1)C(=O)[C@H]1CNC(=O)[C@@H]1Cc1ccccc1]
FP-2 (A/I)
AND ENANTIOMER
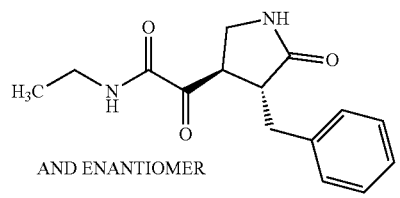 [SMILES: CCNC(=O)C(=O)[C@H]1CNC(=O)[C@@H]1Cc1ccccc1]
FP-3 (A/I)
AND ENANTIOMER
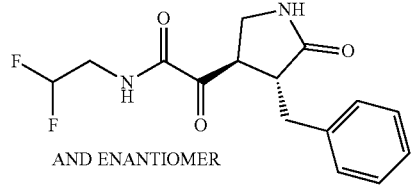 [SMILES: O=C(NCC(F)F)C(=O)[C@H]1CNC(=O)[C@@H]1Cc1ccccc1]
FP-4 (A/I)
AND ENANTIOMER
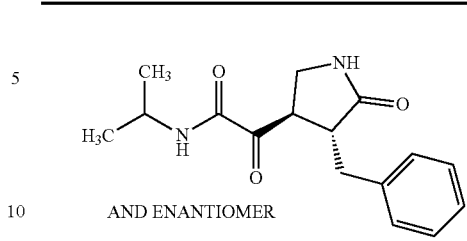
FP-5 (A/I)
AND ENANTIOMER
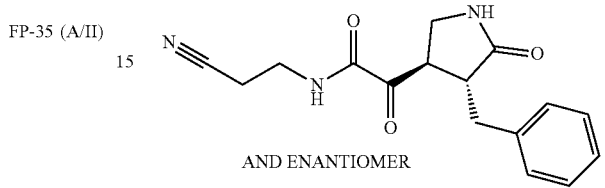
FP-6 (A/II)
AND ENANTIOMER
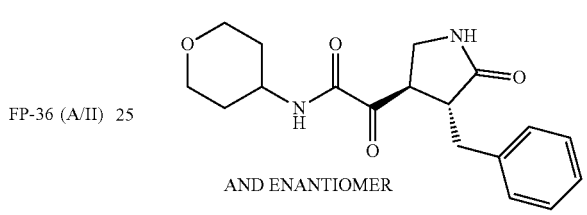
FP-7 (A/II)
AND ENANTIOMER
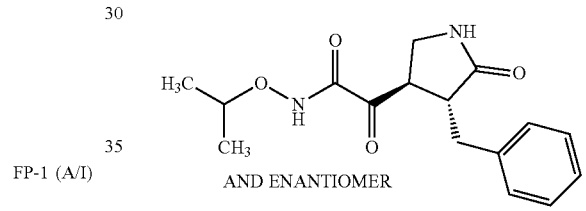
FP-8 (A/II)
AND ENANTIOMER
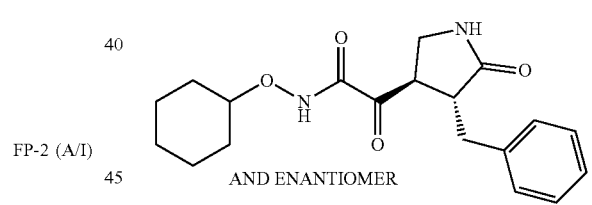
FP-9 (A/II)
AND ENANTIOMER
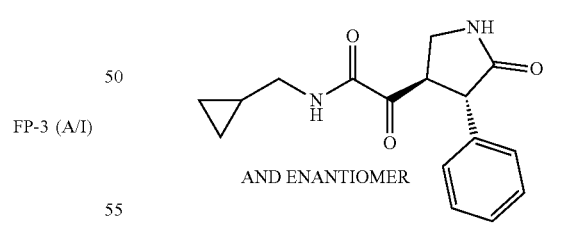
FP-10 (A/I)
AND ENANTIOMER
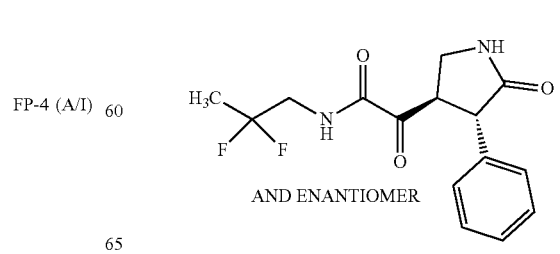
FP-11 (A/II)
AND ENANTIOMER

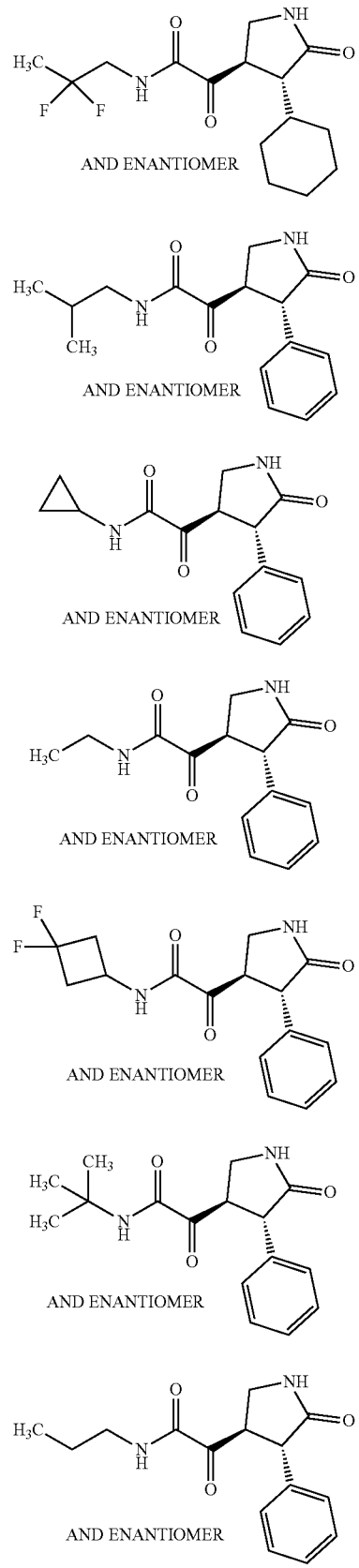
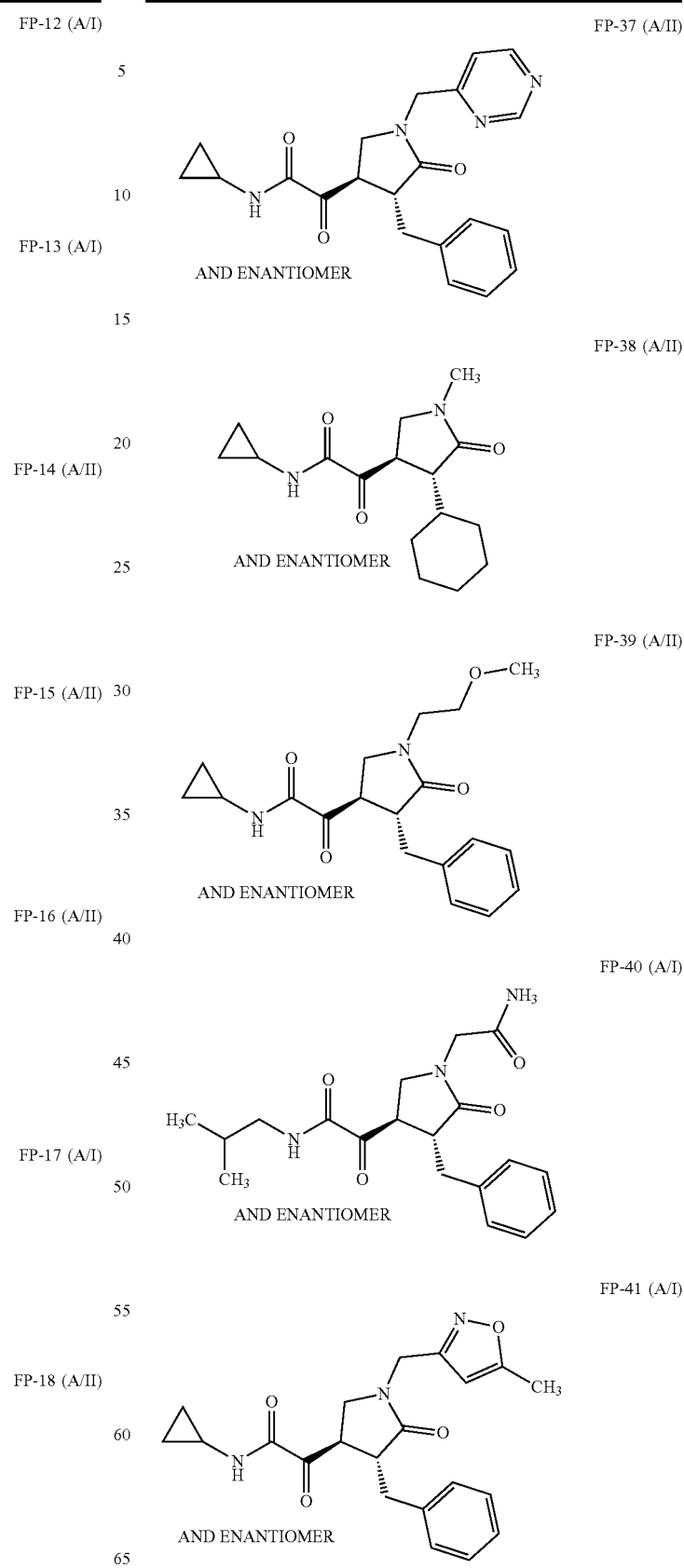

-continued

-continued
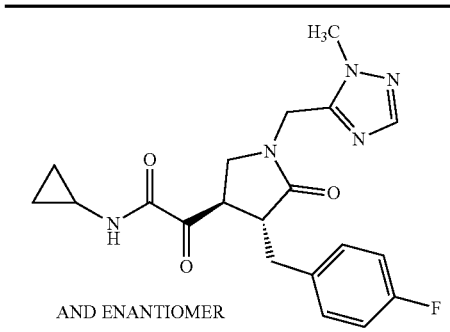
FP-52 (A/III)
AND ENANTIOMER
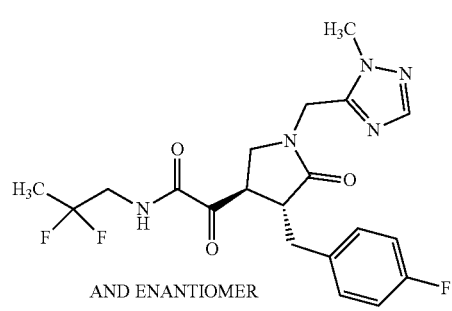 [SMILES: Cn1ncnc1CN1C[C@H](C(=O)C(=O)NCC(C)(F)F)[C@@H](Cc2ccc(F)cc2)C1=O]
FP-53 (A/II)
AND ENANTIOMER
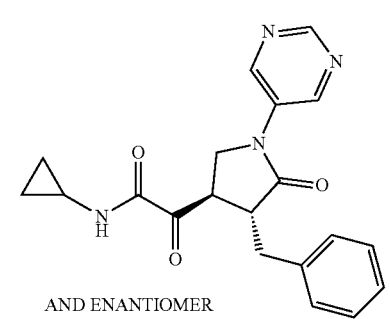
FP-54 (A/I)
AND ENANTIOMER
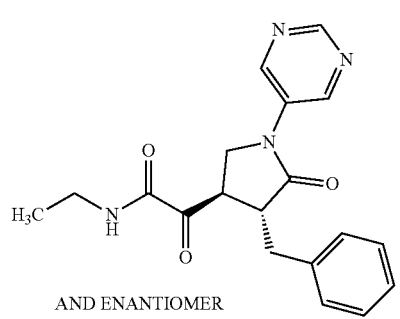 [SMILES: CCNC(=O)C(=O)[C@H]1CN(c2cncnc2)C(=O)[C@@H]1Cc1ccccc1]
FP-55 (A/I)
AND ENANTIOMER
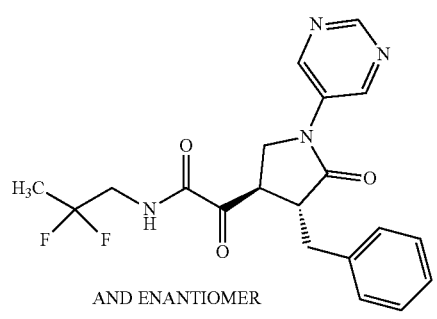 [SMILES: CC(F)(F)CNC(=O)C(=O)[C@H]1CN(c2cncnc2)C(=O)[C@@H]1Cc1ccccc1]
FP-56 (A/I)
AND ENANTIOMER
-continued
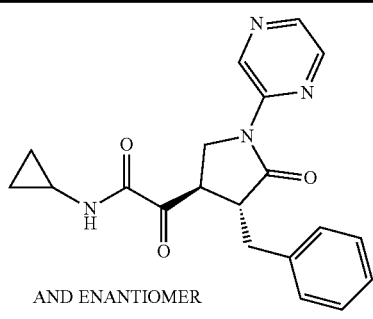
FP-57 (A/I)
AND ENANTIOMER
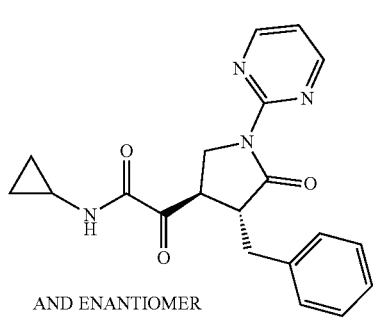 [SMILES: O=C(NC1CC1)C(=O)[C@H]1CN(c2ncccn2)C(=O)[C@@H]1Cc1ccccc1]
FP-58 (A/II)
AND ENANTIOMER
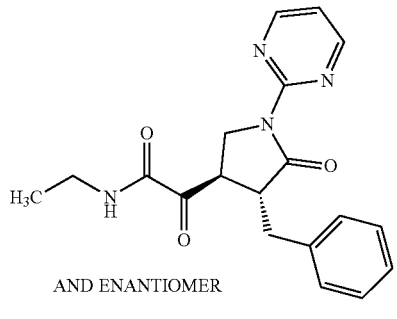 [SMILES: CCNC(=O)C(=O)[C@H]1CN(c2ncccn2)C(=O)[C@@H]1Cc1ccccc1]
FP-59 (A/II)
AND ENANTIOMER
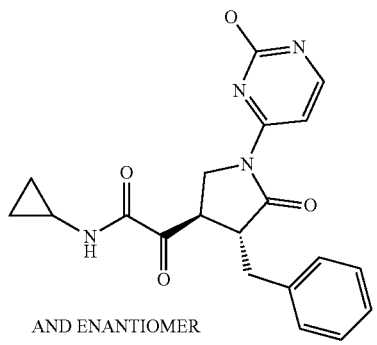 [SMILES: O=C(NC1CC1)C(=O)[C@H]1CN(c2ccnc(O)n2)C(=O)[C@@H]1Cc1ccccc1]
FP-60 (A/II)
AND ENANTIOMER
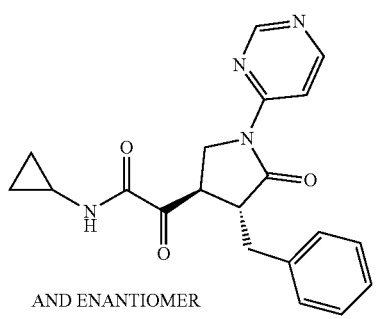 [SMILES: O=C(NC1CC1)C(=O)[C@H]1CN(c2ccncn2)C(=O)[C@@H]1Cc1ccccc1]
FP-61 (A/II)
AND ENANTIOMER 155
-continued
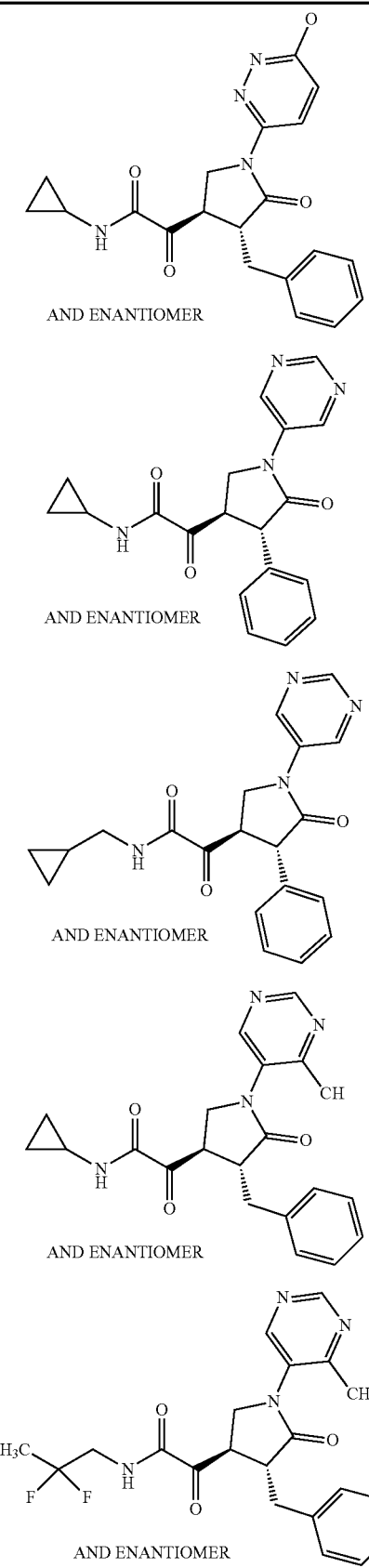
156
-continued
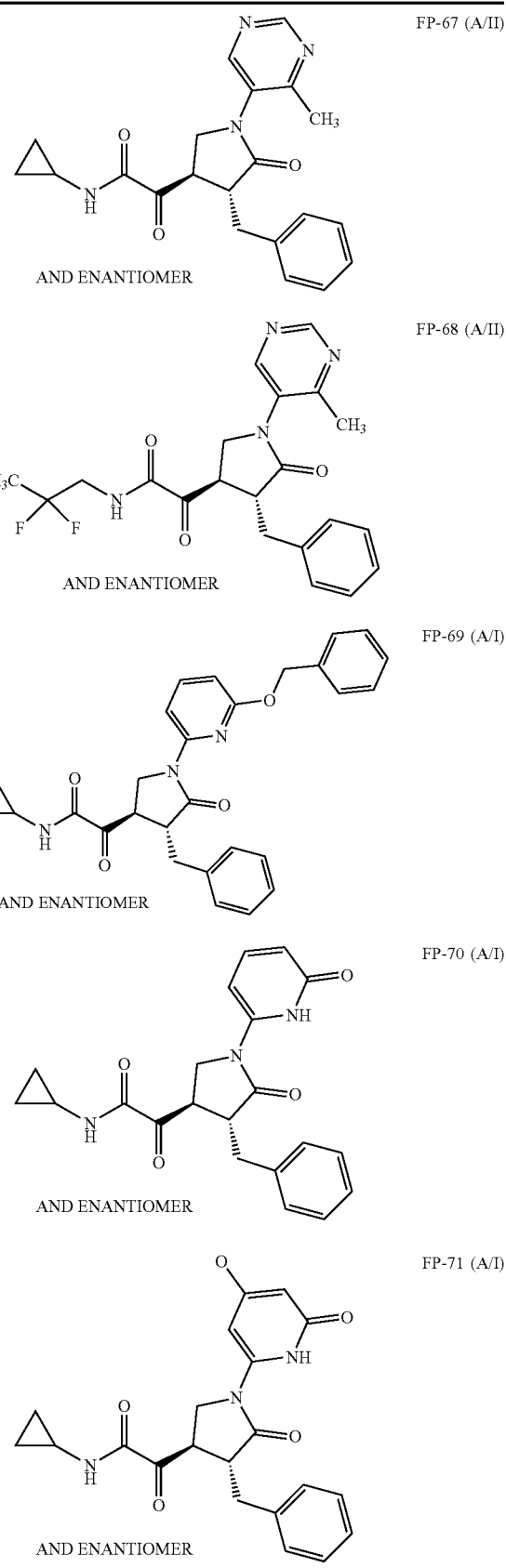

-continued

FP-72 (A/I), FP-73 (A/I), FP-74 (A/I), FP-75 (A/I), FP-76 (A/I), FP-77 (A/II), FP-78 (A/II), FP-79 (A/I), FP-80 (A/I), FP-81 (A/I)

| 159 -continued | | 160 -continued | |
|---|---|---|---|
| 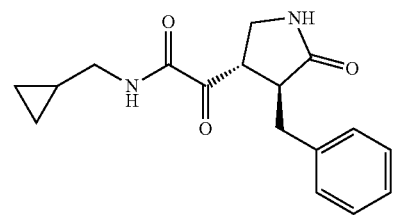 [SMILES: O=C(NCC1CC1)C(=O)[C@@H]1CNC(=O)[C@H]1Cc1ccccc1] | FP-82 (A/II) | 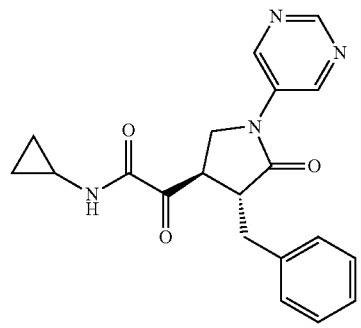 | FP-89 (A/I) |
| 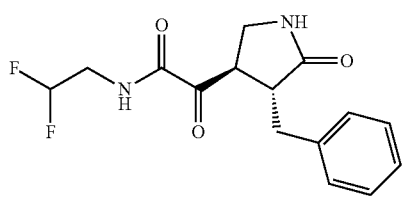 [SMILES: O=C(NCC(F)F)C(=O)[C@H]1CNC(=O)[C@@H]1Cc1ccccc1] | FP-83 (A/I) | | |
| 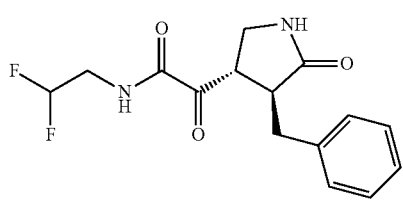 [SMILES: O=C(NCC(F)F)C(=O)[C@@H]1CNC(=O)[C@H]1Cc1ccccc1] | FP-84 (B/III) | 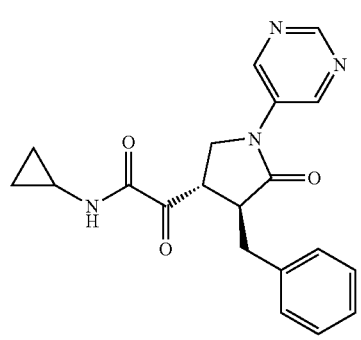 | FP-90 (A/II) |
| 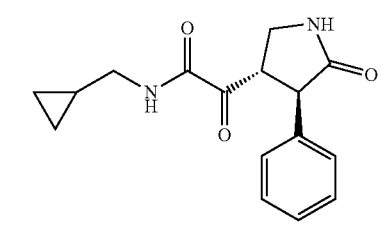 [SMILES: O=C(NCC1CC1)C(=O)[C@@H]1CNC(=O)[C@H]1c1ccccc1] | FP-85 (A/III) | 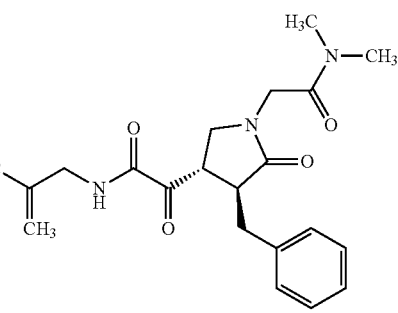 | FP-91 (B/III) |
| 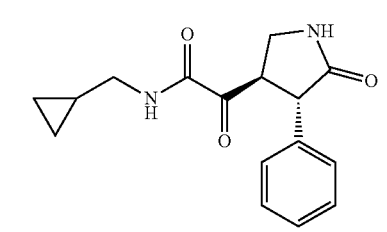 [SMILES: O=C(NCC1CC1)C(=O)[C@H]1CNC(=O)[C@@H]1c1ccccc1] | FP-86 (A/I) | | |
| 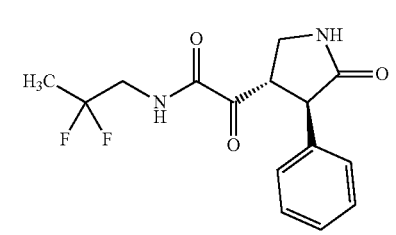 [SMILES: CC(F)(F)CNC(=O)C(=O)[C@@H]1CNC(=O)[C@H]1c1ccccc1] | FP-87 (B/III) | 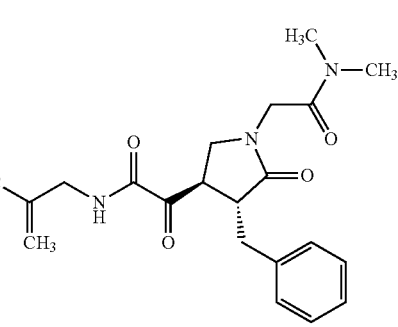 | FP-92 (A/II) |
| 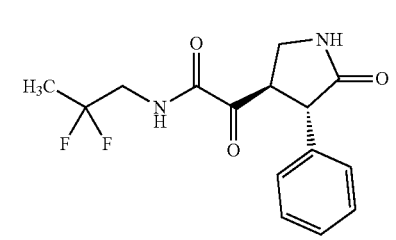 [SMILES: CC(F)(F)CNC(=O)C(=O)[C@H]1CNC(=O)[C@@H]1c1ccccc1] | FP-88 (A/I) | 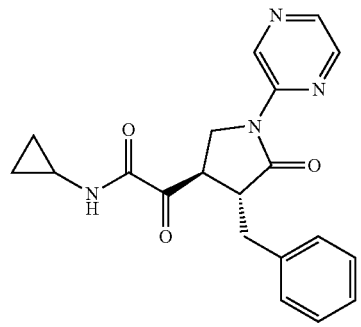 [SMILES: O=C(NC1CC1)C(=O)[C@H]1CN(c2cnccn2)C(=O)[C@@H]1Cc1ccccc1] | FP-93 (A/I) |

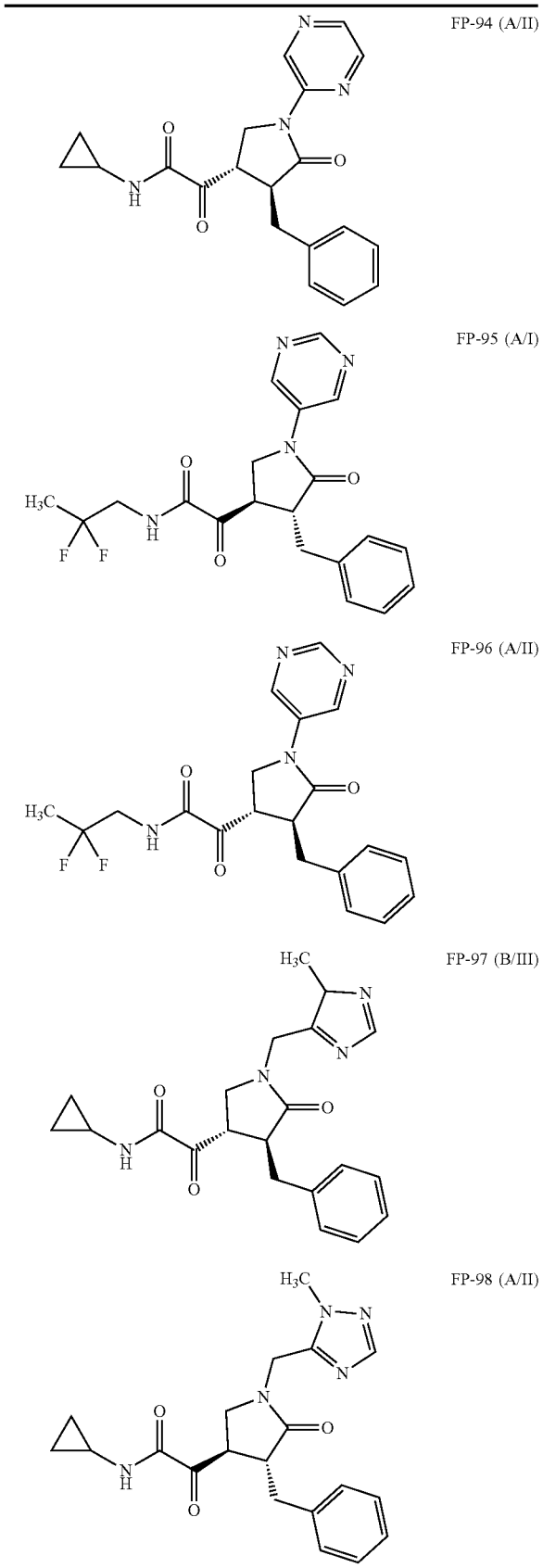
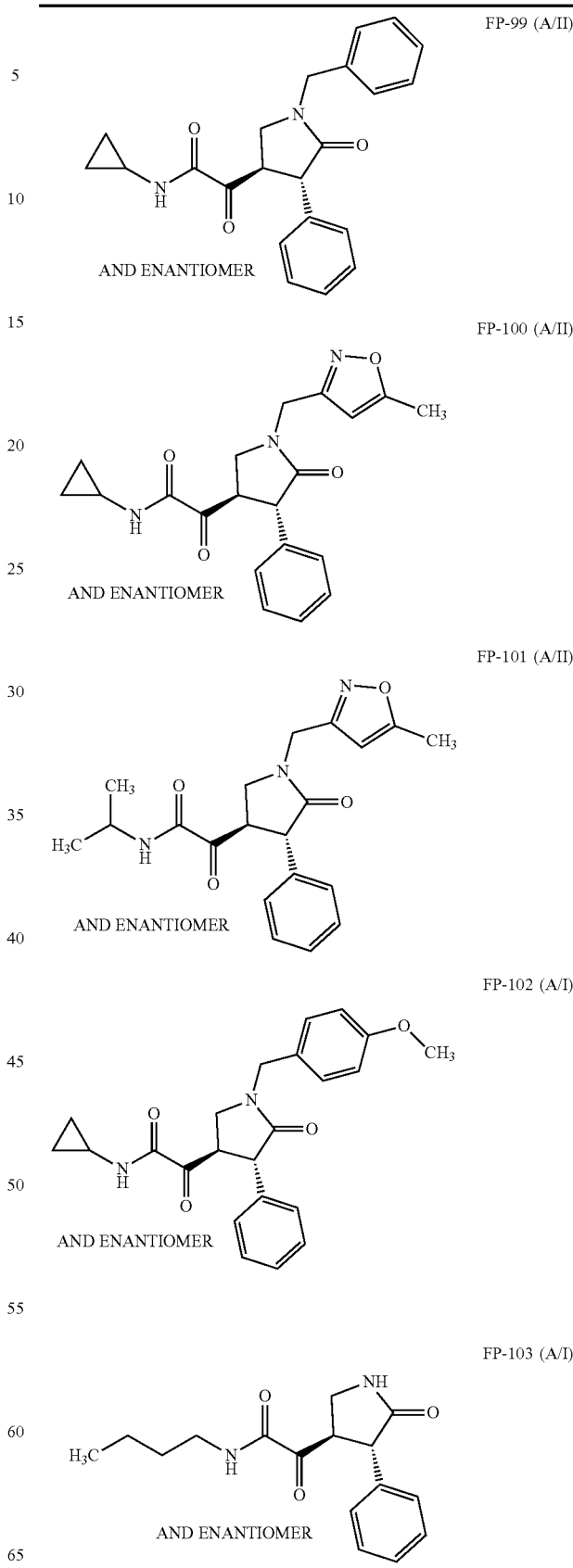

-continued

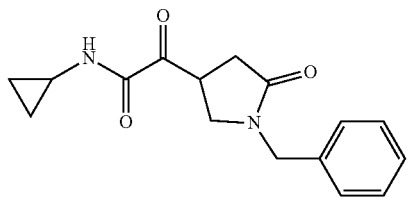 [SMILES: O=C(NC1CC1)C(=O)C1CC(=O)N(Cc2ccccc2)C1]

FP-104 (A/II).

14. A composition comprising the compound according to claim 1 and a pharmaceutically acceptable excipient or carrier.

15. A method of treating an infectious disease, cancer or obesity, comprising the step of administering an effective amount of the compound according to claim 1 to a subject in need thereof.

16. The method of claim 15, wherein the infectious disease is a picornavirus infection.

* * * * *